(12) United States Patent
Chase et al.

(10) Patent No.: US 11,136,335 B2
(45) Date of Patent: Oct. 5, 2021

(54) PRINS REACTION AND INTERMEDIATES USEFUL IN THE SYNTHESIS OF HALICHONDRIN MACROLIDES AND ANALOGS THEREOF

(71) Applicant: EISAI R&D MANAGEMENT CO., LTD., Tokyo (JP)

(72) Inventors: Charles E. Chase, Londonderry, NH (US); Hyeong-Wook Choi, Andover, MA (US); Atsushi Endo, Andover, MA (US); Francis G. Fang, Andover, MA (US); Dae-Shik Kim, Andover, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 0 days.

(21) Appl. No.: 16/313,196

(22) PCT Filed: Jun. 30, 2017

(86) PCT No.: PCT/US2017/040401
§ 371 (c)(1),
(2) Date: Dec. 26, 2018

(87) PCT Pub. No.: WO2018/006031
PCT Pub. Date: Jan. 4, 2018

(65) Prior Publication Data
US 2019/0161495 A1 May 30, 2019

Related U.S. Application Data

(60) Provisional application No. 62/357,031, filed on Jun. 30, 2016.

(51) Int. Cl.
*C07D 493/22* (2006.01)
(52) U.S. Cl.
CPC .................. *C07D 493/22* (2013.01)
(58) Field of Classification Search
CPC .................................................. C07D 493/22
See application file for complete search history.

(56) References Cited

U.S. PATENT DOCUMENTS

| | | |
|---|---|---|
| 5,338,865 A | 8/1994 | Kishi et al. |
| 5,436,238 A | 7/1995 | Kishi et al. |
| 5,451,573 A | 9/1995 | Hemmerle et al. |
| 6,194,586 B1 | 2/2001 | Martinelli et al. |
| 6,214,865 B1 | 4/2001 | Littlefield et al. |
| 6,365,759 B1 | 4/2002 | Littlefield et al. |
| 6,469,182 B1 | 10/2002 | Littlefield et al. |
| 6,653,341 B1 | 11/2003 | Littlefield et al. |
| 7,470,720 B2 | 12/2008 | Littlefield et al. |
| 7,982,060 B2 | 7/2011 | Austad et al. |
| 8,093,410 B2 | 1/2012 | Chase et al. |
| 8,097,648 B2 | 1/2012 | Littlefield et al. |
| 8,148,554 B2 | 4/2012 | Seletsky et al. |
| 8,203,010 B2 | 6/2012 | Endo et al. |
| 8,350,067 B2 | 1/2013 | Endo et al. |
| 8,445,701 B2 | 5/2013 | Austad et al. |
| 8,598,373 B2 | 12/2013 | Hu |
| 8,618,313 B2 | 12/2013 | Benayoud et al. |
| 8,884,031 B2 | 11/2014 | Chase et al. |
| RE45,324 E | 1/2015 | Austad et al. |
| 8,927,597 B2 | 1/2015 | Endo et al. |
| 8,975,422 B2 | 3/2015 | Fang et al. |
| 8,987,479 B2 | 3/2015 | Chase et al. |
| 9,206,194 B2 | 12/2015 | Hu |
| 9,303,039 B2 | 4/2016 | Zhang et al. |
| 9,303,050 B2 | 4/2016 | Benayoud et al. |
| 9,382,262 B2 | 7/2016 | Endo et al. |
| 9,469,651 B2 | 10/2016 | Hu |
| 9,604,993 B2 | 3/2017 | Chase et al. |
| 9,695,188 B2 | 7/2017 | Hu et al. |
| 9,783,549 B2 | 10/2017 | Fang et al. |
| 9,802,953 B2 | 10/2017 | Chase et al. |
| 9,856,276 B2 | 1/2018 | Endo et al. |
| RE46,965 E | 7/2018 | Austad et al. |
| 10,030,032 B2 | 7/2018 | Hu et al. |
| 10,214,539 B2 | 2/2019 | Chase et al. |
| 10,221,189 B2 | 3/2019 | Fang et al. |
| 10,308,661 B2 | 6/2019 | Fang et al. |
| 10,450,324 B2 | 10/2019 | Hu et al. |

(Continued)

FOREIGN PATENT DOCUMENTS

| | | |
|---|---|---|
| CN | 104334562 A | 2/2015 |
| EP | 0572109 A1 | 12/1993 |

(Continued)

OTHER PUBLICATIONS

Wan, Zhao-Kui, et al. "Asymmetric Ni(II)/Cr(II)-Mediated Coupling Reaction: Stoichiometric Process." Organic Letters. (2002), vol. 4 , No. 25, pp. 4431-4434. (Year: 2002).*
Choi et al., "Prins reaction of homoallenyl alcohols: Access to substituted pyrans in the halichondrin series," Org Lett. 19(22): 6092-5 (2017).
Ko, "Prins reactions and applications," http://gbdong.cm.utexas.edu/seminar/old/Prins%20reactions%20and%20Applications_Haye%20Min%20Ko.pdf, retrieved Jan. 21, 2020, dated Nov. 28, 2012 (30 pages).
Partial Supplementary European Search Report for European Patent Application No. 17821400.3, dated Feb. 10, 2020 (17 pages).
U.S. Appl. No. 16/684,332, Benayoud et al.
Gradillas et al., "Macrocyclization by ring-closing metathesis in the total synthesis of natural products: reaction conditions and limitations," Angew Chem Int Ed Engl. 45(37): 6086-6101 (2006).

(Continued)

*Primary Examiner* — John S Kenyon
(74) *Attorney, Agent, or Firm* — Clark & Elbing LLP

(57) ABSTRACT

The invention provides methods for the synthesis of a halichondrin macrolides or analogs thereof through a cyclization reaction strategy. The strategy of the present invention involves subjecting an intermediate to Prins reaction conditions to afford a macrolide. The invention also provides compounds useful as intermediates in the synthesis of a halichondrin macrolides or analogs thereof and methods for preparing the same.

21 Claims, No Drawings

(56) References Cited

U.S. PATENT DOCUMENTS

| | | | |
|---|---|---|---|
| 10,494,388 | B2 | 12/2019 | Endo et al. |
| RE47,797 | E | 1/2020 | Benayoud et al. |
| 10,611,773 | B2 | 4/2020 | Fang et al. |
| 10,676,481 | B2 | 6/2020 | Baran et al. |
| 2002/0103387 | A1 | 8/2002 | Smith et al. |
| 2004/0092581 | A1 | 5/2004 | Burzlaff et al. |
| 2006/0045846 | A1 | 3/2006 | Horstmann et al. |
| 2009/0093649 | A1 | 4/2009 | Nobis |
| 2009/0104285 | A1 | 4/2009 | Littlefield et al. |
| 2009/0203771 | A1 | 8/2009 | Inanaga et al. |
| 2010/0184860 | A1 | 7/2010 | Yoshimura et al. |
| 2011/0184190 | A1 | 7/2011 | Endo et al. |
| 2012/0029213 | A1 | 2/2012 | Austad et al. |
| 2015/0065733 | A1 | 3/2015 | Souza et al. |
| 2015/0225415 | A1 | 8/2015 | Chase et al. |
| 2016/0152631 | A1 | 6/2016 | Souza et al. |
| 2018/0162885 | A1 | 6/2018 | Endo et al. |
| 2019/0010166 | A1 | 1/2019 | Hu et al. |
| 2019/0144463 | A1 | 5/2019 | Fang et al. |
| 2019/0263826 | A1 | 8/2019 | Chase et al. |
| 2019/0300542 | A1 | 10/2019 | Baran et al. |
| 2019/0308992 | A1 | 10/2019 | Fang et al. |
| 2020/0223864 | A1 | 7/2020 | Fang et al. |

FOREIGN PATENT DOCUMENTS

| | | |
|---|---|---|
| JP | 2001-500498 A | 1/2001 |
| JP | 2010-168320 A | 8/2010 |
| SU | 652180 A1 | 3/1979 |
| WO | WO-93/17690 A1 | 9/1993 |
| WO | WO-98/09942 A1 | 3/1998 |
| WO | WO-99/65894 A1 | 12/1999 |
| WO | WO-2005/118565 A1 | 12/2005 |
| WO | WO-2006/076100 A2 | 7/2006 |
| WO | WO-2008/010776 A1 | 1/2008 |
| WO | WO-2009/014105 A1 | 1/2009 |
| WO | WO-2009/046308 A1 | 4/2009 |
| WO | WO-2009/064029 A1 | 5/2009 |
| WO | WO-2009/124237 A1 | 10/2009 |
| WO | WO-2011/094339 A1 | 8/2011 |
| WO | WO-2012/147900 A1 | 11/2012 |
| WO | WO-2013/078559 A1 | 6/2013 |
| WO | WO-2013/142999 A1 | 10/2013 |
| WO | WO-2015/000070 A1 | 1/2015 |
| WO | WO-2015/066729 A1 | 5/2015 |
| WO | WO-2016/038624 A1 | 3/2016 |
| WO | WO-2016/179607 A1 | 11/2016 |
| WO | WO-2017/139664 A1 | 8/2017 |
| WO | WO-2018/217894 A1 | 11/2018 |
| WO | WO-2019/136145 A1 | 7/2019 |

OTHER PUBLICATIONS

Namba et al., "A simple but remarkably effective device for forming the C8-C14 polycyclic ring system of halichondrin B," J Am Chem Soc. 126(25): 7770-1 (2004) (10 pages).
Ward et al., "Catalytic enantioselective diels-alder reaction by self-assembly of the components on a Lewis acid template," Org Lett. 7(16):3533-6 (2005) (Abstract only) (2 pages).
Search Report for Singaporean Patent Application No. 11201811671X, dated Mar. 16, 2020 (5 pages).
International Search Report and Written Opinion dated Oct. 3, 2017 for International Application No. PCT/US2017/40401, Chase et al., "Prins Reaction and Intermediates Useful in the Synthesis of Halichondrin Macrolides and Analogs Thereof," filed Jun. 30, 2017 (16 pages).
Kim et al., "New syntheses of E7389 C14-C35 and Halichondrin C14-C38 building blocks: double-inversion approach," J Am Chem Soc. 131(43):15636-41 (2009).
Pubchem CID 10501910, created Oct. 25, 2006 (8 pages), accessed Aug. 31, 2017.
U.S. Appl. No. 15/944,480, Benayoud et al.
U.S. Appl. No. 16/076,028, Baran et al.
U.S. Appl. No. 16/284,405, Chase et al.
U.S. Appl. No. 16/387,820, Fang et al.
Aicher et al., "Synthetic studies towards halichondrins: synthesis of the C.27-C.38 segment," Tetrahedron Lett. 33(12):1549-52 (1992).
Aicher et al., "Total synthesis of halichondrin B and norhalichondrin B," J Am Chem Soc. 114(8):3162-4 (1992).
Aicher, Thesis, Chapter 4, "Synthetic studies towards halichondrin B," Doctor of Philosophy in Chemistry, Harvard University, 35-54, 1989 (26 pages).
AkzoNobel Polymer Chemicals, "Diisobutylaluminum hydride (DIBAL-H) and other isobutyl aluminum Alkyls (DIBAL-BOT, TIBAL) as specialty organic synthesis reagents," The AkzoNobel Technical Bulletin, 1-14 (2006).
Alley et al. "Comparison of the relative efficacies and toxicities of Halichondrin B analogues," Proceedings of the AACR-NCI-EORTC Conference on Molecular Targets and Cancer Therapeutics. C230:257 (2005).
Anderson, "Developing processes for crystallization-induced asymmetric transformation," Org Process Res Dev. 9:800-13 (2005).
Ando et al., "Z-selective intramolecular Horner-Wadsworth-Emmons reaction for the synthesis of macrocyclic lactones," Org Lett. 12(7):1460-3 (2010).
Austad et al., "Commercial manufacture of Halaven®: chemoselective transformations en route to structurally complex macrocyclic ketones," Synlett. 24 (2013). Supporting Information, (13 pages.).
Austad et al., "Commercial manufacture of Halaven®: chemoselective transformations en route to structurally complex macrocyclic ketones," Synlett. 24(3):333-7 (2013).
Austad et al., "Process development of Halaven®: synthesis of the C14-C35 fragment via iterative Nozaki-Hiyama-Kishi reaction— Williamson ether cyclization," Synlett. 24(3):327-32 (2013).
Bai et al., "Halichondrin B and Homohalichondrin B, marine natural products binding in the vinca domain of tubulin. Discovery of tubulin-based mechanism of action by analysis of differential cytotoxicity data," J Biol Chem. 266(24):15882-9 (1991).
Bernet et al., "Carbocyclische verbindungen aus monosacchariden. Umsetzungen in der glucosereihe," Helv Chim Acta. 62(6):1990-2016 (1979).
Blanchette et al., "Horner-Wadsworth-Emmons reaction: use of lithium chloride and an amine for base-sensitive compounds," Tetrahedron Lett. 25(21):2183-6 (1984).
Burke et al., "Enantioselective synthesis of a Halichondrin B C(20) → C(36) precursor," Tetrahedron Lett. 36(39):7023-6 (1995).
Burke et al., "Synthesis of a C(22)-C(34) Halichondrin B precursor via ring opening—double ring closing metathesis," J Org Chem. 63:8626-7 (1998).
Burke et al., "Synthesis of a C(22) → C(34) Halichondrin precursor via a double dioxanone-to-dihydropyran rearrangement," Tetrahedron Lett. 32(32):3961-4 (1991).
Burke et al., "Synthetic studies toward complex polyether macrolides of marine origin," Spec Publ R Soc Chem. 198:(Anti-Infectives) 73-85 (1997).
Chase et al., "Process development of Halaven®: Synthesis of the C1-C13 fragment from D-(−)-Gulono-1, 4-lactone," Synlett. 24(3):323-6 (2013).
Chen et al., "Ni(II)/Cr(II)-mediated coupling reaction: An asymmetric process," J Org Chem. 60(17):5386-7 (1995).
Choi et al., "Asymmetric Ni(II)/Cr(II)-mediated coupling reaction: catalytic process," Org Lett. 4(25):4435-8 (2002).
Choi et al., "Supporting information for asymmetric Ni(II)/Cr(II)-mediated coupling reaction: catalytic process," Org Lett. 4(25) (2002) (8 pages).
Choi et al., "Synthetic studies on the marine natural product Halichondrins," Pure Appl Chem. 75(1):1-17 (2003).
Cooper et al., "Total Synthesis of Halichondrin B from common sugars: an F-ring intermediate from D-glucose and efficient construction of the C1 to C21 segment," Tetrahedron Lett. 34(51):8193-6 (1993).
Cunningham et al., "The influence of pH on the kinetic constants of alpha-chymotrypsin-catalyzed esterolysis," J Biol Chem. 221(1):287-99 (1956).

(56) References Cited

OTHER PUBLICATIONS

Dabydeen et al. "Comparison of the activities of the truncated Halichondrin B analog NSC 707389 (E7389) with those of the parent compound and a proposed binding site on tubulin," Mol Pharmacol. 70(6):1866-75 (2006).
Del Valle et al., "Total synthesis of (+)-trienomycins A and F via C-C bond-forming hydrogenation and transfer hydrogenation," J Am Chem Soc. 135(30):10986-89 (2013).
Dong et al. "New syntheses of E7389 C14-C35 and halichondrin C14-C38 building blocks: reductive cyclization and oxy-michael cyclization approaches," J Am Chem Soc. 131(43):15642-6 (2009).
Duan et al., "Synthetic studies on halichondrins: a new practical synthesis of the C.1-C.12 segment," Tetrahedron Lett. 34(47):7541-4 (1993).
Fleming et al., "Nitrile anion cyclizations," Tetrahedron. 58(1):1-23 (2002).
Gesinski et al., "Symmetric macrocycles by a Prins dimerization and macrocyclization strategy," available in PMC Nov. 1, 2010, published in final edited form as: Org Lett. 11(22):5342-5 (2009) (13 pages).
Guo et al., "Toolbox approach to the search for effective ligands for catalytic asymmetric Cr-mediated coupling reactions," J Am Chem Soc. 131(42):15387-93 (2009).
Hirata et al., "Halichondrins—antitumor polyether macrolides from a marine sponge," Pure Appl Chem. 58(5):701-10 (1986).
Hori et al., "Efficient synthesis of 2,3-trans-tetrahydropyrans and oxepanes: rearrangement-ring expansion of cyclic ethers having a chloromethanesulfonate," Tetrahedron Lett. 40(11):2145-8 (1999).
Horita et al., "Research on anti-tumor active site of marine source natural product, Halichondrin B.," International Congress Series, 1157 (Towards Natural Medicine Research in the 21st Century), 327-336 (1998).
Horita et al., "Synthetic studies of halichondrin B, an antitumor polyether macrolide isolated from a marine sponge. 2. Efficient synthesis of C16-C26 fragments via construction of the D ring by a highly stereocontrolled iodoetherification," Synlett. 40-43 (1994).
Horita et al., "Synthetic studies of Halichondrin B, an antitumor polyether macrolide isolated from a marine sponge. 3. Synthesis of C27-C36 subunit via completely stereoselective C-glycosylation to the F ring," Synlett. 43-45 (1994).
Horita et al., "Synthetic studies of Halichondrin B, an antitumor polyether macrolide isolated from a marine sponge. 7. Synthesis of two C27-C36 units via construction of the F ring and completely stereoselective C-glycosylation using mixed Lewis acids," Chem Pharm Bull. 45(10):1558-72 (1997).
Horita et al., "Synthetic studies of Halichondrin B, an antitumor polyether macrolide isolated from a marine sponge. 8. Synthesis of the lactone part (C1-C36) via Horner-Emmons coupling between C1-C15 and C16-C36 fragments and yamaguchi lactonization," Tetrahedron Lett. 38(52):8965-8 (1997).
Horita et al., "Synthetic studies on Halichondrin B, an antitumor polyether macrolide isolated from a marine sponge. 9. Synthesis of the C16-C36 unit via stereoselective construction of the D and E rings," Chem Pharm Bull. 46(8):1199-216 (1998).
Horita et al., Synthetic study of a highly antitumorigenic marine phytochemical, Halichondrin B. *Phytochemicals and Phytopharmaceuticals.* Fereidoon Shahidi and Chi-Tang Ho, 386-397 (2000).
Jackson et al., "A total synthesis of norhalichondrin B," Angew Chem Int Ed. 48(13):2346-50 (2009).
Jackson et al., "The halichondrins and E7389," Chem Rev. 109(7):3044-79 (2009).
Jiang et al., "A novel route to the F-ring of Halichondrin B. Diastereoselection in Pd(0)-mediated meso and C2 diol desymmetrization," Org Lett. 4(20):3411-4 (2002).
Jiang et al., "A practical synthesis of the F-ring of halichondrin B via ozonolytic desymmetrization of a C(2)-symmetric dihydroxycyclohexene," J Org Chem. 68(3):1150-3 (2003).
Kawaguchi et al., "Drug and crystal polymorphism," Journal of Human Environmental Engineering. 4(2):310-7 (2002) (10 pages).

Kong et al., "Total synthesis of the spirocyclic imine marine toxin (−)-gymnodimine and an unnatural C4-epimer," J Am Chem Soc. 133(49): 19844-56 (2011).
Kurosu et al., "Fe/Cr- and Co/Cr-mediated catalytic asymmetric 2-Haloallylations of aldehydes," J Am Chem Soc. 126(39):12248-9 (2004).
Kurosu et al., "Supporting information for Fe/Cr- and Co/Cr-mediated catalytic asymmetric 2-haloallylations of aldehydes," J Am Chem Soc. 126(39) (2004) (31 pages).
Mitsunobu, "The use of diethyl azodicarboxylate and triphenylphosphine in synthesis and transformation of natural products," Synthesis. 1-28 (1981).
Namba et al., "New catalytic cycle for couplings of aldehydes with organochromium reagents," Org Lett. 6(26):5031-3 (2004).
Narayan et al., "Novel second generation analogs of eribulin. Part II: Orally available and active against resistant tumors in vivo," Bioorg Med Chem Lett. 21(6):1634-8 (2011).
Newman, "Drug evaluation: eribulin, a simplified ketone analog of the tubulin inhibitor Halichondrin B, for the potential treatment of cancer," Curr Opin Invest Drugs. 8(12):1057-66 (2007).
Nicolaou et al., "Total synthesis of brevetoxin A: Part 3: construction of GHIJ and BCDE ring systems," Chem Eur J. 5(2):628-45 (1999).
Nicolaou et al., "Total synthesis of the CP molecules CP-263,114 and CP-225,917—Part 1: synthesis of key intermediates and intelligence gathering," Angew Chem Int Ed. 38(11):1669-75 (1999).
Ritter, "Synthetic transformations of vinyl and aryl triflates," Synthesis: Reviews. 8:735-62 (1993).
Sakamoto et al., "Stereoselective ring expansion via bicyclooxonium ion. A novel approach to oxocanes," Org Lett. 4(5):675-8 (2002).
Schreiber, "Hydrogen transfer from tertiary amines to trifluoroacetic anhydride," Tetrahedron Lett. 21(11):1027-30 (1980).
Seletsky et al. "Structurally simplified macrolactone analogues of halichondrin B," Bioorg Med Chem Lett. 14(22):5547-50 (2004).
Stamos et al., "A mild preparation of vinyliodides from vinylsilanes," Tetrahedron Lett. 37(48): 8647-50 (1996).
Stamos et al., "New synthetic route to the C.14-C.38 segment of Halichondrins," J Org Chem. 62(22):7552-3 (1997).
Stamos et al., "Ni(II)/Cr(II)-mediated coupling reaction: beneficial effects of 4-tert-butylpyridine as an additive and development of new and improved workup procedures," Tetrahedron Lett. 38(36):6355-8 (1997).
Stamos et al., "Synthetic studies on Halichondrins: a practical synthesis of the C.1-C.13 segment," Tetrahedron Lett. 37(48):8643-6 (1996).
Sutherland et al., "The synthesis of 6alpha- and 6beta-fluoroshikimic acids," J Chem Soc Chem Commun. 18:1386-7 (1989).
Takai et al., "Reactions of alkenylchromium reagents prepared from alkenyl trifluoromethanesulfonates (triflates) with chromium(II) chloride under nickel catalysis" J Am Chem Soc. 108(19):6048-50 (1986).
Tokunaga et al., "Asymmetric catalysis with water: efficient kinetic resolution of terminal epoxides by means of catalytic hydrolysis," Science. 277(5328):936-8 (1997).
Towle et al. "In vitro and in vivo anticancer activities of synthetic macrocyclic ketone analogues of Halichondrin B," Cancer Res. 61(3):1013-21 (2001).
Towle et al., "Halichondrin B macrocyclic ketone analog E7389: medicinal chemistry repair of lactone ester instability generated during structural simplification to clinical Candidate," Annual Meeting of the American Association for Cancer Research, Apr. 6-10, 2002, 5721 (3 pages).
Uemura et al., "Norhalichondrin A: an antitumor polyether macrolide from a marine sponge," J Am Chem Soc. 107(16):4796-8 (1985).
Vandat et al., "Phase II study of eribulin mesylate, a Halichondrin B analog, in patients with metastatic breast cancer previously treated with an anthracycline and a taxane," J Clin Oncol. 27(18):2954-61 (2009).
Varseev et al, "Enantioselective total synthesis of (+)-neosymbioimine," Org Lett. 9(8):1461-4 (2007).

(56) References Cited

OTHER PUBLICATIONS

Wan et al., "Asymmetric Ni(II)/Cr(II)-mediated coupling reaction: Stoichiometric process," Org Lett. 4(25):4431-4 (2002) Supporting Information, 8 pages.

Wan et al., "Asymmetric Ni(II)/Cr(II)-mediated coupling reaction: Stoichiometric process," Org Lett. 4(25):4431-4 (2002).

Wang et al., "Facile preparation of peracetates and per-3-bromobenzoates of alpha-mono- and disaccharides," Molecules. 10(10):1325-34 (2005).

Wang et al., "Structure-activity relationships of halichondrin B analogues: modifications at C.30-C.38" Bioorg Med Chem Lett. 10(10):1029-32 (2000).

Xie et al., "Synthesis of the C20-C26 building block of Halichondrins via a regiospecific and stereoselective SN2' reaction," Org Lett. 4(25): 4427-9 (2002).

Yamamoto et al., "Total synthesis of halichondrin C," J Am Chem Soc. 134(2):893-6 (2012).

Yang et al., "Second generation synthesis of C27-C35 building block of E7389, a synthetic Halichondrin analogue," Org Lett. 11(20): 4516-9 (2009).

Youssefyeh, "Acylations of ketals and enol ethers," J Am Chem Soc. 85(23):3901-2 (1963).

Yu et al., "Atom-based enumeration: new eribulin analogues with low susceptibility to P-glycoprotein-mediated drug efflux," Bioorg Med Chem Lett. 22(24):7363-6 (2012).

Yu et al., "From micrograms to grams: scale-up synthesis of eribulin mesylate," Nat Prod Rep. 30(9):1158-64 (2013).

Yu et al., "Macrocyclic drugs and synthetic methodologies toward macrocycles," Molecules 18(6):6230-68 (2013).

Yu et al., "New synthetic route to the C.14-C.21 fragment of Halichondrin B," Book of Abstracts. 219th ACS National Meeting, San Francisco, CA, Mar. 26-30, 2000 (1 page).

Yu et al., Discovery of E7389 a fully synthetic macrocyclic ketone analog of Halichondrin B. *Anticancer Agents from Natural Products.* CRC Press, 241-265 (2005) (27 pages).

Zheng et al., "Macrocyclic ketone analogues of halichondrin B," Bioorg Med Chem Lett. 14(22): 5551-4 (2004).

Zheng et al., "Synthetic macrocyclic ketone analogs of halichondrin B: structure-activity relationships" Proceedings of the American Association for Cancer Research, 41:301, Abstract #1915 (2000).

Extended European Search Report for European Patent Application No. 17821400.3, dated Jun. 20, 2018 (20 pages).

PubChem Compound Summary for Methyl 2-[(1S,3R,4S,5R,7R,8S,9S,11R)-4,8-diacetyloxy-5--(2-oxoethyl)-2,6,10-trioxatricyclo[7.4.0.03,7]tridecan-11-yl]acetate, <https://pubchem.ncbi.nlm.nih.gov/compound/10501910>, retrieved Jul. 1, 2020 (6 pages).

* cited by examiner

PRINS REACTION AND INTERMEDIATES USEFUL IN THE SYNTHESIS OF HALICHONDRIN MACROLIDES AND ANALOGS THEREOF

BACKGROUND

The invention relates to intermediates useful in the synthesis of pharmaceutically active macrolide compounds and methods of synthesizing macrolide compounds. Halichondrin B is a potent anticancer agent originally isolated from the marine sponge *Halichondria okadai*, and subsequently found in *Axinella* sp., *Phakellia carteri*, and *Lissodendoryx* sp. A total synthesis of halichondrin B was published in 1992 (Aicher, T. D. et al., J. Am. Chem. Soc. 114:3162-3164). Further synthetic and structure-activity relationship studies have been discloses in U.S. Pat. Nos. 5,338,865 and 5,436,238 and in Towle et al., *Annual Meeting of the American Association for Cancer Research*, Apr. 6-10, 2002, 5721 and Wang et al., *Bioorg. Med. Chem. Lett.*, 10:1029-1032, 2000. Eribulin mesylate (also called Halaven®, E7389, and the mesylate salt of B1939), a nontaxane microtubule dynamics inhibitor, is a structurally simplified, synthetic analog of halichondrin B. Methods and intermediates for the synthesis of certain halichondrin B analogs and intermediates are described in International Publication Nos. WO 2005/118565, WO 2009/046308, WO 2009/064029, and WO 2009/124237; U.S. Pat. No. 6,214,865; Austad et al., Synlett 24(3):333-337, 2013; Austad et al., Synlett. 24(3):327-332, 2013; and Chase et al., Synlett 24(3):323-326, 2013. New methods for the synthesis of halichondrin and its analogs (e.g., macrolide analogs) are desirable.

SUMMARY OF THE INVENTION

In general, the present invention provides methods for the preparation of macrocyclic intermediates in the synthesis of a halichondrin macrolide or an analog thereof. In particular, the methods disclosed herein may be useful in the preparation of a halichondrin macrolide or an analog thereof by forming a C.26-C.27 bond through an allene-Prins reaction performed on an intermediate. The invention also provides intermediates that can be employed in the reactions described herein.

In one aspect, the invention provides a method of preparing a macrocyclic intermediate in the synthesis of a halichondrin macrolide or an analog thereof, the method comprising reacting an intermediate of formula (IA) with $R_{12}OH$ and a Lewis acid, the reaction producing the macrocyclic intermediate by forming a bond in the structure of the halichondrin macrolide or an analog thereof, where $R_{12}$ is optionally substituted acyl;

where the compound of formula (IA) is:

(IA)

or a salt or a tautomer thereof, where each of D and D' is independently H, optionally substituted alkyl, or $OP_1$, provided that only one of D and D' is $OP_1$, where $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

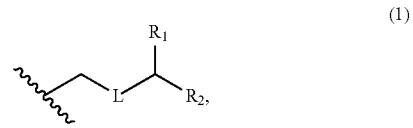

(1)

where

L is —(CH($OP_2$))—, —(C(OH)($OP_2$))—, or —C(O)—;

$R_1$ is H, or $R_1$ and $P_1$ combine to form a bond;

(i) $R_2$ is H, where $P_2$ is absent, H, optionally substituted alkyl, or a hydroxyl protecting group;

(ii) $R_2$ is —$(CH_2)_nNP_3P_4$, where $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;

(iii) $R_2$ is —$(CH_2)_nOP_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_2$ and $P_2$ combine to form an optionally substituted ethylene or a structure selected from the group consisting of:

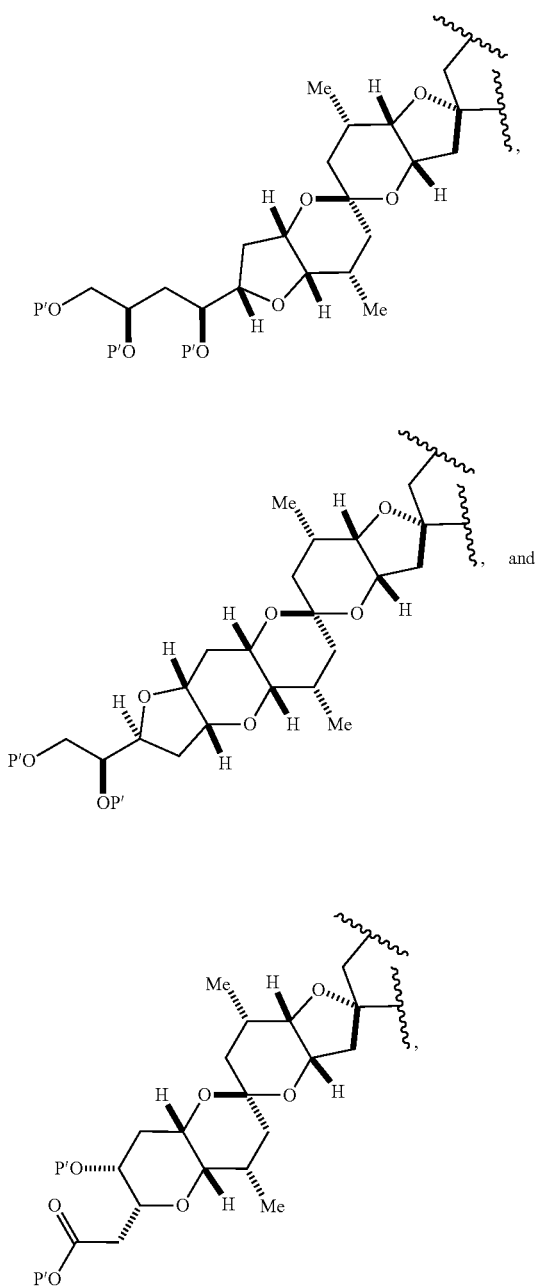

where each P' is independently H or a hydroxyl protecting group;

E is H, optionally substituted alkyl, or optionally substituted alkoxy;

G is O, S, $CH_2$, or $NR_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

$X_1$ is —CH(Y)—, —$CH_2$—, or —O—, $X_2$ is =O or $X_2$, together with the carbon atom to which it is attached, is —$(C(R_X)_2)$—; where each $R_X$ is independently H, —$OR_{X1}$, or —$SR_{X1}$, provided that at least one $R_X$, when present, is —$OR_{X1}$ or —$SR_{X1}$; where each $R_{X1}$ is independently optionally substituted alkyl, or both $R_{X1}$ combine to form optionally substituted alkylene, provided that, when $X_1$ is —O—, $X_2$ is =O;

Y is $SO_2R_C$ or $COOR_C$, where, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;

$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;

$A_1$ and $R_7$ combine to form oxo, $P_7$ is H or a hydroxyl protecting group, and $R_8$ is H;

or $A_1$ is H or OP''', and:

(a) $P_7$ is H or a hydroxyl protecting group, and $R_7$ and $R_8$, together with the atoms to which each is attached, combine to form a double bond;

or (b) $P_7$ and $R_7$ combine to form a bond, and $R_8$ is H or OP''';

(i) each $P_6$ is independently H or a hydroxyl protecting group, or both $P_6$, together with the atoms to which each is attached, combine to form a ketal or acetal; X is =O or X combines with the carbon atom, to which it is attached, to form —$(CH(OP_9))$—, where $P_9$ is H or a hydroxyl protecting group; and each $R_{11}$ is —$OP_{10}$, or both $R_{11}$ combine to form oxo, where $P_{10}$ is alkyl or a hydroxyl protecting group;

(ii) both $P_6$ and X, together with the atoms to which each is attached, combine to form ketal, $P_7$ and $R_7$ combine to form a bond, and $R_8$ is H or OP'''; and each $R_{11}$ is —$OP_{10}$, or both $R_{11}$ combine to form oxo, where $P_{10}$ is alkyl or a hydroxyl protecting group; or (iii) both $P_6$ and both $R_{11}$, together with the atoms to which they are attached, combine to form acetal; and X is =O or X combines with the carbon atom, to which it is attached, to form —$(CH(OP_9))$—, where $P_9$ is H or a hydroxyl protecting group;

$R_9$ is H, OP''', or Y, and $R_{10}$ is H; or $R_9$ and $R_{10}$, together with the atoms to which each is attached, combine to form a double bond;

each P''', when present, is independently H or a hydroxyl protecting group; and $P_8$ is H or silyl; and where the macrocyclic intermediate in the synthesis of a halichondrin macrolide or an analog thereof is a compound of formula (IB):

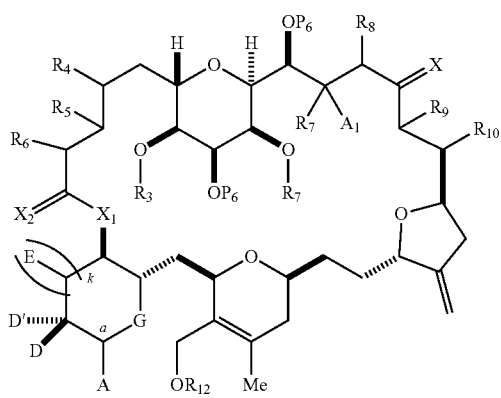

(IB)

or a salt or a tautomer thereof.

In some embodiments, the Lewis acid is an oxophilic Lewis acid (e.g., boron trifluoride or a solvate thereof).

In another aspect, the invention provides a method of preparing a halichondrin macrolide or an analog thereof:

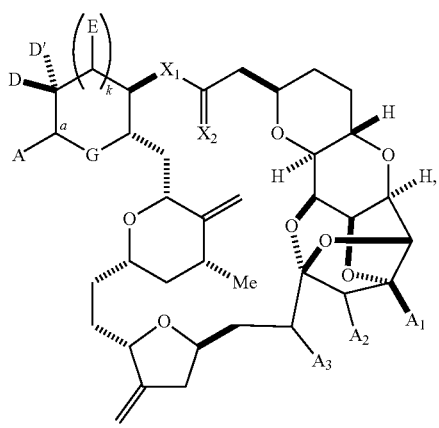

or a salt thereof,
where
each of D and D' is independently H, optionally substituted alkyl, or $OP_1$, provided that only one of D and D' is $OP_1$, where $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

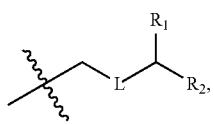

(1)

where
L is —(CH(OP$_2$))—, —(C(OH)(OP$_2$))—, or —C(O)—;
$R_1$ is H, or $R_1$ and $P_1$ combine to form a bond;
(i) $R_2$ is H, where $P_2$ is absent, H, optionally substituted alkyl, or a hydroxyl protecting group;

(ii) $R_2$ is —(CH$_2$)$_n$NP$_3$P$_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;

(iii) $R_2$ is —(CH$_2$)$_n$OP$_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_2$ and $P_2$ combine to form an optionally substituted ethylene or a structure selected from the group consisting of:

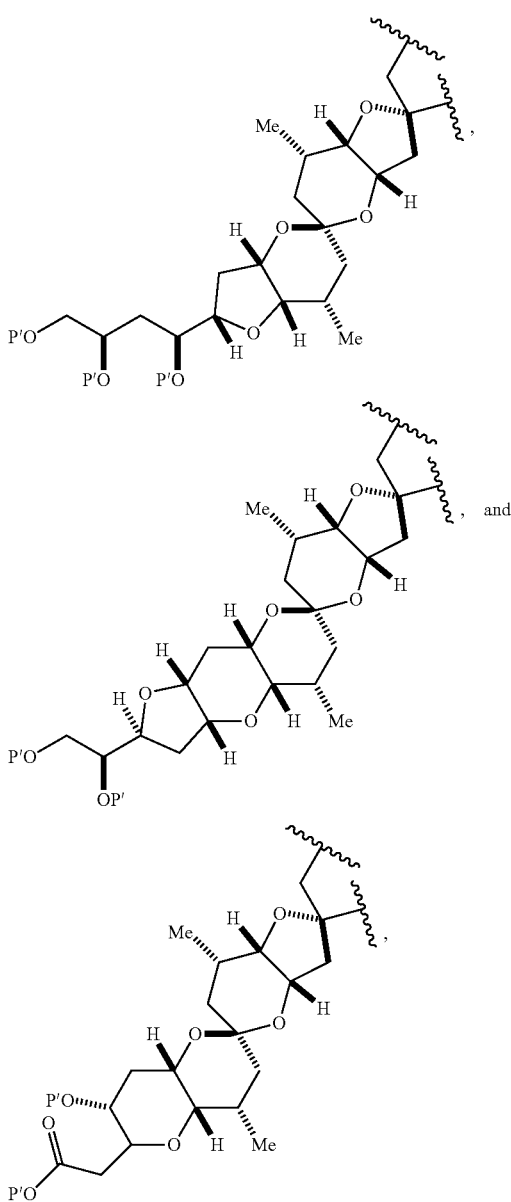

where each P' is independently H or a hydroxyl protecting group;

each of $A_1$, $A_2$, and $A_3$ is independently H or OP''', where each P''' is independently H or a hydroxyl protecting group;

E is H, optionally substituted alkyl, or optionally substituted alkoxy;

G is O, S, $CH_2$, or $NR_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

$X_1$ is —$CH_2$— or —O—, and $X_2$ is =O;

by (A) producing a compound of formula (IB) from a compound of formula (IA) and $R_{12}OH$, where $R_{12}$ is optionally substituted acyl, and the compound of formula (IA) is of the following structure:

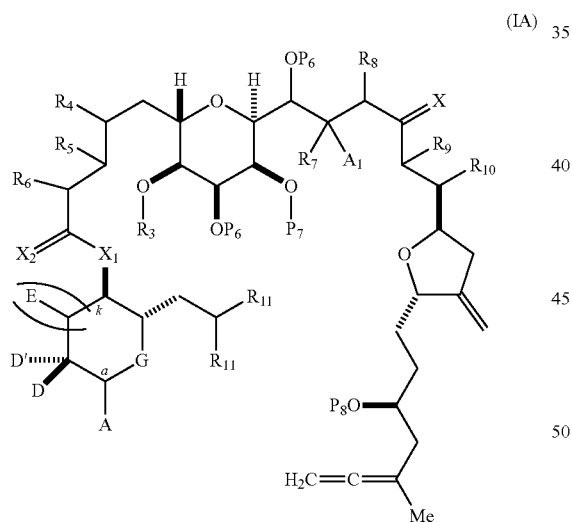

or a salt or a tautomer thereof, where each of D and D' is independently H, optionally substituted alkyl, or $OP_1$, provided that only one of D and D' is $OP_1$, where $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

where

L is —(CH($OP_2$))—, —(C(OH)($OP_2$))—, or —C(O)—;

$R_1$ is H, or $R_1$ and $P_1$ combine to form a bond;

(i) $R_2$ is H, where $P_2$ is absent, H, optionally substituted alkyl, or a hydroxyl protecting group;

(ii) $R_2$ is —$(CH_2)_nNP_3P_4$, where $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;

(iii) $R_2$ is —$(CH_2)_nOP_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_2$ and $P_2$ combine to form an optionally substituted ethylene or a structure selected from the group consisting of:

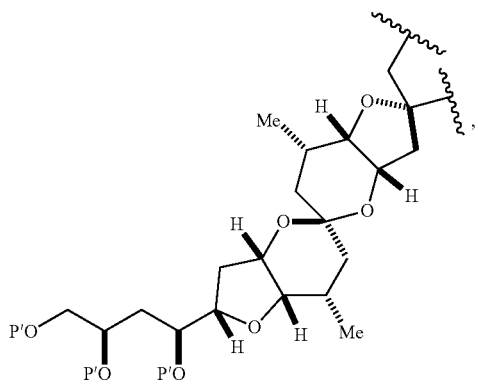

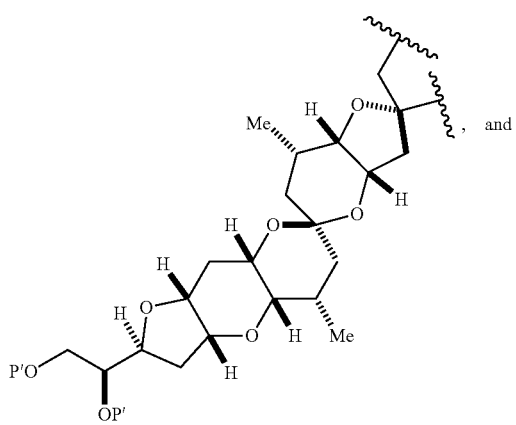

-continued

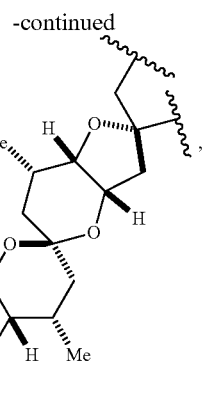

where each P' is independently H or a hydroxyl protecting group;
  E is H, optionally substituted alkyl, or optionally substituted alkoxy;
  G is O, S, $CH_2$, or $NR_N$, where $R_N$ is H, an N-protecting group, or optionally substituted alkyl;
  each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
  n, when present, is 0, 1, or 2;
  k is 0 or 1;
  $X_1$ is —CH(Y)—, —$CH_2$—, or —O—,
  $X_2$ is =O or $X_2$, together with the carbon atom to which it is attached, is —$(C(R_X)_2)$—; where each $R_X$ is independently H, —$OR_{X1}$, or —$SR_{X1}$, provided that at least one $R_X$, when present, is —$OR_{X1}$ or —$SR_{X1}$; where each $R_{X1}$ is independently optionally substituted alkyl, or both $R_{X1}$ combine to form optionally substituted alkylene, provided that, when $X_1$ is —O—, $X_2$ is =O;
  Y is $SO_2R_C$ or $COOR_C$, where, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;
  $R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;
  $A_1$ and $R_7$ combine to form oxo, $P_7$ is H or a hydroxyl protecting group, and $R_8$ is H;
  or
  $A_1$ is H or OP''', and:
    (a) $P_7$ is H or a hydroxyl protecting group, and $R_7$ and $R_8$, together with the atoms to which each is attached, combine to form a double bond;
    or
    (b) $P_7$ and $R_7$ combine to form a bond, and $R_8$ is H or OP''';
  (i) each $P_6$ is independently H or a hydroxyl protecting group, or both $P_6$, together with the atoms to which each is attached, combine to form a ketal or acetal; X is =O or X combines with the carbon atom, to which it is attached, to form —$(CH(OP_9))$—, where $P_9$ is H or a hydroxyl protecting group; and each $R_{11}$ is —$OP_{10}$, or both $R_{11}$ combine to form oxo, where $P_{10}$ is alkyl or a hydroxyl protecting group;
  (ii) both $P_6$ and X, together with the atoms to which each is attached, combine to form ketal, $P_7$ and $R_7$ combine to form a bond, and $R_8$ is H or OP'''; and each $R_{11}$ is —$OP_{10}$, or both $R_{11}$ combine to form oxo, where $P_{10}$ is alkyl or a hydroxyl protecting group; or
  (iii) both $P_6$ and both $R_{11}$, together with the atoms to which they are attached, combine to form acetal; and X is =O or X combines with the carbon atom, to which it is attached, to form —$(CH(OP_9))$—, where $P_9$ is H or a hydroxyl protecting group;
  $R_9$ is H, OP''', or Y, and $R_{10}$ is H; or $R_9$ and $R_{10}$, together with the atoms to which each is attached, combine to form a double bond;
  each P''', when present, is independently H or a hydroxyl protecting group; and
  $P_8$ is H or silyl;
  and
  the compound of formula (IB) is of the following structure:

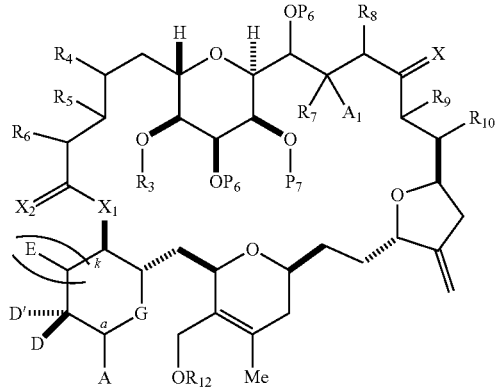

(IB)

or a salt or a tautomer thereof;
where
  $R_{12}$ is optionally substituted acyl; and
  (B) producing the halichondrin macrolide or the analog thereof from compound (IB).

In certain embodiments, producing the compound of formula (IB) includes reacting the compound of formula (IA) with $R_{12}OH$ and a Lewis acid (e.g., an oxophilic Lewis acid (e.g., boron trifluoride or a solvate thereof). In particular embodiments, producing the halichondrin macrolide or the analog thereof includes reacting the compound of formula (IB) with an allylic reducing agent. In further embodiments, $R_3$ and $R_5$ combine to form a bond, and each of $R_4$ and $R_6$ is H. In some embodiments, $R_5$ and $R_6$, together with the atom to which each is attached, combine to form a double bond, $R_4$ is H, and $R_3$ is a hydroxyl protecting group. In other embodiments, each $P_6$ is a hydroxyl protecting group, and X is =O or X combines with the carbon atom, to which it is attached, to form —$(CH(OP_9))$—. In yet other embodiments, $R_7$ and $P_7$ combine to form a bond, and $R_8$ is H. In still other embodiments, $P_7$ is a hydroxyl protecting group, and $R_7$ and $R_8$, together with the atoms to which each is attached, combine to form a double bond. In some embodiments, $R_9$ is H or $SO_2R_C$, and $R_{10}$ is H. In other embodiments, $P_8$ is silyl. In particular embodiments, each $R_{11}$ is —$OP_{10}$, where $P_{10}$ is alkyl. In certain embodiments, G is O. In further embodiments, D is H. In yet further embodiments, D' is $OP_1$, where $P_1$ is alkyl. In other embodiments, the stereogenic center designated by a is (R), and A is of the following structure:

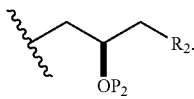

In yet other embodiments, k is 0 and $X_1$ is —$CH_2$—. In still other embodiments, $R_2$ is —$(CH_2)_nNP_3P_4$ or —$(CH_2)_nOP_5$, wherein n is 0. In further embodiments, A and D combine to form the following structure:

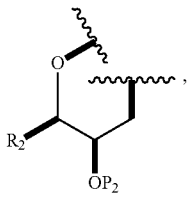

where, the bond to oxygen atom originates at the carbon atom, to which D is attached in formula (IA), and where $R_2$ is —$(CH_2)_nNP_3P_4$ or —$(CH_2)_nOP_5$, where n is 2.

In some embodiments, k is 1, and E is optionally substituted alkyl. In particular embodiments, $X_1$ is —O—.

The methods of the invention may be used in the preparation of eribulin or its salt (e.g., eribulin mesylate). Compounds of formula (IA), (IB), (IC), (IE), (IJ), or (IN), where k is 0, $X_1$ is —CH(Y)— or —$CH_2$—, D is H, D' is $OP_1$, G is O, and A is of the following structure:

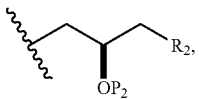

where
(i) $R_2$ is —$(CH_2)_nNP_3P_4$, where n is 0, $P_3$ is H or an N-protecting group, and $P_2$ and $P_4$ combine to form an alkylidene or $P_2$ is H, an optionally substituted alkyl or a hydroxyl protecting group and $P_4$ is an N-protecting group; or
(ii) $R_2$ is —$(CH_2)_nOP_5$, where n is 0, $P_2$ is H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo;
can be used for the synthesis of eribulin or its salt (e.g., eribulin mesylate).

In certain embodiments of formula (IA), (IB), (IC), (IE), (IJ), or (IN), k is 0, $X_1$ is —CH(Y)— or —$CH_2$—, D is H, D' is $OP_1$, G is O, and A is of the following structure:

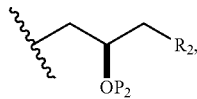

where
(i) $R_2$ is —$(CH_2)_nNP_3P_4$, where n is 0, $P_3$ is an N-protecting group, and $P_2$ and $P_4$ combine to form an alkylidene; or
(ii) $R_2$ is —$(CH_2)_nOP_5$, where n is 0, $P_2$ is H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo;
can be used for the synthesis of eribulin or its salt (e.g., eribulin mesylate).

In another aspect, the invention provides the compounds of formula (IA), (IB), (IC), (ID), (IDa), (IDb), (IDc), (IDd), (IE), (IF), (IH), (IHa), (IHb), (IJ), or (IN).

The structure of the compound of formula (IA) is as follows:

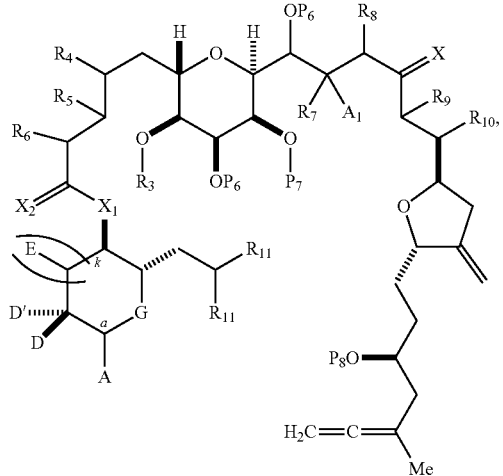

(IA)

or a salt or a tautomer thereof,
where
each of D and D' is independently H, optionally substituted alkyl, or $OP_1$, provided that only one of D and D' is $OP_1$, where $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

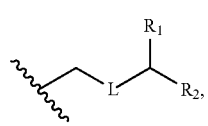

(1)

where

L is —(CH(OP$_2$))—, —(C(OH)(OP$_2$))—, or —C(O)—;

R$_1$ is H, or R$_1$ and P$_1$ combine to form a bond;

(i) R$_2$ is H, where P$_2$ is absent, H, optionally substituted alkyl, or a hydroxyl protecting group;

(ii) R$_2$ is —(CH$_2$)$_n$NP$_3$P$_4$, where P$_3$ is an N-protecting group, and (a) P$_2$ is absent, H, optionally substituted alkyl, or a hydroxyl protecting group, and P$_4$ is an N-protecting group, or (b) P$_2$ and P$_4$ combine to form an alkylidene;

(iii) R$_2$ is —(CH$_2$)$_n$OP$_5$, where P$_2$ is absent, H, optionally substituted alkyl, or a hydroxyl protecting group, and P$_5$ is H, optionally substituted alkyl, or a hydroxyl protecting group; or P$_2$ and P$_5$, together with the atoms to which each is attached, combine to form a ketal, a cyclic carbonate, a dicarbonyl-dioxo, or silylene-dioxo; or (iv) R$_2$ and P$_2$ combine to form an optionally substituted ethylene or a structure selected from the group consisting of:

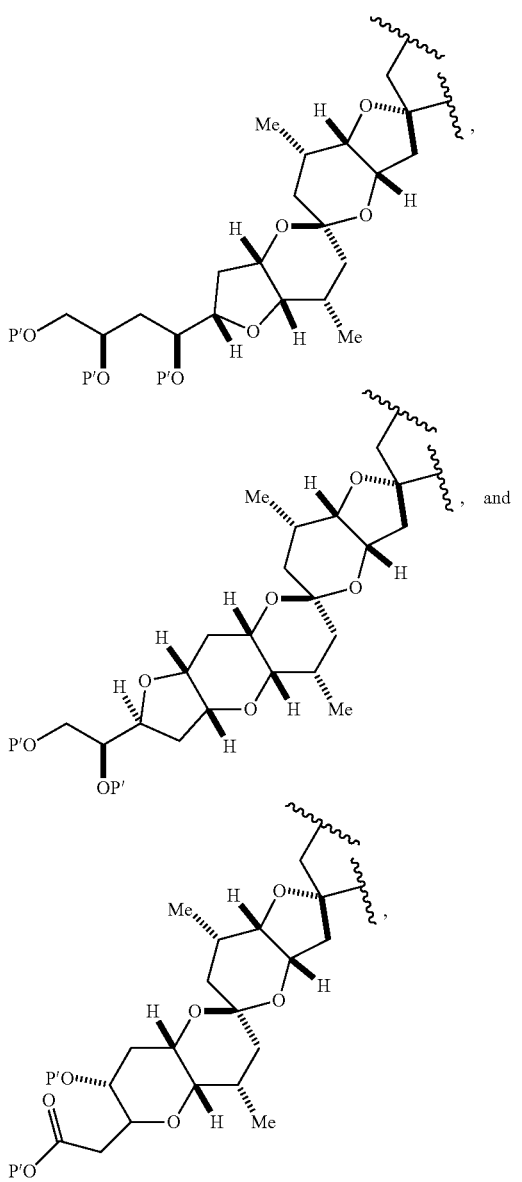

where each P' is independently H or a hydroxyl protecting group;

E is H, optionally substituted alkyl, or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

X$_1$ is —CH(Y)—, —CH$_2$—, or —O—;

X$_2$ is =O or X$_2$, together with the carbon atom to which it is attached, is —(C(R$_X$)$_2$)—; where each R$_X$ is independently H, —OR$_{X1}$, or —SR$_{X1}$, provided that at least one R$_X$, when present, is —OR$_{X1}$ or —SR$_{X1}$; where each R$_{X1}$ is independently optionally substituted alkyl, or both R$_{X1}$ combine to form optionally substituted alkylene, provided that, when X$_1$ is —O—, X$_2$ is =O;

Y is SO$_2$R$_C$ or COOR$_C$, where, when Y is SO$_2$R$_C$, R$_C$ is optionally substituted aryl or optionally substituted non-enolizable alkyl, and when Y is COOR$_C$, R$_C$ is optionally substituted alkyl, optionally substituted aryl, or optionally substituted arylalkyl;

R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;

A$_1$ and R$_7$ combine to form oxo, P$_7$ is H or a hydroxyl protecting group, and R$_8$ is H;

or

A$_1$ is H or OP''', and:

(i) P$_7$ is H or a hydroxyl protecting group, and R$_7$ and R$_8$, together with the atoms to which each is attached, combine to form a double bond;

or (ii) P$_7$ and R$_7$ combine to form a bond, and R$_8$ is H or OP''';

(i) each P$_6$ is independently H or a hydroxyl protecting group, or both P$_6$, together with the atoms to which each is attached, combine to form a ketal or acetal; X is =O or X combines with the carbon atom, to which it is attached, to form —(CH(OP$_9$))—, where P$_9$ is H or a hydroxyl protecting group; and each R$_{11}$ is —OP$_{10}$, or both R combine to form oxo, where P$_{10}$ is alkyl or a hydroxyl protecting group;

(ii) both P$_6$ and X, together with the atoms to which each is attached, combine to form ketal, P$_7$ and R$_7$ combine to form a bond, and R$_8$ is H or OP'''; and each R$_{11}$ is —OP$_{10}$, or both R$_1$ combine to form oxo, where P$_{10}$ is alkyl or a hydroxyl protecting group; or (iii) both P$_6$ and both R$_{11}$, together with the atoms to which they are attached, combine to form acetal; and X is =O or X combines with the carbon atom, to which it is attached, to form —(CH(OP$_9$))—, where P$_9$ is H or a hydroxyl protecting group;

R$_9$ is H, OP''', or Y, and R$_{10}$ is H; or R$_9$ and R$_{10}$, together with the atoms to which each is attached, combine to form a double bond;

each P'', when present, is independently H or a hydroxyl protecting group; and $P_8$ is H or silyl.

The structure of the compound of formula (IB) is as follows:

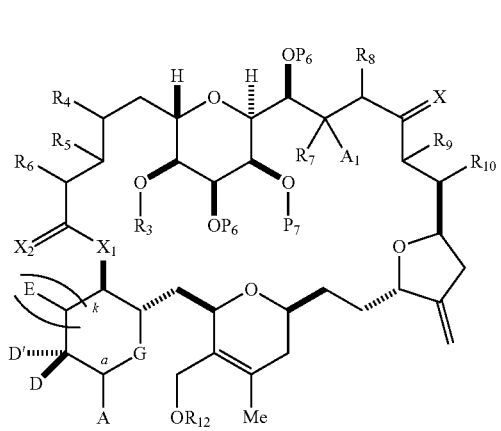

(IB)

or a salt or a tautomer thereof.
wherein
each of D and D' is independently H, optionally substituted alkyl, or $OP_1$, provided that only one of D and D' is $OP_1$, wherein $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

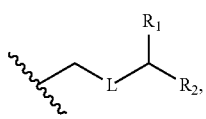

(1)

wherein
L is —(CH(OP$_2$))—, —(C(OH)(OP$_2$))—, or —C(O)—;
$R_1$ is H, or $R_1$ and $P_1$ combine to form a bond;
  (i) $R_2$ is H, wherein $P_2$ is absent, H, optionally substituted alkyl, or a hydroxyl protecting group;
  (ii) $R_2$ is —(CH$_2$)$_n$NP$_3$P$_4$, wherein $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;
  (iii) $R_2$ is —(CH$_2$)$_n$OP$_5$, wherein $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or
  (iv) $R_2$ and $P_2$ combine to form an optionally substituted ethylene or a structure selected from the group consisting of:

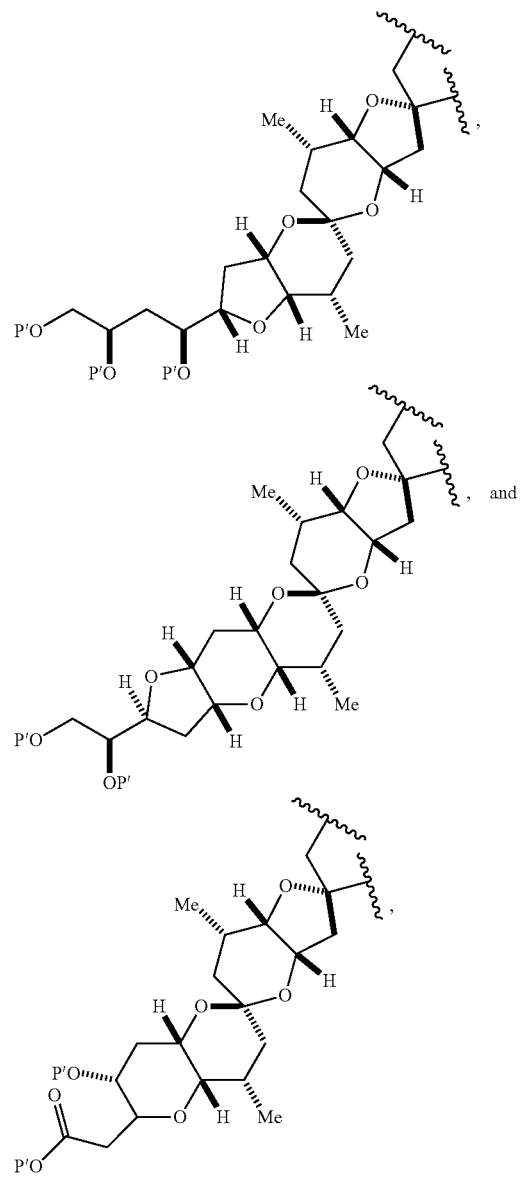

wherein each P' is independently H or a hydroxyl protecting group;
E is H, optionally substituted alkyl, or optionally substituted alkoxy;
G is O, S, CH$_2$, or NR$_N$, wherein R$_N$ is H, an N-protecting group, or optionally substituted alkyl;
each $Q_1$ is independently OR$_4$, SR$_4$, SO$_2$R$_4$, OSO$_2$R$_4$, NR$_B$R$_4$, NR$_B$(CO)R$_4$, NR$_B$(CO)(CO)R$_4$, NR$_B$(CO)NR$_B$R$_4$, NR$_B$(CO)OR$_4$, (CO)OR$_4$, O(CO)R$_4$, (CO)NR$_B$R$_4$, or O(CO)NR$_B$R$_4$, wherein each of R$_4$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$X_1$ is —CH(Y)—, —CH$_2$—, or —O—;
$X_2$ is =O or $X_2$, together with the carbon atom to which it is attached, is —(C(R$_X$)$_2$)—; wherein each R$_X$ is independently H, —OR$_{X1}$, or —SR$_{X1}$, provided that at least one R$_X$, when present, is —OR$_{X1}$ or —SR$_{X1}$; wherein each R$_{X1}$ is independently optionally substituted alkyl, or both R$_{X1}$ combine to form optionally substituted alkylene, provided that, when X$_1$ is —O—, X$_2$ is =O;

Y is SO$_2$R$_C$ or COOR$_C$, where, when Y is SO$_2$R$_C$, R$_C$ is optionally substituted aryl or optionally substituted non-enolizable alkyl, and when Y is COOR$_C$, R$_C$ is optionally substituted alkyl, optionally substituted aryl, or optionally substituted arylalkyl;

R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;

A$_1$ and R$_7$ combine to form oxo, P$_7$ is H or a hydroxyl protecting group, and R$_8$ is H;

or

A$_1$ is H or OP''', and:
  (a) P$_7$ is H or a hydroxyl protecting group, and R$_7$ and R$_8$, together with the atoms to which each is attached, combine to form a double bond;
  or
  (b) P$_7$ and R$_7$ combine to form a bond, and R$_8$ is H or OP''';
  (i) each P$_6$ is independently H or a hydroxyl protecting group, or both P$_6$, together with the atoms to which each is attached, combine to form a ketal or acetal; X is =O or X combines with the carbon atom, to which it is attached, to form —(CH(OP$_9$))—, wherein P$_9$ is H or a hydroxyl protecting group; or
  (ii) both P$_6$ and X, together with the atoms to which each is attached, combine to form ketal, P$_7$ and R$_7$ combine to form a bond, and R$_8$ is H or OP''';

R$_9$ is H, OP''', or Y, and R$_{10}$ is H; or R$_9$ and R$_{10}$, together with the atoms to which each is attached, combine to form a double bond;

each P''', when present, is independently H or a hydroxyl protecting group; and

R$_{12}$ is optionally substituted acyl.

The structure of the compound of formula (IC) is as follows:

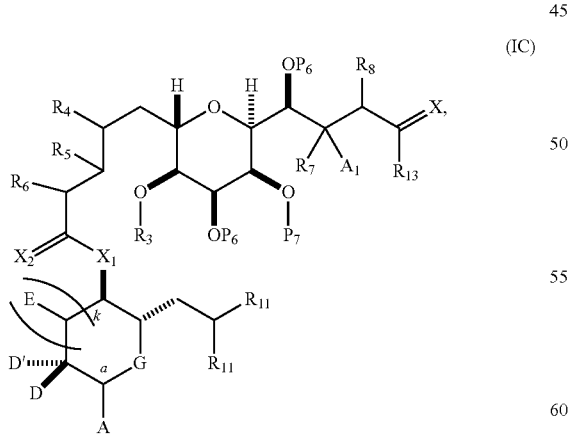

or a salt or tautomer thereof,
where
each of D and D' is independently H, optionally substituted alkyl, or OP$_1$, provided that only one of D and D' is OP$_1$, where P$_1$ is H, alkyl, or a hydroxyl protecting group; and A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, and Q$_1$, the group of formula (1) having the structure:

where
L is —(CH(OP$_2$))— or —C(O)—;
R$_1$ is H, or R$_1$ and P$_1$ combine to form a bond;
  (i) R$_2$ is H, where P$_2$ is absent, H, optionally substituted alkyl, or a hydroxyl protecting group;
  (ii) R$_2$ is —(CH$_2$)$_n$NP$_3$P$_4$, where P$_3$ is an N-protecting group, and (a) P$_2$ is absent, H, optionally substituted alkyl, or a hydroxyl protecting group, and P$_4$ is an N-protecting group, or (b) P$_2$ and P$_4$ combine to form an alkylidene;
  (iii) R$_2$ is —(CH$_2$)$_n$OP$_5$, where P$_2$ is absent, H, optionally substituted alkyl, or a hydroxyl protecting group, and P$_5$ is optionally substituted alkyl or a hydroxyl protecting group; or P$_2$ and P$_5$, together with the atoms to which each is attached, combine to form a ketal, a cyclic carbonate, a dicarbonyl-dioxo, or silylene-dioxo; or
  (iv) R$_2$ and P$_2$ combine to form an optionally substituted ethylene or a structure selected from the group consisting of:

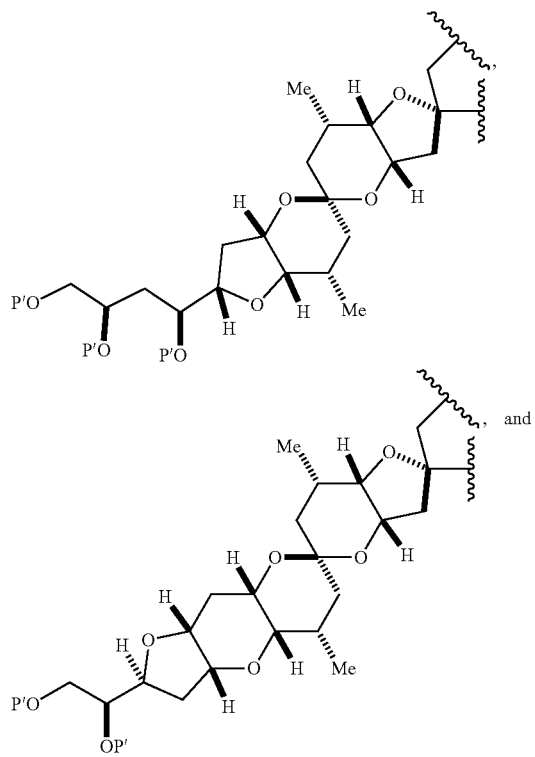

-continued

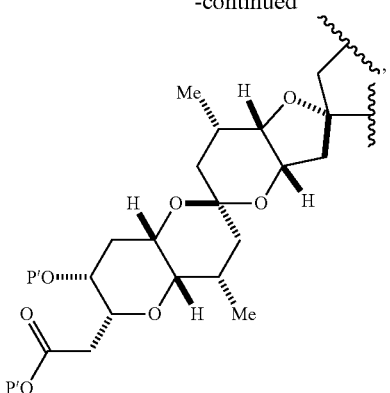

where each P' is independently a hydroxyl protecting group;
E is H, optionally substituted alkyl, or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$X_1$ is —CH(Y)— or —$CH_2$—;
$X_2$ is =O or $X_2$, together with the carbon atom to which it is attached, is —$(C(R_X)_2)$—; where each $R_X$ is independently H, —$OR_{X1}$, or —$SR_{X1}$, provided that at least one $R_X$, when present, is —$OR_{X1}$ or —$SR_{X1}$; where each $R_{X1}$ is independently optionally substituted alkyl, or both $R_{X1}$ combine to form optionally substituted alkylene;
Y is $SO_2R_C$ or $COOR_C$, where, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;
$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;
(a) each $P_6$ is independently a hydroxyl protecting group, or both $P_6$, together with the atoms to which each is attached, combine to form a ketal or acetal; each $R_{11}$ is independently —$OP_{10}$, or both $R_{11}$ combine to form oxo, where $P_{10}$ is alkyl or a hydroxyl protecting group;
or
(b) both $P_6$ and both $R_{11}$, together with the atoms to which they are attached, combine to form an acetal;
$R_{13}$ is H or —$CH_2P(O)(OR_E)_2$, where each $R_E$, when present, is independently optionally substituted alkyl, optionally substituted aryl, or optionally substituted arylalkyl;
X is =O or X combines with the carbon atom, to which it is attached, to form —(CH($OP_9$))—, where $P_9$ is H or a hydroxyl protecting group;

$A_1$ and $R_7$ combine to form oxo, $P_7$ is H or a hydroxyl protecting group, and $R_8$ is H;
or
$A_1$ is H or OP''', and:
(i) $P_7$ is H or a hydroxyl protecting group, and $R_7$ and $R_8$, together with the atoms to which each is attached, combine to form a double bond;
or
(ii) $P_7$ and $R_7$ combine to form a bond, and $R_8$ is H or OP''';
and
each P''', when present, is independently H or a hydroxyl protecting group.

The structure of the compound of formula (ID) is as follows:

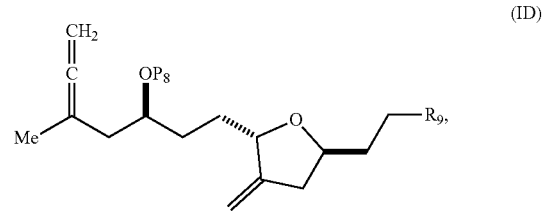

(ID)

where
$P_8$ is H or a hydroxyl protecting group; and
$R_9$ is $SO_2R_C$ or $COOR_C$, when $R_9$ is $SO_2R_C$, $R_C$ is optionally substituted aryl or optionally substituted non-enolizable alkyl, and when $R_9$ is $COOR_C$, $R_C$ is optionally substituted alkyl, optionally substituted aryl, or optionally substituted arylalkyl.

The structure of the compound of formula (IDa) is as follows:

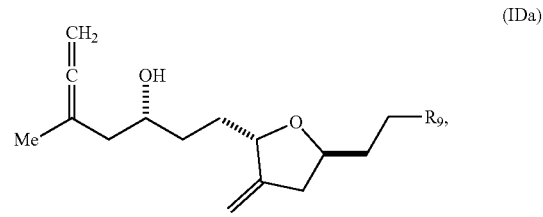

(IDa)

where $R_9$ is $SO_2R_C$ or $COOR_C$, when $R_9$ is $SO_2R_C$, $R_C$ is optionally substituted aryl or optionally substituted non-enolizable alkyl, and when $R_9$ is $COOR_C$, $R_C$ is optionally substituted alkyl, optionally substituted aryl, or optionally substituted arylalkyl.

The structure of the compound of formula (IDb) is as follows:

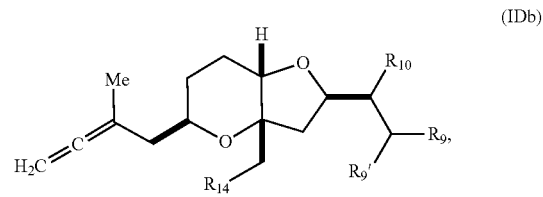

(IDb)

where $R_9$' and $R_{10}$ are both H, or $R_9$' and $R_{10}$ combine to form a double bond; $R_{14}$ is hydroxyl, a halogen (e.g., iodide), or a pseudohalogen (e.g., triflate); and $R_9$ is $SO_2R_C$ or $COOR_C$, when $R_9$ is $SO_2R_C$, $R_C$ is optionally substituted aryl or optionally substituted non-enolizable alkyl, and when $R_9$ is $COOR_C$, $R_C$ is optionally substituted alkyl, optionally substituted aryl, or optionally substituted arylalkyl.

The structure of the compound of formula (IDc) is as follows:

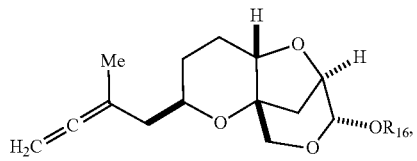
(IDc)

where $R_{16}$ is H, a hydroxyl protecting group, or an optionally substituted alkyl.

The structure of the compound of formula (IDd) is as follows:

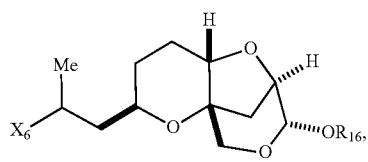
(IDd)

where $X_6$ is $-C(R_{17})=CH_2$, or $-C(O)$-Me, where $R_{17}$ is a pseudohalogen (e.g., triflate) or halogen; and $R_{16}$ is H, a hydroxyl protecting group, or an optionally substituted alkyl.

The structure of the compound of formula (IE) is as follows:

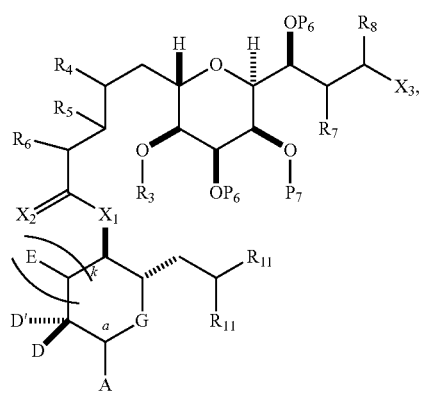
(IE)

or a salt or tautomer thereof,
where
each of D and D' is independently H, optionally substituted alkyl, or $OP_1$, provided that only one of D and D' is $OP_1$, where $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, and $Q_1$, the group of formula (1) having the structure:

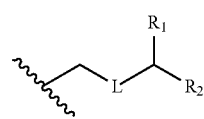
(1)

where

L is $-(CH(OP_2))-$ or $-C(O)-$;

$R_1$ is H, or $R_1$ and $P_1$ combine to form a bond;

(i) $R_2$ is H, where $P_2$ is absent, H, optionally substituted alkyl, or a hydroxyl protecting group;

(ii) $R_2$ is $-(CH_2)_nNP_3P_4$, where $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;

(iii) $R_2$ is $-(CH_2)_nOP_5$, where $P_2$ is absent, H, optionally substituted alkyl, or a hydroxyl protecting group, and $P_5$ is optionally substituted alkyl or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_2$ and $P_2$ combine to form an optionally substituted ethylene or a structure selected from the group consisting of:

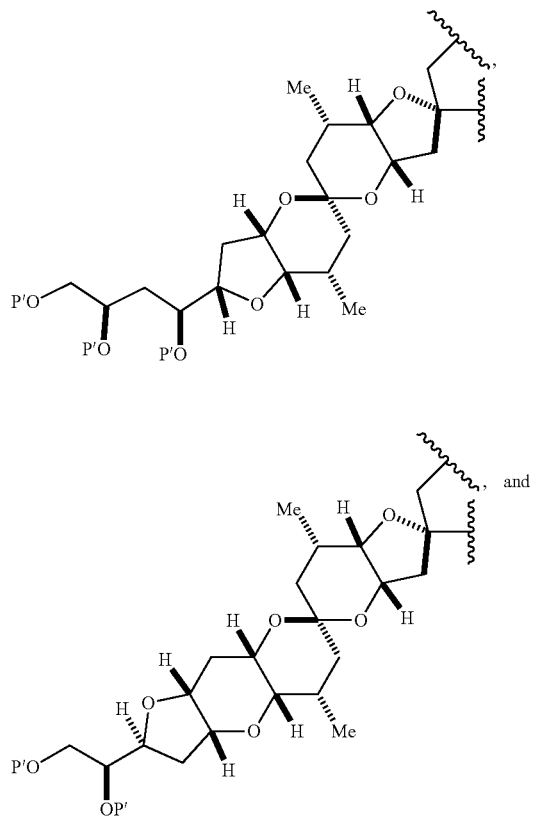

23
-continued

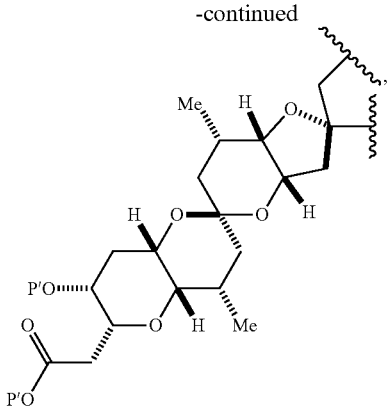

where each P' is independently a hydroxyl protecting group;
E is H, optionally substituted alkyl, or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
X$_1$ is —CH(Y)— or —CH$_2$—;
X$_2$ is =O or X$_2$, together with the carbon atom to which it is attached, is —(C(R$_X$)$_2$)—; where each R$_X$ is independently H, —OR$_{X1}$, or —SR$_{X1}$, provided that at least one R$_X$, when present, is —OR$_{X1}$ or —SR$_{X1}$; where each R$_{X1}$ is independently optionally substituted alkyl, or both R$_{X1}$ combine to form optionally substituted alkylene;
Y is SO$_2$R$_C$ or COOR$_C$, where, when Y is SO$_2$R$_C$, R$_C$ is optionally substituted aryl or optionally substituted non-enolizable alkyl, and when Y is COOR$_C$, R$_C$ is optionally substituted alkyl, optionally substituted aryl, or optionally substituted arylalkyl;
R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;
R$_7$ and P$_7$ combine to form a bond, and R$_8$ is H; or P$_7$ is a hydroxyl protecting group, and R$_7$ and R$_8$, together with the atoms to which each is attached, combine to form a double bond;
(i) each P$_6$ is independently a hydroxyl protecting group, or both P$_6$, together with the atoms to which each is attached, combine to form a ketal or acetal;
each R$_{11}$ is independently —OP$_{10}$, or
both R$_{11}$ combine to form oxo, where P$_{10}$ is alkyl or a hydroxyl protecting group;
or
(ii) both P$_6$ and both R$_{11}$, together with the atoms to which they are attached, combine to form an acetal; and
X$_3$ is —CH$_2$OP$_A$, —CH=CH$_2$, or —CH(OP$_A$)CH$_2$OP$_A$, where each R$_E$ is optionally substituted alkyl, option-

24 ally substituted aryl, or optionally substituted arylalkyl, and where each P$_A$ is independently H or a hydroxyl protecting group, or both P$_A$ combine to form a cyclic protected diol.
The structure of the compound of formula (IF) is as follows:

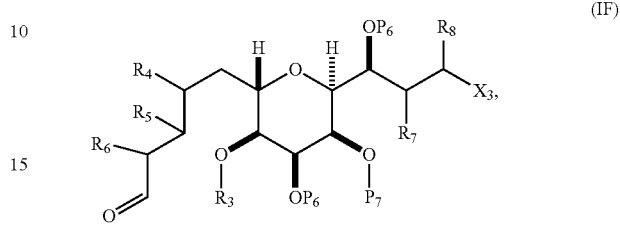

(IF)

where
X$_3$ is —CHO, —CH$_2$OP$_A$, —CH=CH$_2$, or —CH(OP$_A$)CH$_2$OP$_A$;
R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;
R$_7$ and P$_7$ combine to form a bond, and R$_8$ is H; or P$_7$ is a hydroxyl protecting group, and R$_7$ and R$_8$, together with the atoms to which each is attached, combine to form a double bond; and
each P$_6$ is independently a hydroxyl protecting group, or both P$_6$, together with the atoms to which each is attached, combine to form a ketal or acetal.
The structure of the compound of formula (IH) is as follows:

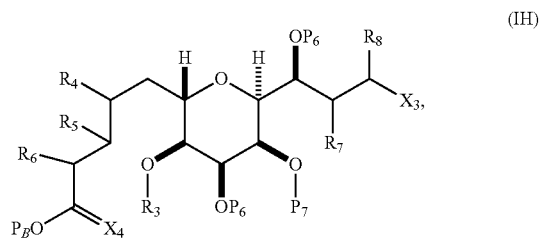

(IH)

or a salt thereof,
where
X$_3$ is —CHO, —CH$_2$OP$_A$, —CH=CH$_2$, or —CH(OP$_A$)CH$_2$OP$_A$;
X$_4$ is =O or X$_4$, together with the carbon atom to which it is attached, combine to form —CH$_2$—;
R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;
R$_7$ and P$_7$ combine to form a bond, and R$_8$ is H; or P$_7$ is a hydroxyl protecting group, and R$_7$ and R$_8$, together with the atoms to which each is attached, combine to form a double bond;
each P$_6$ is independently a hydroxyl protecting group, or both P$_6$, together with the atoms to which each is attached, combine to form a ketal or acetal;

each $P_A$ is independently H or a hydroxyl protecting group, or both $P_A$ combine to form a cyclic protected diol; and $P_B$ is H, a hydroxyl protecting group, or optionally substituted alkyl.

The structure of the compound of formula (IHa) is as follows:

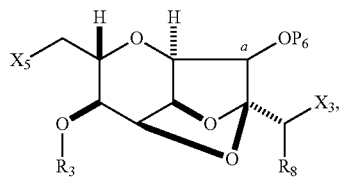

(IHa)

where a identifies the carbon-oxygen bond as | or ⁞, $X_3$ is —CHO, —CH$_2$OP$_A$, —CH=CH$_2$, or —CH(OP$_A$)CH$_2$OP$_A$;

$X_5$ is —CH=CH$_2$ or —CH(R$_4$)—CH(R$_5$)—CH(R$_6$)—C(X$_4$)OP$_B$;

$X_4$ is =O or $X_4$, together with the carbon atom to which it is attached, combine to form —CH$_2$—;

$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;

$P_6$ is a hydroxyl protecting group, or both $P_6$;

each $P_A$ is independently H or a hydroxyl protecting group, or both $P_A$ combine to form a cyclic protected diol; and $P_B$ is H, a hydroxyl protecting group, or optionally substituted alkyl.

The structure of the compound of formula (IHb) is as follows:

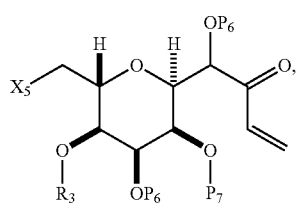

(IHb)

where $X_5$ is —CH=CH$_2$ or —CH(R$_4$)—CH(R$_5$)—CH(R$_6$)—C(X$_4$)OP$_B$;

$X_4$ is =O or $X_4$, together with the carbon atom to which it is attached, combine to form —CH$_2$—;

$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H; and each of $P_6$ and $P_7$ is independently a hydroxyl protecting group, or one $P_6$ and $P_7$, together with the atoms to which each is attached, combine to form a ketal (e.g., one $P_6$ and $P_7$ combine to form cyclohexylidene), and the remaining $P_6$ is a hydroxyl protecting group; or both $P_6$, together with the atoms to which each is attached, combine to form a ketal, and $P_7$ is a hydroxyl protecting group.

The structure of the compound of formula (IJ) is as follows:

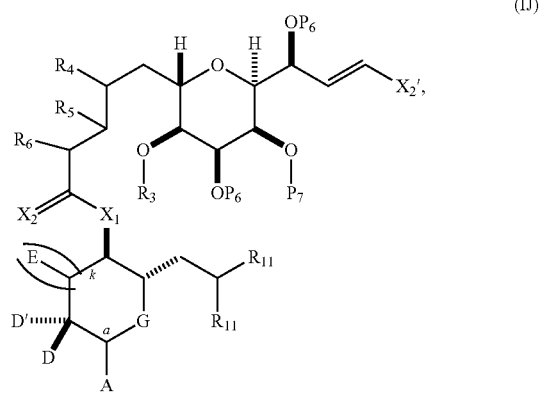

(IJ)

where each of D and D' is independently H, optionally substituted alkyl, or OP$_1$, provided that only one of D and D' is OP$_1$, where $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, and $Q_1$, the group of formula (1) having the structure:

(1)

where

L is —(CH(OP$_2$)) or —C(O)—;

$R_1$ is H, or $R_1$ and $P_1$ combine to form a bond;

(i) $R_2$ is H, where $P_2$ absent, is H, optionally substituted alkyl, or a hydroxyl protecting group;

(ii) $R_2$ is —(CH$_2$)$_n$NP$_3$P$_4$, where $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;

(iii) $R_2$ is —(CH$_2$)$_n$OP$_5$, where $P_2$ is absent, H, optionally substituted alkyl, or a hydroxyl protecting group, and $P_5$ is optionally substituted alkyl or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_2$ and $P_2$ combine to form an optionally substituted ethylene or a structure selected from the group consisting of:

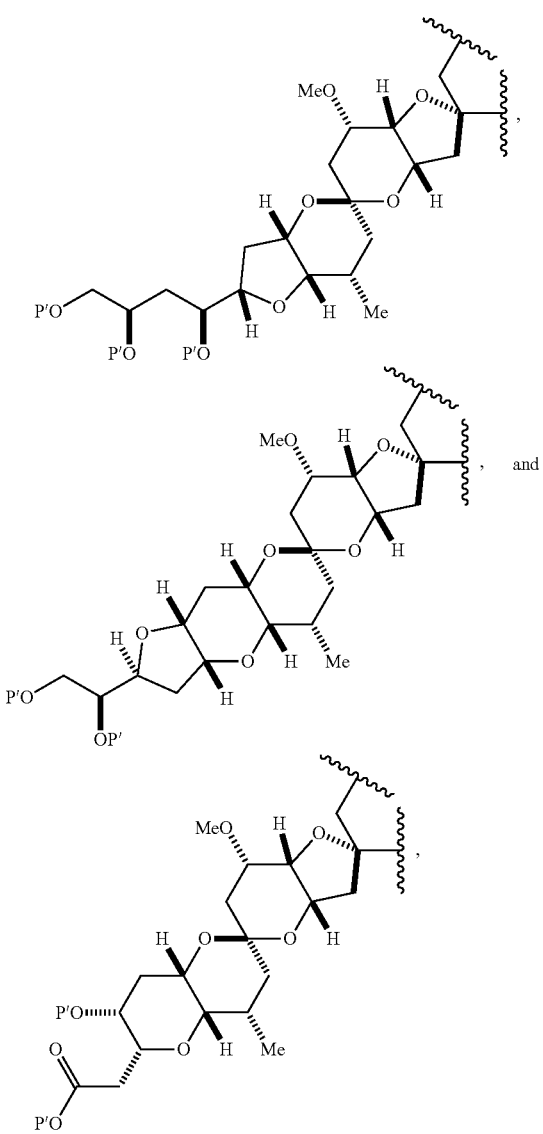

where each P' is independently a hydroxyl protecting group;
E is H, optionally substituted alkyl, or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
X$_1$ is —CH(Y)—, —CH$_2$—, or —O—;
X$_2$ is =O or X$_2$, together with the carbon atom to which it is attached, is —(C(R$_X$)$_2$)—; where each R$_X$ is independently H, —OR$_{X1}$, or —SR$_{X1}$, provided that at least one R$_X$, when present, is —OR$_{X1}$ or —SR$_{X1}$; where each R$_{X1}$ is independently optionally substituted alkyl, or both R$_{X1}$ combine to form optionally substituted alkylene, provided that, when X$_1$ is —O—, X$_2$ is =O;
Y is SO$_2$R$_C$ or COOR$_C$, where, when Y is SO$_2$R$_C$, R$_C$ is optionally substituted aryl or optionally substituted non-enolizable alkyl, and when Y is COOR$_C$, R$_C$ is optionally substituted alkyl, optionally substituted aryl, or optionally substituted arylalkyl;
R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;
(i) each P$_6$ is independently a hydroxyl protecting group, or both P$_6$, together with the atoms to which each is attached, combine to form a ketal or acetal; each R$_{11}$ is independently —OP$_{10}$, or both R$_{11}$ combine to form oxo, where P$_{10}$ is alkyl or a hydroxyl protecting group;
or
(ii) both P$_6$ and both R$_{11}$, together with the atoms to which they are attached, combine to form an acetal;
P$_7$ is a hydroxyl protecting group; and
X$_2$' is a halogen or pseudohalogen.

The structure of the compound of formula (IN) is as follows:

(IN)

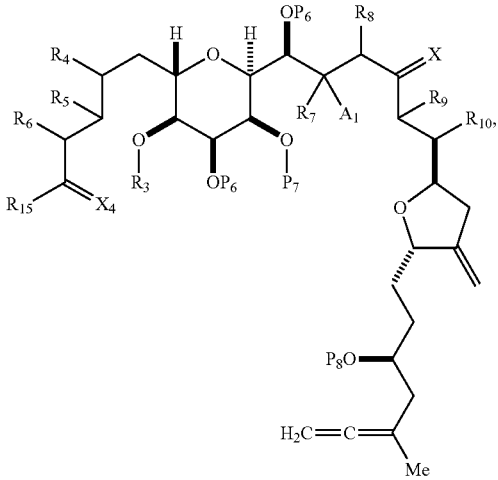

or a salt or tautomer thereof,
where
R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;
A$_1$ and R$_7$ combine to form oxo, P$_7$ is H or a hydroxyl protecting group, and R$_8$ is H;
or
A$_1$ is H or OP'', and:
(i) P$_7$ is H or a hydroxyl protecting group, and R$_7$ and R$_8$, together with the atoms to which each is attached, combine to form a double bond;
or
(ii) P$_7$ and R$_7$ combine to form a bond, and R$_8$ is H or OP''';

each P‴, when present, is independently H or a hydroxyl protecting group;

each $P_6$ is independently H or a hydroxyl protecting group, or both $P_6$, together with the atoms to which each is attached, combine to form a ketal or acetal, and X is =O or X combines with the carbon atom, to which it is attached, to form —(CH(OP$_9$))—, where $P_9$ is H or a hydroxyl protecting group; or both $P_6$ and X, together with the atoms to which each is attached, combine to form ketal; where, when both $P_6$ and X, together with the atoms to which each is attached, combine to form ketal, $P_7$ and $R_7$ combine to form a bond, and $R_8$ is H or OP‴;

$R_9$ is H, $SO_2R_C$, or $COOR_C$, and $R_{10}$ is H; or $R_9$ and $R_{10}$, together with the atoms to which each is attached, combine to form a double bond, where, when $R_9$ is $SO_2R_C$, $R_C$ is optionally substituted aryl or optionally substituted non-enolizable alkyl, and when $R_9$ is $COOR_C$, $R_C$ is optionally substituted alkyl, optionally substituted aryl, or optionally substituted arylalkyl;

$R_{15}$ is H or —OP$_{11}$, where $P_{11}$ is H, a hydroxyl protecting group, or optionally substituted alkyl;

$X_4$ is =O or, together with the carbon atom to which it is attached, is —CH$_2$—, provided that when $R_{15}$ is H, $X_4$ is =O; and $P_8$ is H or silyl.

In some embodiments, each $P_A$ is H, or both $P_A$ combine to form a cyclic protected diol. In other embodiments, $A_1$ is H. In yet other embodiments, each $R_{11}$ is —OP$_{10}$, where $P_{10}$ is alkyl. In still other embodiments, $R_9$ is H or $SO_2R_C$, and $R_{10}$ is H. In certain embodiments, $R_9$ is $SO_2R_C$. In further embodiments, $P_8$ is silyl. In particular embodiments, $P_6$ is a hydroxyl protecting group, and X is =O or X combines with the carbon atom, to which it is attached, to form —(CH(OP$_9$))—. In certain embodiments, $R_3$ and $R_5$ combine to form a bond, and each of $R_4$ and $R_6$ is H. In further embodiments, $R_5$ and $R_6$, together with the atom to which each is attached, combine to form a double bond, $R_4$ is H, and $R_3$ is a hydroxyl protecting group. In yet further embodiments, $R_7$ and $P_7$ combine to form a bond, and $R_8$ is H. In still further embodiments, $P_7$ is a hydroxyl protecting group, and $R_7$ and $R_8$, together with the atoms to which each is attached, combine to form a double bond. In certain embodiments, $A_3$ is H. In particular embodiments, $A_2$ is H.

In further embodiments, the stereogenic center designated by a is (R), and A is of the following structure:

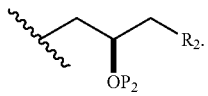

In yet further embodiments, k is 0 and $X_1$ is —CH$_2$—. In still further embodiments, $R_2$ is —(CH$_2$)$_n$NP$_3$P$_4$ or —(CH$_2$)$_n$OP$_5$, wherein n is 0.

In other embodiments, A and D combine to form the following structure:

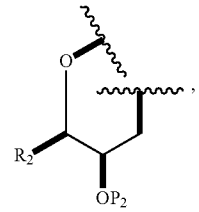

where, the bond to oxygen atom originates at the carbon atom, to which D is attached in formula (IA), and where $R_2$ is —(CH$_2$)$_n$NP$_3$P$_4$ or —(CH$_2$)$_n$OP$_5$, wherein n is 2.

In yet other embodiments, k is 1, and E is optionally substituted alkyl. In still other embodiments, $X_1$ is —O—.

In certain embodiments of the compound of formula (IA), (IB), (IC), (IE), (IJ), or (IN), k is 0, D is H, D' is OP$_1$, and A is of the following structure:

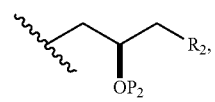

where
(i) $R_2$ is —(CH$_2$)$_n$NP$_3$P$_4$, where n is 0, $P_3$ is H or an N-protecting group, and $P_2$ and $P_4$ combine to form an alkylidene; or
(ii) $R_2$ is —(CH$_2$)$_n$OP$_5$, where n is 0, $P_2$ is H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo.

In particular embodiments of the compound of formula (IA), (IB), (IC), (IE), (IJ), or (IN), k is 0, D is H, D' is OP$_1$, and A is of the following structure:

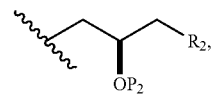

where
(i) $R_2$ is —(CH$_2$)$_n$NP$_3$P$_4$, where n is 0, $P_3$ is an N-protecting group, and $P_2$ and $P_4$ combine to form an alkylidene; or
(ii) $R_2$ is —(CH$_2$)$_n$OP$_5$, where n is 0, each of $P_2$ and $P_5$ is independently H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo.

In yet another aspect, the invention provides compounds 1, 2, 3, 5, 7, 7a, 8, 9, 10, 11, 12, 13, 14, 15, 16, 17, 18, 21, 23, 24, 25, 27, 28, 29, 31, 32, 33, 34, 35, 36, 36b, 36c, 37, 38, 39, 40, 41, 43, 44, 44a, 45, 47, 47a, 47b, 47c, 48, 49, 50, 50a, 51, 52, 53, 54, 55, 56, 57, 58, 59, 61, 62, 63, 66, 67, 68, 69, 70, 71, 72, 73, 77, 78, 79, 80, 81, 82, 83, 84, 85, 86, and 87.

Definitions

Compounds useful in the invention may be isotopically labeled compounds. Useful isotopes include hydrogen, carbon, nitrogen, and oxygen (e.g., $^2$H, $^3$H, $^{13}$O, $^{14}$C, $^{15}$N, $^{18}$O, and $^{17}$O). Isotopically-labeled compounds can be prepared by synthesizing a compound using a readily available isotopically-labeled reagent in place of a non-isotopically-labeled reagent.

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted $C_2$ alkyl group has the formula —CH$_2$CH$_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

By "acetal" is meant —O—(CHR)—O—, where R is H, optionally substituted alkyl, optionally substituted alkenyl, optionally substituted aryl, or optionally substituted arylalkyl, or R group is a bond to an enumerated carbon atom, as shown in Chart 1, within the intermediate or within the halichondrin macrolide or an analog thereof.

By "acetyl" is meant an acyl, in which R is —CX$_n$H$_{3-n}$, where n is 0, 1, 2, or 3, and each X is independently alkoxy or halogen, provided that, when n is 3, each X is independently halogen, and, when n is 2, either both of the X groups are independently halogen or both of the X groups are independently alkoxy. An acetyl group may be substituted (i.e., n is 1, 2, or 3) or unsubstituted (i.e., n is 0).

By "acyl" is meant —C(O)R, where R is H, alkyl, alkenyl, aryl, or arylalkyl. In exemplary acyl groups, R is H, $C_{1-12}$ alkyl (e.g., $C_{1-8}$, $C_{1-6}$, $C_{1-4}$, $C_{2-7}$, $C_{3-12}$, or $C_{3-6}$ alkyl), $C_{2-12}$ alkenyl (e.g., $C_{2-8}$, $C_{2-6}$, $C_{2-4}$, $C_{3-12}$, or $C_{3-6}$ alkenyl), $C_{6-20}$ aryl (e.g., $C_{6-14}$, $C_{6-10}$, $C_{8-20}$, or $C_{8-14}$ aryl), monocyclic $C_{1-6}$ heteroaryl (e.g., monocyclic $C_{1-4}$ or $C_{2-6}$ heteroaryl), $C_{4-19}$ heteroaryl (e.g., $C_{4-10}$ heteroaryl), ($C_{6-14}$)aryl($C_{1-6}$)alkyl, ($C_{1-6}$)heteroaryl($C_{1-6}$)alkyl, or ($C_{4-9}$)heteroaryl($C_{1-6}$)alkyl. As defined herein, any heteroaryl group present in an acyl group has from 1 to 4 heteroatoms selected independently from O, N, and S. An acyl group can be unsubstituted or substituted (e.g., optionally substituted acyl). In the optionally substituted acyl group, the substituent R is H, optionally substituted alkyl, optionally substituted alkenyl, optionally substituted aryl, or optionally substituted arylalkyl. In some embodiments, acyl is $C_{2-10}$ acyl.

By "acylating agent" is meant a compound that reacts with an amine or a hydroxyl group to produce an amide or an ester, respectively. An acylating agent has a formula R-LG, where R is acyl, and LG is halogen, carbonate, or —OR', where R' is acyl.

By "alkoxide" is meant an anionic compound RO—, where R is alkyl. A counterion for alkoxide can be an alkali metal cation, an alkali earth metal cation, or a tetraalkylammonium cation. Alkoxide can be optionally substituted in the same manner as alkyl.

By "alkoxy" is meant —OR, where R is alkyl. Alkoxy can be optionally substituted in the same manner as alkyl.

By "alkoxyalkyl" is meant —OR, where R is alkyl substituted by alkoxy. Each portion of the alkoxyalkyl can be optionally substituted in the same manner as alkyl.

By "alkoxyaryl" is meant —R'(R")$_n$, where n is 1 or 2, R' is arylene and R" is alkoxy, as defined herein. R' can be further optionally substituted in the same manner as aryl. R" can be optionally substituted in the same manner as alkyl.

By "alkoxyarylalkyl" is meant —R'(R"(R'"')$_n$), where n is an integer from 1 to 3, R' is alkylene, R" is arylene, and R'" is alkoxy, as defined herein. R' can be optionally substituted in the same manner as alkyl. R" can be further optionally substituted in the same manner as aryl. R'" can be optionally substituted in the same manner as alkyl.

By "alkyl" is meant a straight or branched chain saturated cyclic (i.e., cycloalkyl) or acyclic hydrocarbon group of from 1 to 12 carbons, unless otherwise specified. In some embodiments, alkyl is $C_{1-6}$ alkyl.

Exemplary alkyl groups include $C_{1-8}$, $C_{1-6}$, $C_{1-4}$, $C_{2-7}$, $C_{3-12}$, and $C_{3-6}$ alkyl. Specific examples include methyl, ethyl, 1-propyl, 2-propyl, 2-methyl-1-propyl, 1-butyl, 2-butyl, and the like. Alkyl group can be optionally substituted with 1, 2, 3, or 4 substituents selected from the group consisting of halogen, hydroxy, alkoxy, aryloxy, arylalkyloxy, amino, oxo, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, and azido.

By "alkylamino" is meant —NHR, where R is alkyl. By "[alkenyl]alkylamino" is meant —NRR', where R is alkyl, and R' is alkenyl. By "[aryl]alkylamino" is meant —NRR', where R is alkyl, and R' is aryl. By "[arylalkyl]alkylamino" is meant —NRR', where R is alkyl, and R' is arylalkyl. By "dialkylamino" is meant —NR$_2$, where each R is alkyl, selected independently.

By "alkylaryl" is meant —R'(R")$_n$, where n is an integer from 1 to 3, R' is arylene, and R" is alkyl. Alkylaryl can be optionally substituted in the same manner as defined for each R' and R" group.

By "alkylene" is meant a multivalent alkyl group. Alkylene groups can be optionally substituted in the same manner as alkyl groups. Alkylene may be a divalent alkylene. For example, a $C_1$ alkylene group is —CH$_2$—.

By "alkylenedithio" is meant —S-alkylene-S—. Alkylenedithio can be optionally substituted in the same manner as an alkylene group.

By "alkylhaloaryl" is meant —R'(R")$_n$—R'", where n is an integer from 1 to 5 and R' is arylene, R" is halogen, and R'" is alkylene, as defined herein. R' can be further optionally substituted in the same manner as aryl. R'" can be further optionally substituted in the same manner as alkyl.

By "alkylthio" is meant —SR, where R is alkyl. Alkylthio can be optionally substituted in the same manner as an alkyl group.

By "alkenyl" is meant a straight or branched chain cyclic or acyclic hydrocarbon group of, unless otherwise specified, from 2 to 12 carbons and containing one or more carbon-carbon double bonds. In some embodiments, alkenyl is $C_{2-6}$ alkenyl. Exemplary alkenyl groups include $C_{2-8}$, $C_{2-7}$, $C_{2-6}$, $C_{2-4}$, $C_{3-12}$, and $C_{3-6}$ alkenyl. Specific examples include ethenyl (i.e., vinyl), 1-propenyl, 2-propenyl (i.e., allyl), 2-methyl-1-propenyl, 1-butenyl, 2-butenyl (i.e., crotyl), and the like. Alkenyl group can be optionally substituted in the same manner as alkyl groups. Alkenyl groups, used in any context herein, may also be substituted with an aryl group.

By "amido" is meant —NHR, where R is acyl. Amido can be optionally substituted in the same manner as acyl.

By "aminal" is meant —O—CR$_2$—NR'—, where each R is independently H, optionally substituted alkyl, optionally substituted alkenyl, optionally substituted aryl, or optionally substituted arylalkyl, or both R groups are together optionally substituted alkylene, and R' is H or an N-protecting group. In particular, R' can be an N-protecting group (e.g., Boc).

By "amino" is meant —NR$_2$, where N and R$_2$ combine to form azido, or each R is independently H or an N-protecting group, or both R combine to form an N-protecting group. Amino can be unmasked, when each R is H, or masked, when at least one R is not H. Thus, optionally masked amino can be masked or unmasked amino.

By "aminoalkyl" is meant —R'(R")$_n$, where n is 1 or 2, R' is alkylene, and R" is amino, as defined herein. R' can be optionally substituted in the same manner as an alkyl group.

By "aryl" is meant a monocyclic or multicyclic ring system having one or more aromatic rings, where the ring system is carbocyclic. Exemplary aryl groups include $C_{6-20}$, $C_{6-15}$, $C_{6-10}$, $C_{8-20}$, and $C_{8-15}$ aryl. A preferred aryl group is a $C_{6-10}$ aryl group. Specific examples of carbocyclic aryl groups include phenyl, indanyl, indenyl, naphthyl, phenanthryl, anthracyl, and fluorenyl. Aryl group can be optionally substituted with 1, 2, 3, 4, or 5 substituents selected from the group consisting of alkyl, alkenyl, aryl, arylalkyl, halogen, alkoxy, aryloxy, arylalkyloxy, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, and azido.

By "arylalkyl" is meant —R'R", where R' is alkylene, and R" is aryl. Arylalkyl can be optionally substituted in the same manner as defined for each R' and R" group.

By "arylalkyloxy" is meant —OR, where R is arylalkyl. Arylalkyloxy can be optionally substituted in the same manner as defined for arylalkyl.

By "arylene" is meant a multivalent aryl group. Arylene groups can be optionally substituted in the same manner as aryl groups. For example, a $C_6$ arylene group is phenylene.

By "aryloxy" is meant —OR, where R is aryl. Aryloxy can be optionally substituted in the same manner as aryl.

By "azido" is meant —N$_3$.

By "boronate" is meant —OB(R)O—, where R is alkyl, alkenyl, aryl, arylalkyl, alkoxy, or 2,6-diacetamidophenyl. Boronate can be substituted, when R is a substituted alkyl, substituted alkenyl, substituted aryl, substituted arylalkyl, or substituted alkoxy. Alternatively, boronate can be unsubstituted, when R is unsubstituted alkyl, unsubstituted alkenyl, aryl, unsubstituted arylalkyl, unsubstituted alkoxy, or 2,6-diacetamidophenyl.

By "carbamate" is meant a group, when a hydroxyl protecting group, having the formula —OC(O)NR$_2$, or, when an amine protecting group, having the formula —NR'—C(O)OR, where each R and R' is independently H, optionally substituted alkyl, optionally substituted alkenyl, optionally substituted aryl, or optionally substituted arylalkyl.

By "carbonate" is meant —OC(O)OR, where R is optionally substituted alkyl, optionally substituted alkenyl, optionally substituted aryl, or optionally substituted arylalkyl.

By "carbonyl" is meant —C(O)—.

By "carboxyl" is meant —C(O)OH, in free acid, ionized, or salt form.

By "carboxylic acid" is meant R—OH, where R is optionally substituted acyl.

By "carboxylic acid anhydride" is meant R—O—R, where each R is independently optionally substituted acyl.

By "cyclic carbonate" is meant —OC(O)O— that is part of a ring.

By "dicarbonyl" is meant —C(O)—C(O)—. Dicarbonyl-dioxo is —OC(O)—COO—.

By "ester" is meant —OC(O)R, where —C(O)R is an optionally substituted acyl group.

By "ether" is meant —OR, where R is alkyl, alkenyl, arylalkyl, silyl, or 2-tetrahydropyranyl. Ether can be optionally substituted as defined for each R group.

By "halichondrin macrolide" is meant a lactone including the structure of carbons 1-30 as shown in Chart 1, wherein carbons 29 and 30 form part of a five- or six-membered ring.

By "haloalkyl" is meant —R'(R")$_n$, where n is an integer from 1 to 5 and R' is alkylene and R" is halogen, as defined herein. R' can be further optionally substituted in the same manner as alkyl By "haloaryl" is meant —R'(R")$_n$, where n is an integer from 1 to 5 and R' is arylene and R" is halogen, as defined herein. R' can be further optionally substituted in the same manner as aryl.

By "haloarylalkyl" is meant —R'(R"(R''')$_n$), where n is an integer from 1 to 5 and R' is alkylene, R" is arylene, and R''' is halogen, as defined herein. R' can be further optionally substituted in the same manner as alkyl. R" can be further optionally substituted in the same manner as aryl.

By "halogen" is meant fluoro, chloro, bromo, or iodo.

By "heterocyclic radical" is meant a 5-, 6- or 7-membered ring, unless otherwise specified, containing one, two, three, or four heteroatoms independently selected from the group containing nitrogen, oxygen, and sulfur. The 5-membered ring has zero to one double bonds, and the 6- and 7-membered rings have zero to two double bonds. Certain heterocyclyl groups include from 1 to 9 carbon atoms. Other such groups may include up to 12 carbon atoms. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl (e.g., 1,3,4-thiadiazole), tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo, 4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d] indolyl; 1,1-dioxo-2H-naphth[1,8-c,d]isothiazolyl; and 1,8-naphthylenedicarboxamido. Heterocyclic groups also include groups of the formula

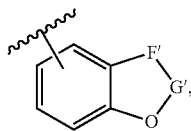

where
F' is selected from the group consisting of —CH$_2$—, —CH$_2$O— and —O—, and G' is selected from the group consisting of —C(O)— and —(C(R')(R''))$_v$—, where each of R' and R'' is, independently, selected from the group consisting of hydrogen or alkyl of one to four carbon atoms, and v is one to three and includes groups, such as 1,3-benzodioxolyl, 1,4-benzodioxanyl, and the like. Any of the heterocyclyl groups mentioned herein may be optionally substituted with one, two, three, four or five substituents independently selected from the group consisting of: (1) alkanoyl (e.g., formyl, acetyl, and the like); (2) alkyl (e.g., alkoxyalkylene, alkylsulfinylalkylene, aminoalkylene, azidoalkylene, acylalkylene, haloalkylene (e.g., perfluoroalkyl), hydroxyalkylene, nitroalkylene, or thioalkoxyalkylene); (3) alkenyl; (4) alkynyl; (5) alkoxy (e.g., perfluoroalkoxy); (6) alkylsulfinyl; (7) aryl; (8) amino; (9) aryl-alkylene; (10) azido; (11) cycloalkyl; (12) cycloalkyl-alkylene; (13) cycloalkenyl; (14) cycloalkenyl-alkylene; (15) halo; (16) heterocyclyl (e.g., heteroaryl); (17) (heterocyclyl)oxy; (18) (heterocyclyl)aza; (19) hydroxy; (20) oxo; (21) nitro; (22) sulfide; (23) thioalkoxy; (24) —(CH$_2$)$_q$CO$_2$R$^A$, where q is an integer from zero to four, and R$^A$ is selected from the group consisting of (a) alkyl, (b) aryl, (c) hydrogen, and (d) aryl-alkylene; (25) —(CH$_2$)$_q$CONR$^B$R$_C$, where q is an integer from zero to four and where R$^B$ and R$^C$ are independently selected from the group consisting of (a) hydrogen, (b) alkyl, (c) aryl, and (d) aryl-alkylene; (26) —(CH$_2$)$_q$SO$_2$R$^D$, where q is an integer from zero to four and where R$^D$ is selected from the group consisting of (a) alkyl, (b) aryl, and (c) aryl-alkylene; (27) —(CH$_2$)$_q$SO$_2$NR$^E$R$^F$, where q is an integer from zero to four and where each of R$^E$ and R$^F$ is, independently, selected from the group consisting of (a) hydrogen, (b) alkyl, (c) aryl, and (d) aryl-alkylene; (28) thiol; (29) aryloxy; (30) cycloalkoxy; (31) arylalkoxy; (31) heterocyclyl-alkylene (e.g., heteroaryl-alkylene); (32) silyl; (33) cyano; and (34) —S(O)R$^H$ where R$^H$ is selected from the group consisting of (a) hydrogen, (b) alkyl, (c) aryl, and (d) aryl-alkylene. In some embodiments, each of these groups can be further substituted as described herein. For example, the alkylene group of an aryl-C$_1$-alkylene or a heterocyclyl-C$_1$-alkylene can be further substituted with an oxo group to afford the respective aryloyl and (heterocyclyl) oyl substituent group. In addition, when a heterocyclyl group is present in a bioreversible group of the invention it may be substituted with an ester, thioester, or disulfide group that is bound to a conjugating moiety, a hydrophilic functional group, or an auxiliary moiety as defined herein.

By "heterocyclic radical alkyl," as used herein, represents an alkyl group substituted with a heterocyclic radical. The heterocyclic radical and alkyl portions may be substituted as the individual groups as described herein.

By "hydroxyalkyl" is meant —R'(R'')$_n$, where n 1 or 2, R' is alkylene and R'' is hydroxyl, as defined herein.

R' can be further optionally substituted in the same manner as alkyl.

By "hydroxyaryl" is meant —R'(R'')$_n$, where n is 1 or 2, R' is arylene and R'' is hydroxyl, as defined herein.

R' can be further optionally substituted in the same manner as aryl.

By "hydroxyl" is meant —OH.

By "hydroxyl protecting group" is meant any group capable of protecting the oxygen atom to which it is attached from reacting or bonding. Hydroxyl protecting groups are known in the art, e.g., as described in Wuts, Greene's Protective Groups in Organic Synthesis, Wiley-Interscience, 4th Edition, 2006.

Exemplary protecting groups (with the oxygen atom to which they are attached) are independently selected from the group consisting of esters, carbonates, carbamates, sulfonates, and ethers. In exemplary ester hydroxyl protecting groups, R of the acyl group is $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), carbocyclic $C_{6-20}$ aryl (e.g., $C_{6-15}$, $C_{6-10}$, $C_{8-20}$, and $C_{8-15}$aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), $(C_{6-15})$aryl$(C_{1-6})$alkyl, $(C_{4-19})$heteroaryl$(C_{1-6})$alkyl, or $(C_{1-6})$heteroaryl$(C_{1-6})$alkyl. Specific examples of acyl groups for use in esters include formyl, benzoylformyl, acetyl (e.g., unsubstituted or chloroacetyl, trifluoroacetyl, methoxyacetyl, triphenylmethoxyacetyl, and p-chlorophenoxyacetyl), 3-phenylpropionyl, 4-oxopentanoyl, 4,4-(ethylenedithio)pentanoyl, pivaloyl (Piv), vinylpivaloyl, crotonoyl, 4-methoxy-crotonoyl, naphthoyl (e.g., 1- or 2-naphthoyl), and benzoyl (e.g., unsubstituted or substituted, e.g., p-methoxybenzoyl, phthaloyl (including salts, such a triethylamine and potassium), p-bromobenzoyl, and 2,4,6-trimethylbenzoyl). As defined herein, any heteroaryl group present in an ester group has from 1 to 4 heteroatoms selected independently from O, N, and S. In exemplary carbonate hydroxyl protecting groups, R is $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), carbocyclic $C_{6-20}$ aryl (e.g., $C_{6-15}$, $C_{6-10}$, $C_{8-20}$, and $C_{8-15}$aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), $(C_{6-15}$ aryl($C_{1-6}$)alkyl, ($C_{4-19}$)heteroaryl($C_{1-6}$)alkyl, or ($C_{1-6}$)heteroaryl($C_{1-6}$)alkyl. Specific examples include methyl, 9-fluorenylmethyl, ethyl, 2,2,2-trichloroethyl, 2-(trimethylsilyl)ethyl, 2-(phenylsulfonyl)ethyl, vinyl, allyl, t-butyl, p-nitrobenzyl, and benzyl carbonates. As defined herein, any heteroaryl group present in a carbonate group has from 1 to 4 heteroatoms selected independently from O, N, and S. In exemplary carbamate hydroxyl protecting groups, each R is independently H, $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), carbocyclic $C_{6-20}$ aryl (e.g., $C_{6-15}$, $C_{6-10}$, $C_{8-20}$, and $C_{8-15}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), ($C_{6-15}$)aryl($C_{1-6}$)alkyl, ($C_{4-19}$)heteroaryl($C_{1-6}$) alkyl, or ($C_{1-6}$)heteroaryl($C_{1-6}$)alkyl. Specific examples include N-phenyl and N-methyl-N-(o-nitrophenyl) carbamates. As defined herein, any heteroaryl group present in a carbamate group has from 1 to 4 heteroatoms selected independently from O, N, and S. Exemplary ether hydroxyl protecting groups include $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), ($C_{6-15}$)aryl($C_{1-6}$)alkyl, ($C_{4-19}$)heteroaryl($C_{1-6}$)alkyl, ($C_{1-6}$)heteroaryl($C_{1-6}$)alkyl, ($C_{1-6}$)alkoxy($C_{1-6}$)alkyl, ($C_{1-6}$)alkylthio($C_{1-6}$)alkyl, ($C_{6-10}$) aryl($C_{1-6}$)alkoxy($C_{1-6}$)alkyl, and silyl (e.g., tri($C_{1-6}$ alkyl) silyl, tri($C_{6-10}$ aryl or $C_{1-6}$ heteroaryl)silyl, di($C_{6-10}$ aryl or $C_{1-6}$ heteroaryl)($C_{1-6}$ alkyl)silyl, and ($C_{6-10}$ aryl or $C_{1-6}$ heteroaryl)di($C_{1-6}$ alkyl)silyl). Specific examples of alkylethers include methyl and t-butyl, and an example of an alkenyl ether is allyl. Ether hydroxyl protecting groups can be used to protect a carboxyl group (e.g., with a $C_{1-12}$ alkyl (e.g., $C_{1-8}$, $C_{1-6}$, $C_{1-4}$, $C_{2-7}$, $C_{3-12}$, and $C_{3-6}$ alkyl), ($C_{6-15}$) aryl($C_{1-6}$)alkyl, ($C_{1-6}$)alkoxy($C_{1-6}$)alkyl, ($C_{1-6}$)alkylthio ($C_{1-6}$)alkyl, or ($C_{6-10}$)aryl($C_{1-6}$)alkoxy($C_{1-6}$)alkyl). Examples of alkoxyalkyls and alkylthioalkyls that can be used as ether hydroxyl protecting groups include methoxymethyl, methylthiomethyl, (2-methoxyethoxy)methyl, and β-(trimethylsilyl)ethoxymethyl. Examples of arylalkyl groups that can be used as ether hydroxyl protecting groups include benzyl, p-methoxybenzyl (MPM), 3,4-dimethoxybenzyl, triphenylmethyl (trityl), o-nitrobenzyl, p-nitrobenzyl, p-halobenzyl, 2,6-dichlorobenzyl, p-cyanobenzyl, naphthylmethyl, and 2- and 4-picolyl ethers. Specific examples of silylethers include trimethylsilyl (TMS), triethylsilyl (TES), t-butyldimethylsilyl (TBS), t-butyldiphenylsilyl (TBDPS), triisopropylsilyl (TIPS), and triphenylsilyl (TPS) ethers. An example of an arylalkyloxyalkylether is benzyloxymethyl ether. As defined herein, any heteroaryl group present in an ether group has from 1 to 4 heteroatoms selected independently from O, N, and S. Vicinal or 1,3-diols may be protected with a diol protecting group (e.g., to produce a "cyclic protected diol"), such as acetal (e.g., containing $C_{1-6}$ alkylene), ketal (e.g., containing $C_{3-6}$ alkylene or $C_{3-6}$ cycloalkyl), cyclic silylene, cyclic carbonate, and cyclic boronate. Examples of acetal and ketal groups include methylene-dioxo, ethylidene-dioxo, benzylidene-dioxo, isopropylidene-dioxo, cyclohexylidene-dioxo, and cyclopentylidene-dioxo. An example of a cyclic silylene is di-t-butylsilylene. Another diol protecting group is 1,1,3,3-tetraisopropylsiloxanediyl. Examples of cyclic boronates include methyl, ethyl, phenyl, and 2,6-diacetamidophenyl boronates. Protecting groups may be substituted as is known in the art; for example, aryl and arylalkyl groups, such as phenyl, benzyl, naphthyl, or pyridinyl, can be substituted with $C_{1-6}$ alkyl, $C_{1-6}$ alkoxy, nitro, cyano, carboxyl, or halogen. Alkyl groups, such as methyl, ethyl, isopropyl, n-propyl, t-butyl, n-butyl, and sec-butyl, and alkenyl groups, such as vinyl and allyl, can also be substituted with oxo, arylsulfonyl, halogen, and trialkylsilyl groups. Preferred protecting groups are TBS and Piv. Protecting groups that are orthogonal are removed under different conditions, as is known in the art.

By "imido" is meant —$NR_2$, where each R is independently optionally substituted acyl.

By "ketal" is meant —O—$CR_2$—O—, where each R is independently optionally substituted alkyl, optionally substituted alkenyl, optionally substituted aryl, or optionally substituted arylalkyl, or both R groups are together optionally substituted alkylene, or each of the R groups is a bond to an enumerated carbon atom, as shown in Chart 1, within the intermediate or within the halichondrin macrolide or an analog thereof.

By "macrocyclic" is meant a compound containing at least one n-membered ring, where n is equal to or greater than 10.

By "non-enolizable" is meant a group that, either alone or in combination with a group to which it is attached, cannot form an enol through a deprotonation/reprotonation sequence. For example, a "non-enolizable alkyl" can be bonded to a sulfone group or to a carbonyl group through a quaternary carbon atom (i.e., the carbon atom that is not bonded to a hydrogen atom).

By "N-protecting group" is meant a group protecting a nitrogen atom in a molecule from participating in one or more undesirable reactions during chemical synthesis (e.g., oxidation reactions, or certain nucleophilic and electrophilic substitutions). Commonly used N-protecting groups are disclosed in Wuts, Greene's Protective Groups in Organic Synthesis, Wiley-Interscience, 4th Edition, 2006. Exemplary N-protecting groups include acyl (e.g., formyl, acetyl, trifluoroacetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, and 4-bromobenzoyl); sulfonyl-containing groups (e.g., benzenesulfonyl, p-toluenesulfonyl, o-nitrobenzenesulfonyl, and p-nitrobenzenesulfonyl); carbamate forming groups (e.g., benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl), arylalkyl (e.g., triphenylmethyl); silyl groups (e.g., trimethylsilyl); and imine-forming groups (e.g., diphenylmethylene). Preferred N-protecting groups are acetyl, benzoyl, phenylsulfonyl, p-toluenesulfonyl, p-nitrobenzenesulfonyl, o-nitrobenzenesulfonyl, t-butyloxycarbonyl (Boc), and benzyloxycarbonyl (Cbz).

By "oxo" or (O) is meant =O.

By "pharmaceutically acceptable salt" is meant a salt within the scope of sound medical judgment, suitable for use in contact with the tissues of humans and animals without undue toxicity, irritation, allergic response and the like and commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. A preferred salt is the mesylate salt.

By "pseudohalogen" is meant —O—SO$_2$R, where R is optionally substituted alkyl, optionally substituted aryl, or optionally substituted arylalkyl. Non-limiting examples of pseudohalogens include trifluoromethanesulfonate and nonaflate.

By "silyl" is meant —SiR$_3$, where each R is independently alkyl, alkenyl, aryl, or arylalkyl. Examples of silyl groups include tri(C$_{1-6}$ alkyl)silyl, tri(C$_{6-10}$ aryl or C$_{1-6}$ heteroaryl)silyl, di(C$_{6-10}$ aryl or C$_{1-6}$ heteroaryl)(C$_{1-6}$ alkyl)silyl, and (C$_{6-10}$ aryl or C$_{1-6}$ heteroaryl)di(C$_{1-6}$ alkyl)silyl. It will be understood that, when a silyl group includes two or more alkyl, alkenyl, aryl, heteroaryl, or arylalkyl groups, these groups are independently selected. As defined herein, any heteroaryl group present in a silyl group has from 1 to 4 heteroatoms selected independently from O, N, and S. Silyl can be optionally substituted in the same manner as defined for each R group.

By "silylene" is meant —SiR$_2$—, where each R is independently alkyl, alkenyl, aryl, arylalkyl, or alkoxy. By "dialkylsilylene" is meant a silylene, where each R is alkyl. Silylene can be optionally substituted in the same manner as defined for each R group. Silylene-dioxo is a group having the formula —O—SiR$_2$—O—.

By "strong base" is meant a Brønsted base, the conjugate acid of which has pKa that is greater than or equal to 13. Non-limiting examples of strong bases include alkyl alkali metals (e.g., butyl lithium or Schlosser's base), Grignard reagents (e.g., alkyl magnesium halide), alkali or alkali earth alkoxides (e.g., tertiary alkoxides, such as t-butoxide), alkali or alkali earth amides (e.g., diisopropylamide, tetramethylpiperidide, or bis(trimethylsilyl)amide), and phosphazene bases (e.g., Schwesinger base). Non-limiting examples of the alkali amides are lithium diisopropylamide, lithium tetramethylpiperidide, lithium bis(trimethylsilyl)amide, sodium bis(trimethylsilyl)amide, and potassium bis(trimethylsilyl)amide.

By "sulfonamide" is meant —NR, where R is sulfonyl.

By "sulfonate" is meant —OS(O)$_2$R, where R is optionally substituted alkyl, optionally substituted alkenyl, optionally substituted aryl, or optionally substituted arylalkyl. In exemplary sulfonates, R is C$_{1-12}$ alkyl (e.g., C$_{1-8}$, C$_{1-6}$, C$_{1-4}$, C$_{2-7}$, C$_{3-12}$, or C$_{3-6}$ alkyl), C$_{2-12}$ alkenyl (e.g., C$_{2-8}$, C$_{2-6}$, C$_{2-4}$, C$_{3-12}$, or C$_{3-6}$ alkenyl), carbocyclic C$_{6-20}$ aryl (e.g., C$_{6-15}$, C$_{6-10}$, C$_{8-20}$, or C$_{8-15}$ aryl), monocyclic C$_{1-6}$ heteroaryl (e.g., C$_{1-4}$ and C$_{2-6}$ heteroaryl), C$_{4-19}$ heteroaryl (e.g., C$_{4-10}$ heteroaryl), (C$_{6-15}$)aryl(C$_{1-6}$)alkyl, (C$_{4-19}$)heteroaryl(C$_{1-6}$)alkyl, or (C$_{1-6}$)heteroaryl(C$_{1-6}$)alkyl. As defined herein, any heteroaryl group present in a sulfonate group has from 1 to 4 heteroatoms selected independently from O, N, and S.

By "sulfonyl" is meant —S(O)$_2$R, where R is optionally substituted alkyl, optionally substituted alkenyl, optionally substituted aryl, optionally substituted arylalkyl, or silyl. Preferred R groups for sulfonyl are the same as those described above for sulfonates.

By "thioacetal" is meant —S—(CHR)—S—, where R is H, optionally substituted alkyl, optionally substituted alkenyl, optionally substituted aryl, or optionally substituted arylalkyl.

By "thioketal" is meant —S—(CR$_2$)—S—, where each R is independently optionally substituted alkyl, optionally substituted alkenyl, optionally substituted aryl, or optionally substituted arylalkyl.

By "triflate" is meant trifluoromethanesulfonate.

The pKa values recited herein refer to the pKa values of a conjugate Brønsted acid in water at room temperature, unless stated otherwise.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

For purposes of this disclosure, any term present in the art which is identical to any term expressly defined in this disclosure, the term's definition presented in this disclosure will control in all respects.

DETAILED DESCRIPTION

The present invention provides methods for the synthesis of a halichondrin macrolide or an analog thereof (see Chart 1). Preferably, the halichondrin macrolide analog is eribulin. Preferably the halichondrin macrolide is a halichondrin B macrolide. The processes of the present invention involve subjecting an intermediate to Prins reaction conditions. The carbon-atom numbering schemes for a halichondrin macrolide and an analog thereof are shown in Chart 1.

Chart 1

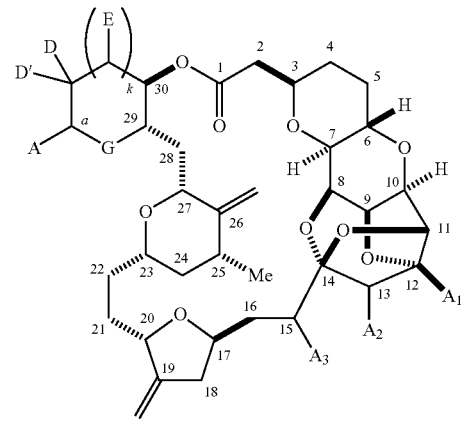

halichondrin macrolide    or

-continued

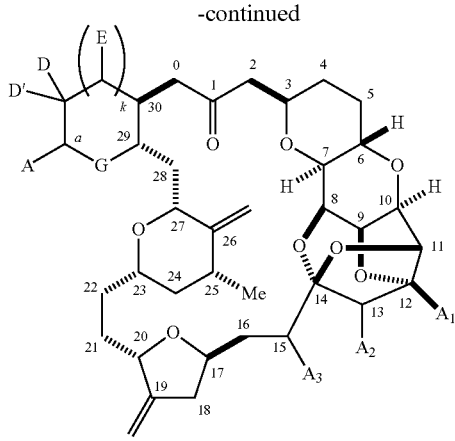

halichondrin macrolide analog

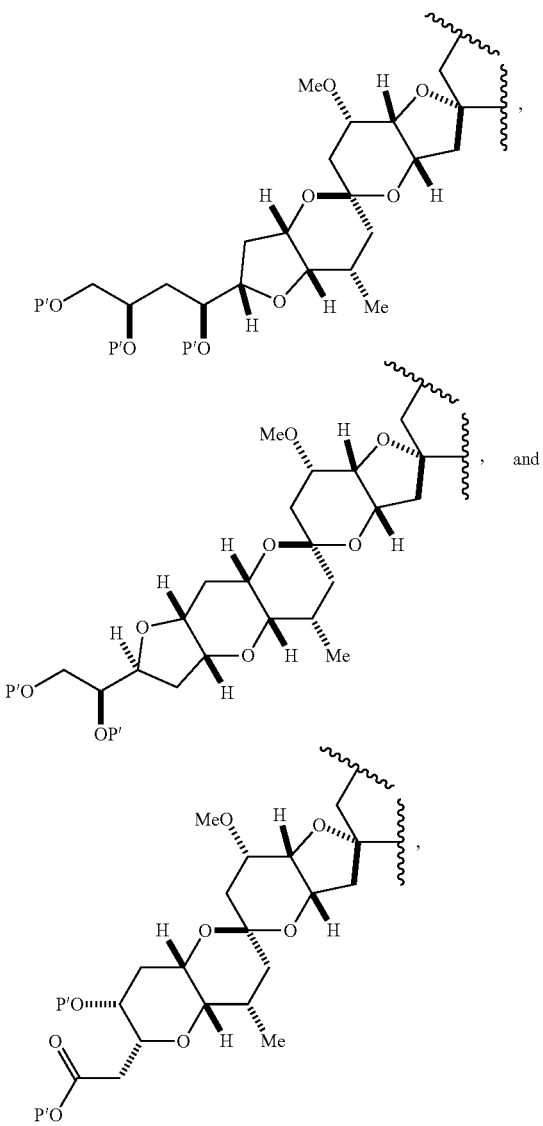

or a salt or tautomer thereof, in which each of D and D' is independently H, optionally substituted alkyl, or $OP_1$, provided that only one of D and D' is $OP_1$, wherein $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

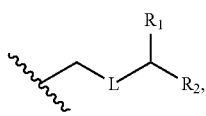 (1)

where

L is —(CH($OP_2$))—, —(C(OH)($OP_2$))—, or —C(O)—;

$R_1$ is H, or $R_1$ and $P_1$ combine to form a bond;

(i) $R_2$ is H, wherein $P_2$ is absent, H, optionally substituted alkyl, or a hydroxyl protecting group;

(ii) $R_2$ is —(CH$_2$)$_n$NP$_3$P$_4$, wherein $P_3$ is H or an N-protecting group, and (a) $P_2$ is absent, H, optionally substituted alkyl, or a hydroxyl protecting group, and $P_4$ is H or an N-protecting group, or (b) $P_2$ and $P_4$ combine to form an alkylidene, or (c) each of $P_2$ and $P_4$ is H;

(iii) $R_2$ is —(CH$_2$)$_n$OP$_5$, wherein $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_2$ and $P_2$ combine to form an optionally substituted ethylene or a structure selected from the group consisting of:

wherein each P' is independently H or a hydroxyl protecting group;

each of $A_1$, $A_2$, and $A_3$ is independently H or OP''', where each P''' is independently H or a hydroxyl protecting group;

E is H, optionally substituted alkyl, or optionally substituted alkoxy;

G is O, S, CH$_2$, or NR$_N$, wherein $R_N$ is H, an N-protecting group, or optionally substituted alkyl;

each $Q_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, wherein each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1; and n is 0, 1, or 2.

Preparation of the halichondrin macrolide or analog thereof involves a reaction between a compound of formula (IA), R$_{12}$OH (R$_{12}$ may be optionally substituted acyl), and a Lewis acid (e.g., an oxophilic Lewis acid (e.g., boron trifluoride or a solvate thereof)) to produce a compound of formula (IB). The compound of formula (IA) is of the following structure:

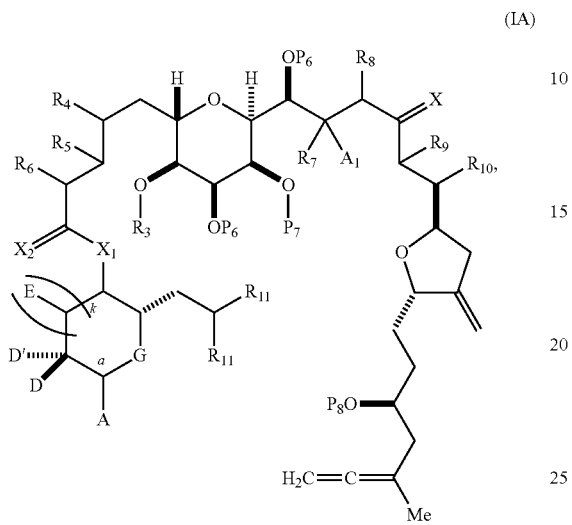

(IA)

or a salt or a tautomer thereof,
where
each of D and D' is independently H, optionally substituted alkyl, or OP$_1$, provided that only one of D and D' is OP$_1$, where P$_1$ is H, alkyl, or a hydroxyl protecting group; and A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

(1)

where
L is —(CH(OP$_2$))—, —(C(OH)(OP$_2$))—, or —C(O)—;
R$_1$ is H, or R$_1$ and P$_1$ combine to form a bond;
  (i) R$_2$ is H, where P$_2$ is absent, H, optionally substituted alkyl, or a hydroxyl protecting group;
  (ii) R$_2$ is —(CH$_2$)$_n$NP$_3$P$_4$, where P$_3$ is an N-protecting group, and (a) P$_2$ is absent, H, optionally substituted alkyl, or a hydroxyl protecting group, and P$_4$ is an N-protecting group, or (b) P$_2$ and P$_4$ combine to form an alkylidene;
  (iii) R$_2$ is —(CH$_2$)$_n$OP$_5$, where P$_2$ is absent, H, optionally substituted alkyl, or a hydroxyl protecting group, and P$_5$ is H, optionally substituted alkyl, or a hydroxyl protecting group; or P$_2$ and P$_5$, together with the atoms to which each is attached, combine to form a ketal, a cyclic carbonate, a dicarbonyl-dioxo, or silylene-dioxo; or
  (iv) R$_2$ and P$_2$ combine to form an optionally substituted ethylene or a structure selected from the group consisting of:

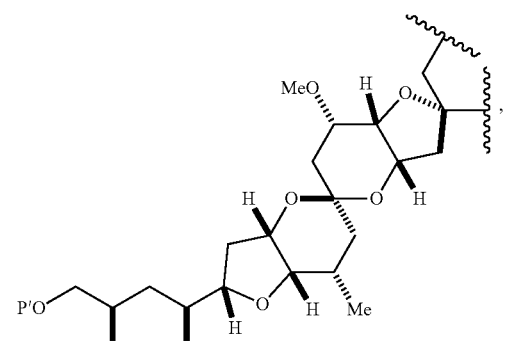

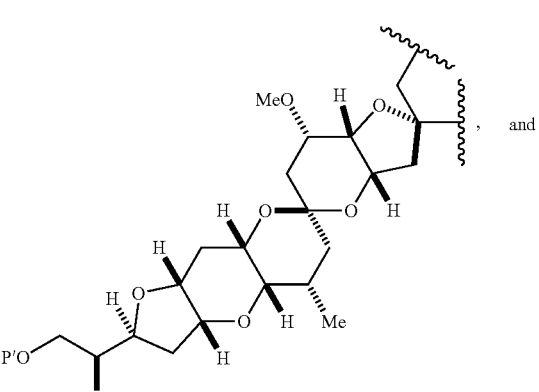

and

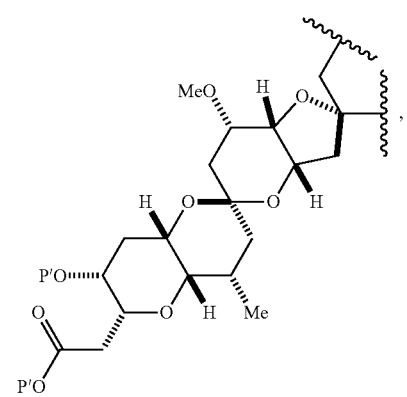

where each P' is independently H or a hydroxyl protecting group;

E is H, optionally substituted alkyl, or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

$X_1$ is —CH(Y)—, —$CH_2$—, or —O—, and $X_2$ is =O or $X_2$, together with the carbon atom to which it is attached, is —$(C(R_X)_2)$—; where each $R_X$ is independently H, —$OR_{X1}$, or —$SR_{X1}$, provided that at least one $R_X$, when present, is —$OR_{X1}$ or —$SR_{X1}$; where each $R_{X1}$ is independently optionally substituted alkyl, or both $R_{X1}$ combine to form optionally substituted alkylene, provided that, when $X_1$ is —O—, $X_2$ is =O; and where Y is $SO_2R_C$ or $COOR_C$, where, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;

$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;

$A_1$ and $R_7$ combine to form oxo, $P_7$ is H or a hydroxyl protecting group, and $R_8$ is H;

or $A_1$ is H or OP''', and:
(i) $P_7$ is H or a hydroxyl protecting group, and $R_7$ and $R_8$, together with the atoms to which each is attached, combine to form a double bond;
or
(ii) $P_7$ and $R_7$ combine to form a bond, and $R_8$ is H or OP''';

(i) each $P_6$ is independently H or a hydroxyl protecting group, or both $P_6$, together with the atoms to which each is attached, combine to form a ketal or acetal; X is =O or X combines with the carbon atom, to which it is attached, to form —$(CH(OP_9))$—, where $P_9$ is H or a hydroxyl protecting group; and each $R_{11}$ is —$OP_{10}$, or both $R_{11}$ combine to form oxo, where $P_{10}$ is alkyl or a hydroxyl protecting group (e.g., silyl);

(ii) both $P_6$ and X, together with the atoms to which each is attached, combine to form ketal, $P_7$ and $R_7$ combine to form a bond, and $R_8$ is H or OP'''; and each $R_{11}$ is —$OP_{10}$, or both $R_{11}$ combine to form oxo, where $P_{10}$ is alkyl or a hydroxyl protecting group (e.g., silyl); or (iii) both $P_6$ and both $R_{11}$, together with the atoms to which they are attached, combine to form acetal; and X is =O or X combines with the carbon atom, to which it is attached, to form —$(CH(OP_9))$—, where $P_9$ is H or a hydroxyl protecting group;

$R_9$ is H, OP''', or Y, and $R_{10}$ is H; or $R_9$ and $R_{10}$, together with the atoms to which each is attached, combine to form a double bond;

$P_8$ is H or silyl; and each P''', when present, is independently H or a hydroxyl protecting group.

The compound of formula (IB) is of the following structure:

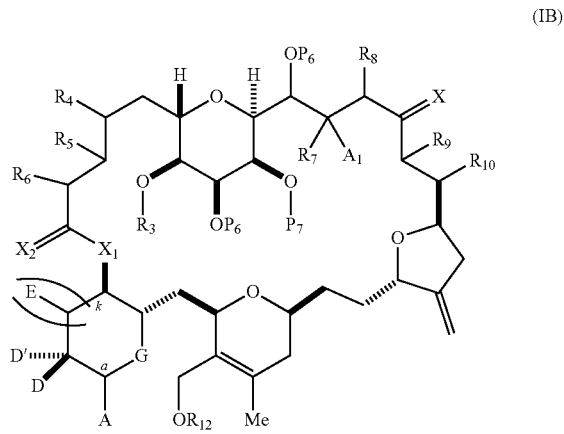

(IB)

or a salt or a tautomer thereof, where $R_{12}$ is optionally substituted acyl, and all other variables are as defined for the compound of formula (IA).

Typically, the reaction conditions for converting the compound of formula (IA) to the compound of formula (IB) are those known in the art for a Prins reaction.

Preparation of the halichondrin macrolide or the analog thereof from the compound of formula (IB) further involves reacting the compound of formula (IB) with an allylic reducing agent to produce the halichondrin macrolide or the analog thereof.

In the halichondrin macrolide, the analog thereof, formula (IA), or formula (IB), G may be O. In the halichondrin macrolide, the analog thereof, formula (IA), or formula (IB), D may be H. In the halichondrin macrolide, the analog thereof, formula (IA), or formula (IB), D' may be $OP_1$, where $P_1$ may be alkyl (e.g., methyl).

In the halichondrin macrolide analog, formula (IA), or formula (IB), k may be 0, and $X_1$ may be —$CH_2$—. In the halichondrin macrolide, formula (IA), or formula (IB), k may be 1, and X, may be —O—.

In the halichondrin macrolide, the analog thereof, formula (IA), or formula (IB), E may be optionally substituted alkyl.

In the halichondrin macrolide, the analog thereof, formula (IA), or formula (IB), $A_1$ may be H.

In the halichondrin macrolide, the analog thereof, formula (IA), or formula (IB), the stereogenic center designated by a may be (R), and A may be of the following structure:

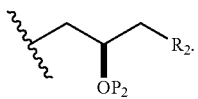

In further embodiments of the halichondrin macrolide, the analog thereof, formula (IA), or formula (IB), k is 0 and $X_1$ is —$CH_2$—. In yet further embodiments of the halichondrin macrolide, the analog thereof, formula (IA), or formula (IB), $R_2$ is —$(CH_2)_nNP_3P_4$ or —$(CH_2)_nOP_5$, wherein n is 0.

Alternatively, in the halichondrin macrolide, the analog thereof, formula (IA), or formula (IB), A and D may combine to form the following structure:

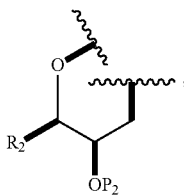

where the bond to the oxygen atom originates at the carbon atom to which D is attached in the halichondrin macrolide, the analog thereof, formula (IA), or formula (IB). In still further embodiments of the halichondrin macrolide, the analog thereof, formula (IA), or formula (IB) $R_2$ is —$(CH_2)_n$NP$_3$P$_4$ or —$(CH_2)_n$OP$_5$, and n is 2.

In other embodiments of the halichondrin macrolide, the analog thereof, formula (IA), or formula (IB), k is 1, and E is optionally substituted alkyl. In still other embodiments of the halichondrin macrolide, the analog thereof, formula (IA), or formula (IB), $X_1$ is —O—.

If, in the compound of formula (IA), $R_3$ is H or a hydroxyl protecting group, $R_5$ and one of $R_4$ and $R_6$, together with the atoms to which each is attached, combine to form a double bond, and the remaining $R_4$ or $R_6$ is H, treatment of the compound of formula (IA) with a Lewis acid (e.g., an oxophilic Lewis acid) and $R_{12}$OH can produce a compound of formula (IB), in which $R_3$ and $R_5$ combine to form a bond, and each of $R_4$ and $R_6$ is H.

Preparation of the halichondrin macrolide or the analog thereof may include further steps, depending on the nature of $A_1$, $R_3$, $R_4$, $R_5$, $R_6$, $R_7$, $R_8$, $R_9$, $R_{10}$, X, $X_1$, $P_6$, and $P_7$.

Preparation of certain compounds of formula (IA) or formula (IB) may further involve conversion of the compound of formula (IA) or formula (IB), in which $A_1$ is H, and $R_7$ and $R_8$ combine to form a double bond, into the compound of formula (IA) or formula (IB) in which $R_7$ and $A_1$ combine to form O. In a non-limiting example, the enone in the compound of formula (IA) or formula (IB), in which $R_7$ and $R_8$ combine to form a double bond can be converted into a C.12-C.13 epoxide using a nucleophilic peroxide agent, e.g., t-butyl hydroperoxide, which can then be converted into the compound of formula (IA) or formula (IB), in which $A_1$ and $R_7$ combine to form oxo, using methods known in the art, e.g., by reacting with a bidentate phosphine ligand and a source of Pd(0) (see, e.g., Muzart, J., *Eur. J. Org. Chem.*, 4717-4741, 2011). Thus, the compound of formula (IA) or formula (IB), in which $A_1$ is OP‴, can be prepared. Other transformations may involve α-oxygenation to produce the compound of formula (IA) or formula (IB), in which $R_8$ and/or $R_9$ is OP‴.

If, in the compound of formula (IA) or formula (IB), $X_1$ is —CH(Y)— and/or $R_9$ is SO$_2$R$_C$ or COOR$_C$, synthesis of the halichondrin macrolide or the analog thereof may further involve a decarboxylation reaction (when $X_1$ is —CH(Y)—, and Y is COOR$_C$ and/or $R_9$ is COOR$_C$) or a desulfonylation reaction (when $X_1$ is —CH(Y)—, and Y is SO$_2$R$_C$ and/or $R_9$ is SO$_2$R$_C$) as described herein. The decarboxylation or desulfonylation reaction may be performed on the compound of formula (IA) or formula (IB) or on an intermediate downstream of the compound of formula (IB) (e.g., after the compound of formula (IB) is reacted with an allylic reducing agent).

If, in the compound of formula (IA) or formula (IB), in which $R_9$ and $R_{10}$, together with the atoms to which each is attached, combine to form a double bond, synthesis of the halichondrin macrolide or the analog thereof may further involve a 1,4-reduction as described herein (e.g., using Stryker's reagent). The 1,4-reduction may be performed on the compound of formula (IA) or formula (IB) or on an intermediate downstream of the compound of formula (IB). Thus, the compound of formula (IA) or formula (IB), in which both $R_9$ and $R_{10}$ are H, may be prepared.

If, in the compound of formula (IA) or formula (IB), X combines with the carbon atom, to which it is attached, to form —(CH(OP$_9$))—, where P$_9$ is H, synthesis of the halichondrin macrolide or the analog thereof may further involve reacting this compound of formula (IB) with an oxidizing agent capable of converting an alcohol to a carbonyl group to produce a compound of formula (IB), in which X is =O. Alternatively, treatment with an oxidizing agent capable of converting an alcohol to a carbonyl group may be performed on an intermediate downstream of the compound of formula (IB) (e.g., after the compound of formula (IB) is reacted with an allylic reducing agent). The reaction, whereby X is converted to oxo, may also be performed on the compound of formula (IA) prior to the macrocylization reaction.

If, in the compound of formula (IB), each $P_6$ is H, and X is =O, synthesis of the halichondrin macrolide or the analog thereof may further involve reacting this compound of formula (IB) with a Brønsted acid (e.g., a Brønsted acid having a pKa of 5±3) to produce the compound of formula (IB), in which both $P_6$ and X, together with the atoms to which each is attached, combine to form ketal. Alternatively, treatment with a Brønsted acid (e.g., a Brønsted acid having a pKa of 5±3) may be performed on an intermediate downstream of the compound of formula (IB) (e.g., after the compound of formula (IB) is reacted with an allylic reducing agent).

If, in the compound of formula (IB), each $P_6$ is a hydroxyl protecting group (e.g., silyl) and X is =O, synthesis of the halichondrin macrolide or the analog thereof may further involve reacting this compound of formula (IB) with a hydroxyl protecting group removing agent (e.g., a fluoride source, if $P_6$ is silyl) to produce the compound of formula (IB), in which each $P_6$ is H and X is =O, which may then be subjected to the treatment with a Brønsted acid (e.g., a Brønsted acid having a pKa of 5±3) to produce the compound of formula (IB), in which both $P_6$ and X, together with the atoms to which each is attached, combine to form ketal. Alternatively, treatment with a hydroxyl protecting group removing agent (e.g., a fluoride source, if $P_6$ is silyl) may be performed on an intermediate downstream of the compound of formula (IB) (e.g., after the compound of formula (IB) is reacted with an allylic reducing agent).

If, in the compound of formula (IB), each $P_6$ is H, X is =O, $P_7$ is H, and $R_7$ and $R_8$, together with the atoms to which each is attached, combine to form a double bond, synthesis of the halichondrin macrolide or the analog thereof may further involve reacting this compound of formula (IB) with a Brønsted acid (e.g., a Brønsted acid having a pKa of 5±3) to produce the compound of formula (IB), in which both $P_6$ and X, together with the atoms to which each is attached, combine to form ketal, and $R_7$ and $R_8$, together with the atoms to which each is attached, combine to form a double bond. Alternatively, treatment with with a Brønsted acid (e.g., a Brønsted acid having a pKa of 5±3) may be performed on an intermediate downstream of the compound of formula (IB) (e.g., after the compound of formula (IB) is reacted with an allylic reducing agent).

If the halichondrin macrolide analog contains A that is a group of formula (1), in which L is —CH(OH)—, $R_1$ is H, and $R_2$ is —$(CH_2)_n$NP$_3$P$_4$ (e.g., eribulin or a salt thereof), and, in a compound of formula (IB), A is a group of formula (1), in which L is —CH(OH)—, $R_1$ is H, and $R_2$ is —$(CH_2)_n$ $OP_5$, where $P_5$ is H, synthesis of the halichondrin macrolide analog may involve amination, as described herein. In some embodiments the halichondrin macrolide analog is eribulin or a salt thereof (e.g., eribulin mesylate).

If the halichondrin macrolide analog is eribulin mesylate, synthesis may further involve salification of eribulin, as described herein.

Additional protecting group manipulations will be readily recognizable in view of the invention disclosed herein and the knowledge in the art. In particular, one of skill in the art will recognize that a transformation, whereby an alcohol is oxidized into a carbonyl, may require deprotecting the alcohol, if the alcohol is protected with a hydroxyl protecting group (e.g., by treating with a hydroxyl protecting group removing agent), unless such deprotection occurs in situ under the oxidation reaction conditions. Likewise, one of skill in the art will recognize that an oxidative transformation performed on a compound including a primary or secondary alcohol may require protecting the primary or secondary alcohol, if such alcohol is to be preserved and if the primary or secondary alcohol is susceptible to oxidation under the conditions present for the oxidative transformation.

Synthesis of Intermediates

The compound of formula (IA) can be prepared using methods and intermediates disclosed, e.g., in U.S. Pat. Nos. 5,338,865; 5,436,238; and 6,214,865; in International Patent application publication Nos. WO 2015/066729 and WO 2016/179607; and in Towle et al., *Annual Meeting of the American Association for Cancer Research*, Apr. 6-10, 2002, 5721; Wang et al., *Bioorg. Med. Chem. Lett.*, 10:1029-1032, 2000; Aicher et al., *J. Am. Chem. Soc.*, 114:3162-3164, 1992; Ueda et al., *J. Am. Chem. Soc.*, 136:5171-5176; and Yamamoto et al., *J. Am. Chem. Soc.*, 134:893-896, 2012; each of which is incorporated herein by reference in its entirety.

Synthesis Via Compound of Formula (IC)

A compound of formula (IA), in which $X_1$ is —CH(Y)— or —$CH_2$—, may be prepared by reacting a compound of formula (IC), in which $R_{13}$ is H, with a compound of formula (ID), which was treated with a strong base (e.g., alkali amide or alkyl lithium).

The compound of formula (IC) has the following structure:

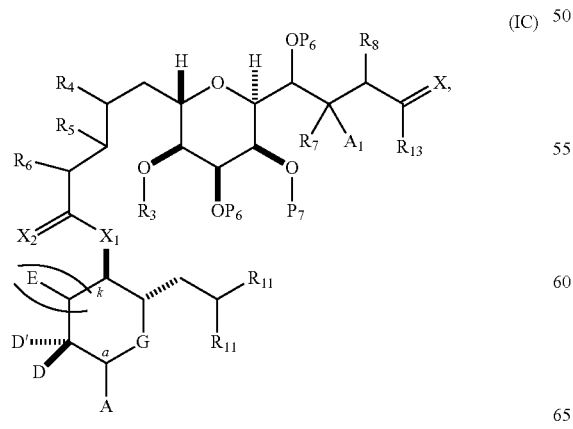

(IC)

where
each of D and D' is independently H, optionally substituted alkyl, or $OP_1$, provided that only one of D and D' is $OP_1$, where $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, and $Q_1$, the group of formula (1) having the structure:

(1)

where
L is —$(CH(OP_2))$— or —C(O)—;
$R_1$ is H, or $R_1$ and $P_1$ combine to form a bond;
(i) $R_2$ is H, where $P_2$ is absent, H, optionally substituted alkyl, or a hydroxyl protecting group;
(ii) $R_2$ is —$(CH_2)_n NP_3P_4$, where $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;
(iii) $R_2$ is —$(CH_2)_n OP_5$, where $P_2$ is absent, H, optionally substituted alkyl, or a hydroxyl protecting group, and $P_5$ is optionally substituted alkyl or a hydroxyl protecting group; or $P_2$ and $P_5$, together with the atoms to which each is attached, combine to form a ketal, a cyclic carbonate, a dicarbonyl-dioxo, or silylene-dioxo; or
(iv) $R_2$ and $P_2$ combine to form an optionally substituted ethylene or a structure selected from the group consisting of:

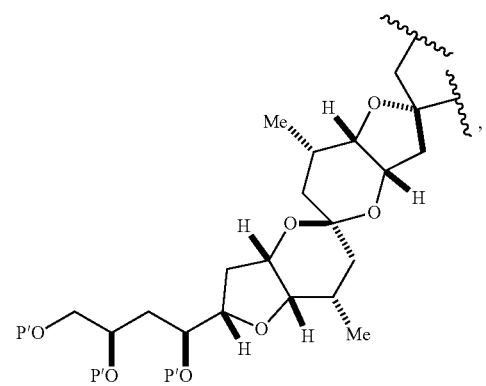

-continued

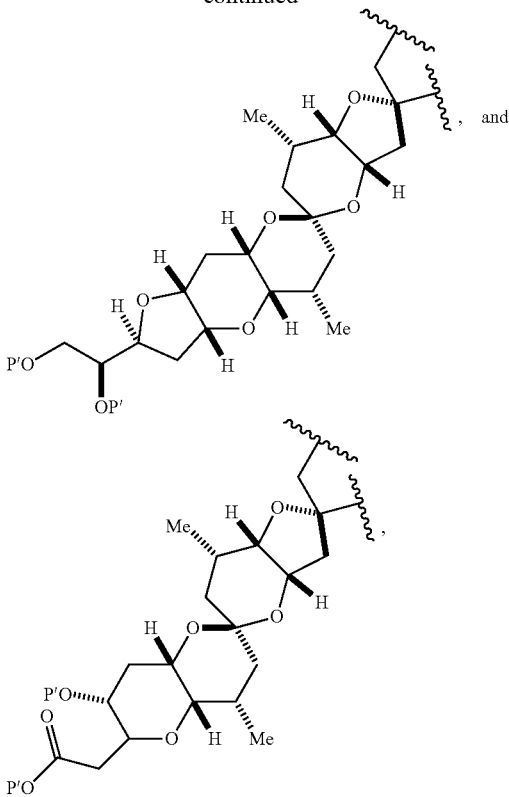

where each P' is independently a hydroxyl protecting group;
E is H, optionally substituted alkyl, or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$X_1$ is —CH(Y)— or —$CH_2$—
$X_2$ is =O or $X_2$, together with the carbon atom to which it is attached, is —$(C(R_X)_2)$—; where each $R_X$ is independently H, —$OR_{X1}$, or —$SR_{X1}$, provided that at least one $R_X$, when present, is —$OR_{X1}$ or —$SR_{X1}$; where each $R_{X1}$ is independently optionally substituted alkyl, or both $R_{X1}$ combine to form optionally substituted alkylene;
Y is $SO_2R_C$ or $COOR_C$, where, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;
$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;

$R_{13}$ is H or —$CH_2P(O)(OR_E)_2$, where each $R_E$, when present, is independently optionally substituted alkyl, optionally substituted aryl, or optionally substituted arylalkyl;
(i) each $P_6$ is independently a hydroxyl protecting group, or both $P_6$, together with the atoms to which each is attached, combine to form a ketal or acetal;
each $R_{11}$ is independently —$OP_{10}$, or
both $R_{11}$ combine to form oxo, where $P_{10}$ is alkyl or a hydroxyl protecting group (e.g., silyl);
or
(ii) both $P_6$ and both $R_{11}$, together with the atoms to which they are attached, combine to form an acetal;
X is =O or X combines with the carbon atom, to which it is attached, to form —$(CH(OP_9))$—, wherein $P_9$ is H or a hydroxyl protecting group;
$A_1$ and $R_7$ combine to form oxo, $P_7$ is H or a hydroxyl protecting group, and $R_8$ is H;
or
$A_1$ is H or OP''', and:
(i) $P_7$ is H or a hydroxyl protecting group, and $R_7$ and $R_8$, together with the atoms to which each is attached, combine to form a double bond;
or
(ii) $P_7$ and $R_7$ combine to form a bond, and $R_8$ is H or OP''';
and
each P''', when present, is H or a hydroxyl protecting group.
In formula (IC), the stereogenic center designated by a may be (R), and A may be of the following structure:

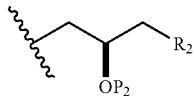

In certain embodiments of formula (IC), k is 0 and $X_1$ is —$CH_2$—. In particular embodiments of formula (IC), $R_2$ is —$(CH_2)_nNP_3P_4$ or —$(CH_2)_nOP_5$, where n is 0.
Alternatively, in formula (IC), A and D may combine to form the following structure:

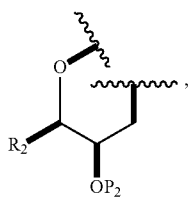

where the bond to the oxygen atom originates at the carbon atom to which D is attached in the formula (IC). In some embodiments of formula (IC) $R_2$ is —$(CH_2)_nNP_3P_4$ or —$(CH_2)_nOP_5$, and n is 2.
In other embodiments of formula (IC), k is 1, and E is optionally substituted alkyl. In still other embodiments of formula (IC), $X_1$ is —O—.

The compound of formula (ID) is of the following structure:

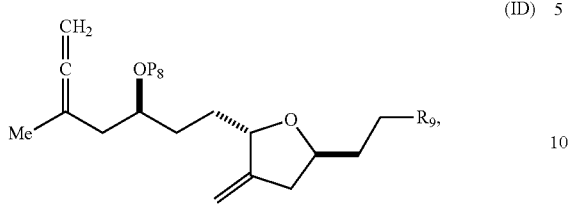

where
P$_8$ is H or a hydroxyl protecting group; and
R$_9$ is SO$_2$R$_C$ or COOR$_C$, when R$_9$ is SO$_2$R$_C$, R$_C$ is optionally substituted aryl or optionally substituted non-enolizable alkyl, and when R$_9$ is COOR$_C$, R$_C$ is optionally substituted alkyl, optionally substituted aryl, or optionally substituted arylalkyl.

Alternatively, a compound of formula (IA), in which X$_1$ is —CH(Y)— or —CH$_2$—, may be prepared by reacting a compound of formula (IC), in which X is =O and R$_{13}$ is —CH$_2$P(O)(OR$_E$)$_2$, with a compound of formula (ID') under Horner-Wadsworth-Emmons reaction conditions.

The compound of formula (ID') is of the following structure:

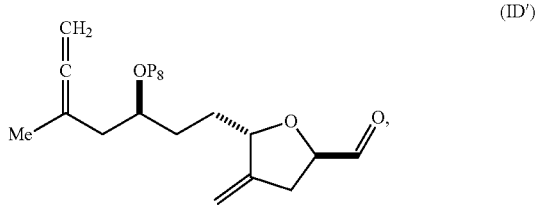

where P$_8$ is H or a hydroxyl protecting group.

The compound of formula (IC), in which X is =O and R$_{13}$ is H, may be reacted with (R$_E$O)$_2$P(O)—CH=N$^+$=N$^-$ (e.g., Seyferth-Gilbert reagent) to produce the compound of formula (IC), in which X is =O and R$_{13}$ is —CH$_2$P(O)(OR$_E$)$_2$.

The compound of formula (IC) may be prepared from the compound of formula (IE)

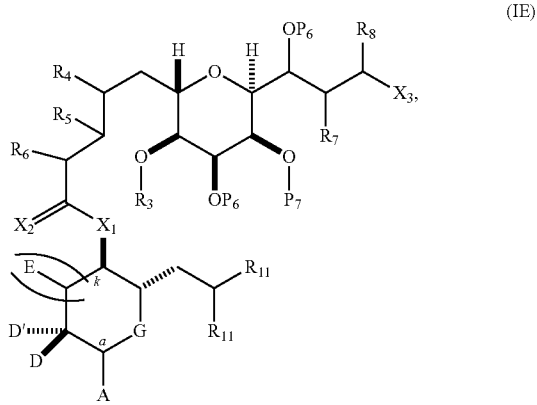

where
X$_3$ is —CH$_2$OP$_A$, —CH=CH$_2$, or —CH(OP$_A$)CH$_2$OP$_A$, where each P$_A$ is independently H or a hydroxyl protecting group, or both P$_A$ combine to form a cyclic protected diol; R$_7$ and P$_7$ combine to form a bond, and R$_8$ is H; or P$_7$ is a hydroxyl protecting group, and R$_7$ and R$_8$, together with the atoms to which each is attached, combine to form a double bond; and all other variables are as defined for the compound of formula (IC).

Preparation of the compound of formula (IC) from the compound of formula (IE) may be performed by reacting the compound of formula (IE), in which X$_3$ is —CH(OP$_A$)CH$_2$OP$_A$, and both P$_A$ are H, with a glycol cleaving agent (e.g., periodic acid or a salt thereof, e.g., NaIO$_4$) to produce the compound of formula (IC), in which X is =O, and R$_{13}$ is H.

Preparation of certain compounds of formula (IC) may further involve conversion of a compound of formula (IC), in which A$_1$ is H, R$_7$ and R$_8$ combine to form a double bond, and X is =O, into a compound of formula (IC) in which R$_7$ and A$_1$ combine to form O. In a non-limiting example, the enal in the compound of formula (IC), in which R$_7$ and R$_8$ combine to form a double bond can be converted into a C.12-C.13 epoxide using a nucleophilic peroxide agent, e.g., t-butyl hydroperoxide, which can then be converted into the compound of formula (IC), in which A$_1$ and R$_7$ combine to form oxo, using methods known in the art, e.g., by reacting with a bidentate phosphine ligand and a source of Pd(0) (see, e.g., Muzart, J., Eur. J. Org. Chem., 4717-4741, 2011). Thus, the compound of formula (IC), in which A$_1$ is OP'', can be prepared. Other transformations may involve α-oxygenation to produce the compound of formula (IC), in which R$_8$ is OP''.

If, in the compound of formula (IE), at least one of P$_A$ is a hydroxyl protecting group, or both P$_A$ combine to form a cyclic protected diol, the compound of formula (IE) may be treated with a hydroxyl protecting group removing agent (e.g., a Brønsted acid (e.g., p-TsOH), if both P$_A$ combine to form a diol protected as a ketal) to prepare the compound of formula (IE), in which both P$_A$ are H.

The compound of formula (IE) may be prepared by reacting a compound of formula (IF) with a compound of formula (IG), which was treated with a strong base (e.g., alkali amide or alkyl lithium). Prior to this reaction, the compound of formula (IF), in which X$_3$ is —CH(OP$_A$)CH$_2$OP$_A$, and both P$_A$ are H, may be converted into the compound of formula (IF), in which X$_3$ is —CH$_2$OP$_A$, where P$_A$ is a hydroxyl protecting group, according to the following procedure. The compound of formula (IF), in which X$_3$ is —CH(OP$_A$)CH$_2$OP$_A$, and both P$_A$ are H, may be reacted with a glycol cleaving agent (e.g., periodic acid or a salt thereof, e.g., NaIO$_4$) to produce the compound of formula (IF), in which X$_3$ is —CHO, which upon reduction with a 1,2-reducing agent and protection with a hydroxyl protecting group, can provide the compound of formula (IF), in which X$_3$ is —CH$_2$OP$_A$, where P$_A$ is a hydroxyl protecting group. For the reduction step, the aldehyde proximal to R$_6$ in formula (IF) may be protected using protecting groups known in the art as suitable for protecting carbonyls.

The compound of formula (IF) is of the following structure:

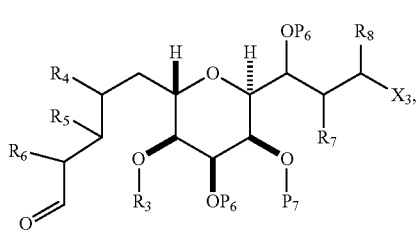

where X₃ is —CHO, —CH₂OP_A, —CH=CH₂, or —CH(OP_A)CH₂OP_A, and all other variables are as defined for the compound of formula (IE).

The compound of formula (IG) is of the following structure:

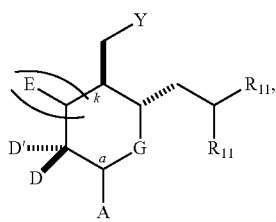

where all variables are as defined for formula (IE).

In formula (IG), the stereogenic center designated by a may be (R), and A may be of the following structure:

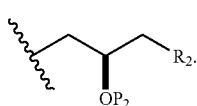

In certain embodiments of formula (IG), k is 0 and X₁ is —CH₂—. In particular embodiments of formula (IG), R₂ is —(CH₂)ₙNP₃P₄ or —(CH₂)ₙOP₅, where n is 0.

The compound of formula (IG) can be prepared using methods known in the art, e.g., those described in WO 2015/066729.

The compound of formula (IF) may be prepared by reacting the compound of formula (IH), in which X₄, together with the carbon atom to which it is attached, combine to form —CH₂—, with an oxidizing agent capable of oxidizing an alcohol to a carbonyl. Alternatively, the compound of formula (IF) may be prepared by reacting the compound of formula (IH), in which X₄ is =O, and P_B is a hydroxyl protecting group or optionally substituted alkyl, with a 1,2-reducing agent (e.g., DIBAL).

The compound of formula (IH) is of the following structure:

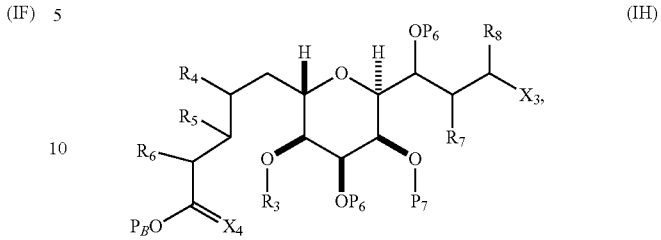

where P_B is H, a hydroxyl protecting group, or optionally substituted alkyl, X₄ is =O or X₄, together with the carbon atom to which it is attached, combine to form —CH₂—, and all of the remaining variables are as defined for the compound of formula (IF).

In some embodiments of formula (IH), R₃ and R₅ combine to form a bond. In particular embodiments, P₇ and R₇ combine to form a bond.

The compound of formula (IH), in which R₇ and P₇ combine to form a bond, can be prepared from the compound of formula (IHa)

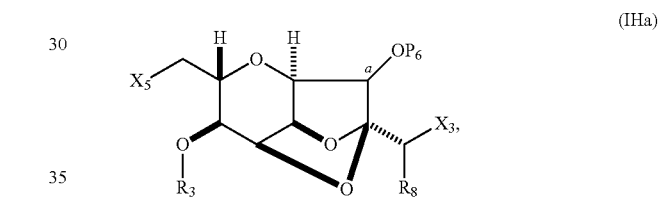

where X₅ is —CH=CH₂ or —CH(R₄)—CH(R₅)—CH(R₆)—C(X₄)OP_B, a identifies the carbon-oxygen bond as ⌐ or ⌐, and the remaining variables are as defined for the compound of formula (IH).

In some embodiments of formula (IHa), X₃ is —CH₂OP_A. In particular embodiments, R₈ is H.

The compound of formula (IHa) can be reacted with a hydrosilane (e.g., Et₃SiH, Ph₂SiH₂, Ph₂MeSiH, or PMHS) and an acid (e.g., a Brønsted acid (e.g., trifluoroacetic acid) or a Lewis acid (e.g., boron trifluoride etherate)) to reduce the ketal thereby producing the compound of formula (IH), if X₅ is —CH(R₄)—CH(R₅)—CH(R₆)—C(X₄)OP_B. If X₅ in the compound of formula (IHa) is —CH=CH₂, the preparation of the compound of formula (IH) may further involve manipulation of X₅, whereby-CH=CH₂ is converted into —CH(R₄)—CH(R₅)—CH(R₆)—C(X₄)OP_B. For example, this conversion can involve hydroboration/oxidation, followed by an olefination reaction (e.g., Horner-Wadsworth-Emmons reaction with P_BO—C(O)—CH₂—P(O)(OR_P)₂, where R_P is optionally substituted alkyl).

If a in formula (IHa) identifies the bond as ⌐, the compound of formula (IHa) may be subjected to an epimerization reaction (e.g., using a reaction sequence involving oxidation of the group —CH(OP₆)— into a carbonyl with subsequent reduction and protection with a hydroxyl protecting group) to provide the compound of formula (IHa), in which a is ⌐.

The compound of formula (IHa), in which X₃ is —CH₂OP_A, can be prepared from the compound of formula (IHb):

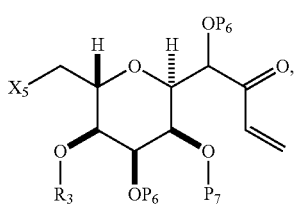

(IHb)

where each of $P_6$ and $P_7$ is independently a hydroxyl protecting group, or one $P_6$ and $P_7$, together with the atoms to which each is attached, combine to form a ketal (e.g., one $P_6$ and $P_7$ combine to form cyclohexylidene), and the remaining $P_6$ is a hydroxyl protecting group; or both $P_6$, together with the atoms to which each is attached, combine to form a ketal, and $P_7$ is a hydroxyl protecting group.

The compound of formula (IHb) can be subjected to oxa-Michael addition, followed by the removal of hydroxyl protecting groups from $OP_6$ and $OP_7$ with concomitant ketalization (e.g., using a hydroxyl protecting group removing agent (e.g., a Brønsted acid (e.g., p-toluenesulfonic acid)) to provide the compound of formula (IHa).

The compound of formula (IH) can also be prepared using methods known in the art, e.g., those described in WO 2015/066729 and WO 2005/118565.

The compound of formula (ID) may be prepared from a compound of formula (Ii):

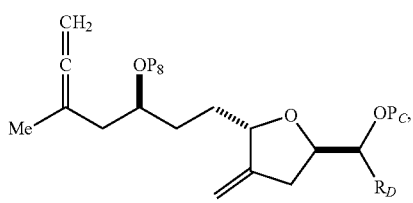

(Ii)

where $P_8$ is H or a hydroxyl protecting group;

(i) $P_C$ is H or a hydroxyl protecting group, and $R^D$ is —$CH_2OP_D$, where $P_D$ is H or a hydroxyl protecting group; or $P_C$ and $P_D$ combine to form a cyclic protected diol; or (ii) $P_C$ and $R_D$, together with the atoms to which each is attached combine to form carbonyl.

Synthesis of the compound of formula (ID) from the compound of formula (Ii), in which $P_8$ is a hydroxyl protecting group, and $P_C$ and $R_D$, together with the atoms to which each is attached combine to form carbonyl, may involve reacting the compound of formula (Ii) with deprotonated $R_9$—$CH_2$—$P(O)(OR_E)_2$ to produce a product, which, upon treatment with a 1,4-reducing agent (e.g., LiHBEt$_3$), may yield the compound of formula (ID), where $R_E$ is optionally substituted alkyl, optionally substituted aryl, or optionally substituted arylalkyl; and $R_9$ is $SO_2R_C$ or $COOR_C$, where, when $R_9$ is $SO_2R_C$, $R_C$ is optionally substituted aryl or optionally substituted non-enolizable alkyl, and when $R_9$ is $COOR_C$, $R_C$ is optionally substituted alkyl, optionally substituted aryl, or optionally substituted arylalkyl. The reaction between the compound of formula (Ii) and $R_9$—$CH_2$—$P(O)(OR_E)_2$ may be carried out under the reaction conditions known in the art for Horner-Wadsworth-Emmons reaction. For example, $R_9$—$CH_2$—$P(O)(OR_E)_2$ may be deprotonated in situ using a strong base (e.g., an alkali amide) prior to the addition of the compound of formula (Ii). If, in the compound of formula (Ii), $P_C$ is H, and $R_D$ is —$CH_2OP_D$, where $P_D$ is H, synthesis of the compound of formula (ID) or formula (ID') may involve reacting this compound of formula (Ii) with a glycol cleaving agent (e.g., periodic acid or a salt thereof, e.g., NaIO$_4$) to produce the compound of formula (Ii), in which $P_C$ and $R_D$, together with the atoms to which each is attached combine to form carbonyl.

The compound of formula (ID') corresponds to the compound of formula (Ii), in which $P_C$ and $R_D$, together with the atoms to which each is attached combine to form carbonyl.

The compound of formula (Ii) can be prepared using methods known in the art, e.g., as described in WO 2015/066729 and in WO 2005/118565.

Alternatively, the compound of formula (ID) may be prepared from the compound of formula (IDa):

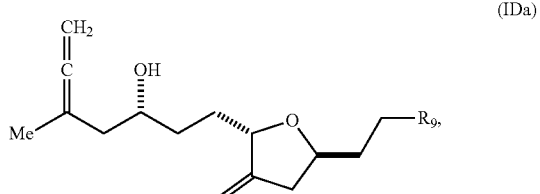

(IDa)

where $R_9$ is as defined for formula (ID).

The compound of formula (IDa) can be converted to the compound of formula (ID), in which $P_8$ is a hydroxyl protecting group, through an epimerization of the secondary carbinol (e.g., through a Mitsunobu reaction with $P_8$—OH, where $P_8$ is a hydroxyl protecting group, such as p-nitrobenzyl)). If the compound of formula (ID), in which $P_8$ is H, is desired, the compounds of formula (ID), in which $P_8$ is a hydroxyl protecting group, may be treated with a hydroxyl protecting group removing agent to produce the compound of formula (ID), in which $P_8$ is H.

The compound of formula (IDa) can be prepared by subjecting the compound of formula (IDb), in which $R_{14}$ is a halogen (e.g., iodide) or a pseudohalogen, and each of $R_9$' and $R_{10}$ is H, to Vasella fragmentation reaction conditions (e.g., Zn and aqueous acetic acid). The compound of formula (IDb) is of the following formula:

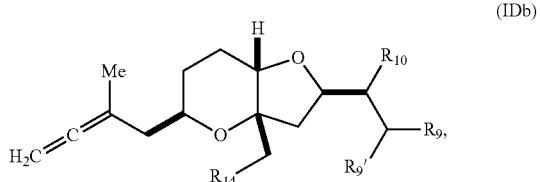

(IDb)

where $R_9$' and $R_{10}$ are both H, or $R_9$' and $R_{10}$ combine to form a double bond; $R_{14}$ is hydroxyl, a halogen (e.g., iodide), or a pseudohalogen (e.g., triflate); and $R_9$ is as defined for formula (ID).

The compound of formula (IDb), in which $R_9$' and $R_{10}$ are both H, can be prepared by treating the compound of formula (IDb), in which $R_9$' and $R_{10}$ combine to form a double bond, with a 1,4-reducing agent (e.g., LiBH$_4$).

The compound of formula (IDb), in which $R_{14}$ is hydroxyl, can be converted into the compound of formula (IDb), in which $R_{14}$ is a pseudohalogen, through a reaction with an appropriate pseudohalogen anhydride (e.g., trifluoromethanesulfonic acid anhydride) under basic conditions (e.g., in the presence of a bulky base, e.g., Hünig's base). The compound of formula (IDb), in which $R_{14}$ is a pseudohalogen, may be treated with a halide salt (e.g., sodium iodide or a tetrabutylammonium iodide) to produce the compound of formula (IDb), in which $R_{14}$ is a halogen (e.g., iodide). The two reactions may be performed as a single pot process.

The compound of formula (IDb), in which $R_{14}$ is hydroxyl, and $R_9'$ and $R_{10}$ combine to form a double bond, can be prepared from the compound of formula (IDc), in which $R_{16}$ is H, through a Horner-Wadsworth-Emmons reaction with $R_9$—$CH_2$—$P(O)(OR_E)_2$, where each $R_E$ is independently optionally substituted alkyl. The compound of formula (IDc) is of the following formula:

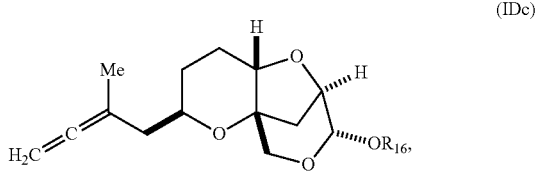

(IDc)

where $R_{16}$ is H, a hydroxyl protecting group, or an optionally substituted alkyl.

The compound of formula (IDc), in which $R_{16}$ is a hydroxyl protecting group or an optionally substituted alkyl, can be converted to the compound of formula (IDc), in which $R_{16}$ is H, through the use of an acid-catalyzed hydrolysis (e.g., using a mixture of an aqueous Brønsted acid and a polar organic solvent, e.g., THF).

The compound of formula (IDc), in which $R_{16}$ is an optionally substituted alkyl or a hydroxyl protecting group, can be prepared from the compound of formula (IDd), in which $X_6$ is —$C(R_{17})$=$CH_2$, through the metal-catalyzed net elimination of H—$R_{17}$ (e.g., using Pd(0), MOP ligand, and Hünig's base). The compound of formula (IDd) is of the following formula:

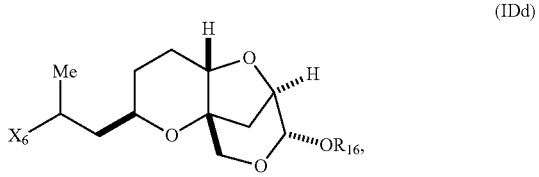

(IDd)

where $X_6$ is —$C(R_{17})$=$CH_2$, —$C(O)$-Me, or cyano, where $R_{17}$ is a pseudohalogen (e.g., triflate) or halogen; and $R_{16}$ is as defined for formula (IDc).

The compound of formula (IDd), in which $R_{16}$ is H and $X_6$ is cyano, is known in the art (e.g., in WO 2009/046308). The compound of formula (IDd), in which $R_{16}$ is H, can be subjected to an acid-catalyzed reaction with an excess of $R_{16}$—OH to give the compound of formula (IDd), in which $R_{16}$ is a hydroxyl protecting group or optionally substituted alkyl. The compound of formula (IDd), in which $X_6$ is cyano, and $R_{16}$ is a hydroxyl protecting group or optionally substituted alkyl, can be reacted with a nucleophilic source of methyl (e.g., MeLi.LiBr) to give the compound of formula (IDd), in which $X_6$ is —$C(O)$-Me. The compound of formula (IDd), in which $X_6$ is —$C(O)$-Me, can be reacted with an electrophilic source of pseudohalogen (e.g., PhNTf$_2$ and a bulky base, e.g., NaHMDS) or an electrophilic source of halogen (e.g., triphenyl phosphite, elemental halogen, and a base, e.g., triethylamine) to give the compound of formula (IDd), in which $X_6$ is —$C(R_{17})$=$CH_2$.

Synthesis Via Compound of Formula (IJ)

The compound of formula (IA) may be prepared by reacting a compound of formula (IJ) with a compound of formula (IK) under Nozaki-Hiyama-Kishi reaction conditions, as described herein. The compound of formula (IJ) is of the following formula:

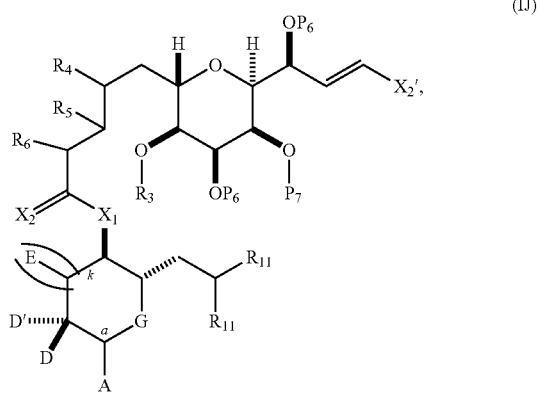

(IJ)

where
each of D and D' is independently H, optionally substituted alkyl, or $OP_1$, provided that only one of D and D' is $OP_1$, where $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, and $Q_1$, the group of formula (1) having the structure:

(1)

where
L is —(CH(OP$_2$))— or —C(O)—;
$R_1$ is H, or $R_1$ and $P_1$ combine to form a bond;
(i) $R_2$ is H, where $P_2$ is absent, optionally substituted alkyl, or a hydroxyl protecting group;
(ii) $R_2$ is —(CH$_2$)$_n$NP$_3$P$_4$, where $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;
(iii) $R_2$ is —(CH$_2$)$_n$OP$_5$, where $P_2$ is absent, optionally substituted alkyl, or a hydroxyl protecting group, and $P_5$ is optionally substituted alkyl or a hydroxyl protecting group; or $P_2$ and $P_5$, together with the atoms to which each is attached, combine to form a ketal, a cyclic carbonate, a dicarbonyl-dioxo, or silylene-dioxo; or (iv) R$_2$ and P$_2$ combine to form an optionally substituted ethylene or a structure selected from the group consisting of:

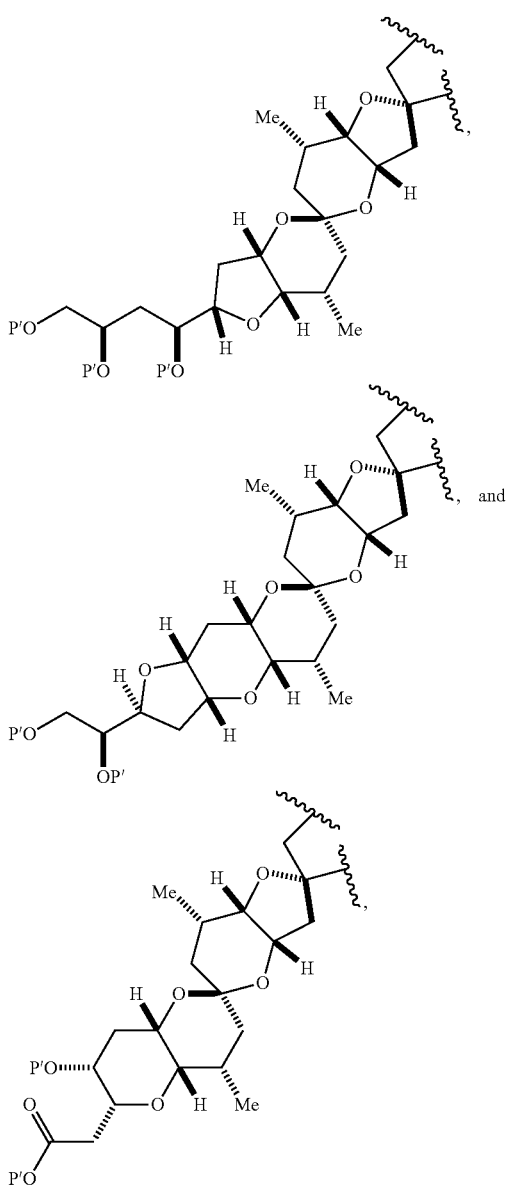

where each P' is independently a hydroxyl protecting group;
E is H, optionally substituted alkyl, or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
X$_1$ is —CH(Y)—, —CH$_2$—, or —O—, and X$_2$ is =O or X$_2$, together with the carbon atom to which it is attached, is —(C(R$_X$)$_2$)—; wherein each R$_X$ is independently H, —OR$_{X1}$, or —SR$_{X1}$, provided that at least one R$_X$, when present, is —OR$_{X1}$ or —SR$_{X1}$; wherein each R$_{X1}$ is independently optionally substituted alkyl, or both R$_{X1}$ combine to form optionally substituted alkylene, provided that, when X$_1$ is —O—, X$_2$ is =O; and where Y is SO$_2$R$_C$ or COOR$_C$, where, when Y is SO$_2$R$_C$, R$_C$ is optionally substituted aryl or optionally substituted non-enolizable alkyl, and when Y is COOR$_C$, R$_C$ is optionally substituted alkyl, optionally substituted aryl, or optionally substituted arylalkyl;

R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;

(i) each P$_6$ is independently a hydroxyl protecting group, or both P$_6$, together with the atoms to which each is attached, combine to form a ketal or acetal;

each R$_{11}$ is independently —OP$_{10}$, or both R$_{11}$ combine to form oxo, where P$_{10}$ is alkyl or a hydroxyl protecting group (e.g., silyl);

or (ii) both P$_6$ and R$_{11}$ both together with the atoms to which they are attached, combine to form an acetal;

each P$_7$ is independently a hydroxyl protecting group; and

X$_2$' is a halogen or pseudohalogen.

In formula (IJ), the stereogenic center designated by a may be (R), and A may be of the following structure:

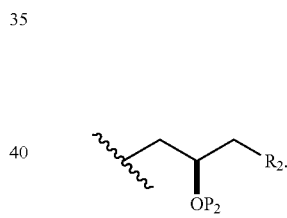

In certain embodiments of formula (IJ), k is 0 and X$_1$ is —CH$_2$—. In particular embodiments of formula (IJ), R$_2$ is —(CH$_2$)$_n$NP$_3$P$_4$ or —(CH$_2$)$_n$OP$_5$, where n is 0.

Alternatively, in formula (IJ), A and D may combine to form the following structure:

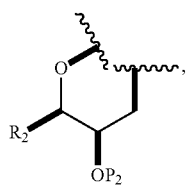

where the bond to the oxygen atom originates at the carbon atom to which D is attached in the formula (IJ). In some embodiments of formula (IJ) R$_2$ is —(CH$_2$)$_n$NP$_3$P$_4$ or —(CH$_2$)$_n$OP$_5$, and n is 2.

In other embodiments of formula (IJ), k is 1, and E is optionally substituted alkyl. In still other embodiments of formula (IJ), X$_1$ is —O—.

The compound of formula (IK) is of the following structure:

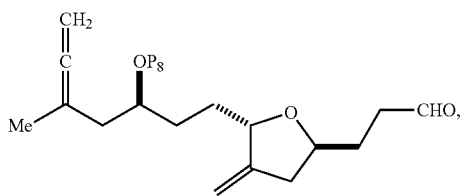

where $P_8$ is a hydroxyl protecting group.

The compound of formula (IK) may be prepared using methods known in the art, e.g., those described in WO 2015/066729 and WO 2005/118565.

The compound of formula (IJ), in which $X_1$ is —CH(Y)— or —CH$_2$—, may be prepared from a compound of formula (IG) and a compound of formula (IL), in which $R_{15}$ is H, and $X_4$ is =O. The compound of formula (IL) is of the following structure:

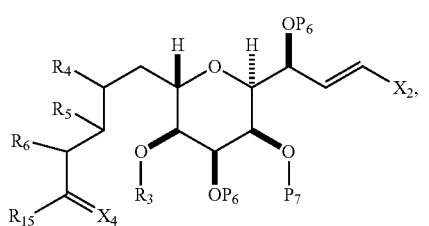

or a salt thereof,
where $R_{15}$ is H or —OP$_{11}$, and $P_{11}$ is H, a hydroxyl protecting group, or optionally substituted alkyl; $X_4$ is =O or, together with the carbon atom to which it is attached, is —CH$_2$—; and all remaining variables are as defined for the compound of formula (IJ); provided that when $R_{15}$ is H, $X_4$ is =O.

The compound of formula (IL) can be prepared using methods known in the art, e.g., those described in International Patent application Nos. WO 2005/118565 and WO 2015/066729, and in U.S. Pat. Nos. 5,338,865; 5,436,238; and 6,214,865.

Synthesis of the compound of formula (IJ), in which $X_1$ is —CH(Y)— or —CH$_2$—, involves reacting the compound of formula (IL), in which $R_{15}$ is H, and $X_4$ is =O, with the compound of formula (IG), which was treated with a strong base (e.g., alkali amide or alkyl lithium) and subsequently oxidizing the alcohol formed from the aldehyde group through the use of an oxidizing agent capable of converting an alcohol to a carbonyl group (e.g., Dess-Martin periodinane).

If a compound of formula (IJ), in which $X_1$ is —CH$_2$—, is to be prepared, synthesis of this compound of formula (IJ) may further involve subjecting the compound of formula (IJ), in which $X_1$ is —CH(Y)—, to decarboxylation (if Y is COOR$_C$) or desulfonylation (if Y is SO$_2$R$_C$) reaction conditions, as described herein.

The compound of formula (IJ), in which $X_1$ is —O—, may be prepared by reacting a compound of formula (IL), in which $R_{15}$ is —OP$_1$, $P_{11}$ is H, and $X_4$, together with the carbon atom to which it is attached, is —CH$_2$—, with a compound of formula (IM) under esterification reaction conditions (e.g., Yamaguchi esterification, as described herein, or using EDCI/DMAP, e.g., as described in Namba and Kishi, *J. Am. Chem. Soc.*, 127:15382-15383, 2005).

The compound of formula (IL), in which $R_{15}$ is —OP$_{11}$, $P_{11}$ is H, and $X_4$, together with the carbon atom to which it is attached, is —CH$_2$—, can be reacted with an oxidizing agent capable of oxidizing hydroxyl to a carbonyl group to give the compound of formula (IL), in which $R_{15}$ is H, and $X_4$ is =O. The compound of formula (IL), in which $R_{15}$ is H, and $X_4$ is =O, can be oxidized using Pinnick oxidation to give the compound of formula (IL), in which $R_{15}$ is —OP$_{11}$, $P_{11}$ is H, and $X_4$ is =O. The compound of formula (IL), in which $X_4$ is =O, $R_{15}$ is —OP$_{11}$, and $P_{11}$ is a hydroxyl protecting group or optionally substituted alkyl, can be treated with a 1,2-reducing agent (e.g., DIBAL) to give the compound of formula (IL), in which $R_{15}$ is —OP$_{11}$, $P_{11}$ is H, and $X_4$, together with the carbon atom to which it is attached, is —CH$_2$—. The compound of formula (IL), in which $X_4$ is =O, and $R_{15}$ is H, can be prepared by reacting the compound of formula (IL), in which $X_4$ is =O, $R_{15}$ is —OP$_{11}$, and $P_{11}$ is a hydroxyl protecting group or optionally substituted alkyl, with a 1,2-reducing agent under the conditions known in the art for conversion of esters to aldehydes (e.g., with DIBAL at low (e.g., from about −80° C. to about −50° C.) temperature).

The compound of formula (IM) is of the following structure:

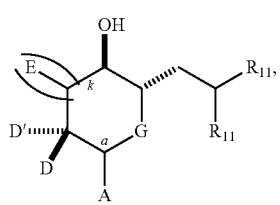

where each $R_{11}$ is independently —OP$_{10}$, or both $R_{11}$ combine to form oxo, where $P_{10}$ is alkyl or a hydroxyl protecting group (e.g., silyl); and all of the remaining variable are as defined for formula (IM).

In formula (IM), A and D may combine to form the following structure:

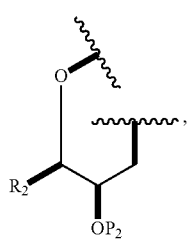

where the bond to the oxygen atom originates at the carbon atom to which D is attached in the formula (IM). In some embodiments of formula (IM) $R_2$ is —(CH$_2$)$_n$NP$_3$P$_4$ or —(CH$_2$)$_n$OP$_5$, and n is 2.

In other embodiments of formula (IM), k is 1, and E is optionally substituted alkyl. In still other embodiments of formula (IM), $X_1$ is —O—.

The compounds of formula (IL) and (IM) may be prepared using methods known in the art, e.g., those described in International Patent application Nos. WO 2005/118565 and WO 2015/066729, and in U.S. Pat. Nos. 5,338,865 and 5,436,238.

Synthesis Via Compound of Formula (IN)

The compound of formula (IA), in which $X_1$ is —O—, may be prepared by reacting the compound of formula (IN), in which $R_{15}$ is —$OP_{11}$, and $P_{11}$ is H, with a compound of formula (IM). This reaction may be performed using esterification reaction conditions known in the art (e.g., Yamaguchi esterification, which may involve the use of 2,4,6-trichlorobenzoyl chloride, an amine base (e.g., Hünig's base), and catalytic quantities of 4-dimethylaminopyridine). Yamaguchi esterification reaction conditions have been described, e.g., in Aicher et al., *J. Am. Chem. Soc.*, 114: 3162-3164, 1992). Alternatively, the esterification conditions may involve the use of a carbodiimide reagent (e.g., EDCI) and a Lewis base catalyst (e.g., DMAP); a non-limiting example of this transformation is described in Namba and Kishi, *J. Am. Chem. Soc.*, 127:15382-15383, 2005.

The compound of formula (IA), in which $X_1$ is —CH(Y)—, may be prepared by reacting the compound of formula (IN), in which $R_{15}$ is H, with a compound of formula (IG), which was treated with a strong base (e.g., alkali amide or alkyl lithium).

The compound of formula (IN) is of the following structure:

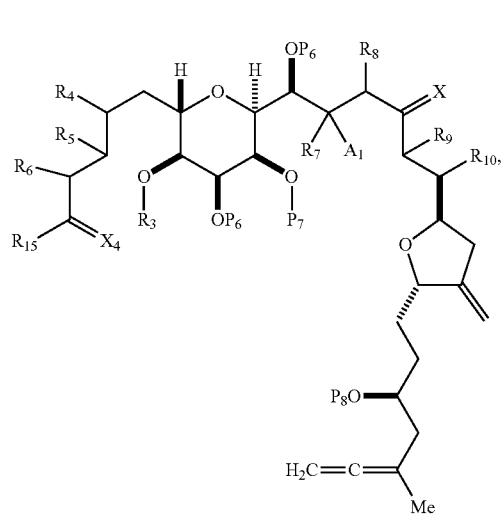

(IN)

or a salt thereof,
where $R_{15}$ is H or —$OP_{11}$, where $P_{11}$ is H, a hydroxyl protecting group, or optionally substituted alkyl; $X_4$ is =O or, together with the carbon atom to which it is attached, is —$CH_2$—; and all remaining variables are as defined for formula (IA); provided that when $R_{15}$ is H, $X_4$ is =O.

The compound of formula (IN), in which $R_{15}$ is —$OP_{11}$, $P_{11}$ is H, and $X_4$, together with the carbon atom to which it is attached, is —$CH_2$—, can be reacted with an oxidizing agent capable of oxidizing hydroxyl to a carbonyl group to give the compound of formula (IN), in which $R_{15}$ is H, and $X_4$ is =O. The compound of formula (IN), in which $R_{15}$ is H, and $X_4$ is =O, can be oxidized using Pinnick oxidation to give the compound of formula (IN), in which $R_{15}$ is —$OP_{11}$, $P_{11}$ is H, and $X_4$ is =O. The compound of formula (IN), in which $X_4$ is =O, $R_{15}$ is —$OP_{11}$, and $P_{11}$ is a hydroxyl protecting group or optionally substituted alkyl, can be treated with a 1,2-reducing agent (e.g., DIBAL) to give the compound of formula (IN), in which $R_{15}$ is —$OP_{11}$, $P_{11}$ is H, and $X_4$, together with the carbon atom to which it is attached, is —$CH_2$—. The compound of formula (IN), in which $X_4$ is =O, and $R_{15}$ is H, can be prepared by reacting the compound of formula (IN), in which $X_4$ is =O, $R_{15}$ is —$OP_{11}$, and $P_{11}$ is a hydroxyl protecting group or optionally substituted alkyl, with a 1,2-reducing agent under the conditions known in the art for conversion of esters to aldehydes (e.g., with DIBAL at low (e.g., from about −80° C. to about −50° C.) temperature).

The compound of formula (IN) in which $R_{15}$ is —$OP_{11}$, and $P_{11}$ is a hydroxyl protecting group or optionally substituted alkyl, may be prepared from the compound of formula (ID) and the compound of formula (IH), in which $P_B$ is a hydroxyl protecting group or optionally substituted alkyl, $X_3$ is —CHO, and $X_4$ is =O.

Synthesis of the compound of formula (IN), in which $R_{15}$ is —$OP_{11}$, from the compound of formula (IH) and the compound of formula (ID) may involve reacting the compound of formula (IH) with the compound of formula (ID), which was treated with a strong base (e.g., alkali amide or alkyl lithium) to produce a product containing an alcohol, which, upon removal of $P_B$ (e.g., using a 1,2-reducing agent, if $P_B$ is an acyl group, such as pivaloyl) and subsequent oxidation (e.g., sequential oxidation using an oxidizing agent capable of converting an alcohol to a carbonyl group, followed by Pinnick oxidation), can provide the compound of formula (IN).

Alternatively, the compound of formula (IN) may be prepared from the compound of formula (IL) and the compound of formula (IK). For example, the compound of formula (IL), in which $X_4$ is =O, $R_{15}$ is —$OP_{11}$, and $P_{11}$ is a hydroxyl protecting group, may be reacted with the compound of formula (IK) under the Nozaki-Hiyama-Kishi reaction conditions to produce the compound of formula (IN), in which $R_{15}$ is —$OP_{11}$, and $P_{11}$ is a hydroxyl protecting group; $R_7$ and $R_8$, together with the atoms to which each is attached, combine to form a double bond; and X combines with the carbon atom, to which it is attached, to form —(CH($OP_9$))—, where $P_9$ is H. Subsequent, deprotection and a reaction with an oxidizing agent capable of converting an alcohol to a carbonyl group can provide the compound of formula (IN), in which X is =O and $R_{15}$ is —$OP_{11}$, and $P_{11}$ is H.

Preparation of certain compounds of formula (IN) may further involve conversion of a compound of formula (IN), in which $A_1$ is H, $R_7$ and $R_8$ combine to form a double bond, and X is =O, into a compound of formula (IN) in which $R_7$ and $A_1$ combine to form O. In a non-limiting example, the enal in the compound of formula (IN), in which $R_7$ and $R_8$ combine to form a double bond can be converted into a C.12-C.13 epoxide using a nucleophilic peroxide agent, e.g., t-butyl hydroperoxide, which can then be converted into the compound of formula (IN), in which $A_1$ and $R_7$ combine to form oxo, using methods known in the art, e.g., by reacting with a bidentate phosphine ligand and a source of Pd(0) (see, e.g., Muzart, J., *Eur. J. Org. Chem.*, 4717-4741, 2011). Thus, the compound of formula (IN), in which $A_1$ is OP''', can be prepared. Other transformations may involve α-oxygenation to produce the compound of formula (IN), in which $R_8$ and/or $R_9$ is OP'''.

In certain embodiments of formula (IA), (IB), (IC), (IE), (IJ), or (IN), k is 0, $X_1$ is —CH(Y)— or —$CH_2$—, D is H, D' is $OP_1$, G is O, and A is of the following structure:

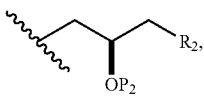

where
(i) $R_2$ is —$(CH_2)_nNP_3P_4$, where n is 0, $P_3$ is H or an N-protecting group, and $P_2$ and $P_4$ combine to form an alkylidene or $P_2$ is H, an optionally substituted alkyl or a hydroxyl protecting group and $P_4$ is an N-protecting group; or
(ii) $R_2$ is —$(CH_2)_nOP_5$, where n is 0, $P_2$ is H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo;

can be used for the synthesis of eribulin or its salt (e.g., eribulin mesylate).

In particular embodiments of formula (IA), (IB), (IC), (IE), (IJ), or (IN), k is 0, $X_1$ is —CH(Y)— or —$CH_2$—, D is H, D' is $OP_1$, G is O, and A is of the following structure:

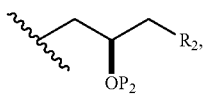

where
(i) $R_2$ is —$(CH_2)_nNP_3P_4$, where n is 0, $P_3$ is an N-protecting group, and $P_2$ and $P_4$ combine to form an alkylidene or $P_2$ is H, an optionally substituted alkyl or a hydroxyl protecting group and $P_4$ is an N-protecting group; or
(ii) $R_2$ is —$(CH_2)_nOP_5$, where n is 0, $P_2$ is H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo;

can be used for the synthesis of eribulin or its salt (e.g., eribulin mesylate).

In further embodiments of the compound of formula (IA), (IB), (IC), (IE), (IJ), or (IN), k is 0, D is H, D' is $OP_1$, and A is of the following structure:

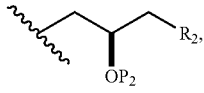

where
(i) $R_2$ is —$(CH_2)_nNP_3P_4$, where n is 0, $P_3$ is an N-protecting group, and $P_2$ and $P_4$ combine to form an alkylidene; or
(ii) $R_2$ is —$(CH_2)_nOP_5$, where n is 0, each of $P_2$ and $P_5$ is independently H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo.

Masked Amines and Amine Unmasking Agents

The compounds used in the methods of the invention can contain a masked or unmasked amine (e.g., at C.35 carbon of the structure of the halichondrin macrolide analog, such as eribulin). An unmasked amine is —$NH_2$. An amine can be masked using methods known in the art, e.g., by protecting the amine with an N-protecting group. Alternatively, an amine can be masked as a nitrogen-containing moiety, which can be reacted with an amine unmasking agent to afford an amine. Non-limiting examples of the nitrogen-containing moieties include azide and an imide (e.g., phthalimide). Amine unmasking agents can be those known in the art for removing N-protecting groups from amines. In a non-limiting example, a Boc group can be removed using amine unmasking agents known in the art, e.g., a Brønsted acid (e.g., HCl in 1,4-dioxane or trifluoroacetic acid). When amine is masked as azide, the amine can be unmasked by subjecting the compound containing the masked amine to Staudinger reaction conditions (e.g., by contacting with a phosphine, such as trialkylphosphine, dialkylarylphosphine, alkyldiarylphosphine, or triarylphosphine) or by reacting the compound containing the masked amine with a reducing agent (e.g., $LiAlH_4$). When amine is masked as an imide (e.g., phthalimide), the amine can be unmasked by reacting with an amine unmasking agent known in the art, e.g., hydrazine.

Oxidizing Agents Capable of Converting an Alcohol to a Carbonyl Group Oxidizing agents capable of converting an alcohol to a carbonyl group are known in the art. Non-limiting examples of these oxidizing agents include Dess-Martin periodinane, TEMPO (in the presence of bleach or BAIB), a dimethylsulfonium compound (e.g., dimethylchlorosulfonium chloride), aluminum trialkoxide with an excess of a ketone (e.g., acetone), and catalytic tetrapropylammonium perruthenate (TPAP) (in the presence of N-methylmorpholine oxide). The dimethylsulfonium compound can be prepared in situ under the conditions known for Parikh-Doering oxidation, Swern oxidation, Corey-Kim oxidation, or Pfitzner-Moffatt oxidation. Alternatively, the dimethylsulfonium compound can be prepared in situ by a reaction between trichloroacetic acid anhydride and dimethyl sulfoxide. An oxidation reaction of an alcohol to a carbonyl group (e.g., a ketone) can be performed using aluminum trialkoxide and an excess of a ketone (e.g., acetone) under the conditions known in the art for Oppenauer oxidation. Allylic and benzylic alcohols can also be oxidized with $MnO_2$.

Reducing Agents

Reducing agents that can be used in the methods of the invention are those known in the art. A reducing agent can be an electron-transfer reducing agent, a metal hydride, or a metalloid hydride. Non-limiting examples of electron-transfer reducing agents include alkali metals in oxidation state (0), alkali earth metals in oxidation state (0), alkali arenides, lanthanide (II) salts (e.g., $SmI_2$), Zn(0), Fe(0), and Mn(0). Non-limiting examples of metal hydrides and metalloid hydrides include boron hydride compounds (e.g., $NaBH_4$, $LiBH_4$, $LiHBEt_3$, selectrides (e.g., L-selectride), and boranes (e.g., 9-BBN and alpine borane)), aluminum hydride compounds (e.g., $LiAlH_4$, Red-Al®, and alanes (e.g., diisobutylaluminum hydride (DIBAL))), hydrosilanes (e.g., PMHS and $Ph_2SiH_2$), hydrostannanes (e.g., $Bu_3SnH$), copper hydride complexes (e.g., Stryker's reagent), palladium hydride complexes, platinum hydride complexes, iridium hydride complexes, rhodium hydride complexes, and ruthenium hydride complexes. Reducing agents can be formed in situ, e.g., a copper hydride complex can be formed by a reaction of a copper salt with, e.g., a boron hydride compound or a hydrosilane. Thus, some reducing reagents (e.g., boron hydride compounds, hydrosilanes, and hydrostannanes) can be used in combination with a catalytic quantity of a metal salt (e.g., Cu, Pd, Pt, Ir, Rh, or Ru salt). Alternatively, catalytic reducing agents can be metal salts (e.g., aluminum isopropoxide or a ruthenium complex) in combination with an alcohol, which undergo transfer hydrogenation of carbonyl-containing compounds without intermediacy of a metal hydride. Non-limiting examples of transfer hydrogenation reactions include Meerwein-Ponndorf-Verley reduction (e.g., using aluminum isopropoxide/isopropanol) and Ru-catalyzed transfer hydrogenation (e.g., Hashiguchi et al., *J. Am. Chem. Soc.*, 117:7562-7563, 1995).

When a substrate is an α,β-unsaturated carbonyl or sulfone compound (e.g., an α,β-enone or a vinyl sulfone), a reducing agent can be a 1,2-reducing agent or a 1,4-reducing agent. For example, a reaction between an α,β-unsaturated carbonyl compound and a 1,2-reducing agent can afford, e.g., an allylic alcohol (or an allylic amine, if the starting compound is an enamide), whereas a reaction between an α,β-unsaturated carbonyl compound and a 1,4-reducing agent can afford an α,β-saturated compound and can leave the carbonyl group intact after work up of the reaction mixture. Non-limiting examples of 1,2-reducing agents include metal hydrides and metalloid hydrides, e.g., aluminum hydride compounds, boron hydride compounds (e.g., $CeCl_3$ with $NaBH_4$), and ruthenium hydride complexes. Non-limiting examples of 1,4-reducing agents include boron hydride compounds (e.g., $LiHBEt_3$ and L-selectride), hydrostannanes, copper hydride complexes (e.g., Stryker's reagent), palladium hydride complexes, platinum hydride complexes, iridium hydride complexes, rhodium hydride complexes, and ruthenium hydride complexes.

A compound having an allylic leaving group (e.g., a carboxylate, a halide, or a sulfonate) can be treated with an allylic reducing agent to replace the leaving group with a hydrogen atom. A non-limiting example of allylic reducing agent is a palladium salt or complex (e.g., $Pd(PPh_3)_4$) in combination with a formic acid salt (e.g., trialkylammonium formate).

Hydroxyl Protecting Groups and Hydroxyl Protecting Group Removing Agents

Hydroxyl protecting groups can be as defined herein. In particular, a hydroxyl protecting group can be an acyl, a sulfonyl, an arylalkyl (e.g., benzyl or p-methoxybenzyl), an aryl (e.g., p-methoxyphenyl), or an optionally substituted silyl (e.g., TMS, TES, TBS, TIPS, TBDPS, or TPS). Hydroxyl protecting groups, hydroxyl protecting agents, and hydroxyl protecting reaction conditions can be selected to protect selectively certain hydroxyl groups in a compound, while leaving other hydroxyl groups unprotected. The choice of hydroxyl protecting groups for a compound can facilitate subsequent deprotection strategies, as some hydroxyl protecting groups can be removed in the presence of others using appropriate hydroxyl protecting group removing agents. Some of these strategies involving the choice of silyl hydroxyl protecting groups are discussed in, e.g., *Silicon-Based Blocking Agents*, Gelest, Inc., 2011.

Hydroxyl protecting group removing agents are those agents that can react with a compound having a protected hydroxyl group to afford the compound with a deprotected hydroxyl group. Hydroxyl protecting group removing agents and deprotection reaction conditions can be those known in the art. In a non-limiting example, hydroxyl masked as silyl ether can be unmasked by a reaction with a fluoride source (e.g., a fluoride salt, such as KF or TBAF). Alternatively, hydroxyl protected as TMS or TES ether can be deprotected by a reaction with a Brønsted acid (e.g., a carboxylic acid).

In another non-limiting example, hydroxyl protected as an ester can be deprotected by a reaction with a base (e.g., alkali hydroxide (e.g., lithium hydroxide, sodium hydroxide, or potassium hydroxide) or $C_{1-6}$ alkoxide (e.g., alkali $C_{1-6}$ alkoxide or alkali earth $C_{1-6}$ alkoxide)). Alternatively, hydroxyl protected as an ester (e.g., pivaloyl ester) can be deprotected by a reaction with a 1,2-reducing agent (e.g., DIBAL-H). In yet another non-limiting example, hydroxyl protected as an arylalkyl ether (e.g., 1-arylalk-1-yl ether) can be deprotected using a reduction reaction, e.g., with Pd/C and $H_2$ or with $Na/NH_3$. Alternatively, hydroxyl protected as an alkoxy-arylalkyl ether (e.g., MPM ether) can be deprotected by a reaction with 2,3-dichloro-5,6-dicyano-1,4-benzoquinone (DDQ). In still another non-limiting example, hydroxyl protected as alkoxyalkyl ether (e.g., 1-alkoxyalk-1-yl) or THP ether can be deprotected by a reaction with a Brønsted acid. Cyclic protected diols, such as acetals or ketals (e.g., as 2-alkyl-1,3-dioxolane, 2,2-dialkyl-1,3-dioxolane, 2-alkyl-1,3-dioxane, or 2,2-dialkyl-1,3-dioxane), can be deprotected by a reaction with a Brønsted acid (e.g., a carboxylic acid).

Decarboxylation and Desulfonylation

The conditions for the decarboxylation reaction can be those known in the art, e.g., Krapcho decarboxylation or a sequence including deprotection, if $R_C$ is not H, by converting $R_C$ to H and subsequent protodecarboxylation. The conditions for the desulfonylation reaction can be those known in the art. For example, the desulfonylation reaction can include contacting the compound of formula (IA) or formula (IB) or an intermediate downstream of the compound of formula (IA) or formula (IB) with an electron-transferring reducing agent (e.g., $SmI_2$; Cr(III) salt and Mn(0); or Mg(0)). For exemplary desulfonylation conditions, see WO 2009/064029.

Nozaki-Hiyama-Kishi Reaction

Nozaki-Hiyama-Kishi reaction conditions that may be used in transformation described herein can be those known in the art. Nozaki-Hiyama-Kishi reaction can include reacting substrates (an aldehyde and a vinyl halide or pseudohalide) with a Cr(II) salt and a Ni(II) salt. Ancillary ligands can be used in combination with the metal salts. In a non-limiting example, a substituted 1,10-phenanthroline can be used in combination with a Ni(II) salt. Chiral ancillary ligands can be used to render the reaction stereoselective. In a non-limiting example, chiral N-(dihydrooxazolyl-phenyl)-sulfonamides can be used with a Cr(II) salt to control the stereochemistry of the carbonyl carbon, to which a vinyl nucleophile is added in the course of Nozaki-Hiyama-Kishi reaction.

Salification

Salification reaction conditions are known in the art. Salification of eribulin can afford a pharmaceutically acceptable salt of eribulin (e.g., eribulin mesylate). In particular, salification reaction can involve contacting eribulin with a Brønsted acid (e.g., a pharmaceutically acceptable Brønsted acid (e.g., methanesulfonic acid)) to afford a pharmaceutically acceptable salt of eribulin (e.g., *Handbook of Pharmaceutical Salts: Properties, Selection and Use*, ed.: Stahl and Wermuth, Wiley-VCH/VHCA, Weinheim/Zurich, 2002). Pharmaceutically acceptable salts of eribulin, e.g., eribulin mesylate, can be formed by methods known in the art, e.g., in situ during the final isolation and purification of the compound or separately by reacting the free base group with a suitable organic acid. In one example, eribulin is treated with a solution of MsOH and $NH_4OH$ in water and acetonitrile. The mixture is concentrated. The residue is dissolved in DCM-pentane, and the solution is added to anhydrous pentane. The resulting precipitate is filtered and dried under high vacuum to provide eribulin mesylate.

Epimerizations

Epimerization reactions can be used to invert a stereogenic center having an undesired stereochemical identity. For example, through epimerization, an R stereogenic center can be converted to an S stereogenic center and vice versa. Epimerization of a stereogenic sp$^3$-carbon bonded to one hydrogen atom and to one hydroxyl group can be achieved through a reaction sequence involving oxidation of the hydroxyl group to a carbonyl group followed by a 1,2-reduction reaction. The 1,2-reduction reaction can provide the desired stereochemical identity diastereoselectively, or the reaction can be carried out using a chiral catalyst, chiral auxiliary, or a chiral reducing agent. Non-limiting examples of chiral reducing agents include alpine borane and prapine borane. Non-limiting examples of 1,2-reduction reactions involving chiral catalysts are Corey-Bakshi-Shibata reduction, Noyori hydrogenation, and Noyori transfer hydrogenation. The oxidation/reduction reaction sequence can be carried out in situ using dynamic kinetic resolution. A dynamic kinetic resolution can further involve a reaction with a hydroxyl protecting agent, which removes the desired stereoisomer from the reduction/oxidation equilibrium. In a non-limiting example, a dynamic kinetic resolution of chiral secondary alcohols can involve reduction/oxidation equilibration using $\eta^5$-Ph$_5$CpRu(CO)$_2$H in combination with enantioselective esterification using isopropenyl acetate catalyzed by a lipase enzyme (e.g., lipase B from *Candida Antarctica*, see, e.g., Martin-Matute et al., *J. Am. Chem. Soc.*, 127:8817-8825, 2005).

Epimerization can also be carried out on a compound containing a tetrahydropyran-2-yl-acetaldehyde moiety, in which carbon 2 of the pyran ring exhibits an undesired stereochemical identity. Contacting this compound with L-proline can provide equilibrium between two stereoisomers. If other, non-equilibrating stereogenic centers are present in the compound, the most stable stereoisomer will be present in a larger quantity relative to other stereoisomer(s) in equilibrium with the most stable stereoisomer.

The following examples are meant to illustrate the invention. They are not meant to limit the invention in any way.

EXAMPLES

Example 1—Preparation of a Halichondrin Macrolide Analog Via a Compound of Formula (IC)

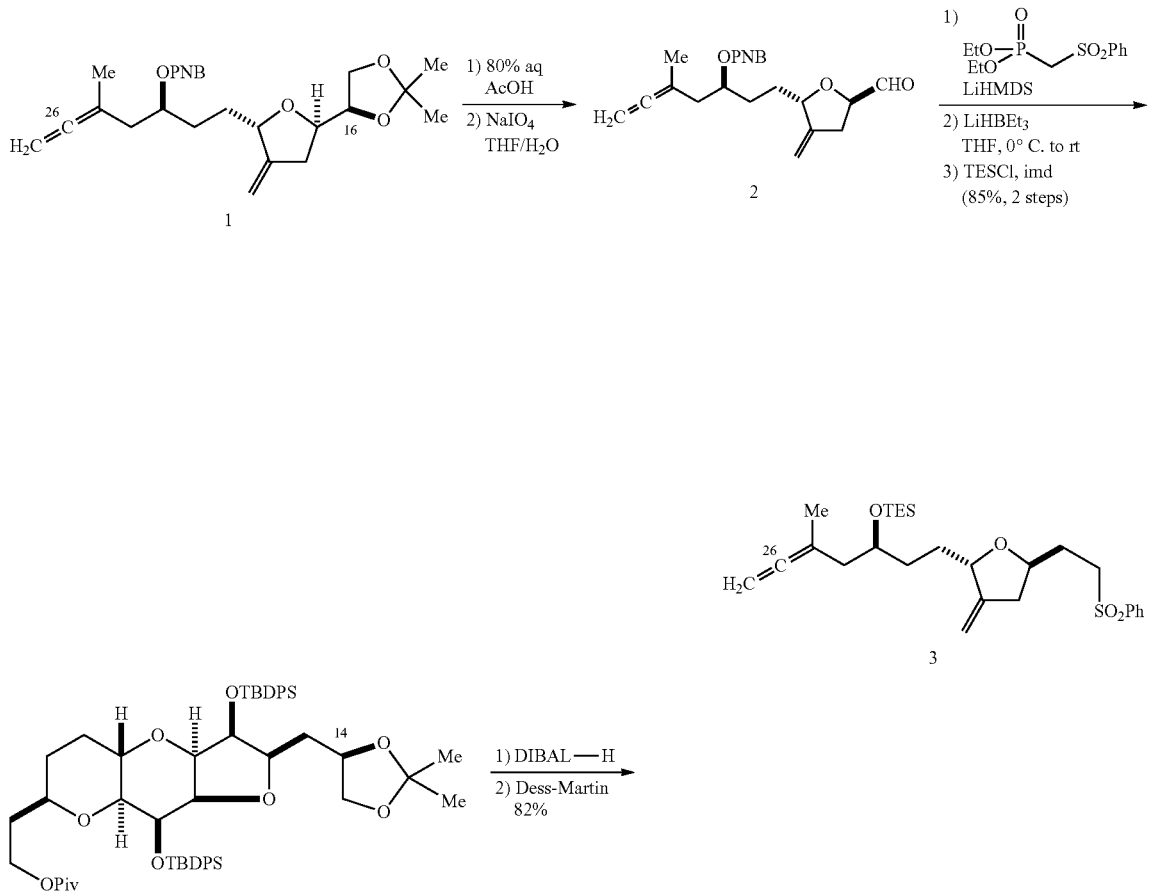

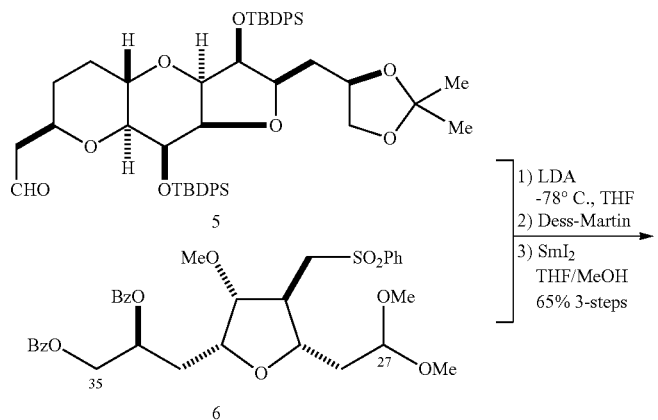
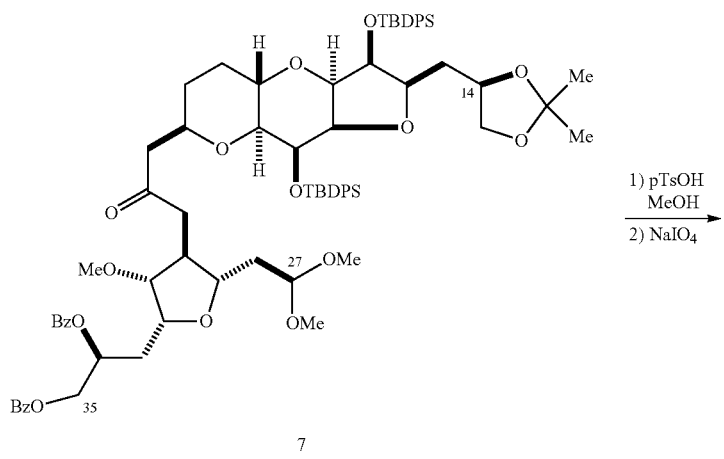
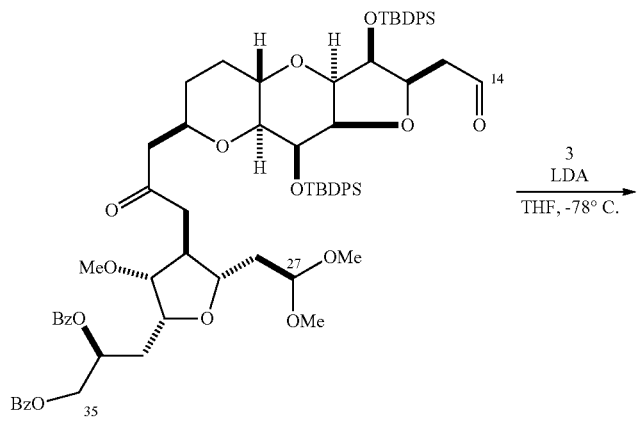

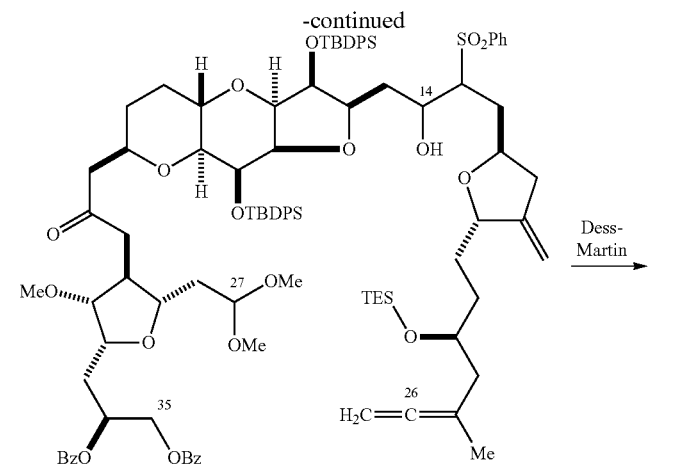
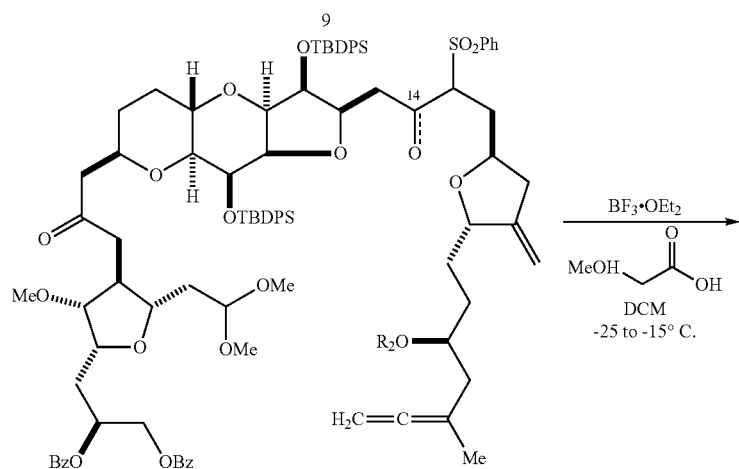
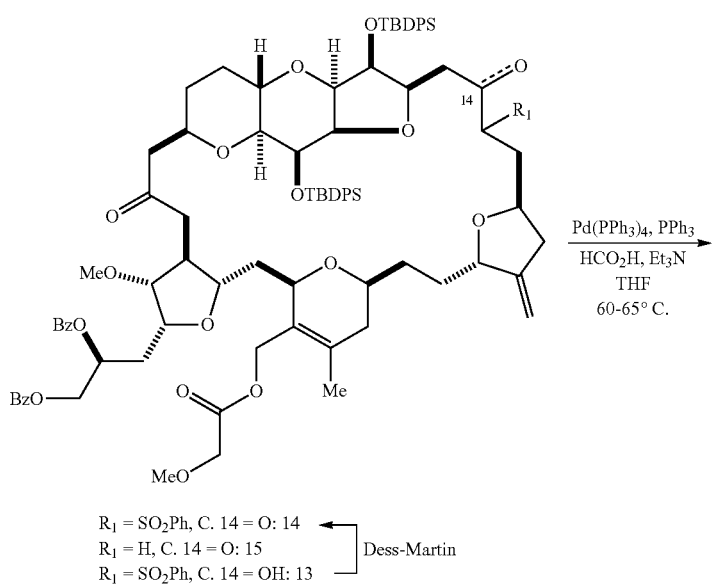

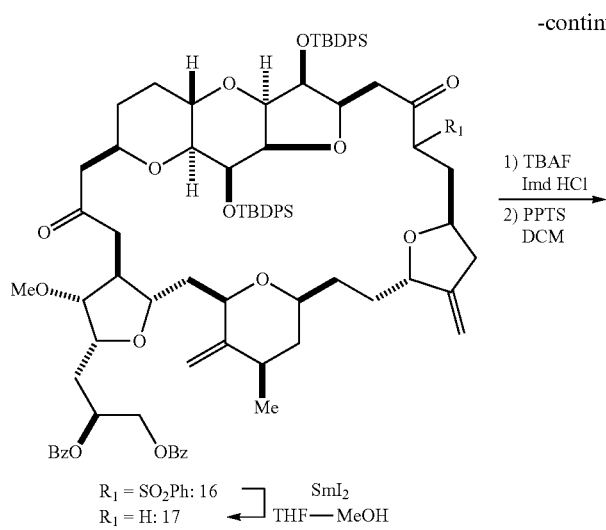

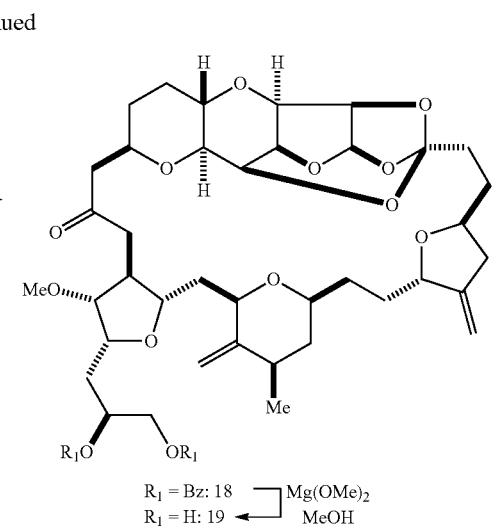

(S)-1-((2S,5R)-5-((R)-1,2-dihydroxyethyl)-3-methylenetetrahydrofuran-2-yl)-5-methylhepta-5,6-dien-3-yl 4-nitrobenzoate (S)-5-methyl-1-((2S,5R)-3-methylene-5-((E)-2-(phenylsulfonyl)vinyl)tetrahydrofuran-2-yl)hepta-5,6-dien-3-yl 4-nitrobenzoate

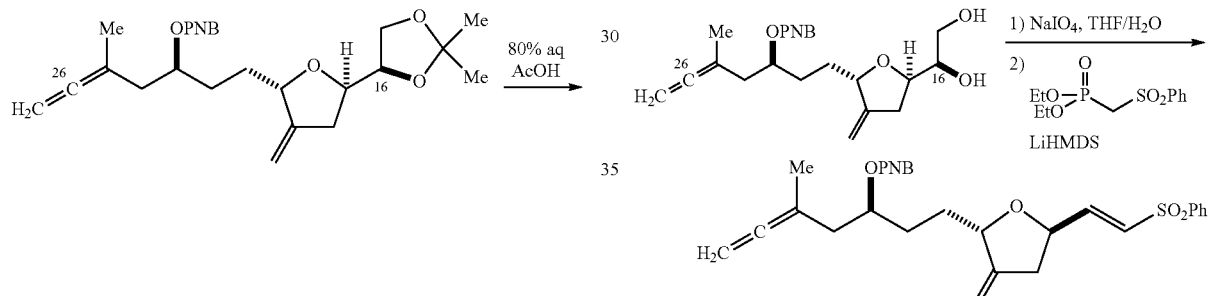

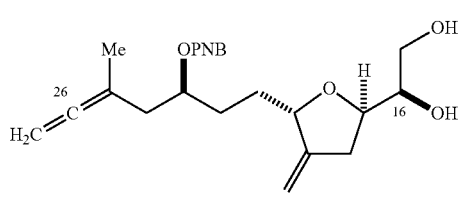

To a solution of (S)-1-((2S,5R)-5-((R)-2,2-dimethyl-1,3-dioxolan-4-yl)-3-methylenetetrahydrofuran-2-yl)-5-methylhepta-5,6-dien-3-yl 4-nitrobenzoate (0.70 g, 1.53 mmol) in acetic acid (8 mL) at ambient temperature was added water (2 mL). The resulting mixture was stirred at ambient temperature until all starting material was consumed. Upon completion, the reaction mixture was concentrated in vacuo and azeotroped with toluene twice to give 0.62 g of the target product.

$^1$H NMR (400 MHz, CHLOROFORM-d) δ ppm 1.56-1.70 (m, 2H) 1.73 (t, J=3.13 Hz, 3H) 1.81-1.94 (m, 2H) 2.25-2.32 (m, 1H) 2.37-2.47 (m, 1H) 2.50-2.59 (m, 1H) 2.60-2.70 (m, 1H) 3.51-3.59 (m, 1H) 3.60-3.68 (m, 1H) 3.69-3.76 (m, 1H) 4.04-4.14 (m, 1H) 4.42-4.50 (m, 2H) 4.50-4.59 (m, 1H) 4.84 (q, J=2.21 Hz, 1H) 5.02 (q, J=1.95 Hz, 1H) 5.31-5.39 (m, 1H) 8.16-8.23 (m, 2H) 8.26-8.32 (m, 2H)

((S)-1-((2S,5R)-5-((R)-1,2-dihydroxyethyl)-3-methylenetetrahydrofuran-2-yl)-5-methylhepta-5,6-dien-3-yl 4-nitrobenzoate (0.62 g, 1.49 mmol) was dissolved in THF (12.4 ml) at ambient temperature. Water (6.20 ml) and sodium periodate (0.953 g, 4.46 mmol) were then added. The resulting mixture was stirred at ambient temperature until all starting material was consumed. Upon completion, the reaction mixture was diluted with MTBE (30 mL), washed twice with 30% (w/v) aqueous NaCl (15 mL), and dried over MgSO$_4$. Filtration and concentration in vacuo provided 573 mg of (S)-1-((2S,5R)-5-formyl-3-methylenetetrahydrofuran-2-yl)-5-methylhepta-5,6-dien-3-yl 4-nitrobenzoate. The crude product was dissolved in THF (8.6 mL) and cooled to −78° C. In a separate flask, dimethyl ((phenylsulfonyl)methyl)phosphonate (589 mg, 2.23 mmol) was dissolved in THF (7 mL) and treated with 1.0 M LiHMDS (2304 µl, 2.304 mmol) for 20 min at 0° C. The resulting solution was added into the aldehyde solution at −78° C. The resulting reaction mixture was stirred until all the aldehyde was consumed. Upon complete conversion, the reaction was quenched with a saturated aqueous NH$_4$Cl (9 mL) and water (3 mL). The resulting mixture was warmed to ambient temperature and extracted twice with MTBE (12 mL each). The combined organic layers were washed with 30% aqueous NaCl (10 ml) and dried over MgSO$_4$. Filtration, concentration in vacuo, and purification by silica gel column chromatography using a 20-50% gradient of ethyl acetate in n-heptane as eluent provided 438 mg of the target product as a colorless oil.

$^1$H NMR (400 MHz, CHLOROFORM-d) δ ppm 1.60-1.75 (m, 5H) 1.80-1.92 (m, 2H) 2.21-2.30 (m, 1H) 2.33-2.54 (m, 2H) 2.78-2.98 (m, 1H) 4.42-4.48 (m, 2H) 4.48-4.56 (m, 1H) 4.61-4.75 (m, 1H) 4.87 (d, J=1.95 Hz, 1H) 5.00-5.10 (m, 1H) 5.24-5.47 (m, 1H) 6.54 (dd, J=15.05, 1.76 Hz, 1H) 6.92 (dd, J=14.85, 3.91 Hz, 1H) 7.49-7.58 (m, 2H) 7.58-7.68 (m, 1H) 7.80-7.95 (m, 2H) 8.11-8.23 (m, 2H) 8.24-8.33 (m, 2H)

(S)-5-methyl-1-((2S,5R)-3-methylene-5-(2-(phenylsulfonyl)ethyl)tetrahydrofuran-2-yl)hepta-5,6-dien-3-ol

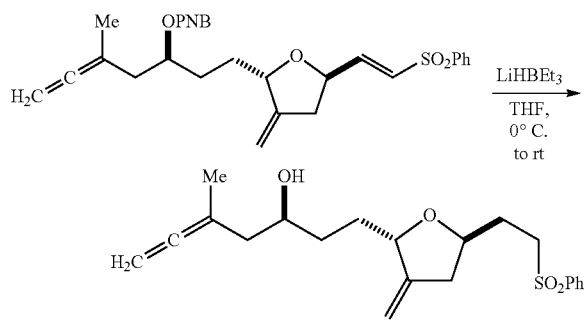

(S)-5-methyl-1-((2S,5R)-3-methylene-5-((E)-2-(phenylsulfonyl)vinyl)tetrahydrofuran-2-yl)hepta-5,6-dien-3-yl 4-nitrobenzoate (438 mg, 0.837 mmol) was dissolved in THF (15 mL) and cooled to 0° C. 1.0 M Super hydride in THF (3.35 mL, 3.35 mmol) was added, and the resulting mixture was brought to ambient temperature. Upon complete consumption of the starting material, a sat. aq. NH$_4$Cl solution (30 mL) was added. The resulting mixture was extracted twice with MTBE (30 mL each). The combined organic layers were washed with 30% (w/v) aqueous NaCl solution (10 mL) and dried over MgSO$_4$. Filtration, concentration in vacuo, and purification by silica gel column chromatography using a 30-50% gradient of ethyl acetate in n-heptane as eluent provided 280 mg of the target product as a colorless oil.

$^1$H NMR (400 MHz, CHLOROFORM-d) δ ppm 1.48-1.66 (m, 3H) 1.69 (t, J=3.12 Hz, 3H) 1.83-1.94 (m, 2H) 2.06 (dt, J=5.08, 2.54 Hz, 2H) 2.19-2.31 (m, 1H) 2.43 (d, J=2.73 Hz, 1H) 2.64-2.76 (m, 1H) 3.05-3.17 (m, 1H) 3.20-3.32 (m, 1H) 3.65-3.78 (m, 1H) 4.01-4.14 (m, 1H) 4.32 (br s, 1H) 4.58-4.69 (m, 2H) 4.85 (q, J=2.21 Hz, 1H) 4.98 (q, J=1.95 Hz, 1H) 7.52-7.60 (m, 2H) 7.61-7.68 (m, 1H) 7.88-7.92 (m, 2H)

Triethyl(((S)-5-methyl-1-((2S,5R)-3-methylene-5-(2-(phenylsulfonyl)ethyl)tetrahydrofuran-2-yl)hepta-5,6-dien-3-yl)oxy)silane

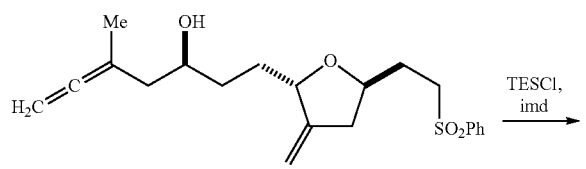

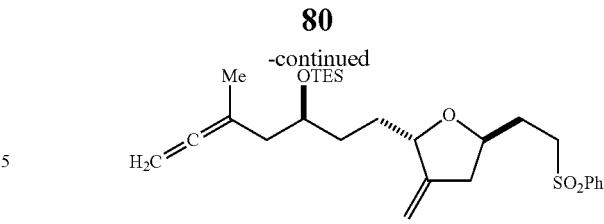

To a solution of (S)-5-methyl-1-((2S,5R)-3-methylene-5-(2-(phenylsulfonyl)ethyl)tetrahydrofuran-2-yl)hepta-5,6-dien-3-ol (0.14 g, 0.372 mmol) in dichloromethane (4 mL) at 0° C. were added imidazole (101 mg, 1.4 mmol) and chlorotriethylsilane (0.127 mL, 0.744 mmol). The resulting reaction mixture was stirred at ambient temperature until all the starting material was consumed. Upon completion, the reaction was quenched with a sat'd NH$_4$Cl solution (10 mL). The resulting mixture was extracted with MTBE (20 mL), washed with 30% (w/v) aqueous NaCl (5 mL) and dried over MgSO$_4$. Filtration, concentration in vacuo, and purification by silica gel column chromatography using a 0-25% gradient of ethyl acetate in n-heptane as eluent provided 128 mg of the target product as a colorless oil.

$^1$H NMR (400 MHz, CHLOROFORM-d) δ ppm 0.57 (q, J=8.08 Hz, 6H) 0.94 (t, J=7.82 Hz, 9H) 1.44-1.58 (m, 4H) 1.67 (t, J=3.13 Hz, 3H) 1.79-1.95 (m, 2H) 1.99-2.07 (m, 1H) 2.07-2.16 (m, 1H) 2.18-2.30 (m, 1H) 2.63-2.72 (m, 1H) 3.05-3.18 (m, 1H) 3.24-3.37 (m, 1H) 3.72-3.87 (m, 1H) 3.96-4.06 (m, 1H) 4.21-4.33 (m, 1H) 4.48-4.60 (m, 2H) 4.83 (d, J=1.95 Hz, 1H) 4.97 (d, J=1.95 Hz, 1H) 7.49-7.59 (m, 2H) 7.61-7.71 (m, 1H) 7.84-7.95 (m, 2H).

2-((2R,3S,3aR,4aS,7R,8aS,9S,9aR)-3,9-bis((tert-butyldiphenylsilyl)oxy)-2-(((R)-2,2-dimethyl-1,3-dioxolan-4-yl)methyl)decahydrofuro[3,2-b]pyrano[2,3-e]pyran-7-yl)acetaldehyde

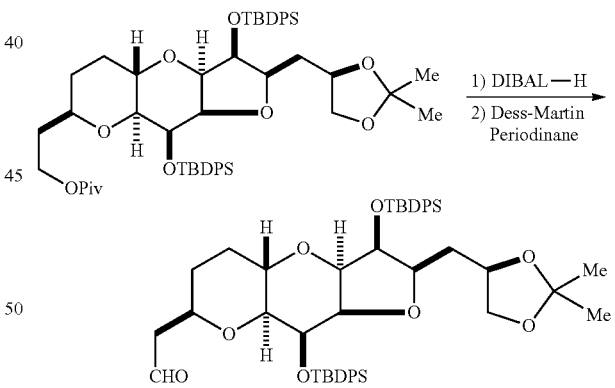

To a solution of 2-((2R,3S,3aR,4aS,7R,8aS,9S,9aR)-3,9-bis((tert-butyldiphenylsilyl)oxy)-2-(((R)-2,2-dimethyl-1,3-dioxolan-4-yl)methyl)decahydrofuro[3,2-b]pyrano[2,3-e]pyran-7-yl)ethyl pivalate (0.100 g, 0.107 mmol) in dichloromethane (2.0 mL) at −78° C. was added 1.0 M Dibal-H in toluene (0.214 mL, 0.214 mmol). The reaction mixture was stirred at −78° C. until all the starting material was consumed. Upon completion, the reaction was quenched with methanol (0.043 mL, 1.07 mmol) and a solution of Rochelle's Salt (0.453 g) in water (2.0 mL). The resulting mixture was brought to ambient temperature overnight. The organic layer was set aside, and the aqueous layer was extracted twice with dichloromethane (4.00 mL). The combined organic layers were dried over MgSO$_4$. Filtration and concentration in vacuo provided 89 mg of [2-((2R,3S,3aR,4aS,7R,8aS,9S,9aR)-3,9-bis((tert-butyldiphenylsilyl)oxy)-2-(((R)-2,2-dimethyl-1,3-dioxolan-4-yl)methyl)decahydrofuro[3,2-b]pyrano[2,3-e]pyran-7-yl)ethanol]. The crude product was dissolved in dichloromethane (1.8 mL) at ambient temperature and treated with sodium bicarbonate (43.9 mg, 0.523 mmol) and Dress-Martin periodinane (111 mg, 0.261 mmol). Once the reaction was complete, MTBE (1.8 mL), a saturated aqueous NaHCO$_3$ (8% w/v) (1 mL), water (0.5 mL) and sodium thiosulfate (165 mg, 1.05 mmol) were added. The resulting mixture was stirred at ambient temperature for 1 h, and the layers were separated. The organic layer was washed with 30% aqueous NaCl (1 mL) and dried over MgSO$_4$. Filtration, concentration in vacuo, and purification by silica gel column chromatography using a 2/1 mixture of n-heptane and ethyl acetate as eluent provided 73 mg of the target product as a white foam solid.

$^1$H NMR (400 MHz, CHLOROFORM-d) δ ppm 1.09 (s, 9H) 1.11 (s, 9H) 1.21-1.30 (m, 6H) 1.32-1.44 (m, 3H) 1.58-1.68 (m, 1H) 1.82-1.90 (m, 1H) 1.96-2.20 (m, 1H) 2.10-2.29 (m, 2H) 3.05 (dd, J=9.57, 3.71 Hz, 1H) 3.17-3.26 (m, 1H) 3.64-3.83 (m, 4H) 3.85-3.92 (m, 1H) 3.99-4.09 (m, 1H) 4.14-4.20 (m, 1H) 4.23 (t, J=5.28 Hz, 1H) 4.36 (dd, J=6.45, 3.71 Hz, 1H) 7.29-7.41 (m, 12H) 7.68-7.80 (m, 8H) 9.54 (br s, 1H).

(R)-3-((2R,3R,4S,5S)-4-(3-((2R,3S,3aR,4aS,7R,8aS,9S,9aR)-3,9-bis((tert-butyldiphenylsilyl)oxy)-2-(((R)-2,2-dimethyl-1,3-dioxolan-4-yl)methyl)decahydrofuro[3,2-b]pyrano[2,3-e]pyran-7-yl)-2-oxopropyl-5-(2,2-dimethoxyethyl)-3-methoxytetrahydrofuran-2-yl)propane-1,2-diyl dibenzoate

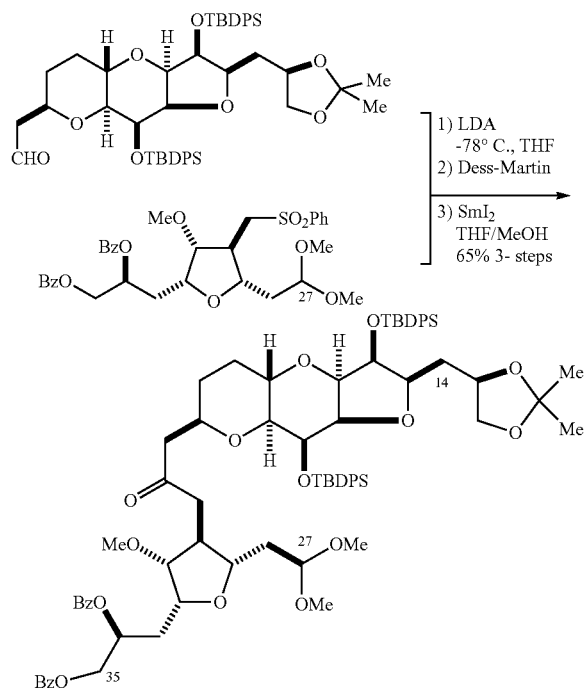

To a solution of (S)-3-((2R,3R,4S,5S)-5-(2,2-dimethoxyethyl)-3-methoxy-4-((phenylsulfonyl)methyl)tetrahydrofuran-2-yl)propane-1,2-diyl dibenzoate (593 mg, 0.946 mmol) in THF (3.6 mL) at −78° C. was added 0.35 M lithium diisopropylamide (LDA) in THF (2.65 mL, 0.927 mmol). After 1 h, a solution of 2-((2R,3S,3aR,4aS,7R,8aS,9S,9aR)-3,9-bis((tert-butyldiphenylsilyl)oxy)-2-(((R)-2,2-dimethyl-1,3-dioxolan-4-yl)methyl)decahydrofuro[3,2-b]pyrano[2,3-e]pyran-7-yl)acetaldehyde (358 mg, 0.422 mmol) in n-heptane (5.4 mL) was added. The reaction mixture was stirred at −78° C. until all the aldehyde was consumed. Upon completion, the reaction was quenched with a sat. aq. NH$_4$Cl solution (7 mL). The resulting mixture was extracted twice MTBE (50 mL). The combined organic layers were washed with 30% (w/v) aqueous NaCl (4 mL) and dried over MgSO$_4$. Filtration, concentration in vacuo, and purification by silica gel column chromatography using a 33-66% gradient of ethyl acetate in n-heptane as eluent provided 576 mg of (2R)-3-((2R,3R,4S,5S)-4-((1S)-3-((2R,3S,3aR,4aS,7R,8aS,9S,9aR)-3,9-bis((tert-butyldiphenylsilyl)oxy)-2-(((R)-2,2-dimethyl-1,3-dioxolan-4-yl)methyl)decahydrofuro[3,2-b]pyrano[2,3-e]pyran-7-yl)-2-hydroxy-1-(phenylsulfonyl)propyl)-5-(2,2-dimethoxyethyl)-3-methoxytetrahydrofuran-2-yl)propane-1,2-diyl dibenzoate contaminated with by-products. The crude product (658 mg) was dissolved in dichloromethane (13 mL) and treated with sodium bicarbonate (0.187 g, 2.229 mmol) and Dess-Martin periodinane (0.473 g, 1.115 mmol) at ambient temperature. The reaction mixture was stirred at ambient temperature until all the starting material was consumed. Upon completion, MTBE (30 mL), a sat. aq. NaHCO$_3$ solution (15 mL), a sat. aq. Na$_2$S$_2$O$_3$ (10 mL), and water (10 mL) were added. The resulting mixture was stirred for 1 h at ambient temperature, and the layers were separated. The organic layer was set aside, and the aqueous layer was extracted with MTBE (30 mL). The combined organic layers were washed with 30% (w/v) aqueous NaCl (10 mL) and dried over MgSO$_4$. Filtration and concentration in vacuo provided 0.590 g of (R)-3-((2R,3R,4S,5S)-4-((S)-3-((2R,3S,3aR,4aS,7R,8aS,9S,9aR)-3,9-bis((tert-butyldiphenylsilyl)oxy)-2-(((R)-2,2-dimethyl-1,3-dioxolan-4-yl)methyl)decahydrofuro[3,2-b]pyrano[2,3-e]pyran-7-yl)-2-oxo-1-(phenylsulfonyl)propyl)-5-(2,2-dimethoxyethyl)-3-methoxytetrahydrofuran-2-yl)propane-1,2-diyl dibenzoate as white foam solid. The crude ketone product was dissolved in THF/methanol (9/6 mL) and cooled to −78° C. 0.1 M SmI$_2$ in THF (18.0 mL, 1.80 mmol) was added until the green color sustained. Once the reaction was complete, a saturated aqueous Rochelle's salt solution (30 mL), MTBE (7.2 mL), and water (4 mL) were added. The resulting mixture was warmed to ambient temperature over 4 h. The organic layer was separated, and the aqueous layer was extracted with MTBE (7.2 mL). The combined organic layers were washed with 30% (w/v) aqueous NaCl (2.4 mL) and dried over MgSO$_4$. Filtration, concentration in vacuo, and purification by silica gel column chromatography using a 33-88% gradient of ethyl acetate in n-heptane as eluent provided 353 mg of the target product as a white foam solid.

$^1$H NMR (400 MHz, CHLOROFORM-d) δ ppm 1.07 (s, 9H) 1.10 (s, 9H) 1.22-1.45 (m, 6H) 1.57-1.66 (m, 1H) 1.73-1.95 (m, 4H) 1.97-2.07 (m, 1H) 2.12-2.30 (m, 5H) 2.31-2.41 (m, 1H) 3.03 (dd, J=9.57, 3.32 Hz, 1H) 3.17-3.22 (m, 1H) 3.23 (s, 3H) 3.25 (s, 3H) 3.33 (s, 3H) 3.29-3.39 (m, 1H) 3.40-3.49 (m, 1H) 3.64 (t, J=6.45 Hz, 1H) 3.68-3.79 (m, 3H) 3.81-3.90 (m, 2H) 3.98-4.08 (m, 1H) 4.09-4.17 (m, 1H) 4.21 (t, J=5.28 Hz, 1H) 4.31 (dd, J=6.64, 3.52 Hz, 1H) 4.43 (dd, J=7.62, 3.71 Hz, 1H) 4.55 (d, J=4.69 Hz, 2H) 5.53-5.64 (m, 1H) 7.28-7.45 (m, 16H) 7.50-7.59 (m, 2H) 7.67-7.73 (m, 6H) 7.78 (d, J=6.64 Hz, 2H) 8.00 (d, J=7.43 Hz, 2H) 8.05 (d, J=7.43 Hz, 2H).

(R)-3-((2R,3R,4S,5S)-4-(3-((2R,3S,3aR,4aS,7R,8aS,9S,9aR)-3,9-bis((tert-butyldiphenylsilyl)oxy)-2-((R)-2,3-dihydroxypropyl)decahydrofuro[3,2-b]pyrano[2,3-e]pyran-7-yl)-2-oxopropyl)-5-(2,2-dimethoxyethyl)-3-methoxytetrahydrofuran-2-yl)propane-1,2-diyl dibenzoate. Compound 7a

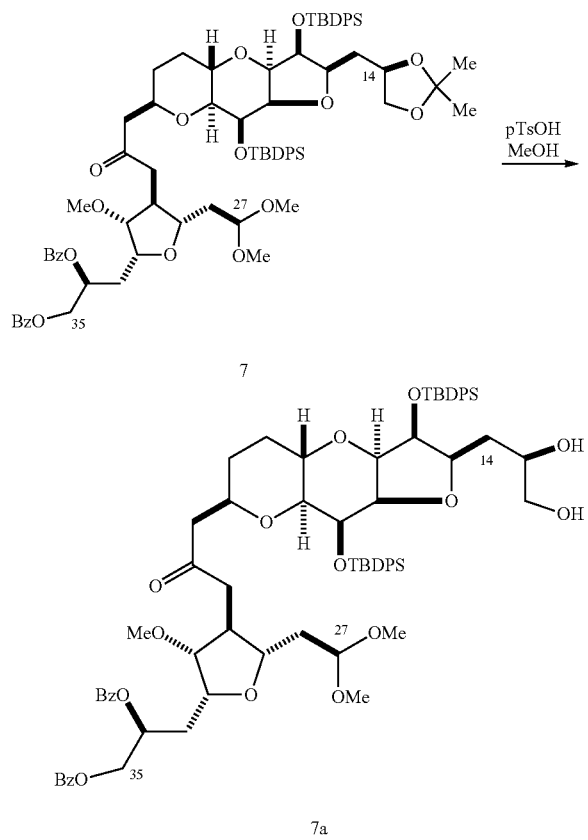

To a solution of (R)-3-((2R,3R,4S,5S)-4-(3-((2R,3S,3aR,4aS,7R,8aS,9S,9aR)-3,9-bis((tert-butyldiphenylsilyl)oxy)-2-(((R)-2,2-dimethyl-1,3-dioxolan-4-yl)methyl)decahydrofuro[3,2-b]pyrano[2,3-e]pyran-7-yl)-2-oxopropyl)-5-(2,2-dimethoxyethyl)-3-methoxytetrahydrofuran-2-yl)propane-1,2-diyl dibenzoate (87 mg, 0.065 mmol) in methanol (5 mL) was added p-toluenesulfonic acid monohydrate (3.10 mg, 0.016 mmol) at ambient temperature. The reaction mixture was stirred until all the starting material was consumed. Upon completion, the reaction was quenched with a sat. aq. NaHCO₃ solution (5 mL) and water (5 mL). The resulting mixture was extracted with MTBE (10 mL each) twice, and the combined organic layers were washed with 30% (w/v) aqueous NaCl (2 mL) and dried over MgSO₄. Filtration, concentration in vacuo, and purification by silica gel column chromatography using a 50-100% gradient of ethyl acetate in n-heptane as eluent provided 51 mg of the target product.

¹H NMR (400 MHz, CHLOROFORM-d) δ ppm 1.06 (s, 9H) 1.08 (s, 9H) 1.33-1.48 (m, 2H) 1.59-1.67 (m, 1H) 1.70-1.95 (m, 4H) 1.99-2.04 (m, 1H) 2.07-2.31 (m, 5H) 2.32-2.42 (m, 1H) 2.75 (d, J=5.08 Hz, 1H) 3.02 (dd, J=9.97, 4.49 Hz, 1H) 3.22 (s, 3H) 3.24 (s, 3H) 3.29-3.33 (m, 1H) 3.34 (s, 3H) 3.38 (br s, 3H) 3.57 (dd, J=6.64, 4.69 Hz, 1H) 3.62 (t, J=4.89 Hz, 1H) 3.67-3.77 (m, 1H) 3.86 (br s, 3H) 4.05 (td, J=10.26, 4.49 Hz, 1H) 4.23 (s, 2H) 4.43 (dd, J=7.62, 3.71 Hz, 1H) 4.55 (d, J=5.08 Hz, 2H) 5.54-5.66 (m, 1H) 7.29-7.43 (m, 16H) 7.49-7.59 (m, 2H) 7.61-7.69 (m, 6H) 7.72-7.78 (m, 2H) 7.97-8.01 (m, 2H) 8.02-8.08 (m, 2H)

(R)-3-((2R,3R,4S,5S)-4-(3-((2R,3S,3aR,4aS,7R,8aS,9S,9aR)-3,9-bis((tert-butyldiphenylsilyl)oxy)-2-(2-oxoethyl)decahydrofuro[3,2-b]pyrano[2,3-e]pyran-7-yl)-2-oxopropyl)-5-(2,2-dimethoxyethyl)-3-methoxytetrahydrofuran-2-yl)propane-1,2-diyl dibenzoate

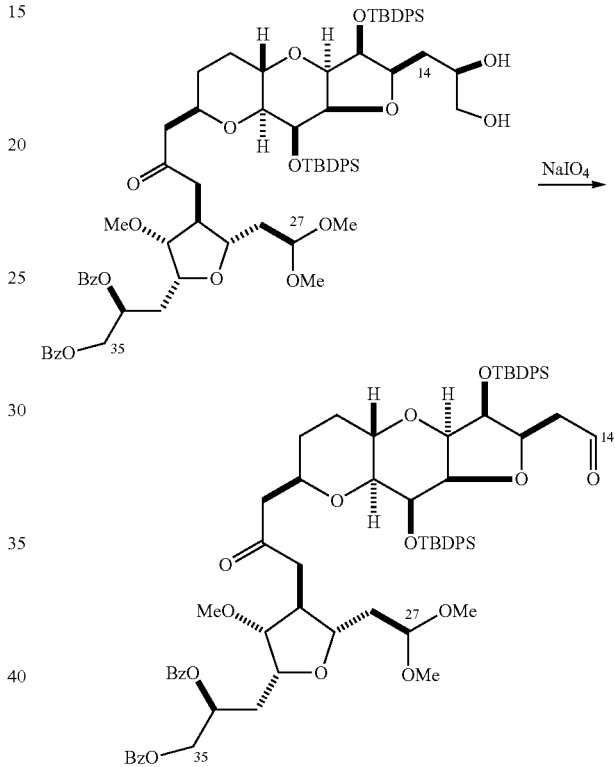

To a solution of (R)-3-((2R,3R,4S,5S)-4-(3-((2R,3S,3aR,4aS,7R,8aS,9S,9aR)-3,9-bis((tert-butyldiphenylsilyl)oxy)-2-((R)-2,3-dihydroxypropyl)decahydrofuro[3,2-b]pyrano[2,3-e]pyran-7-yl)-2-oxopropyl)-5-(2,2-dimethoxyethyl)-3-methoxytetrahydrofuran-2-yl)propane-1,2-diyl dibenzoate (51 mg, 0.039 mmol) in THF (2 mL) were added water (0.7 mL, 39 mmol) and sodium periodate (50.6 mg, 0.237 mmol) at ambient temperature. The reaction mixture was stirred until all the starting material was consumed. Upon completion, the reaction was quenched with 30% (w/v) aqueous NaCl (5 mL). The resulting mixture was extracted with MTBE (12 mL), and the organic layer was washed with 30% (w/v) aqueous NaCl (3 mL) twice and dried over MgSO₄. Filtration and concentration in vacuo provided 48 mg of the target product as white foam solid. The crude product was used in the next step without further purification.

¹H NMR (400 MHz, BENZENE-d₆) δ ppm 1.19 (s, 9H) 1.30 (s, 9H) 1.35-1.44 (m, 2H) 1.75 (dd, J=16.61, 4.89 Hz, 1H) 1.85-1.92 (m, 1H) 1.92-1.99 (m, 2H) 2.08-2.22 (m, 3H) 2.27-2.44 (m, 2H) 2.50-2.61 (m, 2H) 2.78-2.85 (m, 1H) 2.85-2.93 (m, 1H) 2.99 (dd, J=7.23, 4.10 Hz, 1H) 3.12-3.17 (m, 1H) 3.15 (s, 3H) 3.18-3.21 (m, 1H) 3.23 (s, 3H) 3.28 (s, 3H) 3.33 (d, J=3.13 Hz, 1H) 3.62-3.75 (m, 2H) 3.95-4.02 (m, 1H) 4.05 (dd, J=6.45, 5.28 Hz, 1H) 4.12 (dd, J=7.62, 2.54 Hz, 2H) 4.24 (q, J=6.38 Hz, 1H) 4.48-4.62 (m, 2H) 4.76 (dd, J=7.23, 4.10 Hz, 1H) 5.84-5.97 (m, 1H) 6.92-6.98 (m, 2H) 6.99-7.08 (m, 4H) 7.19-7.38 (m, 12H) 7.72-7.79 (m, 2H) 7.82-7.95 (m, 6H) 8.12 (d, J=7.43 Hz, 2H) 8.17 (d, J=6.64 Hz, 2H) 9.59 (s, 1H)

(2R)-3-((2R,3R,4S,5S)-4-(3-((2R,3S,3aR,4aS,7R,8aS,9S,9aR)-3,9-bis((tert-butyldiphenylsilyl)oxy)-2-(4-((2R,5S)-5-((S)-5-methyl-3-((triethylsilyl)oxy)hepta-5,6-dien-1-yl)-4-methylenetetrahydrofuran-2-yl)-2-oxo-3-(phenylsulfonyl)butyl)decahydrofuro[3,2-b]pyrano[2,3-e]pyran-7-yl)-2-oxopropyl)-5-(2,2-dimethoxyethyl)-3-methoxytetrahydrofuran-2-yl) propane-1,2-diyl dibenzoate mixture was brought to ambient temperature, and the layers were separated. The aqueous layer was extracted with MTBE (10 mL), and the combined organic layers were washed with 30% (w/v) aqueous NaCl (2 mL) twice and dried over MgSO$_4$. Filtration, concentration in vacuo, and purification by silica gel column chromatography using a 15-50% gradient of ethyl acetate in n-heptane as eluent provided 36 mg of a mixture of (2R)-3-((2R,3R,4S,5S)-4-(3-((2R,3S,3aR,4aS,7R,8aS,9S,9aR)-3,9-bis((tert-butyldiphenylsilyl)oxy)-2-(2-hydroxy-4-((2R,5S)-5-((S)-5-methyl-3-((triethylsilyl)oxy)hepta-5,6-dien-1-yl)-4-methylenetetrahydrofuran-2-yl)-3-(phenylsulfonyl)butyl)decahydrofuro[3,2-b]pyrano[2,3-e]pyran-7-yl)-2-oxopropyl)-5-(2,2-dimethoxyethyl)-3-methoxytetrahydrofuran-2-yl)propane-1,2-diyl dibenzoate

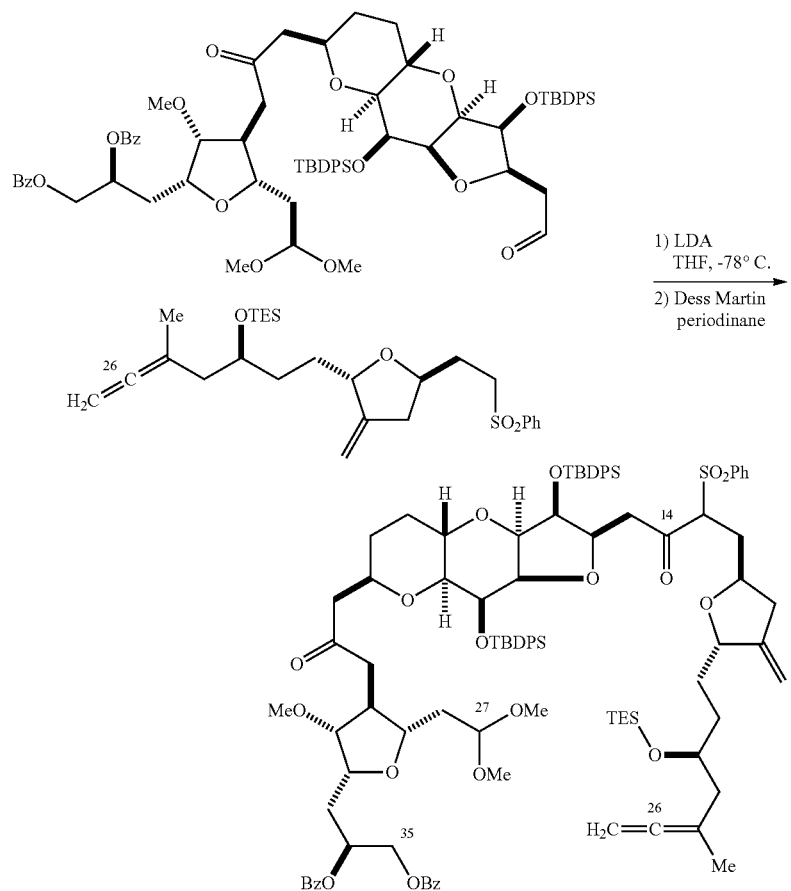

To a solution of triethyl(((S)-5-methyl-1-((2S,5R)-3-methylene-5-(2-(phenylsulfonyl)ethyl)tetrahydrofuran-2-yl)hepta-5,6-dien-3-yl)oxy)silane (25.09 mg, 0.051 mmol) in THF (1.5 mL) at −78° C. was added 0.35 M LDA in THF (0.156 mL, 0.055 mmol). After 30 min at −78° C., a solution of (R)-3-((2R,3R,4S,5S)-4-(3-((2R,3S,3aR,4aS,7R,8aS,9S,9aR)-3,9-bis((tert-butyldiphenylsilyl)oxy)-2-(2-oxoethyl)decahydrofuro[3,2-b]pyrano[2,3-e]pyran-7-yl)-2-oxopropyl)-5-(2,2-dimethoxyethyl)-3-methoxytetrahydrofuran-2-yl)propane-1,2-diyl dibenzoate (43 mg, 0.034 mmol) in THF (1.5 mL) was added. After stirring for 30 min at −78° C., the reaction mixture was treated with a sat. aq. NH$_4$Cl solution (3 mL), water (2 mL), and MTBE (5 mL). The resulting and the starting aldehyde, which was used in next step without further purification. To a solution of the crude product in dichloromethane (1 mL) were added sodium bicarbonate (10.35 mg, 0.123 mmol) and Dess-Martin periodinane (26.1 mg, 0.062 mmol) at ambient temperature. After stirring for 6 h, the reaction mixture was diluted with MTBE (5 mL) and treated with a sat. aq. NaHCO$_3$ solution (3 mL) and a sat. aq. Na$_2$S$_2$O$_3$ (2 mL). The resulting mixture was stirred for 20 min, and the layers were separated. The aqueous layer was extracted with MTBE (12 mL), and the combined organic layers were washed with 30% (w/v) aqueous NaCl twice and dried over MgSO$_4$. Filtration, concentration in vacuo, and purification by silica gel column chromatography using a 33-50% gradient of ethyl acetate in n-heptane as eluent provided 24 mg of the target product as a 1:1 diastereomeric mixture.

$^1$H NMR (400 MHz, CHLOROFORM-d) δ ppm 0.49-0.64 (m, 6H) 0.90-1.00 (m, 9H) 1.04-1.14 (m, 18H) 1.20-1.55 (m, 7H) 1.60-1.64 (m, 1.5H) 1.65-1.70 (m, 1.5H) 1.71-2.70 (m, 18H) 2.97-3.09 (m, 1H) 3.22 (s, 1.5H) 3.22 (s, 1.5H) 3.24 (s, 1.5H) 3.24 (s, 1.5H) 3.25-3.31 (m, 1H) 3.33 (s, 3H) 3.36-3.48 (m, 1H) 3.49-3.63 (m, 1H) 3.65-3.90 (m, 3H) 3.94-4.30 (m, 8H) 4.39-4.45 (m, 1H) 4.48-4.53 (m, 1H) 4.53-4.58 (m, 3H) 4.80 (br d, J=8.99 Hz, 1H) 4.88-4.98 (m, 1H) 5.52-5.64 (m, 1H) 7.27-7.83 (m, 31H) 8.00 (br d, J=7.43 Hz, 2H) 8.05 (br d, J=7.82 Hz, 2H)

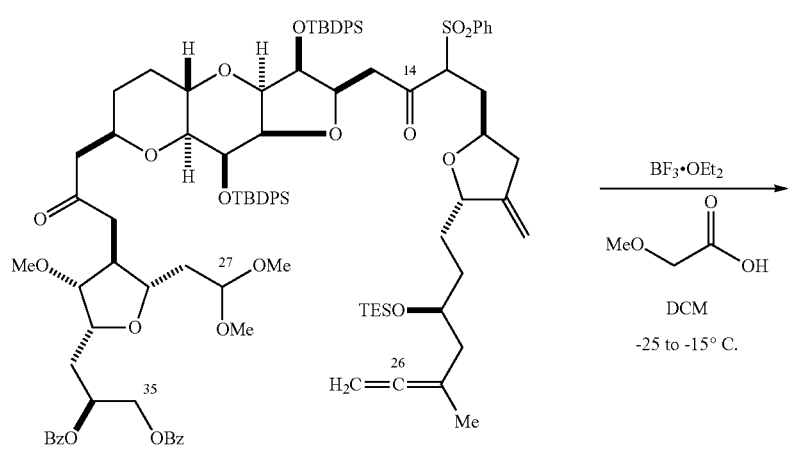

Compound 14

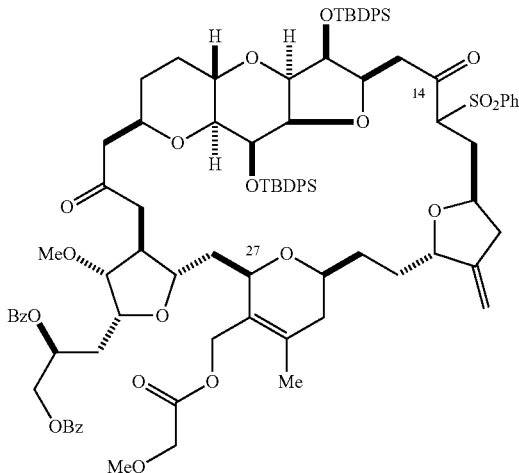

14

To a solution of (2R)-3-((2R,3R,4S,5S)-4-(3-((2R,3S,3aR,4aS,7R,8aS,9S,9aR)-3,9-bis((tert-butyldiphenylsilyl)oxy)-2-(4-((2R,5S)-5-((S)-5-methyl-3-((triethylsilyl)oxy)hepta-5,6-dien-1-yl)-4-methylenetetrahydrofuran-2-yl)-2-oxo-3-(phenylsulfonyl)butyl)decahydrofuro[3,2-b]pyrano[2,3-e]pyran-7-yl)-2-oxopropyl)-5-(2,2-dimethoxyethyl)-3-methoxytetrahydrofuran-2-yl)propane-1,2-diyl dibenzoate (12 mg, 5.484 μmol) in dichloromethane (2.4 mL) at −18° C. were added methoxyacetic acid (0.017 mL, 0.219 mmol) and BF$_3$·OEt$_2$ (5.6 μL, 0.044 mmol). The reaction mixture was stirred between −25° C. and −15° C. until the cyclization was complete. Upon completion, the reaction was quenched with sat. aq. NaHCO$_3$ (5 mL). The resulting mixture was extracted twice with MTBE (10 mL). The combined organic layers were washed with 30% (w/v) aqueous NaCl (3 mL) and dried over MgSO$_4$. Filtration, concentration in vacuo, and purification by silica gel column chromatography using a 10-40% gradient of ethyl acetate in n-heptane as eluent provided 5.5 mg of the target product as a 3:2 diastereomeric mixture.

$^1$H NMR (400 MHz, CHLOROFORM-d) δ ppm 0.93 (s, 5H) 0.99 (s, 4H) 1.11 (s, 4H) 1.13 (s, 5H) 1.31-1.58 (m, 9H)

1.70 (s, 1.2H) 1.74 (s, 1.8H) 1.74-2.12 (m, 6H) 2.19 (br t, J=6.25 Hz, 2H) 2.27-2.78 (m, 7H) 2.95 (t, J=9.18 Hz, 0.4H) 3.07 (t, J=8.99 Hz, 0.6H) 3.32 (s, 1.8H) 3.34 (s, 1.2H) 3.35-3.39 (m, 2H) 3.41 (s, 1.2H) 3.42 (s, 1.8H) 3.49-3.55 (m, 1H) 3.56-3.62 (m, 1H) 3.64-3.90 (m, 4H) 3.99 (s, 0.8H) 3.99 (s, 1.2H) 4.01-4.10 (m, 2H) 4.20-4.44 (m, 3H) 4.50-4.59 (m, 2H) 4.60-4.73 (m, 2H) 4.77 (s, 0.4H) 4.82 (s, 0.6H) 4.87 (s, 0.4H) 4.96 (s, 0.6H) 5.50-5.64 (m, 1H) 7.27-7.81 (m, 31H) 7.96-8.10 (m, 4H)

1H) 3.44-3.51 (m, 1H) 3.52-3.57 (m, 0.33H) 3.60-3.86 (m, 5H) 3.88-4.06 (m, 3H) 4.13-4.21 (m, 2H) 4.27 (t, J=6.25 Hz, 0.66H) 4.32 (t, J=6.84 Hz, 0.33H) 4.54-4.62 (m, 3H) 4.71 (s, 0.33H) 4.74 (s, 0.66H) 4.78 (s, 0.33H) 4.81 (s, 0.33H) 4.84 (br s, 1.3H) 4.87 (br s, 0.33H) 4.95 (s, 0.66H) 5.59-5.67 (m, 1H) 7.27-7.74 (m, 31H) 7.98-8.02 (m, 2H) 8.05 (br d, J=7.03 Hz, 2H)

Compound 16

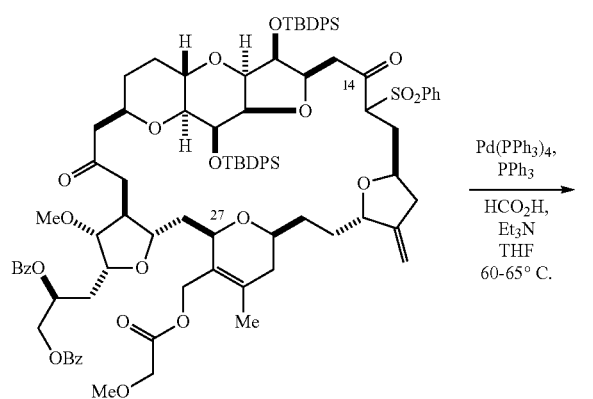

14

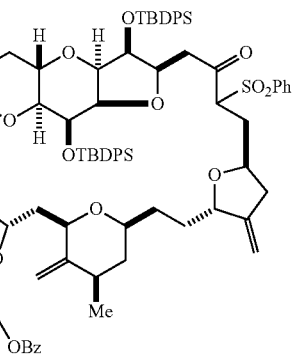

16

Compound 17

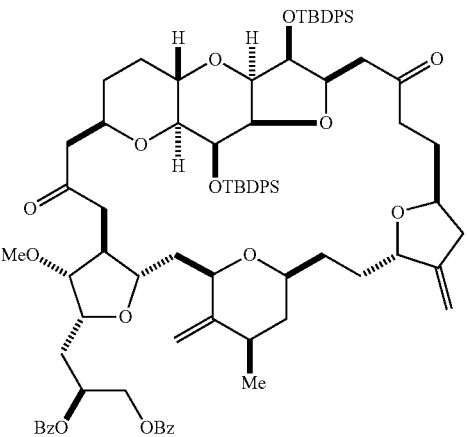

17

To a solution of compound 14 (5.5 mg, 3.309 μmol) in THF (1 mL) were added formic acid (6.35 μL, 0.165 mmol), triethylamine (0.023 mL, 0.165 mmol), and a solution of Pd(Ph$_3$P)$_4$ (1.147 mg, 0.993 μmol) and triphenylphosphine (1.041 mg, 3.971 μmol) in THF (0.1 mL). The resulting mixture was stirred at 60-65° C. overnight and cooled to ambient temperature. The reaction mixture was diluted with MTBE (10 mL), washed with a sat. aq. NaHCO$_3$ (3 mL) and dried over MgSO$_4$. Filtration, concentration in vacuo, and purification by silica gel column chromatography using a 30-50% gradient of ethyl acetate in n-heptane as eluent provided 1.8 mg of the target product (2:1 diastereomeric mixture)

$^1$H NMR (400 MHz, CHLOROFORM-d) δ ppm 0.94 (s, 6H) 0.98 (s, 3H) 1.03 (br d, J=6.25 Hz, 3H) 1.10 (s, 3H) 1.12 (s, 6H) 1.27-1.76 (m, 8H) 1.90-2.12 (m, 7H) 2.21 (br t, J=6.25 Hz, 2H) 2.27-2.82 (m, 8H) 2.95-3.03 (m, 0.33H) 3.10 (t, J=9.18 Hz, 0.66H) 3.37 (s, 2H) 3.38 (s, 1H) 3.34-3.43 (m, To a solution of compound 16 (1.8 mg, 1.144 μmol) in THF (0.5 mL)/methanol (0.25 mL) at −78° C. was added 0.1 M samarium diiodide in THF (0.057 mL, 5.718 μmol) until green color persisted. The reaction mixture was stirred at −78° C. for 10 min, and treated with sat. aq. Rochelle's salt (3 mL) and MTBE (5 mL) and water (2 mL). The resulting mixture was warmed to ambient temperature and then extracted with MTBE (7 mL). The organic layer was washed with 30% (w/v) aqueous NaCl (3 mL) and dried over MgSO$_4$. Filtration, concentration in vacuo, and purification by silica gel column chromatography using a 10-33% gradient of ethyl acetate in n-heptane as eluent provided 1.4 mg of the target product.

¹H NMR (400 MHz, CHLOROFORM-d) δ ppm 0.98 (s, 9H) 1.03 (br d, J=6.25 Hz, 3H) 1.06 (s, 9H) 1.27-2.15 (m, 11H) 2.20-2.33 (m, 3H) 2.56-2.81 (m, 5H) 2.89-2.94 (m, 1H) 3.02-3.12 (m, 2H) 3.41 (s, 3H) 3.45-3.48 (m, 2H) 3.68 (dd, J=5.86, 4.69 Hz, 1H) 3.76 (br d, J=8.60 Hz, 2H) 3.79-3.86 (m, 2H) 3.86-3.96 (m, 2H) 4.03 (dd, J=8.99, 3.52 Hz, 1H) 4.10-4.19 (m, 1H) 4.30-4.39 (m, 1H) 4.55-4.60 (m, 2H) 4.76 (s, 1H) 4.82 (br s, 1H) 4.85 (s, 1H) 4.95 (d, J=1.17 Hz, 1H) 5.57-5.66 (m, 1H) 7.27-7.67 (m, 26H) 8.01 (d, J=7.43 Hz, 2H) 8.05 (d, J=7.43 Hz, 2H).

Compound 18

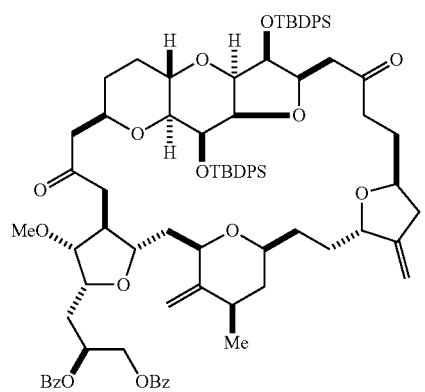

17

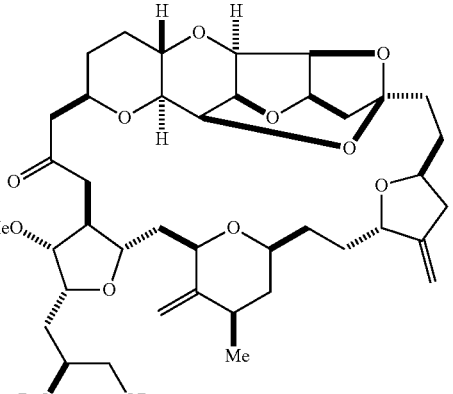

18

To compound 17 (1.4 mg, 0.976 μmol) in a vial was added THF (280 μL) and N,N-dimethylacetamide (98 μL) at ambient temperature. A mixture of TBAF (1.0 M in THF, 49 μL, 0.049 mmol) and imidazole hydrochloride (2.6 mg, 0.024 mmol) was added. The resulting mixture was stirred over 15 h at ambient temperature and then treated with 30% (w/v) aqueous NaCl (2 mL) and MTBE (3 mL). The layers were separated, and the aqueous layer was extracted twice with MTBE (3 mL each time). The combined organic layers were concentrated in vacuo. The residue was dissolved in dichloromethane (0.5 mL) at ambient temperature and PPTS (0.9 mg, 3.6 μmol) was added. Once the starting material was consumed, the reaction mixture was purified by silica gel column chromatography using heptane/ethyl acetate (1/1) and ethyl acetate as eluent to give 0.6 mg of the target product, which was confirmed by NMR analysis with an authentic sample.

(S)-3-((2R,3R,4S,5S)-4-(3-((2R,3S,3aR,4aS,7R,8aS, 9S,9aR)-3,9-bis((tert-butyldiphenylsilyl)oxy)-2-(4-((2S,5S)-5-((S)-5-methyl-3-((triethylsilyl)oxy)hepta-5,6-dien-1-yl)-4-methylenetetrahydrofuran-2-yl)-2-oxobutyl)decahydrofuro[3,2-b]pyrano[2,3-e]pyran-7-yl)-2-oxopropyl)-5-(2,2-dimethoxyethyl)-3-methoxytetrahydrofuran-2-yl)propane-1,2-diyl dibenzoate

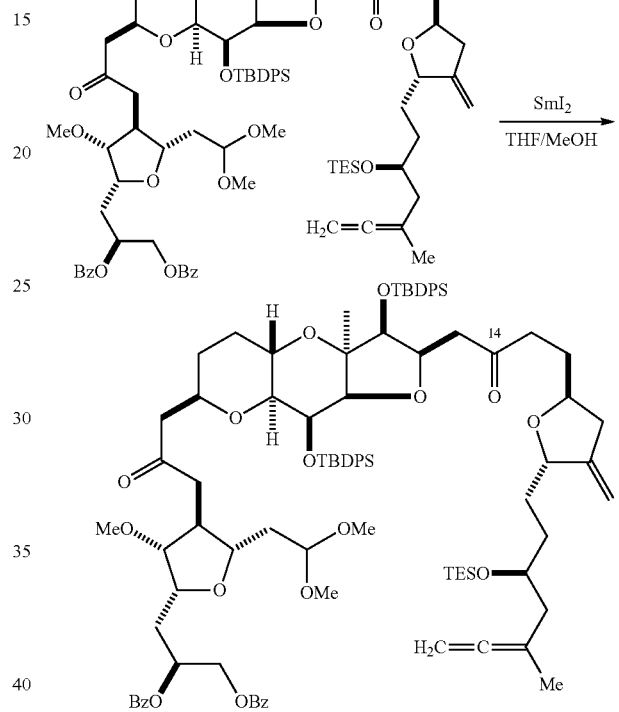

To a solution of (S)-3-((2R,3R,4S,5S)-4-(3-((2R,3S,3aR, 4aS,7R,8aS,9S,9aR)-3,9-bis((tert-butyldiphenylsilyl)oxy)-2-(4-((2R,5S)-5-((S)-5-methyl-3-((triethylsilyl)oxy)hepta-5, 6-dien-1-yl)-4-methylenetetrahydrofuran-2-yl)-2-oxo-3-(phenylsulfonyl)butyl)decahydrofuro[3,2-b]pyrano[2,3-e] pyran-7-yl)-2-oxopropyl)-5-(2,2-dimethoxyethyl)-3-methoxytetrahydrofuran-2-yl)propane-1,2-diyl dibenzoate (12 mg, 6.856 μmol) in THF (1.2 mL)/methanol (0.4 mL) at −78° C. was added a solution of samarium diiodide in THF (0.1 M, 0.34 mL, 34 μmol) until green color persisted. The reaction mixture was stirred at −78° C. for 10 min and treated with sat. aq. Rochelle's salt (1.5 mL), MTBE (3 mL), and water (1 mL). The resulting mixture was warmed to ambient temperature and extracted with MTBE (7 mL). The organic layer was washed with 30% (w/v) aqueous NaCl (3 mL) and dried over MgSO₄. Filtration, concentration in vacuo, and purification by silica gel column chromatography using a 33-50% gradient of ethyl acetate in n-heptane as eluent provided 6.0 mg of the target product.

¹H NMR (400 MHz, CHLOROFORM-d) δ ppm 0.60 (q, J=7.82 Hz, 6H) 0.96 (t, J=7.82 Hz, 9H) 1.05 (s, 9H) 1.06 (s, 9H) 1.32-1.67 (m, 8H) 1.69 (t, J=3.13 Hz, 3H) 1.73-1.89 (m, 2H) 1.90-1.98 (m, 1H) 2.02-2.45 (m, 12H) 2.54-2.64 (m, 1H) 2.73-2.80 (m, 2H) 2.97 (dd, J=9.77, 3.13 Hz, 1H) 3.23 (s, 3H) 3.24 (s, 3H) 3.33 (br s, 4H) 3.39-3.48 (m, 1H)

3.52-3.63 (m, 2H) 3.66-3.77 (m, 1H) 3.78-3.93 (m, 3H) 4.04-4.16 (m, 1H) 4.18-4.25 (m, 2H) 4.27-4.32 (m, 1H) 4.35 (q, J=6.12 Hz, 1H) 4.42 (dd, J=7.62, 3.71 Hz, 1H) 4.51-4.58 (m, 4H) 4.82 (d, J=1.56 Hz, 1H) 4.95 (d, J=1.95 Hz, 1H) 5.52-5.63 (m, 1H) 7.26-7.46 (m, 16H) 7.50-7.57 (m, 2H) 7.63-7.70 (m, 6H) 7.72-7.79 (m, 2H) 7.98-8.01 (m, 2H) 8.03-8.06 (m, 2H)
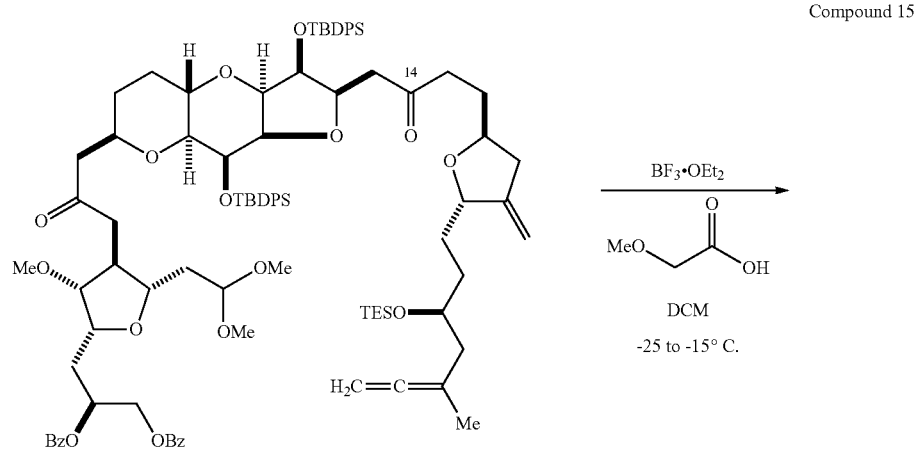
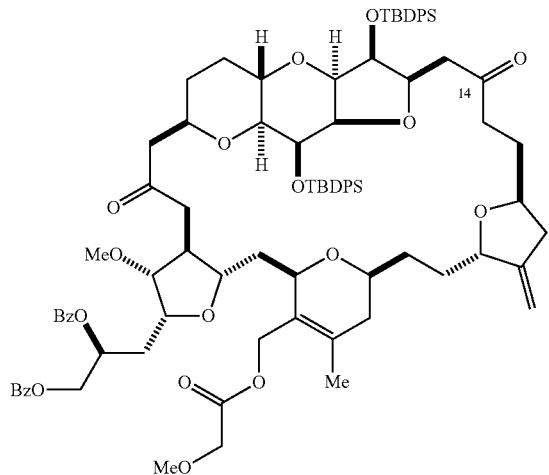

To a solution (R)-3-((2R,3R,4S,5S)-4-(3-((2R,3S,3aR, 4aS,7R,8aS,9S,9aR)-3,9-bis((tert-butyldiphenylsilyl)oxy)-2-(4-((2S,5S)-5-((S)-5-methyl-3-((triethylsilyl)oxy)hepta-5,6-dien-1-yl)-4-methylenetetrahydrofuran-2-yl)-2-oxobutyl)decahydrofuro[3,2-b]pyrano[2,3-e]pyran-7-yl)-2-oxopropyl)-5-(2,2-dimethoxyethyl)-3-methoxytetrahydrofuran-2-yl)propane-1,2-diyl dibenzoate (6.0 mg, 3.726 μmol) in dichloromethane (1.8 mL) at −25° C. were added methoxyacetic acid (8.6 μL, 0.112 mmol) and BF$_3$.OEt$_2$ (3.8 μL, 0.03 mmol). The reaction mixture was stirred between −20° C. and −15° C., and the reaction was monitored by TLC. Upon completion, the reaction was quenched with sat. aq. NaHCO$_3$ (2 mL). The resulting mixture was extracted twice with MTBE (10 mL). The combined organic layers were washed with 30% (w/v) aqueous NaCl (2 mL) and dried over MgSO$_4$. Filtration, concentration in vacuo, and purification by silica gel column chromatography using a 10-40% gradient of ethyl acetate in n-heptane as eluent provided 2.8 mg of the target product.

$^1$H NMR (400 MHz, CHLOROFORM-d) δ ppm 0.98 (s, 9H) 1.07 (s, 9H) 1.40-1.70 (m, 4H) 1.73 (s, 3H) 1.75-2.11 (m, 11H) 2.20 (t, J=6.45 Hz, 2H) 2.23-2.31 (m, 1H) 2.49 (br d, J=2.74 Hz, 1H) 2.50-2.55 (m, 1H) 2.58-3.10 (m, 4H) 2.92-3.02 (m, 1H) 3.03-3.12 (m, 2H) 3.39 (s, 3H) 3.37-3.42 (m, 1H) 3.42 (s, 3H) 3.45-3.51 (m, 2H) 3.63-3.70 (m, 2H) 3.74-3.89 (m, 3H) 3.94 (ddd, J=11.43, 7.72, 3.52 Hz, 1H) 4.00 (s, 2H) 4.04 (dd, J=8.79, 3.71 Hz, 1H) 4.11-4.26 (m, 2H) 4.33 (t, J=6.64 Hz, 2H) 4.56 (d, J=4.69 Hz, 2H) 4.60-4.72 (m, 2H) 4.82 (s, 1H) 4.95 (s, 1H) 5.54-5.67 (m, 1H) 7.29-7.45 (m, 16H) 7.49-7.57 (m, 2H) 7.57-7.70 (m, 8H) 7.98-8.02 (m, 2H) 8.02-8.08 (m, 2H)

Compound 17

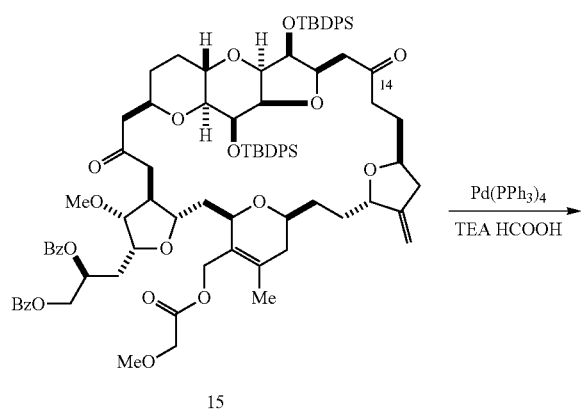

15

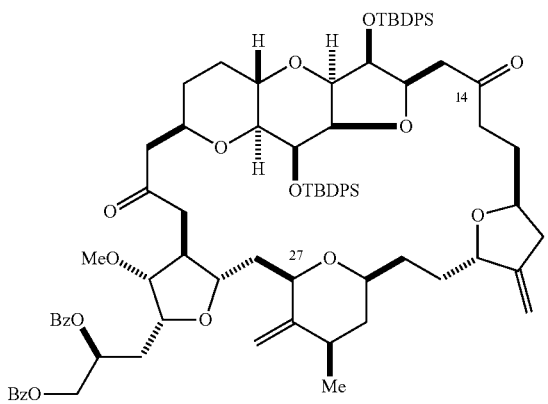

17

To a solution of compound 15 (1.3 mg, 0.85 μmol) in THF (0.5 mL) was added formic acid (1.6 μL, 0.043 mmol), triethylamine (6.0 μL, 0.043 mmol), and a solution of Pd(Ph$_3$P)$_4$ (0.5 mg, 0.42 μmol) and triphenylphosphine (0.5 mg, 1.7 μmol) in THF (0.1 mL). The resulting mixture was stirred at 60-65° C. overnight and cooled to ambient temperature. The reaction mixture was diluted with MTBE (5 mL), washed with sat. aq. NaHCO$_3$ (1 mL) and 30% (w/v) aqueous NaCl (1 mL), and dried over MgSO$_4$. Filtration, concentration in vacuo, and purification by silica gel column chromatography using a 20-50% gradient of ethyl acetate in n-heptane as eluent provided 0.2 mg of the target product, which was confirmed by NMR comparison with an authentic sample.

Alternative Synthesis Via Compound (IC)

Compound 17 may also be prepared according to the following reaction sequence from compound 8.

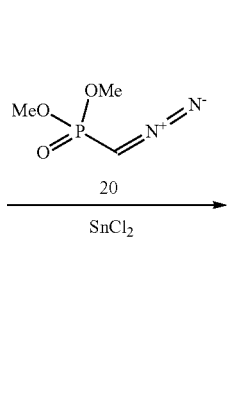

8

97
98
-continued
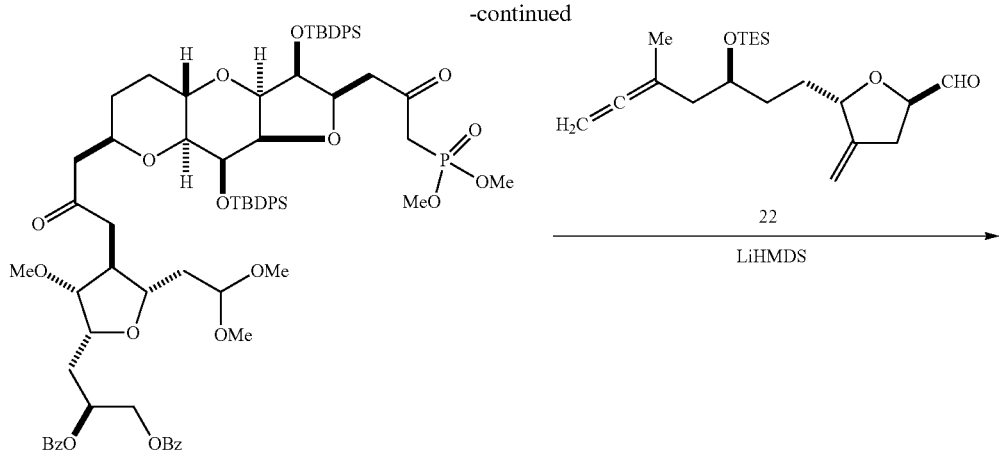
21
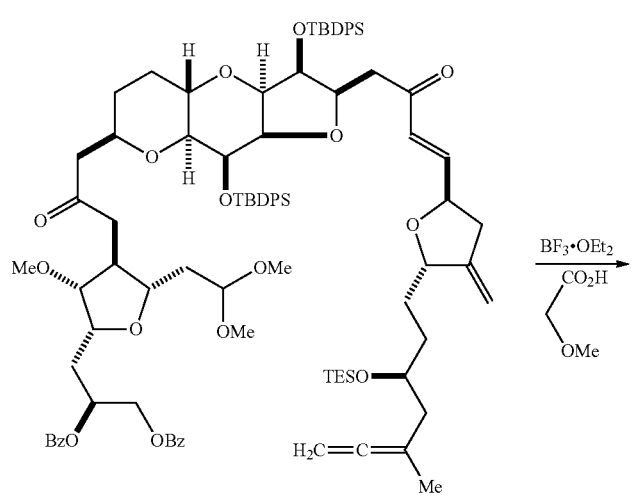
23
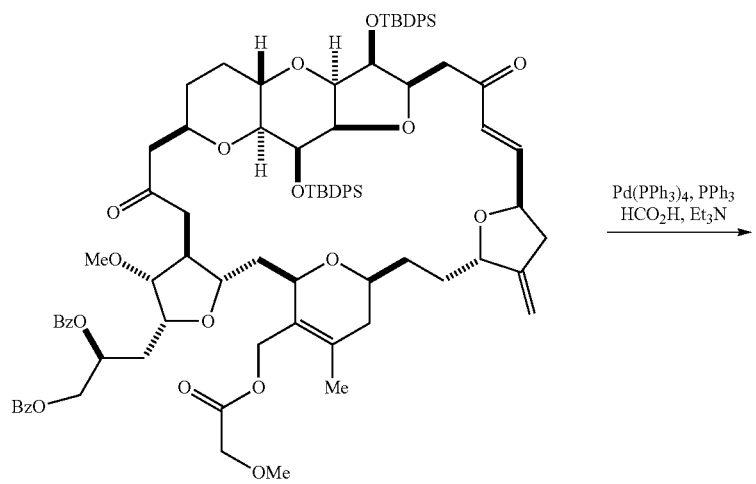
24

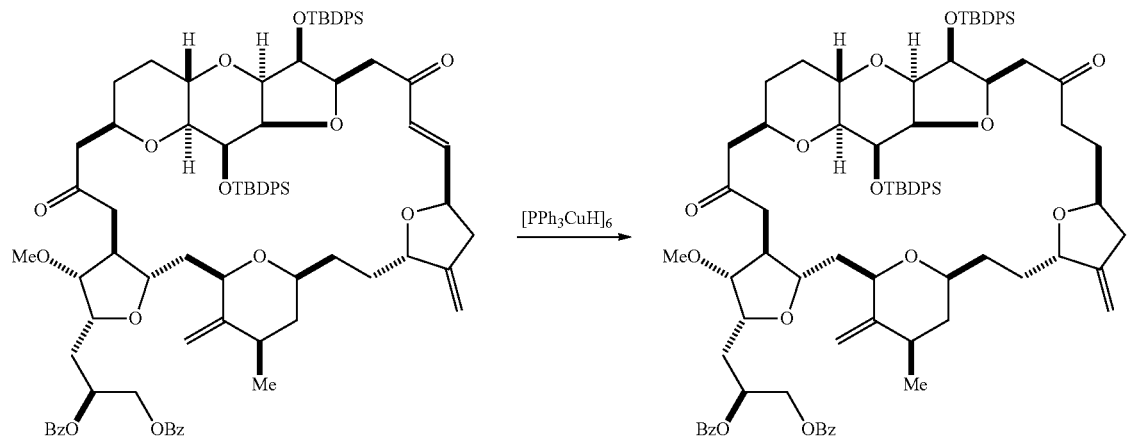

As illustrated in the above scheme, compound 8 can be reacted with Seyferth-Gilbert reagent 20 in the presence of $SnCl_2$ to give compound 21, which, upon reaction with a strong base (e.g., LiHMDS) and compound 22, can give compound 23. Compound 23 may be subjected to Prins reaction with an oxophilic Lewis acid and a carboxylic acid to give compound 24, which, upon allylic reduction (e.g., Pd-catalyzed allylic reduction) and 1,4-reduction (e.g., with Stryker's reagent), gives compound 17.

Example 2—Preparation of a Halichondrin Macrolide Analog Via a Compound of Formula (IJ)

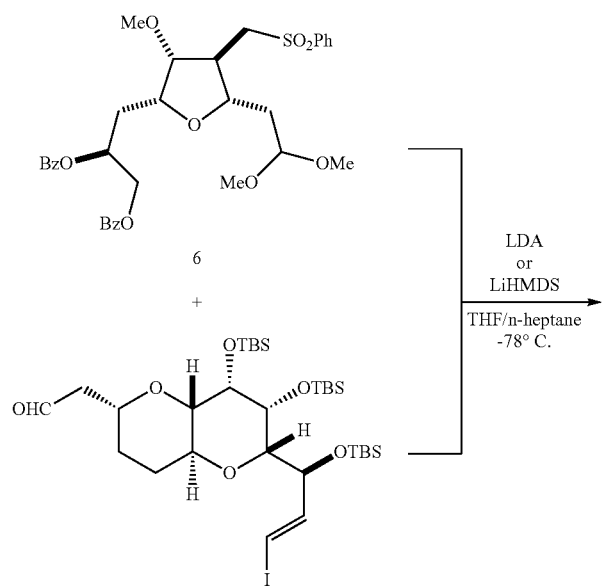

-continued
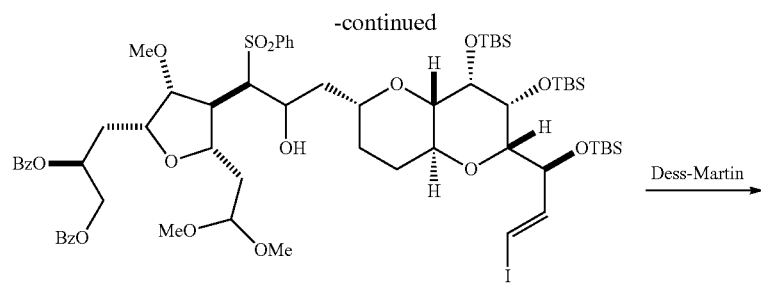
27
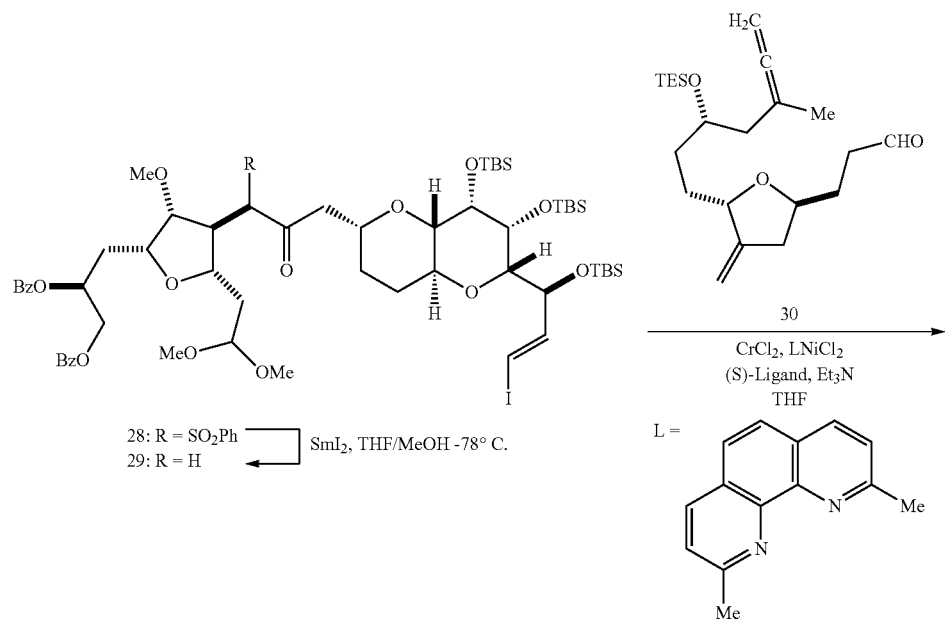
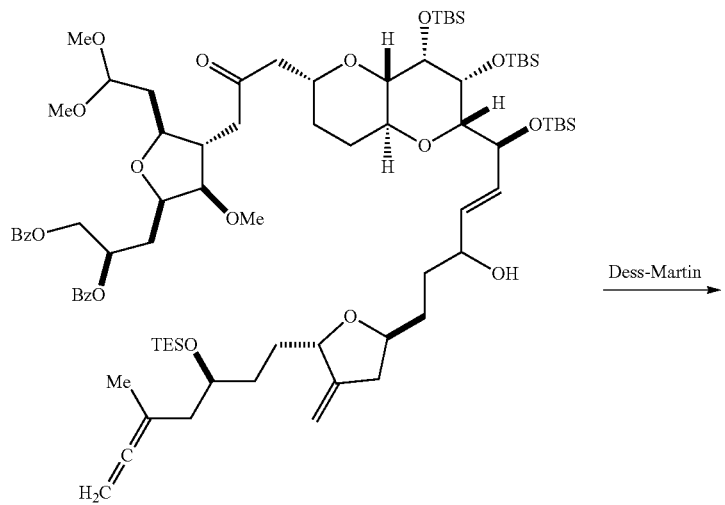
31

-continued
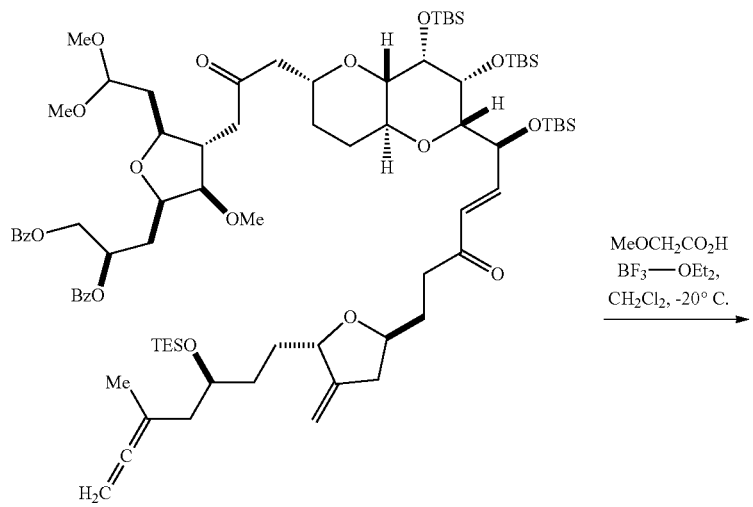
32
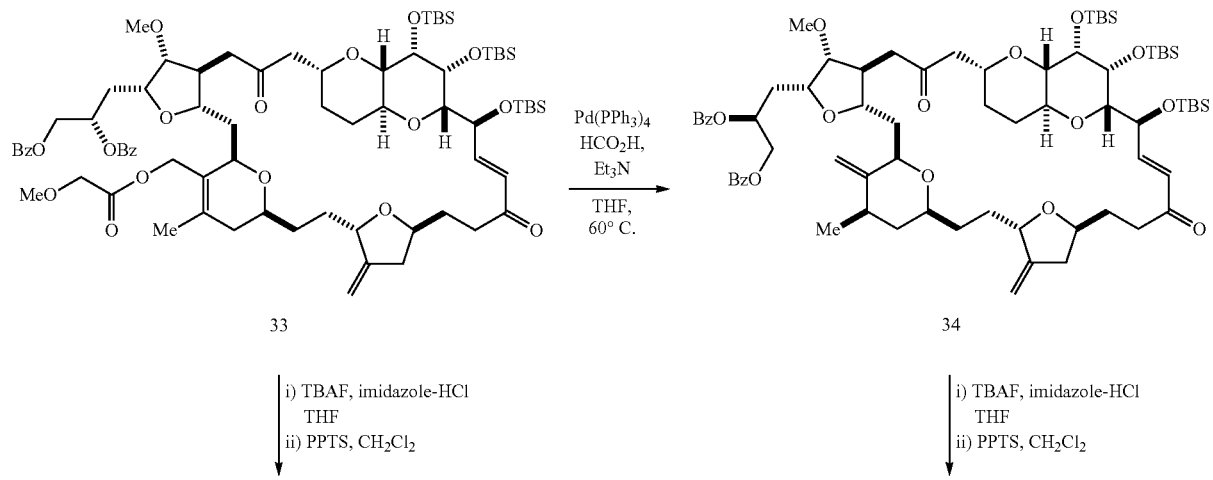
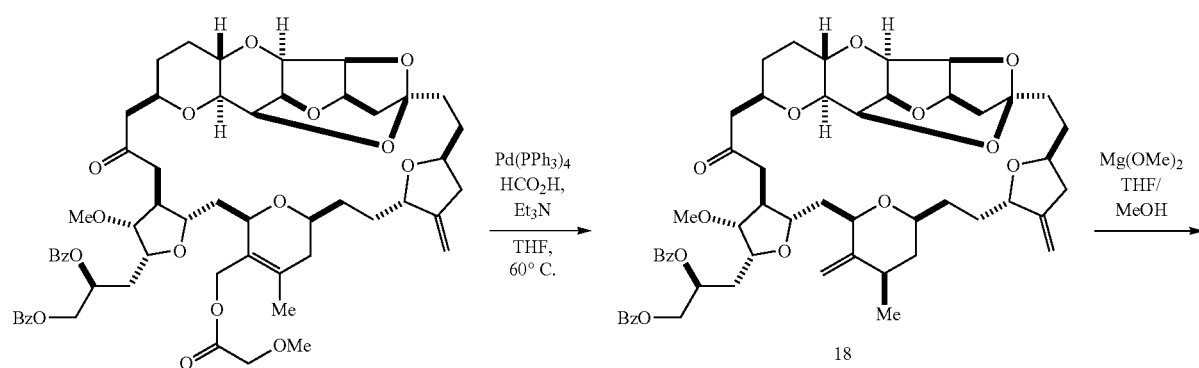

-continued

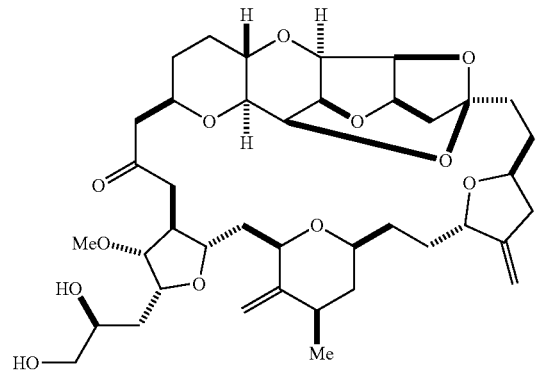

19

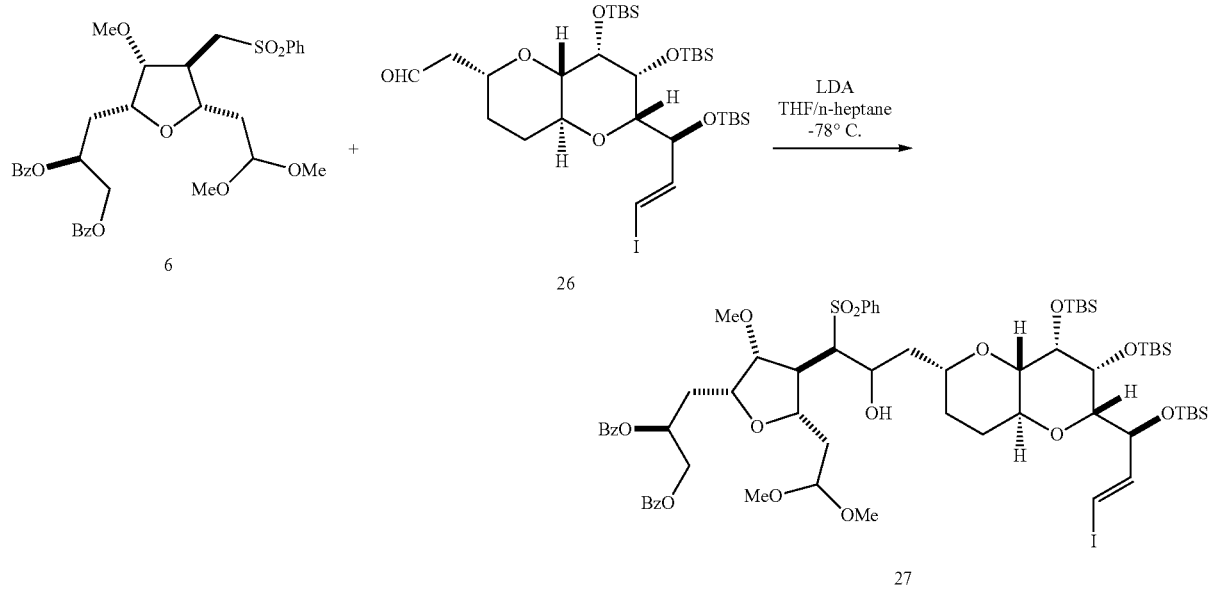

(2S)-3-((2R,3R,4S,5S)-4-((1R)-3-((2R,4aS,6S,7R, 8S,8aS)-7,8-bis((tert-butyldimethylsilyl)oxy)-6-((S, E)-1-((tert-butyldimethylsilyl)oxy)-3-iodoallyl)octa-hydropyrano[3,2-b]pyran-2-yl)-2-hydroxy-1-(phenylsulfonyl)propyl)-5-(2,2-dimethoxyethyl)-3-methoxytetrahydrofuran-2-yl)propane-1,2-diyl dibenzoate A solution of (S)-3-((2R,3R,4S,5S)-5-(2,2-dimethoxyethyl)-3-methoxy-4-((phenylsulfonyl)methyl)tetrahydrofuran-2-yl)propane-1,2-diyl dibenzoate (4.95 g, 7.89 mmol) (azeotroped twice with THF) in THF (40.5 mL) was cooled to −78° C. and treated with the freshly prepared lithium diisopropylamide (LDA, 19.7 mL, 0.40 M) maintaining the internal temperature below −68° C. After stirring at −78° C. for 30 min, the mixture was treated with a solution of 2-((2R,4aS,6S,7R,8S,8aS)-7,8-bis((tert-butyldimethylsilyl)oxy)-6-((S,E)-1-((tert-butyldimethylsilyl)oxy)-3-iodoallyl)octahydropyrano[3,2-b]pyran-2-yl)acetaldehyde (4.50 g, 6.07 mmol) in n-heptane (54.0 mL) over 15 min maintaining the internal temperature below −65° C. The mixture was stirred at −78° C. for 2 h, at which time the reaction was quenched with sat. aq. NH₄Cl (45.0 mL) and extracted twice with methyl tert-butyl ether (MTBE, 45.0 mL). The organic layers were combined, dried over MgSO₄ and concentrated in vacuo to give the title compound (8.6 g, 104%).

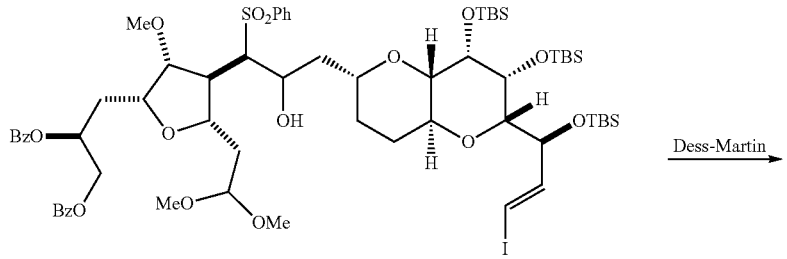

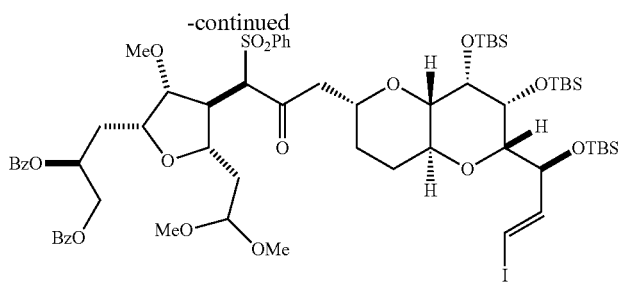

28

(S)-3-((2R,3R,4S,5S)-4-((R)-3-((2R,4aS,6S,7R,8S,8aS)-7,8-bis((tert-butyldimethylsilyl)oxy)-6-((S,E)-1-((tert-butyldimethylsilyl)oxy)-3-iodoallyl)octahydropyrano[3,2-b]pyran-2-yl)-2-oxo-1-(phenylsulfonyl)propyl)-5-(2,2-dimethoxyethyl)-3-methoxytetrahydrofuran-2-yl)propane-1,2-diyl dibenzoate A solution of a crude (2R)-3-((2R,3R,4S,5S)-4-((1S)-3-((2R,4aS,6S,7R,8S,8aS)-7,8-bis((tert-butyldimethylsilyl)oxy)-6-((S,E)-1-((tert-butyldimethylsilyl)oxy)-3-iodoallyl)octahydropyrano[3,2-b]pyran-2-yl)-2-hydroxy-1-(phenylsulfonyl)propyl)-5-(2,2-dimethoxyethyl)-3-methoxytetrahydrofuran-2-yl)propane-1,2-diyl dibenzoate (10.8 g, 7.88 mmol) in CH$_2$Cl$_2$ (162 mL) was treated with Dess-Martin periodinane (4.01 g, 9.45 mmol) and stirred at room temperature for 2 h. The reaction was quenched with sat. aq. NaHCO$_3$ (86 mL) and 20% (w/v) aq. Na$_2$SO$_3$ (86 mL). The mixture was extracted twice with MTBE (86 mL). The organic layers were combined, dried over MgSO$_4$, and concentrated in vacuo to give the title compound (11.23 g, 104%).

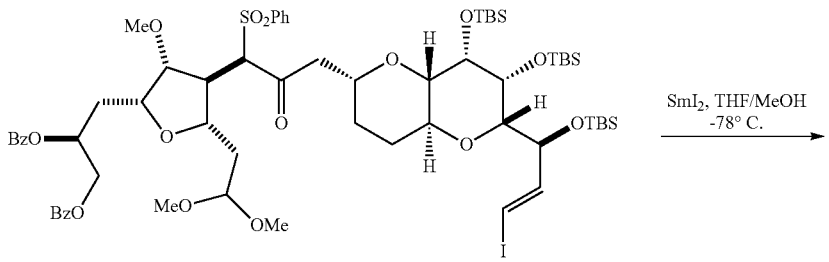

28

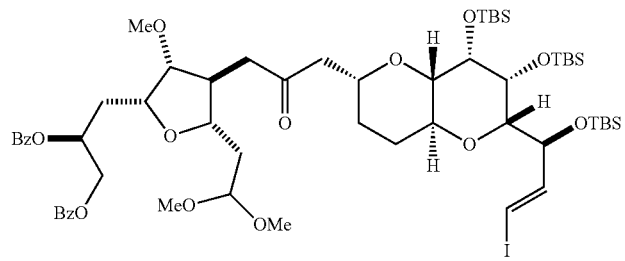

29

(S)-3-((2R,3R,4S,5S)-4-(3-((2R,4aS,6S,7R,8S,8aS)-7,8-bis((tert-butyldimethylsilyl)oxy)-6-((S,E)-1-((tert-butyldimethylsilyl)oxy)-3-iodoallyl)octahydro-pyrano[3,2-b]pyran-2-yl)-2-oxopropyl)-5-(2,2-dimethoxyethyl)-3-methoxytetrahydrofuran-2-yl)propane-1,2-diyl dibenzoate A solution of a crude (R)-3-((2R,3R,4S,5S)-4-((S)-3-((2R,4aS,6S,7R,8S,8aS)-7,8-bis((tert-butyldimethylsilyl)oxy)-6-((SE)-1-((tert-butyldimethylsilyl)oxy)-3-iodoallyl)octahydropyrano[3,2-b]pyran-2-yl)-2-oxo-1-(phenylsulfonyl)propyl)-5-(2,2-dimethoxyethyl)-3-methoxytetrahydrofuran-2-yl)propane-1,2-diyl dibenzoate (10.75 g, 7.87 mmol) in a mixture of THF (82 mL) and methanol (56 mL) and cooled to −78° C. and treated with 0.1 M SmI$_2$ in THF (197 mL, 19.7 mmol) over 40 min maintaining the internal temperature below −60° C. The resulting mixture was stirred at −78° C. for 1 h. The reaction was quenched with 40% (w/v) Rochelle's salt in water (153 mL), and the resulting mixture was warmed to room temperature. After treating with potassium carbonate (32.6 g, 236 mmol), the mixture was stirred at room temperature for 30 min and extracted twice with MTBE (108 mL). The organic layers were combined, washed with brine, and concentrated in vacuo. The residue was purified by silica gel column chromatography (ethyl acetate/n-heptane=10% to 25%) to give the title compound (6.65 g, 69% for 3 steps). $^1$H NMR (400 MHz, CHLOROFORM-d) δ ppm −0.01 (s, 3H), 0.01 (s, 3H), 0.02 (s, 3H), 0.08 (s, 6H), 0.09 (s, 3H), 0.85 (s, 9H), 0.91 (s, 9H), 0.92 (s, 9H), 1.21-1.40 (m, 2H), 1.67-1.76 (m, 1H), 1.82-1.97 (m, 3H), 2.12-2.25 (m, 2H), 2.34 (dd, J=16.61, 4.89 Hz, 1H), 2.42-2.46 (m, 3H), 2.66 (dd, J=16.41, 7.82 Hz, 1H), 2.92 (dd, J=9.57, 2.15 Hz, 1H), 3.26 (s, 3H), 3.27 (s, 3H), 3.35 (s, 3H), 3.39-3.48 (m, 2H), 3.49-3.57 (m, 1H), 3.77-3.94 (m, 4H), 4.03 (s, 1H), 4.45 (dd, J=6.64, 4.69 Hz, 1H), 4.55 (d, J=5.08 Hz, 2H), 4.87 (dd, J=8.01, 3.32 Hz, 1H), 5.50-5.67 (m, 1H), 6.27 (d, J=14.46 Hz, 1H), 6.84 (dd, J=14.46, 7.82 Hz, 1H), 7.35-7.48 (m, 4H), 7.49-7.63 (m, 2H), 7.91-8.11 (m, 4H).

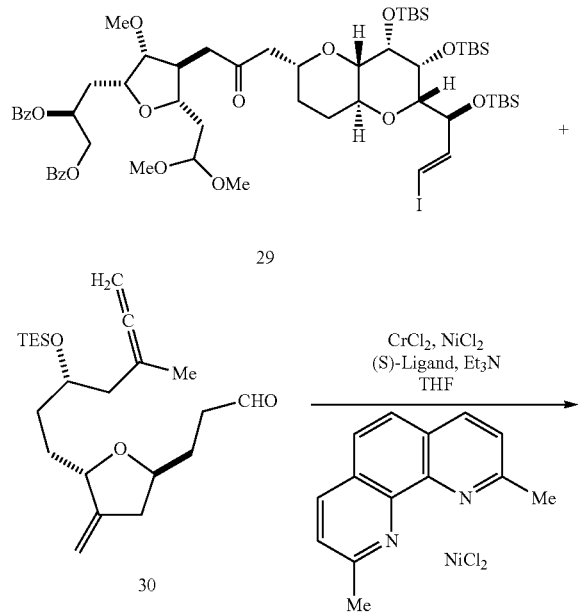

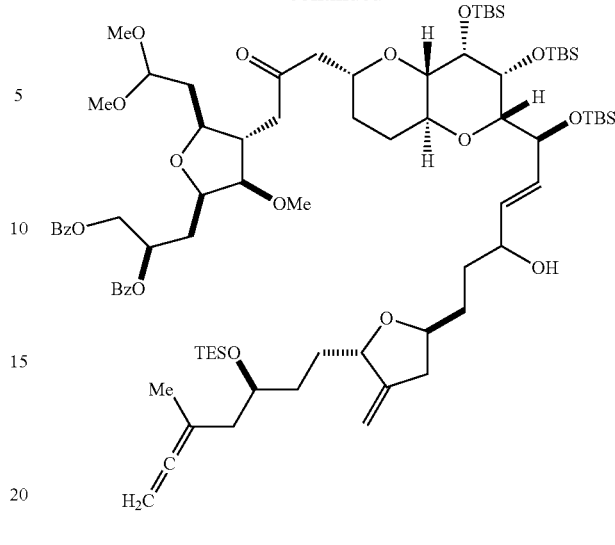

31

(2R)-3-((2R,3R,4S,5S)-4-(3-((2R,4aS,6S,7R,8S,8aS)-7,8-bis((tert-butyldimethylsilyl)oxy)-6-((1S,E)-1-((tert-butyldimethylsilyl)oxy)-4-hydroxy-6-((2S,5S)-5-((S)-5-methyl-3-((triethylsilyl)oxy)hepta-5,6-dien-1-yl)-4-methylenetetrahydrofuran-2-yl)hex-2-en-1-yl)octahydropyrano[3,2-b]pyran-2-yl)-2-oxopropyl)-5-(2,2-dimethoxyethyl)-3-methoxytetrahydrofuran-2-yl)propane-1,2-diyl dibenzoate A three-necked flask was purged with nitrogen and charged with (S)—N-(2-(4-isopropyl-4,5-dihydrooxazol-2-yl)-6-methylphenyl)methanesulfonamide ((S)-Ligand, 2.42 g, 8.16 mmol). After purging with nitrogen for 5 min, chromous chloride (1.00 g, 8.16 mmol) was added. After purging with nitrogen for 5 min, the mixture was heated to 35° C. and treated with Et$_3$N (1.14 mL, 8.16 mmol) maintaining the internal temperature below 35° C. The mixture was stirred at 30-35° C. for 1 h. After cooling to 0° C., the mixture was treated with nickel(II) chloride 2,9-dimethyl-1,10-phenanthroline complex (0.069 g, 0.20 mmol) and a solution of 3-((2S,5S)-5-((S)-5-methyl-3-((triethylsilyl)oxy)hepta-5,6-dien-1-yl)-4-methylenetetrahydrofuran-2-yl)propanal (1.066 g, 2.815 mmol) and (R)-3-((2R,3R,4S,5S)-4-(3-((2R,4aS,6S,7R,8S,8aS)-7,8-bis((tert-butyldimethylsilyl)oxy)-6-((S,E)-1-((tert-butyldimethylsilyl)oxy)-3-iodoallyl)octahydropyrano[3,2-b]pyran-2-yl)-2-oxopropyl)-5-(2,2-dimethoxyethyl)-3-methoxytetrahydrofuran-2-yl)propane-1,2-diyl dibenzoate (2.5 g, 2.04 mmol) in THF (11.25 mL). The mixture was stirred at 0° C. for 5 min and at room temperature for 16 h. After cooling to 0° C., the mixture was treated with 1,2-ethylenediamine (2.05 mL, 30.6 mmol) and stirred at room temperature for 1 h. The mixture was treated with water (25 mL) and n-heptane (37.5 mL). The organic layer was separated, and the aqueous layer was extracted twice with MTBE (30.0 mL). The organic layers were combined, dried over MgSO$_4$, and concentrated in vacuo. The residue was treated with 2-propanol (ca. 10 mL) and stirred at room temperature for 1 h. The precipitated ligand was filtered off and rinsed with 2-propanol. The filtrate was concentrated in vacuo. The residue was purified by silica gel column chromatography (ethyl acetate/n-heptane=10% to 40%) to give the title compound (1.398 g, 46%, a mixture of two isomers). ¹H NMR (400 MHz, CHLOROFORM-d, a mixture of two isomers) δ ppm −0.01 (s, 6H), 0.01-0.04 (m, 3H), 0.06 (s, 3H), 0.08-0.12 (m, 6H), 0.59 (q, J=8.08 Hz, 6H), 0.79-0.87 (m, 9H), 0.88-0.92 (m, 9H), 0.92-0.94 (m, 9H), 0.96 (t, J=8.21 Hz, 9H), 1.48-1.66 (m, 12H), 1.68 (t, J=2.93 Hz, 3H), 1.77-1.85 (m, 1H), 1.85-1.92 (m, 2H), 2.06-2.35 (m, 7H), 2.41-2.52 (m, 3H), 2.58-2.73 (m, 2H), 2.87-2.97 (m, 1H), 3.26 (2s, 6H), 3.35 (s, 3H), 3.38-3.42 (m, 1H), 3.43-3.60 (m, 2H), 3.73-3.85 (m, 3H), 3.86-3.94 (m, 2H), 3.96-4.07 (m, 2H), 4.31-4.40 (m, 1H), 4.42-4.47 (m, 1H), 4.50-4.64 (m, 4H), 4.83 (s, 1H), 4.96 (s, 1H), 4.99-5.10 (m, 1H), 5.49-5.62 (m, 1H), 5.62-5.75 (m, 1H), 5.78-5.99 (m, 1H), 7.35-7.47 (m, 4H), 7.48-7.64 (m, 2H), 7.93-8.13 (m, 4H).

methylenetetrahydrofuran-2-yl)hex-2-en-1-yl) octahydropyrano[3,2-b]pyran-2-yl)-2-oxopropyl)-5-(2,2-dimethoxyethyl)-3-methoxytetrahydrofuran-2-yl)propane-1,2-diyl dibenzoate (0.957 g, 0.647 mmol) in $CH_2Cl_2$ (9.6 mL) was treated with aq. sodium bicarbonate (0.163 g, 1.94 mmol) and Dess-Martin periodinane (0.33 g, 0.78 mmol). The mixture was stirred at room temperature for 40 min. The reaction was quenched with 20% (w/v) aq. $Na_2SO_3$ (7.66 mL) and sat. aq. $NaHCO_3$ (7.66 mL). The mixture was extracted twice with MTBE (9.57 mL). The organic layers were combined, washed with brine (9.6 mL), and concentrated in vacuo. The residue was purified by silica gel column chromatography (ethyl acetate in n-heptane=10% to 40%) to give the title compound (828 mg, 87%). ¹H NMR (400 MHz, CHLOROFORM-d) δ ppm −0.03 (s, 3H), −0.01 (s, 3H), 0.04 (s, 3H), 0.09 (s, 3H), 0.11 (s, 6H), 0.58 (q, J=7.43 Hz, 6H), 0.86 (s, 9H), 0.92 (s, 9H), 0.93 (s, 9H), 0.96 (t, J=7.82 Hz, 9H), 1.47-1.66 (m, 7H), 1.68 (t, J=3.32 Hz, 3H), 1.71-1.84 (m, 4H), 1.85-1.93 (m, 2H), 2.05-2.17 (m, 2H), 2.18-2.34 (m, 5H), 2.52-2.78 (m, 5H), 2.86-2.97 (m, 1H), 3.26 (2s, 6H), 3.28-3.32 (m, 1H), 3.35 (s, 3H), 3.37-3.45 (m, 1H), 3.46-3.56 (m, 1H), 3.73-3.86 (m, 2H), 3.87-3.97 (m, 3H), 3.97-4.07 (m, 2H), 4.33 (br s, 1H), 4.39-4.49 (m, 1H), 4.51-4.63 (m, 4H), 4.83 (s, 1H), 4.96 (s, 1H), 5.04-5.18 (m, 1H), 5.49-5.66 (m, 1H), 6.29 (d, J=16.02 Hz, 1H), 7.07 (dd, J=16.22, 7.23 Hz, 1H), 7.33-7.48 (m, 4H), 7.48-7.62 (m, 2H), 7.97-8.13 (m, 4H).

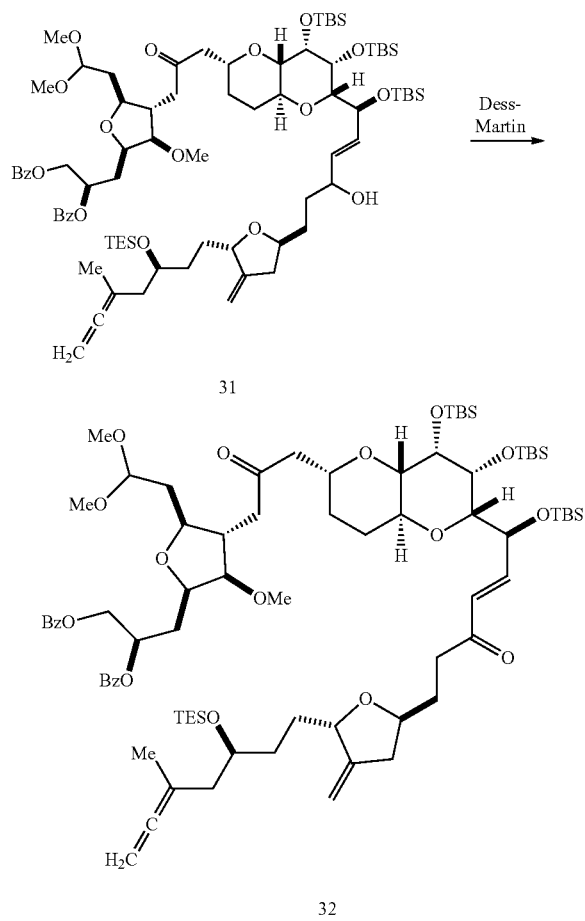

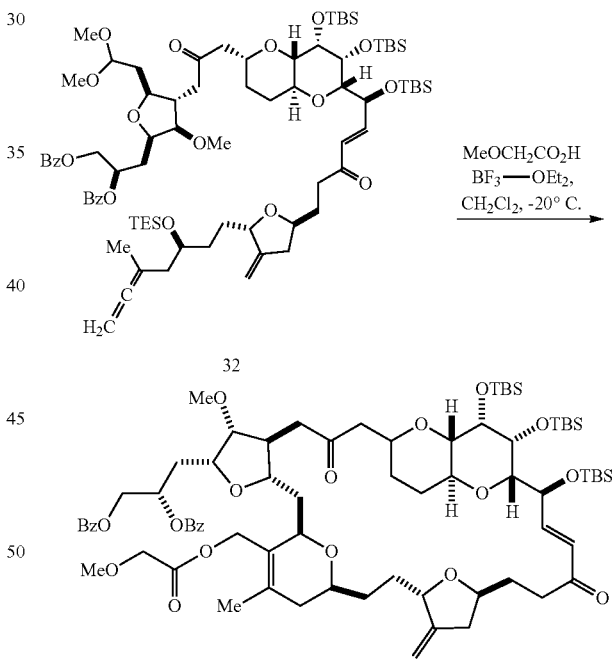

Compound 33.

A solution of (R)-3-((2R,3R,4S,5S)-4-(3-((2R,4aS,6S,7R,8S,8aS)-7,8-bis((tert-butyldimethylsilyl)oxy)-6-((S,E)-1-((tert-butyldimethylsilyl)oxy)-6-((2S,5S)-5-((S)-5-methyl-3-((triethylsilyl)oxy)hepta-5,6-dien-1-yl)-4-methylenetetrahydrofuran-2-yl)-4-oxohex-2-en-1-yl) octahydropyrano[3,2-b]pyran-2-yl)-2-oxopropyl)-5-(2,2-dimethoxyethyl)-3-methoxytetrahydrofuran-2-yl)propane-1,2-diyl dibenzoate (0.10 g, 0.068 mmol) in $CH_2Cl_2$ (22 mL) was cooled to −25° C. and treated with methoxyacetic acid (R)-3-((2R,3R,4S,5S)-4-(3-((2R,4aS,6S,7R,8S,8aS)-7,8-bis((tert-butyldimethylsilyl)oxy)-6-((S,E)-1-((tert-butyldimethylsilyl)oxy)-6-((2S,5S)-5-((S)-5-methyl-3-((triethylsilyl)oxy)hepta-5,6-dien-1-yl)-4-methylenetetrahydrofuran-2-yl)-4-oxohex-2-en-1-yl) octahydropyrano[3,2-b]pyran-2-yl)-2-oxopropyl)-5-(2,2-dimethoxyethyl)-3-methoxytetrahydrofuran-2-yl)propane-1,2-diyl dibenzoate A solution of (2R)-3-((2R,3R,4S,5S)-4-(3-((2R,4aS,6S,7R,8S,8aS)-7,8-bis((tert-butyldimethylsilyl)oxy)-6-((1S,E)-1-((tert-butyldimethylsilyl)oxy)-4-hydroxy-6-((2S,5S)-5-((S)-5-methyl-3-((triethylsilyl)oxy)hepta-5,6-dien-1-yl)-4-

(0.104 mL, 1.36 mmol) and BF$_3$.OEt$_2$ (0.026 mL, 0.20 mmol). The mixture was stirred at −25° C. to −15° C. for 3 h. Additional BF$_3$.OEt$_2$ (0.017 mL, 0.135 mmol) was added, and stirring was continued at −15 to −25° C. for another 1 h. The reaction was quenched with sat. aq. NaHCO$_3$ (20 mL). The mixture was extracted twice with MTBE (20 mL). The organic layers were combined, washed with brine, and concentrated in vacuo. The residue was purified by silica gel column chromatography (ethyl acetate in n-heptane=10% to 40%) to give the title compound (26 mg, 28%). $^1$H NMR (400 MHz, CHLOROFORM-d) δ ppm −0.05 (s, 3H), 0.03 (s, 3H), 0.12 (s, 9H), 0.16 (s, 3H), 0.87 (s, 9H), 0.93 (s, 9H), 0.96 (s, 9H), 1.29-1.43 (m, 3H), 1.44-1.55 (m, 2H), 1.62-1.80 (m, 5H), 1.73 (s, 3H), 1.80-2.02 (m, 5H), 2.13-2.23 (m, 2H), 2.24-2.36 (m, 1H), 2.38-2.51 (m, 3H), 2.51-2.61 (m, 1H), 2.63-2.75 (m, 3H), 2.83 (dd, J=16.41, 6.64 Hz, 1H), 2.92 (dd, J=9.38, 1.95 Hz, 1H), 3.31 (s, 3H), 3.35-3.44 (m, 2H), 3.41 (s, 3H), 3.49-3.63 (m, 2H), 3.72-3.85 (m, 1H), 3.85-3.94 (m, 2H), 3.98 (s, 2H), 4.00-4.08 (m, 3H), 4.16-4.24 (m, 1H), 4.25-4.33 (m, 1H), 4.45-4.59 (m, 2H), 4.61-4.75 (m, 1H), 4.83 (br s, 1H), 4.94-5.05 (m, 2H), 5.48-5.73 (m, 1H), 6.34 (d, J=16.02 Hz, 1H), 7.19-7.29 (m, 1H), 7.34-7.48 (m, 4H), 7.49-7.61 (m, 2H), 7.91-8.16 (m, 4H).

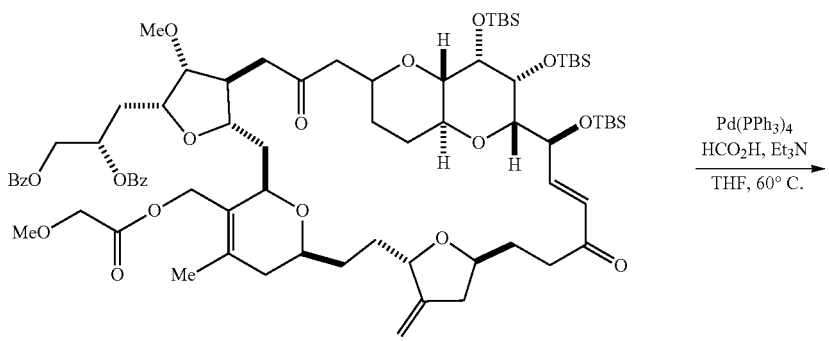

33

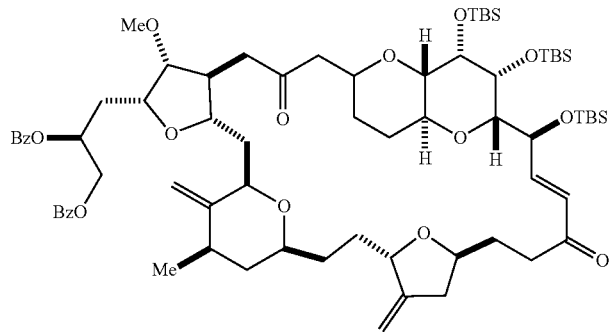

34

Compound 34.

To a mixture of Pd(Ph₃P)₄ (2.1 mg, 1.80 μmol) and triphenylphosphine (1.9 mg, 7.2 μmol) in THF (1.0 mL) was added a solution of compound 33 (25 mg, 0.018 mmol) in THF (1.0 mL), formic acid (0.017 mL, 0.45 mmol), and triethylamine (0.063 mL, 0.45 mmol). The mixture was stirred at 60° C. for 3 d. Additional Pd(Ph₃P)₄ (2.1 mg, 1.8 μmol), triethylamine (0.063 mL, 0.45 mmol), and formic acid (0.017 mL, 0.45 mmol) were added, and stirring was continued at 60° C. for 1 d. The mixture was diluted with MTBE and washed with sat. aq. NaHCO₃. The organic layer was concentrated in vacuo and purified by silica gel column chromatography (ethyl acetate in n-heptane=10% to 25%) to give the title compound (17 mg, 73%). ¹H NMR (400 MHz, CHLOROFORM-d) δ ppm −0.06 (s, 3H), 0.02 (s, 3H), 0.11 (s, 9H), 0.18 (s, 3H), 0.88 (s, 9H), 0.95 (s, 9H), 0.98 (s, 9H), 1.07 (d, J=6.25 Hz, 3H), 1.24-1.34 (m, 2H), 1.35-1.45 (m, 1H), 1.47-1.56 (m, 3H), 1.56-1.64 (m, 1H), 1.64-1.73 (m, 3H), 1.74-1.84 (m, 3H), 1.85-1.94 (m, 1H), 1.96-2.04 (m, 1H), 2.15-2.36 (m, 4H), 2.43-2.58 (m, 3H), 2.59-2.77 (m, 4H), 2.83 (dd, J=16.02, 7.03 Hz, 1H), 2.92 (dd, J=9.38, 1.95 Hz, 1H), 3.34 (s, 3H), 3.37-3.46 (m, 1H), 3.48-3.60 (m, 2H), 3.71-3.84 (m, 2H), 3.84-3.94 (m, 2H), 3.96-4.10 (m, 4H), 4.21 (br s, 1H), 4.51-4.64 (m, 2H), 4.76 (s, 1H), 4.84 (br s, 2H), 4.95-5.10 (m, 2H), 5.52-5.71 (m, 1H), 6.35 (d, J=16.41 Hz, 1H), 7.34-7.47 (m, 4H), 7.50-7.64 (m, 2H), 7.91-8.13 (m, 4H).

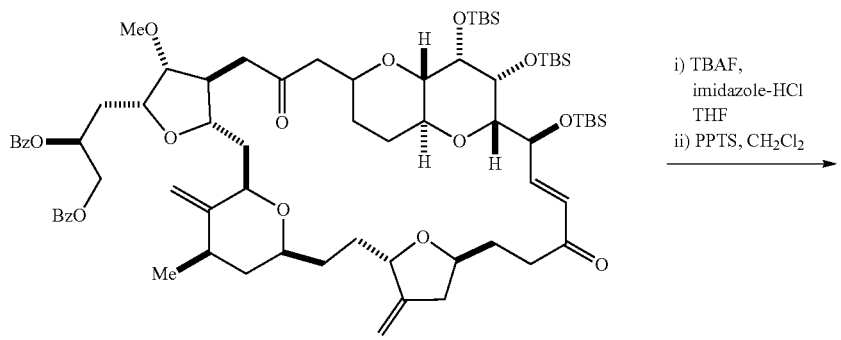

34 i) TBAF, imidazole-HCl THF
ii) PPTS, CH₂Cl₂

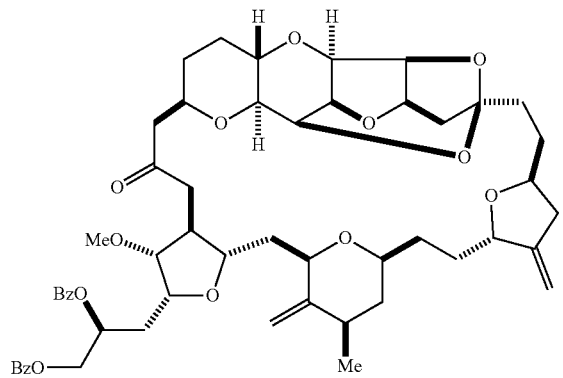

18

Compound 18.

A mixture of imidazole hydrochloride (0.011 g, 0.11 mmol) and 1 M tetrabutylammonium fluoride (TBAF) in THF (0.23 mL, 0.23 mmol) was diluted with THF (0.46 mL) and treated with a solution of compound 34 (0.023 g, 0.018 mmol) in THF (0.69 mL). After stirring at room temperature for 2 d, the mixture was treated with toluene (2.3 mL) and water (1.2 mL). The organic layer was separated and the aqueous layer was extracted twice with a mixture of toluene (1.2 mL) and THF (1.2 mL). The organic layers were combined and concentrated in vacuo. The residue was azeotroped twice with acetonitrile (1.2 mL).

The residue was dissolved in $CH_2Cl_2$ (3 mL), treated with PPTS (0.045 g, 0.18 mmol), and stirred at room temperature for 1 d. The mixture was concentrated in vacuo and purified by silica gel column chromatography (ethyl acetate in n-heptane=10% to 80%) to give the title compound (12 mg, 72%).

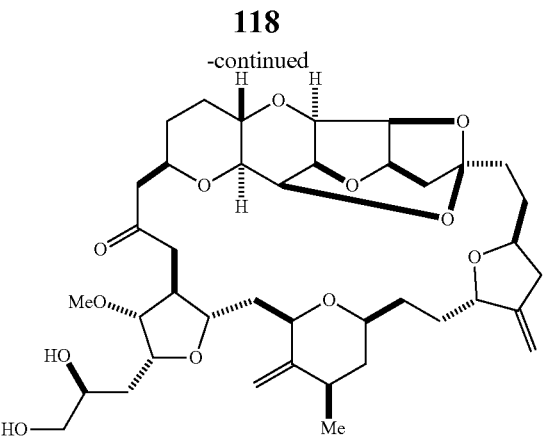

19

Compound 19.

A solution of compound 18 (0.012 g, 0.013 mmol) in a mixture of THF (0.024 mL) and methanol (0.48 mL) was treated with 6-10% (w/v) $Mg(OMe)_2$ in methanol (0.051 g, 0.038 mmol), and the resulting mixture was stirred at room temperature for 20 h. Additional 6-10% $Mg(OMe)_2$ in methanol (0.051 g, 0.038 mmol) was added and stirring was continued at rt for another 1 d. After concentration, the mixture was purified by silica gel column chromatography (ethyl acetate in n-heptane=30% to 100% and then 5% MeOH in ethyl acetate) to give the title compound (4 mg, 43%).

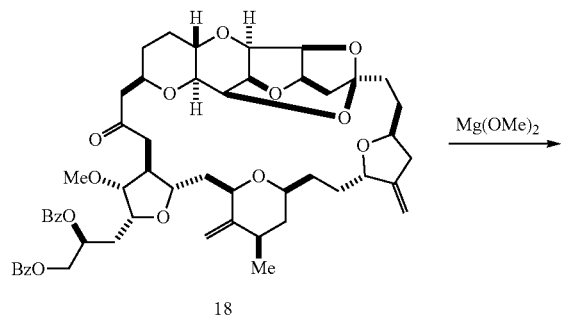

18

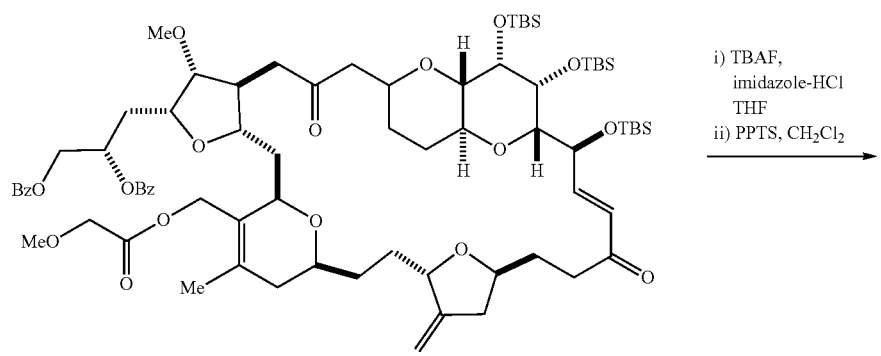

33

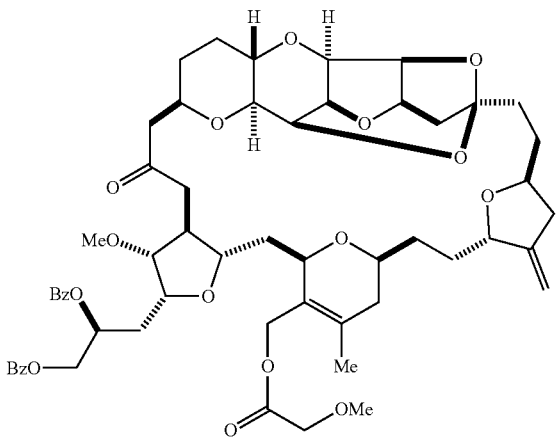

35

Compound 35.

A mixture of imidazole hydrochloride (0.022 g, 0.21 mmol) and 1 M TBAF in THF (0.44 mL, 0.44 mmol) was diluted with THF (0.94 mL) and treated with a solution of compound 33 (0.094 g, 0.068 mmol) in THF (2.256 mL). The mixture was stirred at room temperature for 7 d. After dilution with toluene (2.35 mL) and water (2.35 mL), the organic layer was separated, and the aqueous layer was extracted twice with a mixture of toluene (1.6 mL) and THF (1.6 mL). The organic layers were combined, concentrated in vacuo, and azeotroped twice with acetonitrile (4.7 mL).

The residue was dissolved in $CH_2Cl_2$ (3.55 mL), treated with pyridinium p-tolunesulfonate (PPTS, 0.094 g, 0.37 mmol), and stirred at room temperature for 1 d. Additional PPTS (0.094 g, 0.37 mmol) was added, and stirring was continued at room temperature for another 3 d. After concentration, the mixture was dissolved in ethyl acetate and filtered through a glass filter to remove insoluble solid (PPTS). The filtrate was concentrate in vacuo and purified by silica gel column chromatography (ethyl acetate in n-heptane=10% to 80%) to give the title compound (18 mg, 26%). $^1$H NMR (400 MHz, CHLOROFORM-d) δ ppm 1.29-1.48 (m, 3H), 1.50-1.71 (m, 4H), 1.74 (s, 3H), 1.78-2.35 (m, 13H), 2.37-2.61 (m, 3H), 2.68-2.81 (m, 2H), 2.82-2.96 (m, 1H), 3.38-3.46 (m, 2H), 3.40 (s, 3H), 3.44 (s, 3H), 3.48-3.59 (m, 1H), 3.68-3.76 (m, 1H), 3.77-3.84 (m, 1H), 3.85-3.96 (m, 2H), 3.97-4.07 (m, 4H), 4.08-4.21 (m, 2H), 4.24-4.37 (m, 3H), 4.50-4.62 (m, 3H), 4.62-4.70 (m, 2H), 4.76 (d, J=12.51 Hz, 1H), 4.87 (br s, 1H), 5.01 (br s, 1H), 5.45-5.71 (m, 1H), 7.32-7.47 (m, 4H), 7.48-7.62 (m, 2H), 7.90-8.14 (m, 4H).

Compound 18.

To a mixture of $Pd(Ph_3P)_4$ (2.0 mg, 1.8 μmol) and triphenylphosphine (1.8 mg, 7.0 μmol) in THF (0.72 mL) was added a solution of compound 35 (0.018 g, 0.018 mmol), formic acid (0.013 mL, 0.35 mmol), and triethylamine (0.049 mL, 0.35 mmol) in THF (0.72 mL). The mixture was stirred at 60° C. for 20 h. Additional triethylamine (0.049 mL, 0.35 mmol) and formic acid (0.013 mL, 0.35 mmol) were added and stirring was continued at 60° C. for another 2.5 d. After dilution with MTBE, the mixture was washed with sat. aq. $NaHCO_3$. The organic layer was concentrated in vacuo and purified by silica gel column chromatography (ethyl acetate in n-heptane=10% to 80%) to give the title compound (18 mg). $^1$H NMR (400 MHz, CHLOROFORM-d) δ 1.08 (d, J=6.25 Hz, 3H), 1.28-1.35 (m, 2H), 1.36-1.48 (m, 3H), 1.56-1.62 (m, 1H), 1.63-1.77 (m, 3H), 1.81-1.99 (m, 3H), 2.05-2.34 (m, 11H), 2.37-2.53 (m, 3H), 2.67 (dd, J=16.22, 9.97 Hz, 1H), 2.78-2.89 (m, 2H), 3.32 (d, J=3.52 Hz, 1H), 3.39-3.46 (m, 3H), 3.51-3.64 (m, 2H), 3.72-3.79 (m, 1H), 3.79-3.86 (m, 1H), 3.89-3.98 (m, 1H), 4.02 (d, J=6.45, 4.49 Hz, 1H), 4.06-4.15 (m, 1H), 4.18 (dd, J=6.45, 4.49 Hz, 1H), 4.24-4.37 (m, 3H), 4.56 (d, J=5.08 Hz, 2H), 4.60 (t, J=4.30 Hz, 1H), 4.68 (t, J=5.08 Hz, 1H), 4.79 (s, 1H), 4.86 (br s, 1H), 4.88 (s, 1H), 4.97-5.03 (m, 1H), 5.50-5.62 (m, 1H), 7.35-7.47 (m, 4H), 7.49-7.62 (m, 2H), 7.97-8.09 (m, 4H).

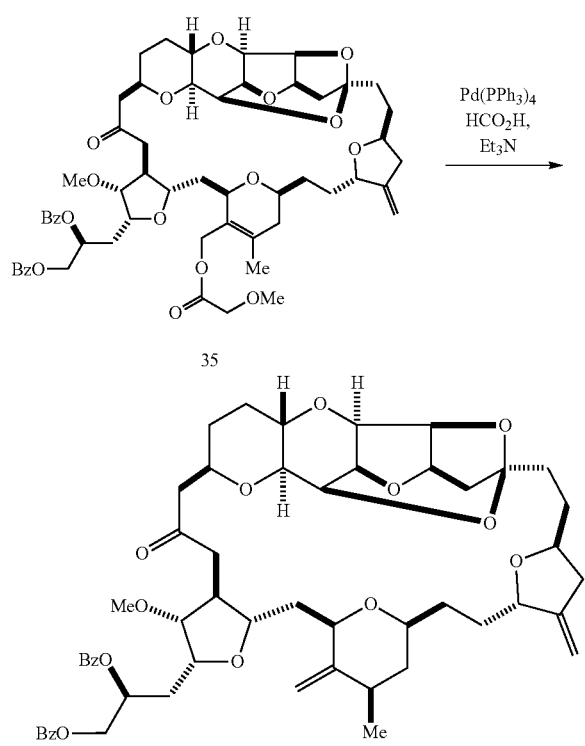

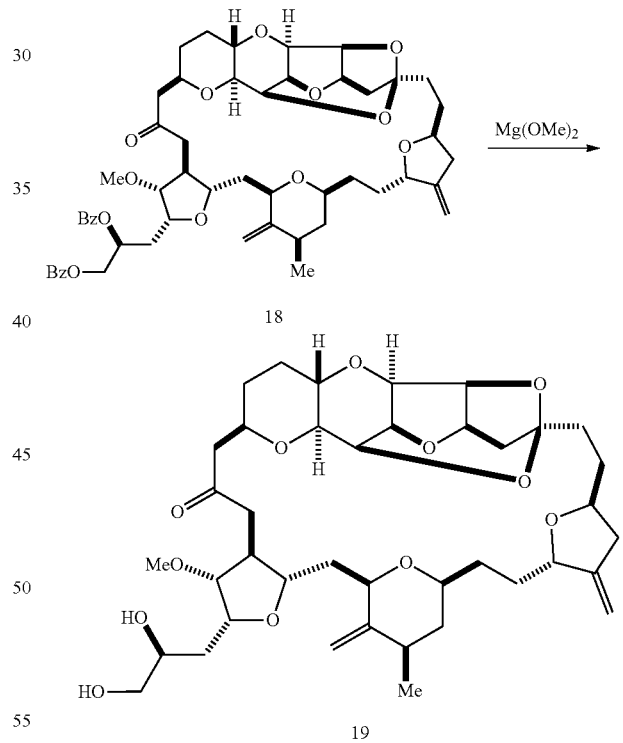

Compound 19.

A solution of compound 18 (0.018 g, 0.019 mmol) in a mixture of THF (0.045 mL) and methanol (0.9 mL) was treated with 6-10% (w/v) $Mg(OMe)_2$ in methanol (0.186 mL, 0.134 mmol), and stirred at rt for 3 d. After concentration, the mixture was purified by silica gel column chromatography (ethyl acetate in n-heptane=30% to 100% and 5% MeOH in ethyl acetate) to give the title compound (3 mg, 23% for 2 steps). $^1$H NMR (400 MHz, CHLOROFORM-d) δ 1.08 (d, J=6.25 Hz, 3H), 1.28-1.51 (m, 5H), 1.58-1.63 (m, 2H), 1.66-1.79 (m, 4H), 1.88-2.02 (m, 4H), 2.06-2.56 (m, 12H), 2.71 (dd, J=15.83, 9.97 Hz, 1H), 2.81-2.92 (m, 2H), 3.29 (d, J=0.78 Hz, 1H), 3.30-3.35 (m, 1H), 3.43 (s, 3H), 3.50-3.70 (m, 4H), 3.85 (dt, J=9.48, 3.27 Hz, 1H), 3.88-3.98 (m, 3H), 4.03 (dd, J=6.25, 4.30 Hz, 1H), 4.09-4.12 (m, 1H), 4.18 (dd, J=6.64, 4.69 Hz, 1H), 4.29 (dd, J=10.55, 3.52 Hz, 1H), 4.31-4.39 (m, 2H), 4.60 (t, J=4.49 Hz, 1H), 4.69 (t, J=4.30 Hz, 1H), 4.81 (s, 1H), 4.89 (s, 1H), 4.93 (br s, 1H), 5.07 (br s, 1H).
Example 3—Preparation of a Halichondrin Macrolide Analog Via a Compound of Formula (IJ)
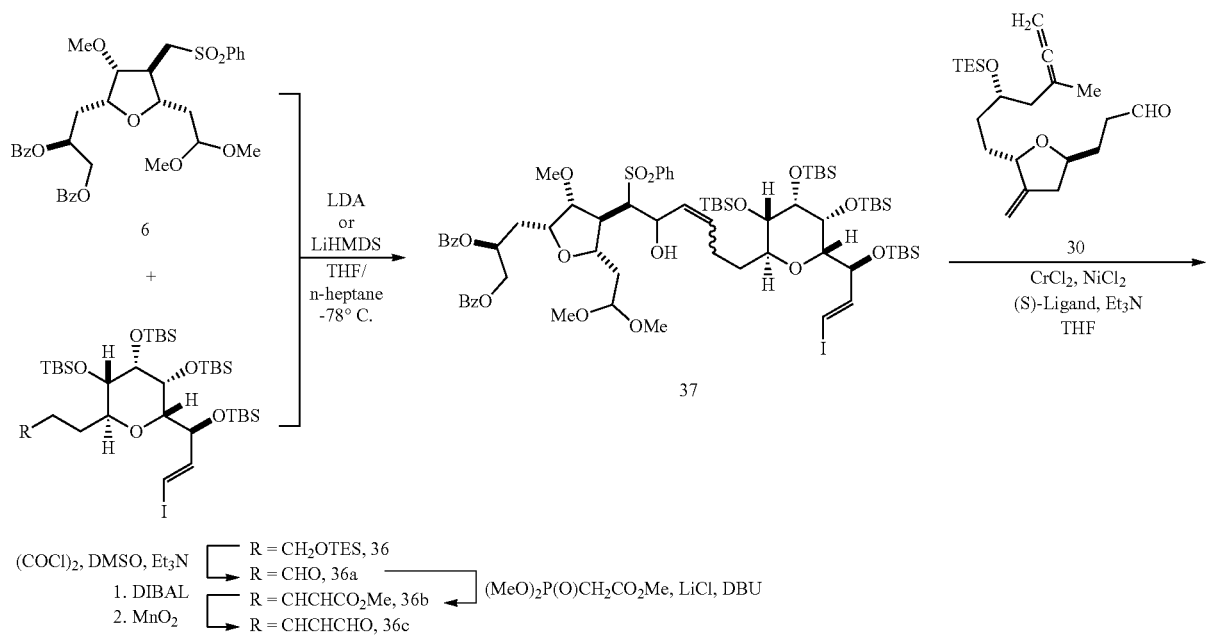
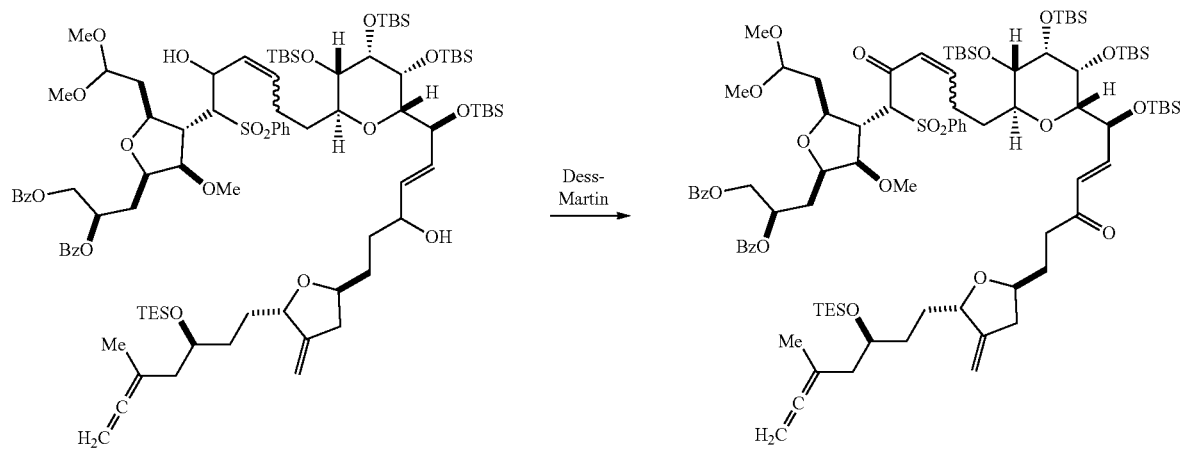

-continued

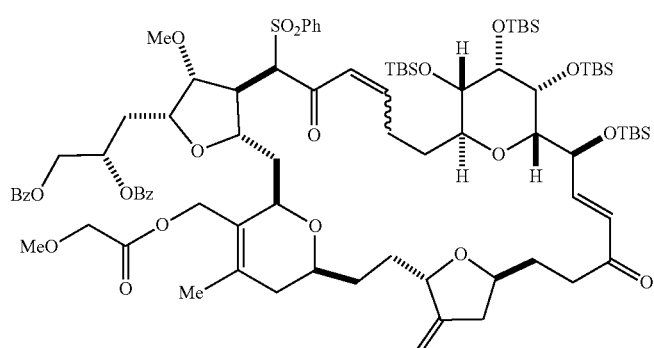

40

An exemplary compound of formula (IA) can be prepared as shown in the above scheme. Compound 36 can be homologated in accordance with the following sequence: Swern oxidation, Horner-Wadsworth-Emmons reaction (Masamune/Roush conditions), reduction with DIBAL-H, and oxidation with $MnO_2$. The homologated compound 36 can then be treated with compound 6, which can be deprotonated with, e.g., LDA or LiHMDS, to give compound 37. Reacting compound 37 with compound 30 under Nozaki-Hiyama-Kishi reaction conditions provides compound 38 (an exemplary compound of formula (IA)). Subsequent oxidation of compound 38 with Dess-Martin periodinane gives compound 39 (another exemplary compound of formula (IA)). Compound 39 can be converted to compound 40 (an exemplary compound of formula (IB)) by a reaction with methoxyacetic acid and $BF_3 \cdot OEt_2$ (exemplary Prins reaction conditions).

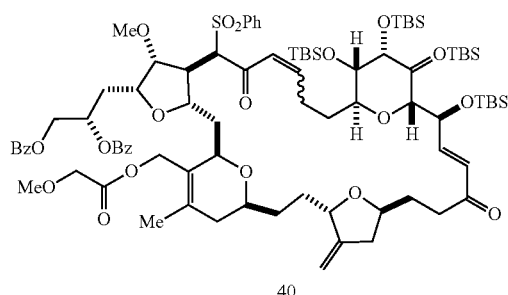

40 i) TBAF, imidazole-HCl
  THF
ii) PPTS, $CH_2Cl_2$
iii) $SmI_2$, THF, MeOH,
  -78° C.

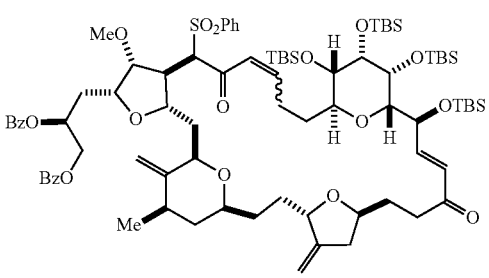

41 i) TBAF, imidazole-HCl
  THF
ii) PPTS, $CH_2Cl_2$
iii) $SmI_2$, THF, MeOH,
  -78° C.

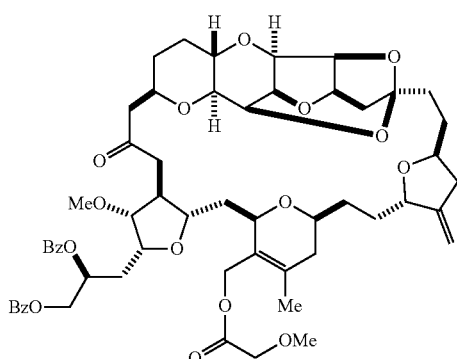

35

Pd(PPh₃)₄
HCO₂H,
Et₃N
———→
THF, 60° C.

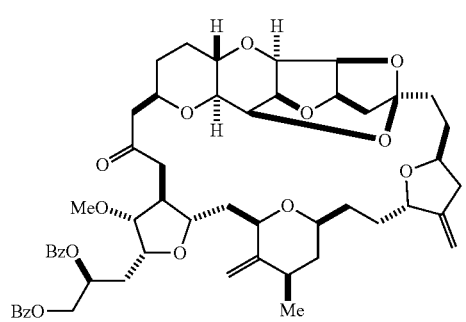

18

An exemplary halichondrin macrolide analog can be prepared from a compound of formula (IB) as shown in the above scheme. Provided herein are two pathways that can be used to access compound 18 from compound 40. In one approach, compound 40 can be reacted with an allylic reducing agent (e.g., Pd(PPh$_3$)$_4$/HCO$_2$H/Et$_3$N) to give compound 41, which upon global desilylation with a fluoride source (e.g., TBAF, buffered with imidazolium hydrochloride), PPTS-catalyzed ketalization, and reductive desulfonylation (e.g., with SmI$_2$) can afford compound 18. Alternatively, compound 40 can be first converted to compound 35 through global desilylation with a fluoride source (e.g., TBAF, buffered with imidazolium hydrochloride), PPTS-catalyzed ketalization, and reductive desulfonylation (e.g., with SmI$_2$). Compound 35 was reacted with an allylic reducing agent (e.g., Pd(PPh$_3$)$_4$/HCO$_2$H/Et$_3$N) to give compound 18, as described in Example 2. Compound 18 was converted to compound 19 as described in Example 1.

Example 4—Preparation of a Halichondrin Macrolide Via a Compound of Formula (IN)

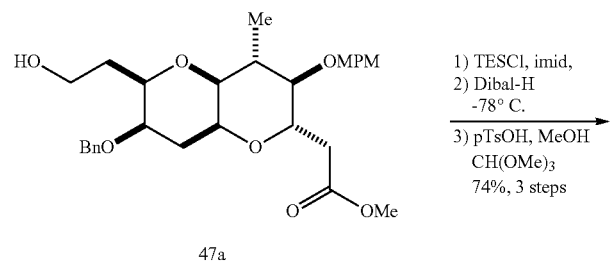

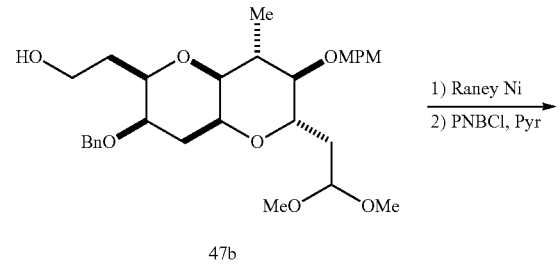

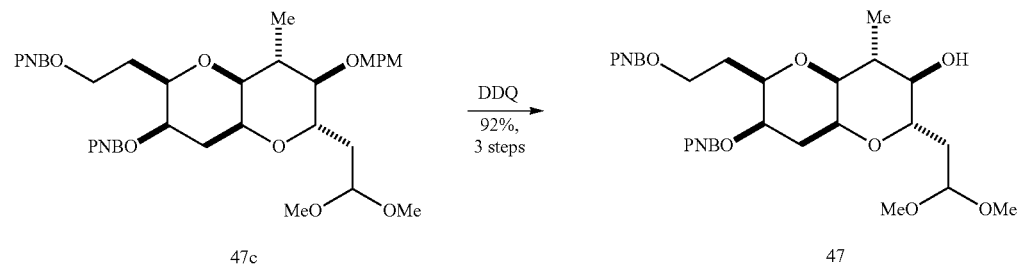

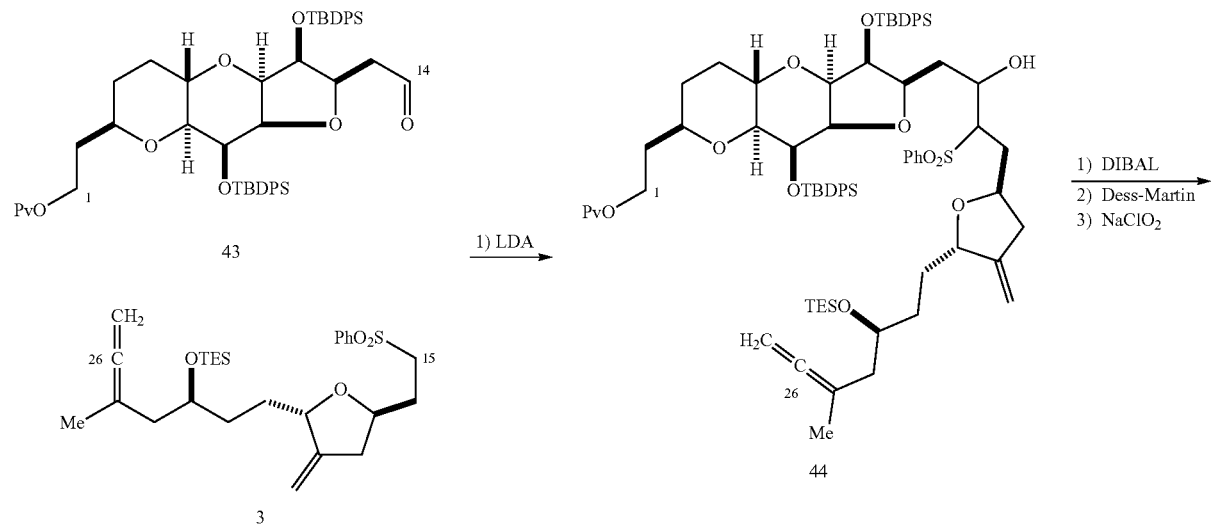

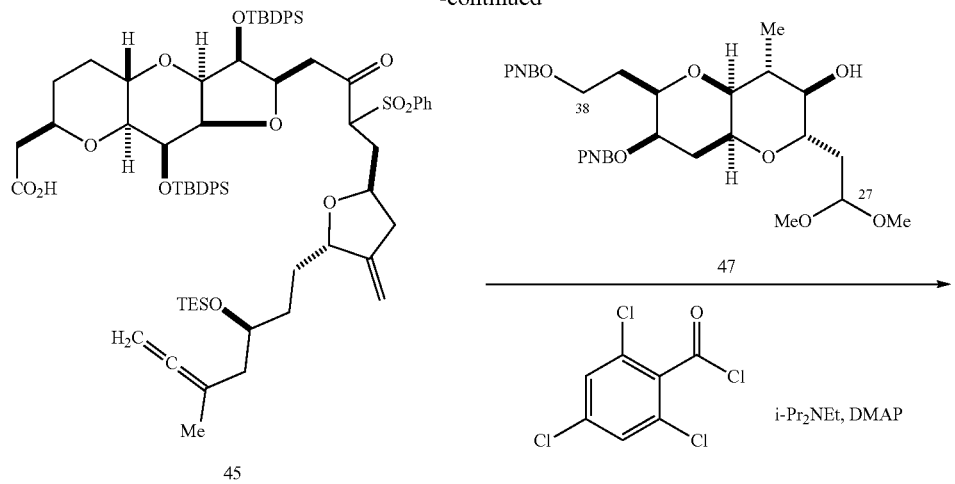
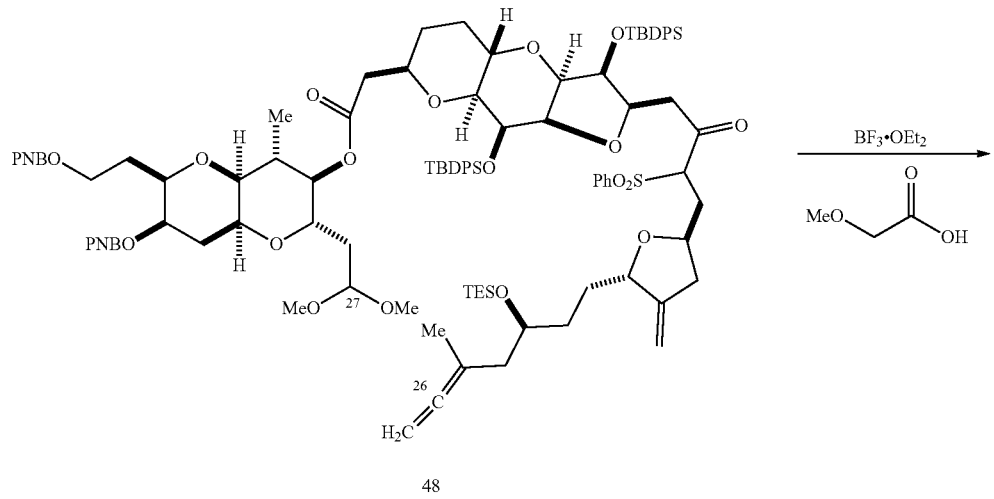
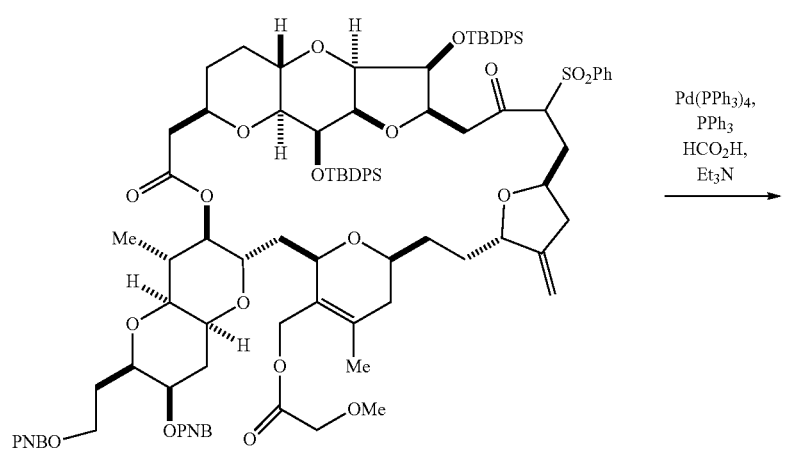

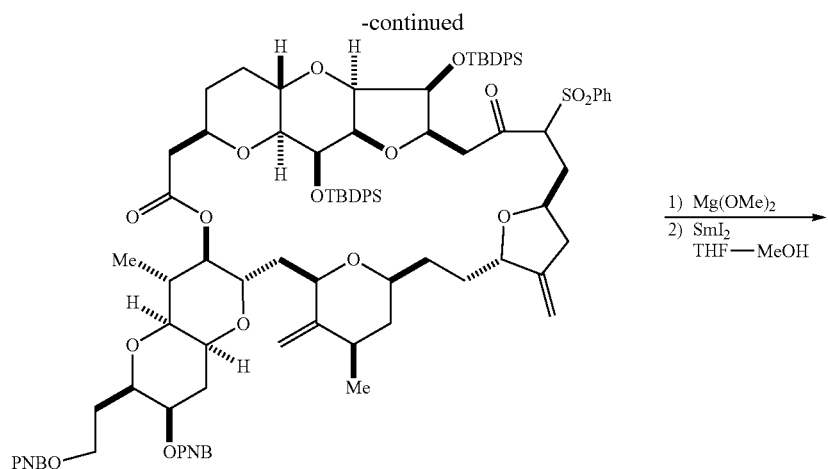
50
1) Mg(OMe)₂
2) SmI₂
   THF—MeOH
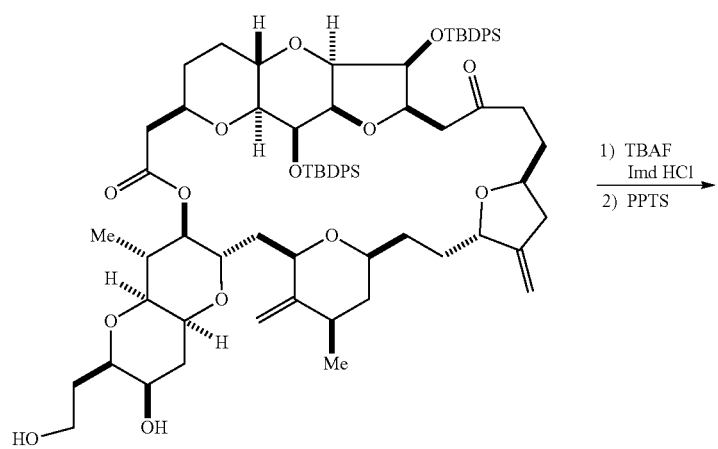
51
1) TBAF
   Imd HCl
2) PPTS
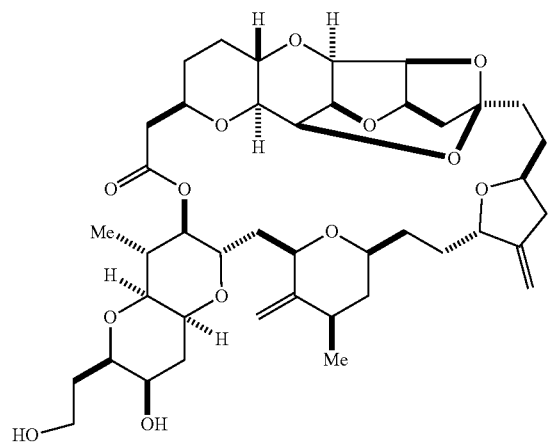
52

2-((2R,3R,4aS,6S,7R,8R,8aS)-3-(benzyloxy)-6-(2,2-dimethoxyethyl)-7-((4-methoxybenzyl)oxy)-8-methyloctahydropyrano[3,2-b]pyran-2-yl)ethanol

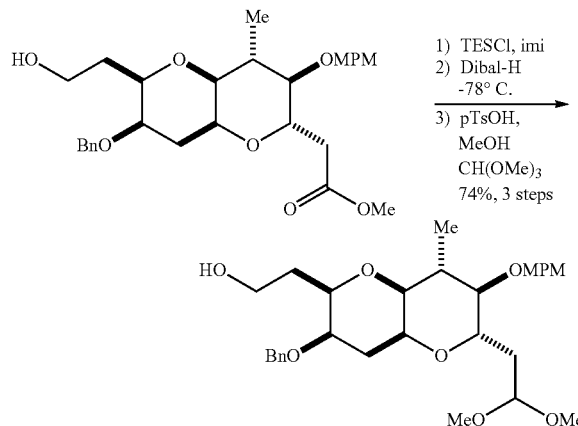

To a solution of methyl 2-((2S,3R,4R,4aS,6R,7R,8aS)-7-(benzyloxy)-6-(2-hydroxyethyl)-3-((4-methoxybenzyl)oxy)-4-methyloctahydropyrano[3,2-b]pyran-2-yl)acetate (1.0 g, 1.94 mmol) in dichloromethane (10.00 mL, 155.417 mmol) at 0° C. was added imidazole (0.397 g, 5.83 mmol) and chlorotriethylsilane (0.652 mL, 3.89 mmol). The resulting mixture was stirred at ambient temperature for 1 h and then treated with MTBE (20 mL) and a sat. aq. NH$_4$Cl solution (15 mL). The organic layer was separated, washed twice with 30% (w/v) aqueous NaCl (10 mL), and dried over MgSO$_4$. Filtration and concentration in vacuo provided 1.329 g of methyl 2-((2S,3R,4R,4aS,6R,7R,8aS)-7-(benzyloxy)-3-((4-methoxybenzyl)oxy)-4-methyl-6-(2-((triethylsilyl)oxy)ethyl)octahydropyrano[3,2-b]pyran-2-yl)acetate. The crude product was dissolved in dichloromethane (24 mL) and cooled to –78° C. 1.0 M DIBAL-H in toluene (3.08 mL, 3.077 mmol) was added while the internal temperature was kept below –74° C. After stirring for 2 h at –78° C., the reaction was quenched with methanol (0.778 mL, 19.231 mmol), and Rochelle's salt solution (30 mL) and water (20 mL) were added. The resulting mixture was warmed to ambient temperature overnight. The layers were separated, and the aqueous layer was extracted twice with dichloromethane (30 mL). The combined organic layers were dried over MgSO$_4$, filtered, and concentrated in vacuo to give 1.314 g of crude 2-((2S,3R,4R,4aS,6R,7R,8aS)-7-(benzyloxy)-3-((4-methoxybenzyl)oxy)-4-methyl-6-(2-((triethylsilyl)oxy)ethyl)octahydropyrano[3,2-b]pyran-2-yl)acetaldehyde. The crude product was dissolved in methanol (20 mL) at ambient temperature. To the resulting solution were added trimethyl orthoformate (2 mL) and p-toluenesulfonic acid monohydrate (0.018 g, 0.097 mmol). The reaction mixture was stirred overnight at ambient temperature and treated with saturated aqueous NaHCO$_3$ (34.7 mL) and water (12 mL). The resulting mixture was extracted with MTBE (40 mL) three times. The combined organic layers were washed with 30% (w/v) aqueous NaCl (20 mL) and dried over MgSO$_4$. Filtration, concentration in vacuo, and purification by silica gel column chromatography using a 50-100% gradient of ethyl acetate in n-heptane as eluent provided 0.79 g of the target product.

$^1$H NMR (400 MHz, CHLOROFORM-d) δ ppm 1.12 (d, J=7.42 Hz, 3H) 1.59-1.75 (m, 3H) 1.97 (ddd, J=14.17, 7.13, 2.93 Hz, 1H) 2.05-2.23 (m, 2H) 2.32 (dt, J=14.75, 4.74 Hz, 1H) 2.51-2.60 (m, 1H) 2.99 (dd, J=8.79, 7.23 Hz, 1H) 3.24 (s, 3H) 3.28 (s, 3H) 3.35-3.40 (m, 1H) 3.46 (dd, J=5.08, 3.91 Hz, 1H) 3.57-3.66 (m, 1H) 3.72-3.83 (m, 3H) 3.79 (s, 3H) 4.04 (td, J=9.18, 2.74 Hz, 1H) 4.42 (d, J=4.30 Hz, 1H) 4.45 (d, J=2.74 Hz, 1H) 4.50-4.55 (m, 1H) 4.59 (dd, J=7.42, 3.91 Hz, 1H) 4.75 (d, J=12.50 Hz, 1H) 6.86 (d, J=8.99 Hz, 2H) 7.21-7.29 (m, 3H) 7.30-7.38 (m, 4H)

(2R,3R,4aS,6S,7R,8R,8aS)-6-(2,2-dimethoxyethyl)-7-((4-methoxybenzyl)oxy)-8-methyl-2-(2-((4-nitrobenzoyl)oxy)ethyl)octahydropyrano[3,2-b]pyran-3-yl 4-nitrobenzoate

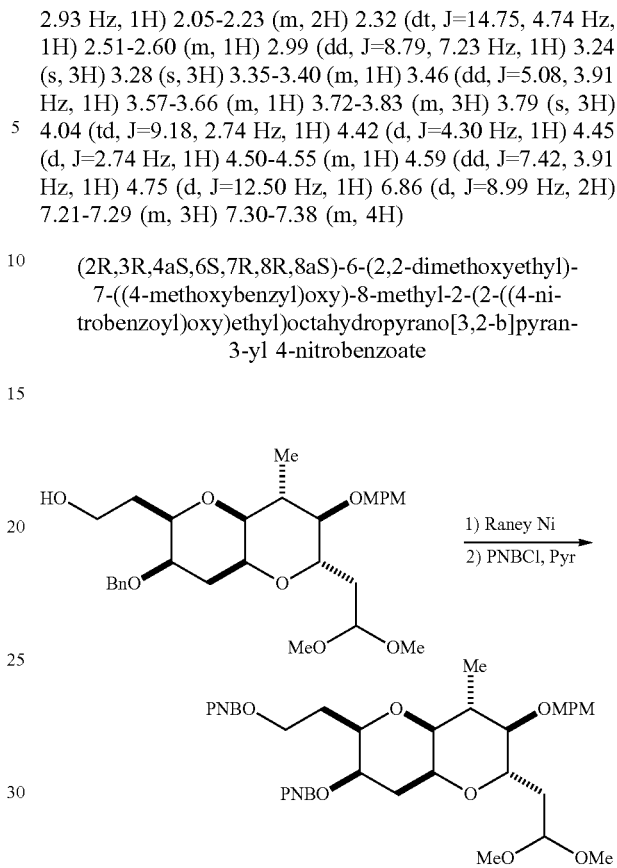

To a solution of 2-((2R,3R,4aS,6S,7R,8R,8aS)-3-(benzyloxy)-6-(2,2-dimethoxyethyl)-7-((4-methoxybenzyl)oxy)-8-methyloctahydropyrano[3,2-b]pyran-2-yl)ethanol (0.77 g, 1.451 mmol) in methanol (31 mL) was added a slurry of Raney-Nickel in water (ca. 8 mL). The resulting mixture was stirred under H$_2$ (balloon) until all starting material was consumed. Upon completion, the mixture was diluted with MeOH and filtered through a Celite pad, which was then rinsed with MeOH until all soluble products were removed. Concentration of the filtrates provided 0.639 g of (2R,3R,4aS,6S,7R,8R,8aS)-6-(2,2-dimethoxyethyl)-2-(2-hydroxyethyl)-7-((4-methoxybenzyl)oxy)-8-methyloctahydropyrano[3,2-b]pyran-3-ol. The crude product was dissolved in pyridine (12.8 ml) and treated with 4-nitrobenzoyl chloride (1.077 g, 5.802 mmol) and 4-dimethylaminopyridine (0.018 g, 0.145 mmol) at ambient temperature. The resulting mixture was stirred until all starting material was consumed. Upon completion, the reaction mixture was diluted with EtOAc (30 mL) and treated with a sat. aq. NaHCO$_3$ solution (40 mL) and water (10 mL). The layers were separated, and the aqueous layer was extracted twice with a mixture of EtOAc/MTBE (1/1, 30 mL each). The combined organic layers were washed with 30% (w/v) aqueous NaCl (25 mL) and dried over MgSO$_4$. Filtration, concentration in vacuo, and purification by silica gel column chromatography using a 25-50% gradient of ethyl acetate in n-heptane as eluent provided 0.72 g of the target product.

$^1$H NMR (400 MHz, CHLOROFORM-d) δ ppm 1.15 (d, J=7.42 Hz, 3H) 1.72 (ddd, J=13.97, 9.28, 4.10 Hz, 1H) 1.81-1.89 (m, 1H) 1.91-1.95 (m, 1H) 1.95-2.00 (m, 1H) 2.15 (s, 2H) 2.37 (dt, J=15.34, 2.88 Hz, 1H) 3.06-3.11 (m, 1H) 3.08 (s, 3H) 3.16 (s, 3H) 3.30-3.44 (m, 1H) 3.64-3.72 (m, 1H) 3.74 (br s, 1H) 3.77 (s, 3H) 3.95 (ddd, J=9.09, 7.52, 3.71

Hz, 1H) 4.38 (dd, J=7.23, 4.10 Hz, 1H) 4.50-4.59 (m, 3H) 5.01-5.07 (m, 1H) 5.48-5.49 (m, 1H) 6.84 (d, J=8.60 Hz, 2H) 7.26 (d, J=8.60 Hz, 2H) 8.14-8.19 (m, 4H) 8.22-8.29 (m, 4H).

(2R,3R,4aS,6S,7R,8R,8aS)-6-(2,2-dimethoxyethyl)-7-hydroxy-8-methyl-2-(2-((4-nitrobenzoyl)oxy)ethyl)octahydropyrano[3,2-b]pyran-3-yl 4-nitrobenzoate

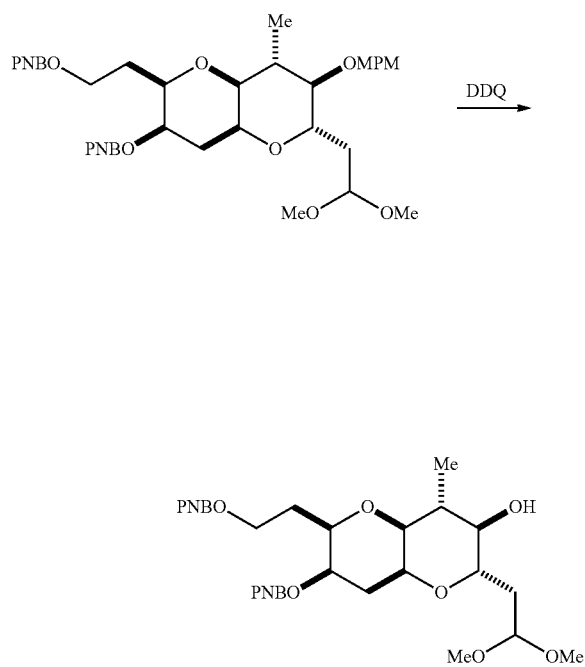

To a solution of (2R,3R,4aS,6S,7R,8R,8aS)-6-(2,2-dimethoxyethyl)-7-((4-methoxybenzyl)oxy)-8-methyl-2-(2-((4-nitrobenzoyl)oxy)ethyl)octahydropyrano[3,2-b]pyran-3-yl 4-nitrobenzoate (0.70 g, 0.948 mmol) in dichloromethane (22.4 mL) were added tert-butanol (0.224 mL), pH 7 phosphate buffer (2.2 mL) and DDQ (0.430 g, 1.895 mmol) at ambient temperature. The resulting mixture was stirred at ambient temperature until all the starting material was consumed (ca. 2 h). Upon completion, the reaction mixture was treated with sat. aq. NaHCO₃ aqueous solution (30 mL). The layers were separated, and the aqueous layer was extracted twice with CH₂Cl₂ (30 mL each). The combined organic layer were washed with 30% aqueous NaCl (10 mL) and dried over MgSO₄. Filtration, concentration in vacuo, and purification by silica gel column chromatography using a 50-80% gradient of ethyl acetate in n-heptane as eluent provided 574 mg of the target product as a white solid. ¹H NMR (400 MHz, CHLOROFORM-d) δ ppm 1.13 (d, J=7.82 Hz, 3H) 1.70 (ddd, J=14.17, 7.33, 4.30 Hz, 1H) 1.93-2.01 (m, 3H) 2.13 (ddt, J=14.80, 9.33, 5.52, 5.52 Hz, 1H) 2.26 (q, J=7.82 Hz, 1H) 2.41 (dt, J=15.63, 2.34 Hz, 1H) 3.19 (s, 3H) 3.25 (s, 3H) 3.34 (dt, J=10.06, 2.78 Hz, 1H) 3.38-3.42 (m, 1H) 3.73 (dd, J=9.77, 3.13 Hz, 1H) 3.85 (br s, 1H) 3.88 (d, J=10.16 Hz, 1H) 4.09 (br d, J=7.03 Hz, 1H) 4.38 (dd, J=7.42, 3.91 Hz, 1H) 4.51 (t, J=6.25 Hz, 2H) 5.07-5.12 (m, 1H) 8.13-8.18 (m, 2H) 8.20-8.31 (m, 6H)

1-((2R,3S,3aR,4aS,7R,8aS,9S,9aR)-3,9-bis((tert-butyldiphenylsilyl)oxy)-7-(2-hydroxyethyl)decahydrofuro[3,2-b]pyrano[2,3-e]pyran-2-yl)-4-((2R,5S)-5-((S)-5-methyl-3-((triethylsilyl)oxy)hepta-5,6-dien-1-yl)-4-methylenetetrahydrofuran-2-yl)-3-(phenylsulfonyl)butan-2-ol. Compound 44a

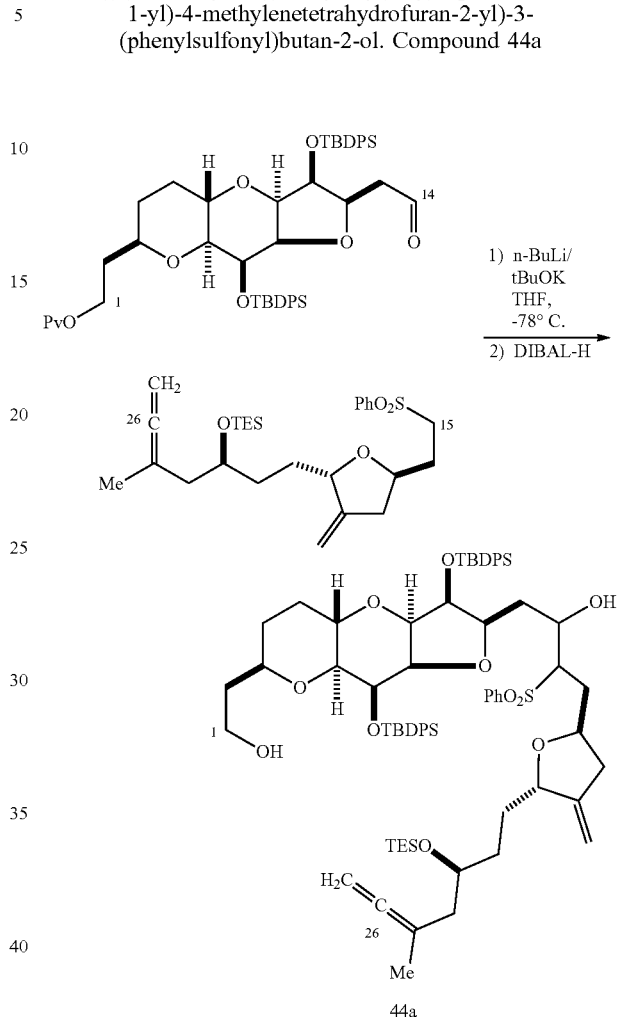

To a solution of triethyl(((S)-5-methyl-1-((2S,5R)-3-methylene-5-(2-(phenylsulfonyl)ethyl)tetrahydrofuran-2-yl)hepta-5,6-dien-3-yl)oxy)silane (178 mg, 0.363 mmol) in THF (4.6 mL) at −78° C. were added potassium tert-butoxide (1.0 M in THF, 0.363 mL, 0.363 mmol) and n-BuLi (1.6 M in hexane, 0.227 mL, 0.363 mmol). The resulting mixture was stirred for 10 min at −78° C. and treated with a solution of 2-((2R,3S,3aR,4aS,7R,8aS,9S,9aR)-3,9-bis((tert-butyldiphenylsilyl)oxy)-2-(2-oxoethyl)decahydrofuro[3,2-b]pyrano[2,3-e]pyran-7-yl)ethyl pivalate (116 mg, 0.134 mmol) in THF (3 mL). The resulting reaction mixture was stirred at −78° C. until all of the aldehyde was consumed. Upon completion, the reaction was quenched with a sat. aq. NH₄Cl solution (4 mL) and water (2 mL). The resulting mixture was diluted with MTBE (5 mL) and warmed to ambient temperature. The layers were separated, and the aqueous layer was extracted with MTBE (10 mL). The combined organic layers were washed with 30% (w/v) aqueous NaCl (4 mL) twice and dried over MgSO₄. Filtration and concentration in vacuo provided 2-((2R,3S,3aR,4aS,7R,8aS,9S,9aR)-3,9-bis((tert-butyldiphenylsilyl)oxy)-2-(2-hydroxy-4-((2R,5S)-5-((S)-5-methyl-3-((triethylsilyl)oxy)hepta-5,6-dien-1-yl)-4-methylenetetrahydrofuran-2- yl)-3-(phenylsulfonyl)butyl)decahydrofuro[3,2-b]pyrano[2,3-e]pyran-7-yl)ethyl pivalate (MS m/z 1376.8 [M+Na]+). The crude product (182 mg in theory) was dissolved in dichloromethane (8 mL) and cooled to −78° C. 1.0 M DIBAL-H in toluene (0.672 mL, 0.672 mmol) was added, and the resulting solution was stirred for 1.5 h at −78° C. The reaction was then quenched with methanol (0.27 mL, 6.72 mmol) and a saturated Rochelle's salt solution (10 mL). The resulting mixture was diluted with dichloromethane (10 mL) and warmed up to ambient temperature overnight. The layers were separated, and the aqueous layer was extracted with dichloromethane (5 mL). The combined organic layers were dried over MgSO4. Filtration, concentration in vacuo, and purification by silica gel column chromatography using a 20-50% gradient of ethyl acetate in n-heptane as eluent provided 148 mg of the target product as a mixture of four diastereomers (MS m/z 1291.7 [M+Na]+).

2-((2R,3S,3aR,4aS,7R,8aS,9S,9aR)-3,9-bis((tert-butyldiphenylsilyl)oxy)-2-(4-((2R,5S)-5-((S)-5-methyl-3-((triethylsilyl)oxy)hepta-5,6-dien-1-yl)-4-methylenetetrahydrofuran-2-yl)-2-oxo-3-(phenylsulfonyl)butyl)decahydrofuro[3,2-b]pyrano[2,3-e]pyran-7-yl)acetic acid

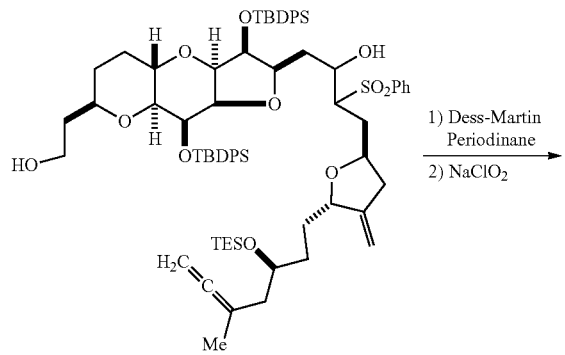

To a solution of 1-((2R,3S,3aR,4aS,7R,8aS,9S,9aR)-3,9-bis((tert-butyldiphenylsilyl)oxy)-7-(2-hydroxyethyl)decahydrofuro[3,2-b]pyrano[2,3-e]pyran-2-yl)-4-((2R,5S)-5-((S)-5-methyl-3-((triethylsilyl)oxy)hepta-5,6-dien-1-yl)-4-methylenetetrahydrofuran-2-yl)-3-(phenylsulfonyl)butan-2-ol (148 mg, 0.117 mmol) in dichloromethane (4.4 mL) at ambient temperature were added sodium bicarbonate (78 mg, 0.932 mmol) and Dess-Martin periodinane (198 mg, 0.466 mmol). The resulting mixture was stirred at ambient temperature for 4 h and treated with a sat. aq. NaHCO3 solution (6 mL) and sat. aq. Na2S2O3 solution (6 mL). The resulting mixture was diluted with MTBE (15 mL) and stirred for 30 min. The layers were separated, and the aqueous layer was extracted with MTBE (10 mL). The combined organic layers were washed twice with 30% (w/v) aqueous NaCl (5 mL each) and dried over MgSO4. Filtration and concentrated in vacuo provided 148 mg of 2-((2R,3S,3aR,4aS,7R,8aS,9S,9aR)-3,9-bis((tert-butyldiphenylsilyl)oxy)-2-(4-((2R,5S)-5-((S)-5-methyl-3-((triethylsilyl)oxy)hepta-5,6-dien-1-yl)-4-methylenetetrahydrofuran-2-yl)-2-oxo-3-(phenylsulfonyl)butyl)decahydrofuro[3,2-b]pyrano[2,3-e]pyran-7-yl)acetaldehyde (MS m/z 1287.6 [M+Na]+). To the crude product were added tert-butanol (4.4 mL) and n-amylene (0.444 mL, 4.19 mmol). The resulting mixture was treated with a solution of sodium phosphate monobasic (49.1 mg, 0.409 mmol) and sodium chlorite (31.7 mg, 0.351 mmol) in water (2.2 mL). The reaction mixture was stirred at ambient temperature until all starting material was consumed. Upon completion, the mixture was diluted with MTBE (15 mL) and treated with a sat. aq. NH4Cl solution (10 mL). The organic layer was separated, and the aqueous layer was extracted with MTBE (10 mL). The combined organic layers were washed twice with 30% (w/v) aqueous NaCl (5 mL each) and dried over MgSO4. Filtration, concentration in vacuo, and purification by silica gel column chromatography using a 33-75% gradient of ethyl acetate in n-heptane as eluent provided 118 mg of the target product as a 1:1 mixture of two diastereomers (MS m/z 1303.8 [M+Na]+).

$^1$H NMR (400 MHz, CHLOROFORM-d) δ ppm 0.54-0.62 (m, 6H) 0.90-0.98 (m, 9H) 1.05 (s, 4.5H) 1.10 (s, 4.5H) 1.11 (s, 4.5H) 1.13 (s, 4.5H) 1.29-1.75 (m, 8H) 1.62 (t, J=3.12 Hz, 1.5H) 1.68 (t, J=3.12 Hz, 1.5H) 1.87-2.19 (m, 6.5H) 2.25-2.38 (m, 2H) 2.47 (dd, J=18.94, 2.54 Hz, 0.5H) 2.50-2.57 (m, 0.5H) 2.58-2.68 (m, 0.5H) 3.04 (dd, J=18.55, 2.15 Hz, 0.5H) 3.13 (dd, J=9.76, 5.86 Hz, 0.5H) 3.23 (dd, J=9.76, 6.64 Hz, 0.5H) 3.31 (dd, J=18.74, 8.98 Hz, 0.5H) 3.40-3.50 (m, 1.5H) 3.63-3.76 (m, 2.5H) 3.77-3.85 (m, 1H) 3.90 (ddd, J=9.18, 6.25, 2.54 Hz, 0.5H) 3.96-4.12 (m, 3.5H) 4.16 (dd, J=8.39, 4.10 Hz, 0.5H) 4.20 (t, J=5.47 Hz, 0.5H) 4.23-4.28 (m, 1.5H) 4.32 (dd, J=10.15, 2.73 Hz, 0.5H) 4.47-4.52 (m, 1H) 4.52-4.58 (m, 1H) 4.80 (dd, J=4.49, 2.15 Hz, 1H) 4.94 (dd, J=3.51, 1.95 Hz, 1H) 7.27-7.60 (m, 15H) 7.65-7.81 (m, 10H)

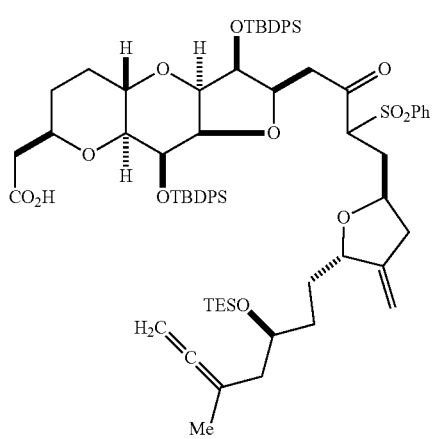

(2R,3R,4aS,6S,7R,8S,8aS)-7-(2-((2R,3S,3aR,4aS, 7R,8aS,9S,9aR)-3,9-bis((tert-butyldiphenylsilyl) oxy)-2-(4-((2R,5S)-5-((S)-5-methyl-3-((triethylsilyl) oxy)hepta-5,6-dien-1-yl)-4-methylenetetrahydrofuran-2-yl)-2-oxo-3-(phenylsulfonyl)butyl)decahydrofuro[3,2-b]pyrano[2,3-e]pyran-7-yl)acetoxy)-6-(2,2-dimethoxyethyl)-8-methyl-2-(2-((4-nitrobenzoyl)oxy)ethyl)octahydropyrano[3,2-b]pyran-3-yl 4-nitrobenzoate

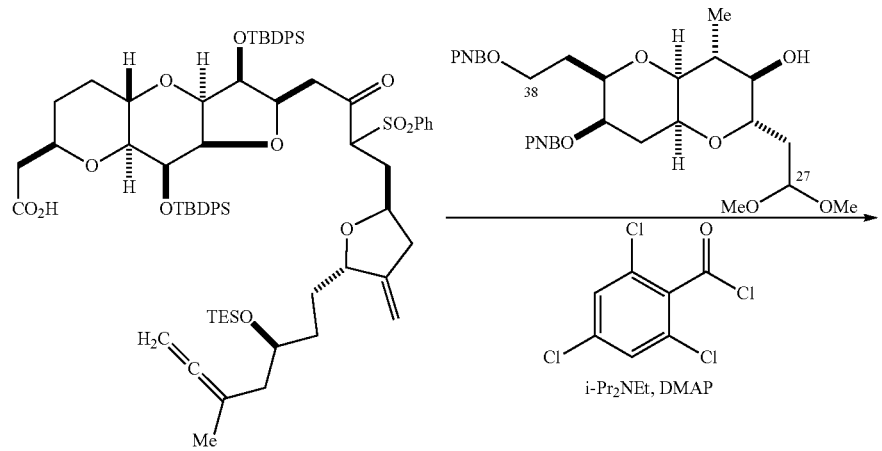

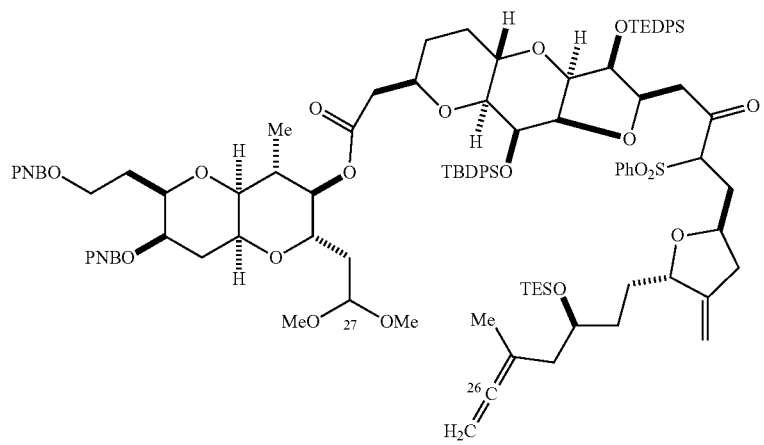

To a solution of 2-((2R,3S,3aR,4aS,7R,8aS,9S,9aR)-3,9-bis((tert-butyldiphenylsilyl)oxy)-2-(4-((2R,5S)-5-((S)-5-methyl-3-((triethylsilyl)oxy)hepta-5,6-dien-1-yl)-4-methylenetetrahydrofuran-2-yl)-2-oxo-3-(phenylsulfonyl)butyl)decahydrofuro[3,2-b]pyrano[2,3-e]pyran-7-yl)acetic acid (118 mg, 0.092 mmol) and (2R,3R,4aS,6S,7R,8R,8aS)-6-(2,2-dimethoxyethyl)-7-hydroxy-8-methyl-2-(2-((4-nitrobenzoyl)oxy)ethyl)octahydropyrano[3,2-b]pyran-3-yl 4-nitrobenzoate (159 mg, 0.258 mmol) in dichloromethane (3.0 mL) at ambient temperature were added triethyl amine (TEA, 0.026 mL, 0.184 mmol), 6-nitro-o-toluic anhydride (47.5 mg, 0.138 mmol), and 4-dimethylaminopyridine (5.62 mg, 0.046 mmol). After being stirred overnight, the reaction mixture was concentrated in vacuo. Purification by silica gel column chromatography using a 33-66% gradient of ethyl acetate in n-heptane as eluent provided 152 mg of the target product as a 1:1 diastereomeric mixture.

$^1$H NMR (400 MHz, CHLOROFORM-d) δ ppm 0.52-0.62 (m, 6H) 0.90-0.97 (m, 9H) 1.04 (d, J=7.42 Hz, 3H) 1.06 (s, 4.5H) 1.08 (s, 4.5H) 1.11 (s, 4.5H) 1.13 (s, 4.5H) 1.17-1.53 (m, 5H) 1.62 (t, J=3.13 Hz, 1.5H) 1.67 (t, J=3.13 Hz, 1.5H) 1.72-2.24 (m, 16H) 2.35-2.46 (m, 3H) 2.55-2.66 (m, 1H) 3.02-3.06 (m, 0.5H) 3.07 (s, 1.5H) 3.08 (s, 1.5H) 3.16 (s, 1.5H) 3.16 (s, 1.5H) 3.22 (d, J=5.47 Hz, 1H) 3.29 (dd, J=18.95, 8.40 Hz, 0.5H) 3.38 (br s, 1H) 3.56-3.63 (m, 1H) 3.64-3.75 (m, 4H) 3.76-3.81 (m, 1.5 H) 3.86-3.94 (m, 1H) 3.95-4.17 (m, 4H) 4.18-4.30 (m, 2.5H) 4.30-4.37 (m, 1H) 4.46-4.57 (m, 4H) 4.58-4.65 (m, 1H) 4.78 (s, 1H) 4.89 (d, J=1.95 Hz, 0.5H) 4.93 (d, J=1.95 Hz, 0.5H) 5.09 (br s, 1H) 7.27-7.57 (m, 15H) 7.65-7.81 (m, 10H) 8.14-8.32 (m, 8H)

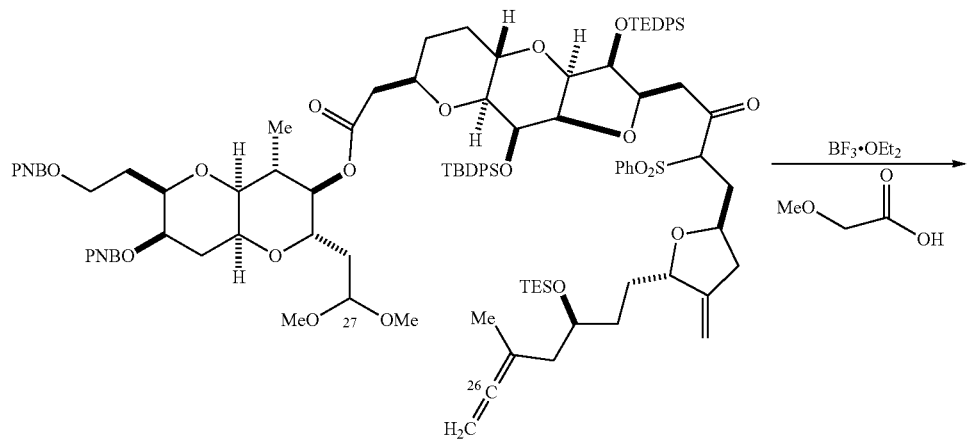

Compound 49

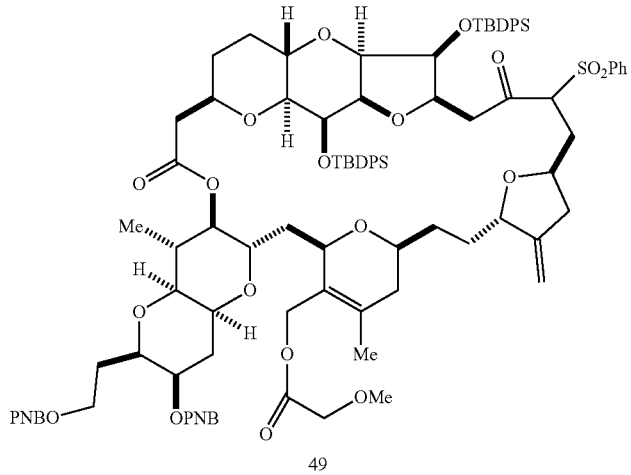

To a solution of (2R,3R,4aS,6S,7R,8S,8aS)-7-(2-((2R,3S,3aR,4aS,7R,8aS,9S,9aR)-3,9-bis((tert-butyldiphenylsilyl)oxy)-2-(4-((2R,5S)-5-((S)-5-methyl-3-((triethylsilyl)oxy)hepta-5,6-dien-1-yl)-4-methylenetetrahydrofuran-2-yl)-2-oxo-3-(phenylsulfonyl)butyl)decahydrofuro[3,2-b]pyrano[2,3-e]pyran-7-yl)acetoxy)-6-(2,2-dimethoxyethyl)-8-methyl-2-(2-((4-nitrobenzoyl)oxy)ethyl)octahydropyrano[3,2-b]pyran-3-yl 4-nitrobenzoate (76 mg, 0.04 mmol) in dichloromethane (38 mL) at −20° C. were added methoxyacetic acid (0.155 mL, 2.02 mmol) and $BF_3 \cdot OEt_2$ (51 μL, 0.40 mmol). The reaction mixture was stirred between −20° C. and −10° C., and the reaction was monitored by TLC and LCMS. Upon completion, the reaction was quenched with sat. aq. $NaHCO_3$ (20 mL). The organic layer was separated and washed with 30% (w/v) aqueous NaCl (5 mL) and dried over $MgSO_4$. Filtration, concentration in vacuo, and purification by silica gel column chromatography using a 50-66% gradient of ethyl acetate in n-heptane as eluent provided 58 mg of the target product as a 1:1 diastereomeric mixture.

$^1$H NMR (400 MHz, CHLOROFORM-d) δ ppm 0.96 (s, 4.5H) 1.02 (s, 4.5H) 1.09 (s, 4.5H) 1.12 (s, 4.5H) 1.35 (s, 1.5H) 1.45 (s, 1.5H) 1.18-2.24 (m, 19H) 2.31-2.54 (m, 3H) 2.56-2.80 (m, 3H) 2.98-3.10 (m, 1H) 3.18-3.42 (m, 2H) 3.40 (s, 1.5H) 3.41 (s, 1.5H) 3.47 (dd, J=5.28, 2.15 Hz, 1H) 3.54 (t, J=4.10 Hz, 0.5H) 3.59-3.78 (m, 5.5H) 3.82 (td, J=10.26, 4.10 Hz, 1H) 3.95 (s, 2H) 3.97-4.04 (m, 1H) 4.09-4.37 (m, 6H) 4.48-4.73 (m, 6H) 4.77 (br d, J=5.86 Hz, 1H) 4.83 (br s, 1H) 4.94 (s, 1H) 5.13 (br s, 1H) 7.27-7.55 (m, 15H) 7.56-7.82 (m, 10H) 8.15-8.35 (m, 8H)

Compound 50

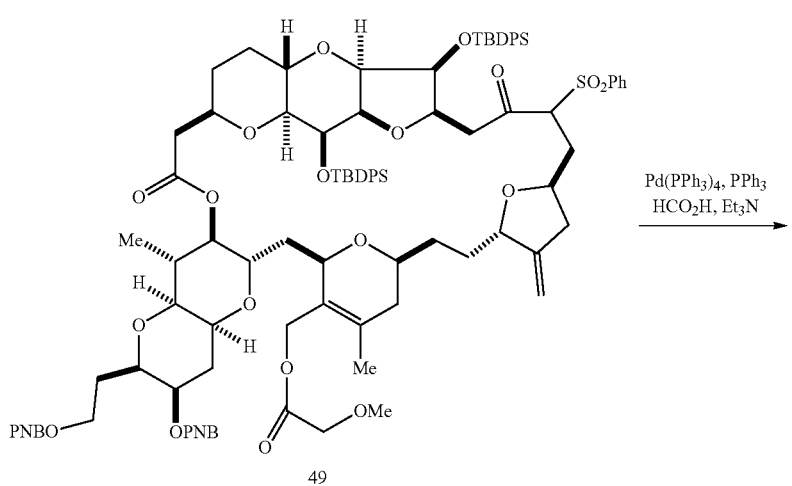

To a solution of Pd(Ph$_3$P)$_4$ (8.05 mg, 6.967 μmol) and triphenylphosphine (7.31 mg, 0.028 mmol) in THF (1.0 mL) was added a solution of compound 49 (25 mg, 0.014 mmol) in THF (0.5 mL) at ambient temperature. Formic acid (3.2 μL, 0.084 mmol) and triethylamine (0.012 mL, 0.084 mmol) were added by syringe. The resulting mixture was stirred at 60-65° C. for 15 h and cooled to ambient temperature. The reaction mixture was diluted with MTBE (10 mL), washed with sat. aq. NaHCO$_3$ (3 mL) and dried over MgSO$_4$. Filtration, concentration in vacuo, and purification by silica gel column chromatography using a 25-60% gradient of ethyl acetate in n-heptane as eluent provided 10 mg of the target product as a 2:1 mixture of diastereomers.

$^1$H NMR (400 MHz, CHLOROFORM-d) δ ppm 0.97 (s, 6H) 1.02 (s, 3H) 1.05 (s, 3H) 1.08 (br d, J=6.64 Hz, 3H) 1.12 (s, 6H) 1.23 (br d, J=7.42 Hz, 3H) 1.28-1.88 (m, 8H) 1.90-2.24 (m, 12H) 2.32-2.84 (m, 6H) 2.99-3.10 (m, 1H) 3.22-3.95 (m, 10H) 4.00-4.07 (m, 1H) 4.07-4.39 (m, 4H) 4.47-4.93 (m, 9H) 5.21 (br s, 0.3H) 5.26 (br s, 0.7H) 7.28-7.50 (m, 14H) 7.54-7.80 (m, 11H) 8.11-8.42 (m, 8H)

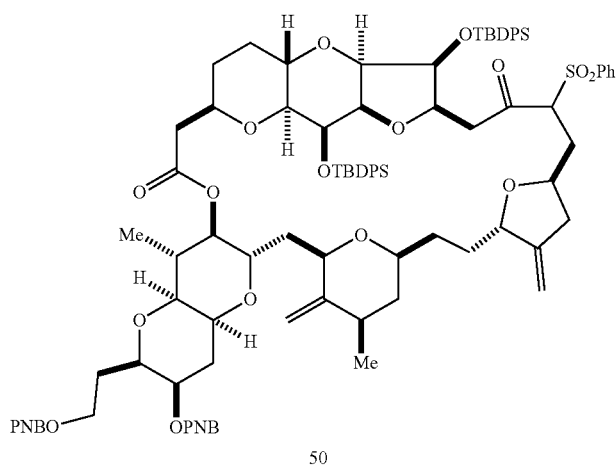

50

Compound 50a

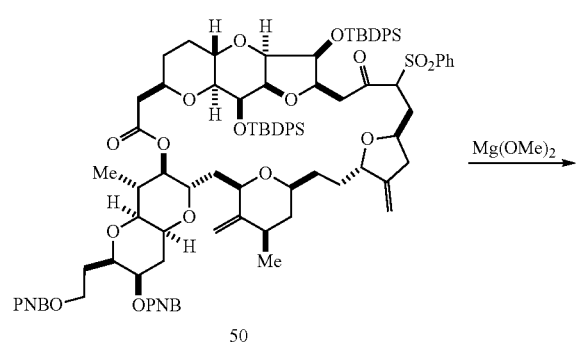

50

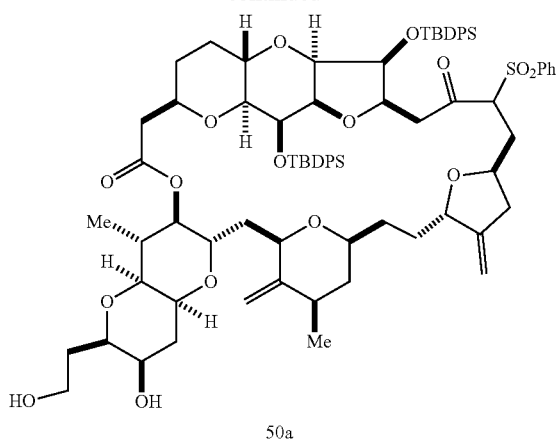

50a

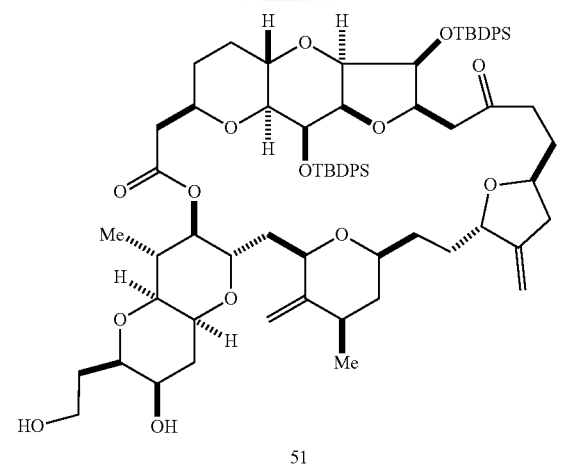

51

To a solution of compound 50 (10 mg, 5.861 μmol) in MeOH (0.5 mL, 12.359 mmol) and THF (0.20 mL, 2.441 mmol) was added a solution of magnesium methoxide (3.88 μL, 2.931 μmol) at ambient temperature. The reaction was monitored by LCMS and TLC, and additional the magnesium methoxide solution (0.16 mL) was added over 6 days. The resulting mixture was diluted with EtOAc (6 ml) and washed with a sat. aq. NH$_4$Cl solution (5 mL). The aqueous layer was extracted with EtOAc (5 mL), and the combined organic layers were washed with 30% aqueous NaCl (2 mL) and dried over MgSO$_4$. Filtration, concentration in vacuo, and purification by silica gel column chromatography using a 50-100% gradient of ethyl acetate in n-heptane as eluent provided 5 mg of the target product.

$^1$H NMR (400 MHz, CHLOROFORM-d) δ ppm 0.97 (s, 9H) 1.07 (br d, J=6.64 Hz, 3H) 1.10 (s, 9H) 1.19 (d, J=7.82 Hz, 3H) 1.28-1.54 (m, 4H) 1.65-2.04 (m, 9H) 2.06-2.35 (m, 8H) 2.41 (dd, J=16.02, 9.38 Hz, 1H) 2.62-2.71 (m, 1H) 2.75 (dd, J=16.02, 5.47 Hz, 1H) 2.82-2.90 (m, 2H) 3.13 (dd, J=9.38, 8.21 Hz, 1H) 3.25-3.34 (m, 3H) 3.37-3.45 (m, 1H) 3.53 (dd, J=4.69, 3.13 Hz, 1H) 3.58 (s, 2H) 3.59-3.63 (m, 1H) 3.70-3.88 (m, 6H) 3.91 (br s, 1H) 4.00 (dd, J=7.82, 5.08 Hz, 1H) 4.03-4.09 (m, 1H) 4.18 (dd, J=7.62, 4.88 Hz, 1H) 4.23-4.31 (m, 1H) 4.36 (br d, J=11.33 Hz, 1H) 4.55 (d, J=8.60 Hz, 1H) 4.71 (s, 1H) 4.80 (br s, 2H) 4.83 (s, 1H) 4.98 (s, 1H) 7.27-7.47 (m, 12H) 7.49-7.55 (m, 2H) 7.58-7.72 (m, 9H) 7.76-7.81 (m, 2H)

To a solution of compound 50a (5.0 mg, 3.551 μmol) in THF (0.9 mL)/methanol (0.3 mL) at −78° C. was added samarium diiodide as a 0.1 M solution in THF (0.2 mL, 0.02 mmol). After 10 min, a sat. aq. Rochelle's salt solution (1.5 mL), MTBE (3 mL), and water (1 mL) were added. The resulting mixture was warmed to ambient temperature and extracted with MTBE (5 mL). The organic layer was washed with 30% (w/v) aq. NaCl (3 mL) and dried over MgSO$_4$. Filtration, concentration in vacuo, and purification by silica gel column chromatography using a 50-75% gradient of ethyl acetate in n-heptane as eluent provided 4.0 mg of the target product as a foam solid.

$^1$H NMR (400 MHz, CHLOROFORM-d) δ ppm 1.01 (s, 9H) 1.06 (s, 9H) 1.09 (br d, J=6.64 Hz, 3H) 1.19 (br d, J=7.82 Hz, 3H) 1.28-1.53 (m, 6H) 1.67-1.88 (m, 6H) 1.91-1.99 (m, 1H) 2.06-2.36 (m, 8H) 2.54 (dd, J=6.84, 2.93 Hz, 1H) 2.59-2.67 (m, 1H) 2.68-2.84 (m, 3H) 2.91-3.01 (m, 1H) 3.05 (t, J=8.99 Hz, 1H) 3.09-3.16 (m, 1H) 3.31 (s, 1H) 3.44-3.49 (m, 1H) 3.50 (t, J=4.10 Hz, 1H) 3.54-3.62 (m, 3H) 3.64 (dd, J=5.67, 4.10 Hz, 1H) 3.73 (br d, J=11.72 Hz, 1H) 3.76-3.86 (m, 2H) 3.89-3.98 (m, 2H) 4.04-4.18 (m, 3H) 4.25-4.35 (m, 2H) 4.41 (br d, J=8.99 Hz, 1H) 4.76 (br s, 1H) 4.81 (d, J=1.17 Hz, 1H) 4.82 (br s, 1H) 4.84 (s, 1H) 4.96 (d, J=1.56 Hz, 1H) 7.28-7.46 (m, 12H) 7.57-7.73 (m, 8H)

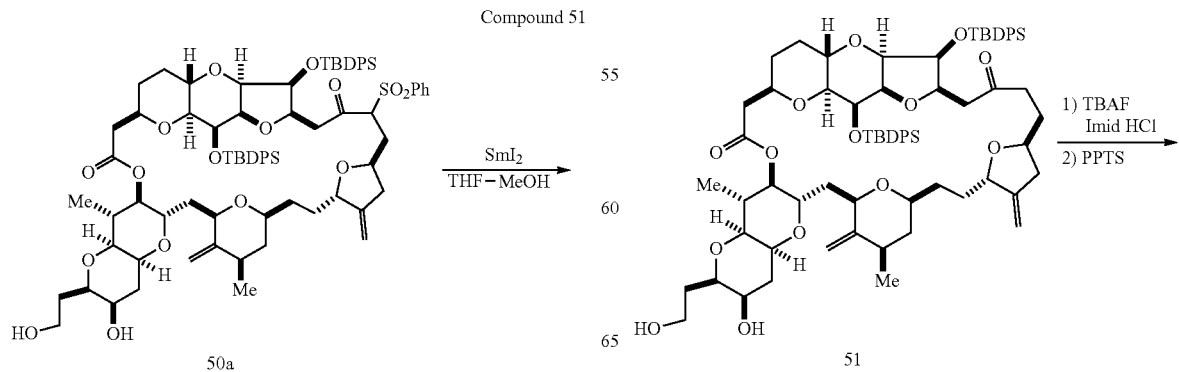

Compound 51 · · · Compound 52

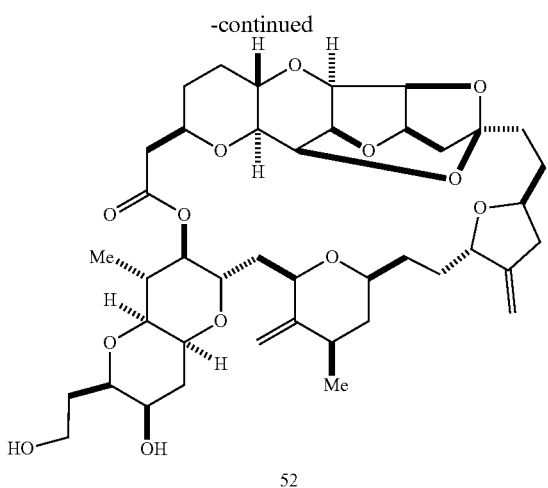

52

To compound 51 (2.5 mg, 3.2 μmol) in a vial were added THF (0.8 mL) and N,N-dimethylacetamide (0.28 mL) at ambient temperature. TBAF (1.0 M in THF, 95 μL, 0.095 mmol) and imidazole hydrochloride (5.0 mg, 0.047 mmol) were added. The resulting mixture was stirred over 2 days at ambient temperature. 30% (w/v) aqueous NaCl (2.0 mL) was added, and the resulting mixture was extracted twice with a mixture of THF (5.0 mL) and toluene (5.0 mL). The combined organic layer was concentrated under a stream of nitrogen. The residue was dissolved in dichloromethane (1.5 mL) at ambient temperature, and PPTS (33 mg, 132 μmol) was added. Once all starting material was consumed, the reaction mixture was purified by silica gel column chromatography using a 0-10% gradient of methanol in ethyl acetate as eluent to give 0.7 mg of the target product, which was confirmed by LCMS (MS m/z 795.4 [M+Na]$^+$) and $^1$H NMR comparison with that previously reported.

$^1$H NMR (400 MHz, CHLOROFORM-d) δ ppm 1.10 (br d, J=6.25 Hz, 3H) 1.18 (d, J=7.82 Hz, 3H) 1.27-2.40 (m, 25H) 2.39-2.45 (m, 1H) 2.48-2.57 (m, 1H) 2.77-2.86 (m, 1H) 2.91 (dd, J=9.38, 2.34 Hz, 1H) 3.29 (s, 1H) 3.51-3.57 (m, 2H) 3.65 (br d, J=10.94 Hz, 1H) 3.72-3.89 (m, 5H) 4.04 (dd, J=6.25, 4.30 Hz, 1H) 4.19 (dd, J=6.25, 4.69 Hz, 1H) 4.24 (td, J=10.06, 3.71 Hz, 1H) 4.36-4.44 (m, 3H) 4.50 (t, J=2.34 Hz, 1H) 4.60 (t, J=4.30 Hz, 1H) 4.65-4.72 (m, 1H) 4.76-4.85 (m, 2H) 4.98 (br s, 1H) 5.08 (s, 1H)

Example 5—Preparation of a Halichondrin Macrolide Via a Compound of Formula (IJ)

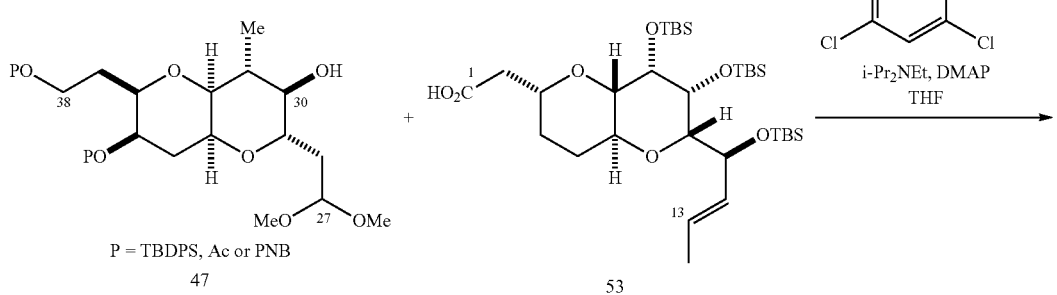

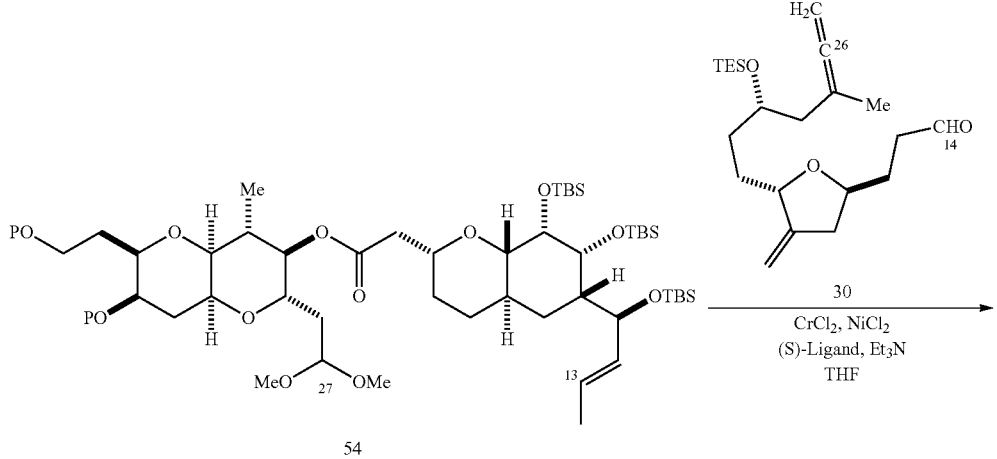

147 148
-continued
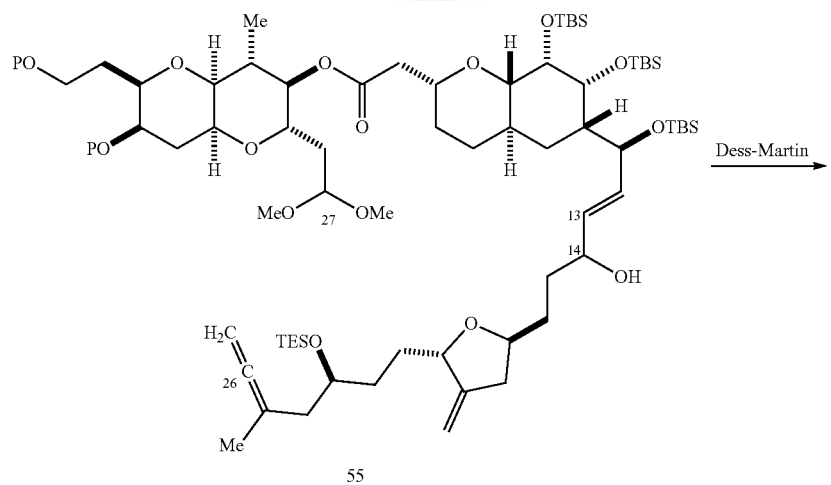
55
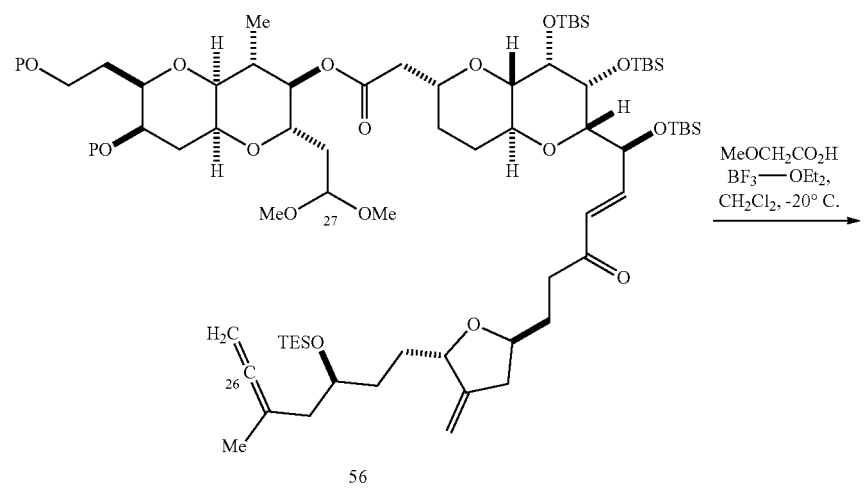
56
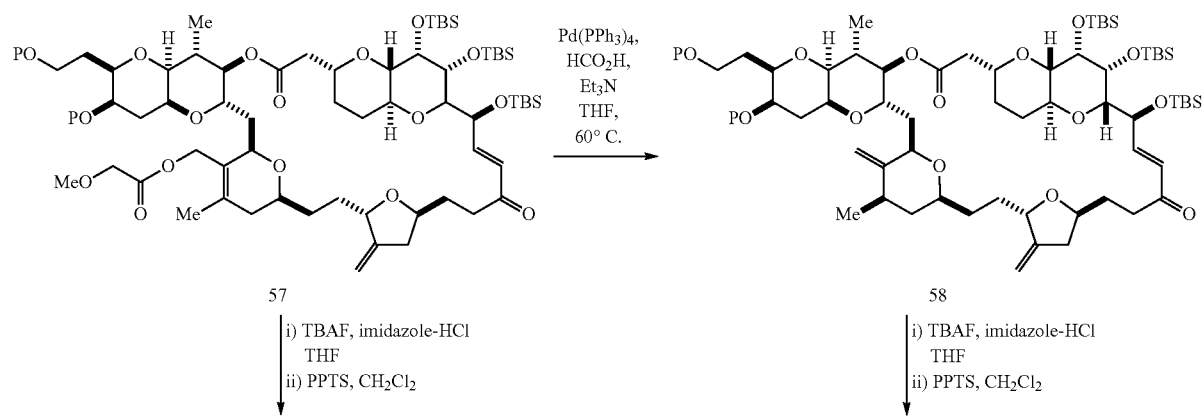
57 58
i) TBAF, imidazole-HCl
  THF
ii) PPTS, CH$_2$Cl$_2$
i) TBAF, imidazole-HCl
  THF
ii) PPTS, CH$_2$Cl$_2$ -continued

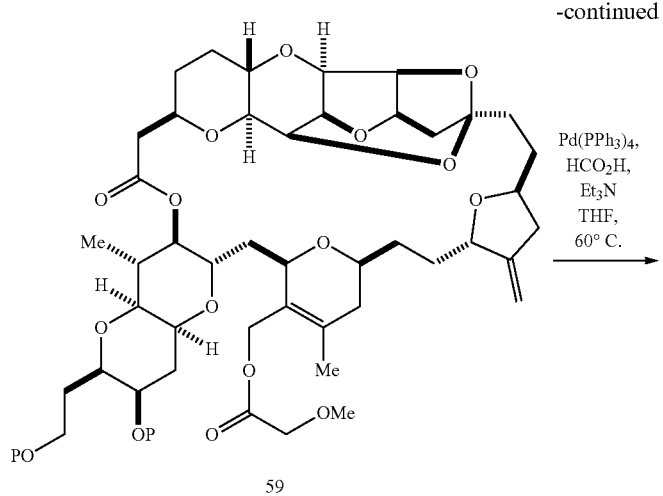

59

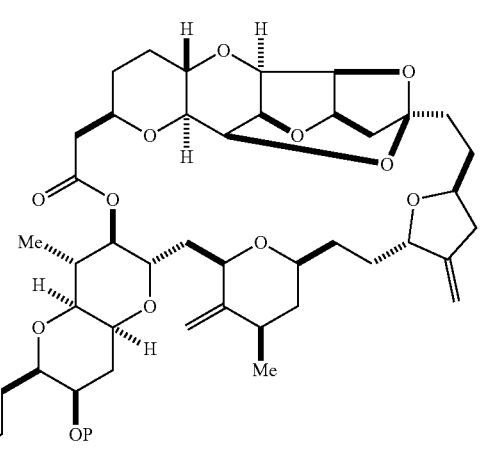

51

Pd(PPh₃)₄, HCO₂H, Et₃N THF, 60° C.

An exemplary compound of formula (IA) can be prepared as shown in the above scheme. Subjecting compound 52 to Yamaguchi esterification with compound 53 gives compound 54, which, upon reacting with compound 30 under Nozaki-Hiyama-Kishi reaction conditions, affords compound 55 (an exemplary compound of formula (IA)). Oxidation of compound 55 with Dess-Martin periodinane gives compound 56 (another exemplary compound of formula (IA)).

An exemplary halichondrin macrolide can be prepared as shown in the above scheme. Compound 56 can be converted to compound 57 by a reaction with methoxyacetic acid and BF₃·OEt₂ (exemplary Prins reaction conditions). Provided herein are two pathways to accessing exemplary halichondrin macrolide 51 from compound 57. In one approach, compound 57 can be reacted with an allylic reducing agent (e.g., Pd(PPh₃)₄/HCO₂H/Et₃N) to produce compound 58, which upon global desilylation with a fluoride source (e.g., TBAF, buffered with imidazolium hydrochloride) and PPTS-catalyzed ketalization, can afford compound 51. Alternatively, global desilylation with a fluoride source (e.g., TBAF, buffered with imidazolium hydrochloride) of compound 57, followed by PPTS-catalyzed ketalization and a reaction with an allylic reducing agent (e.g., Pd(PPh₃)₄/HCO₂H/Et₃N), to yield compound 51.

In some embodiments, P is PNB.

Example 6—Preparation of a Halichondrin Macrolide Via a Compound of Formula (IN)

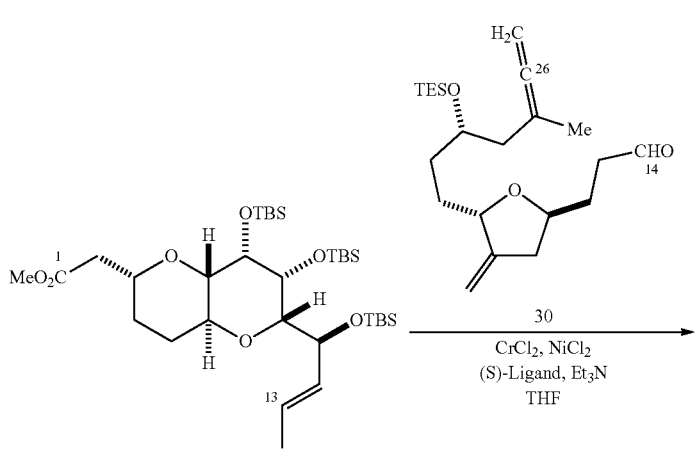

60

-continued
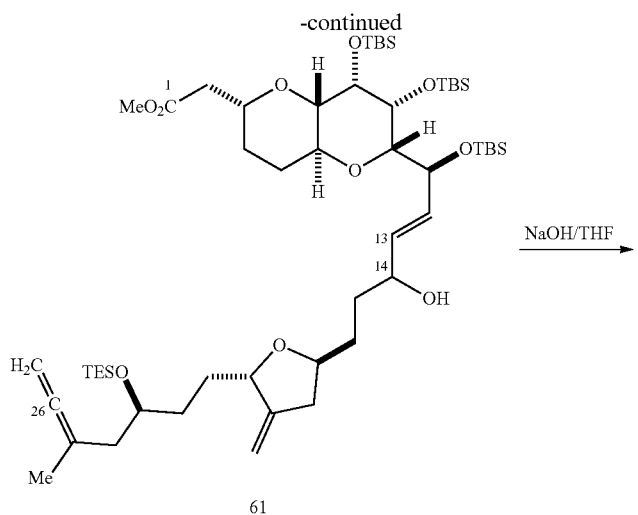
61
NaOH/THF →
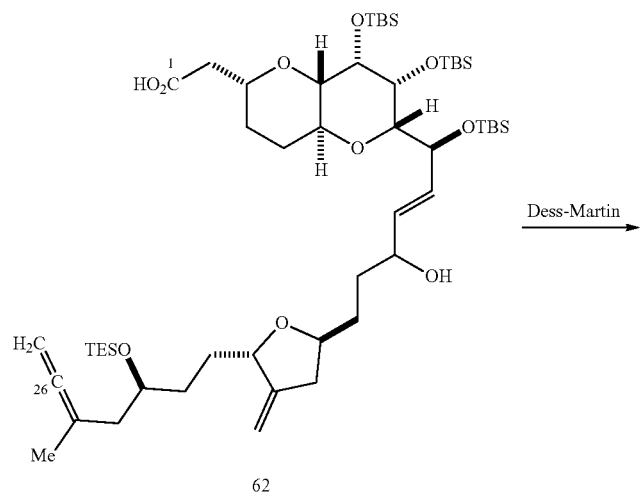
62
Dess-Martin →
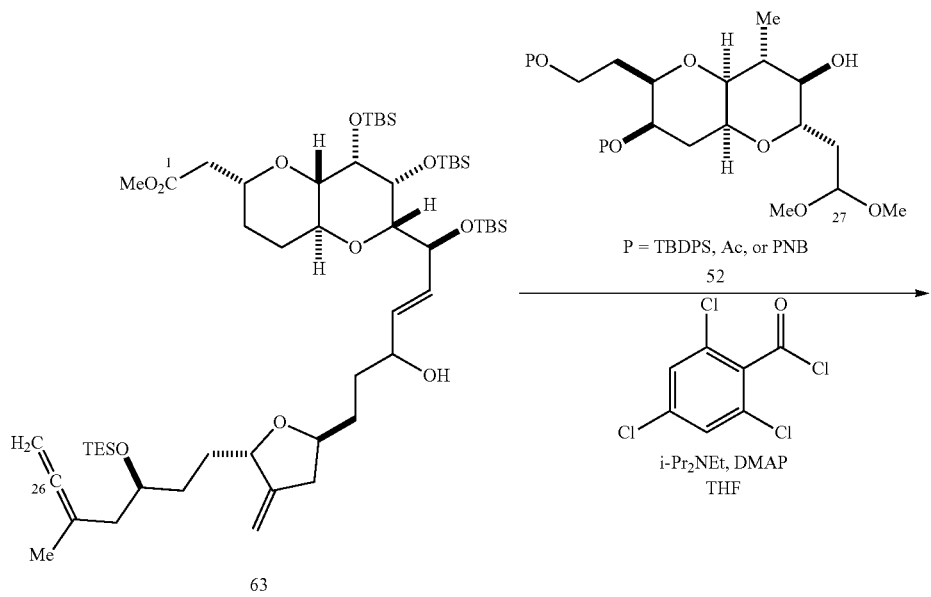
63

-continued

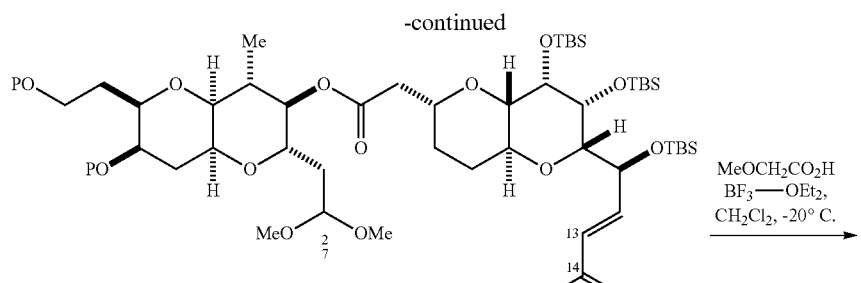

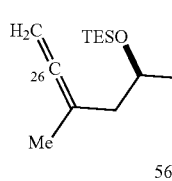

56

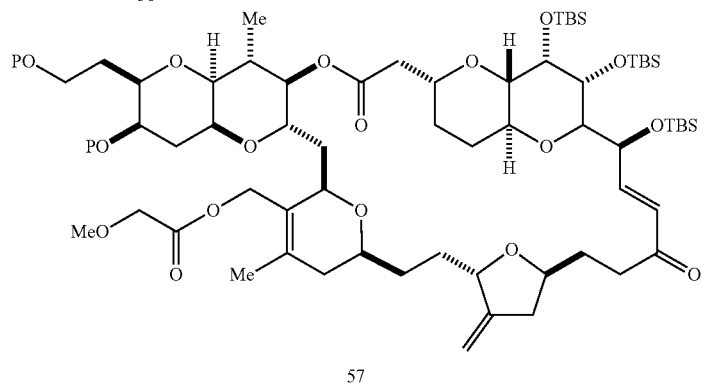

57

An exemplary compound of formula (IA) can be prepared as shown in the above scheme. Reacting compound 60 with compound 30 under Nozaki-Hiyama-Kishi reaction conditions affords compound 61 (an exemplary compound (IN). Hydrolysis of the ester in compound 61 provides compound 62. Oxidation (e.g., with Dess-Martin periodinane) of compound 62 gives compound 63. Yamaguchi esterification of compound 63 with compound 52 affords compound 56 (an exemplary compound of formula (IA)). Prins reaction (methoxyacetic acid and $BF_3.OEt_2$; exemplary Prins reaction conditions) of compound 56 furnishes compound 57 (an exemplary compound of formula (IB)).

Example 7—Preparation of Compound (IH)

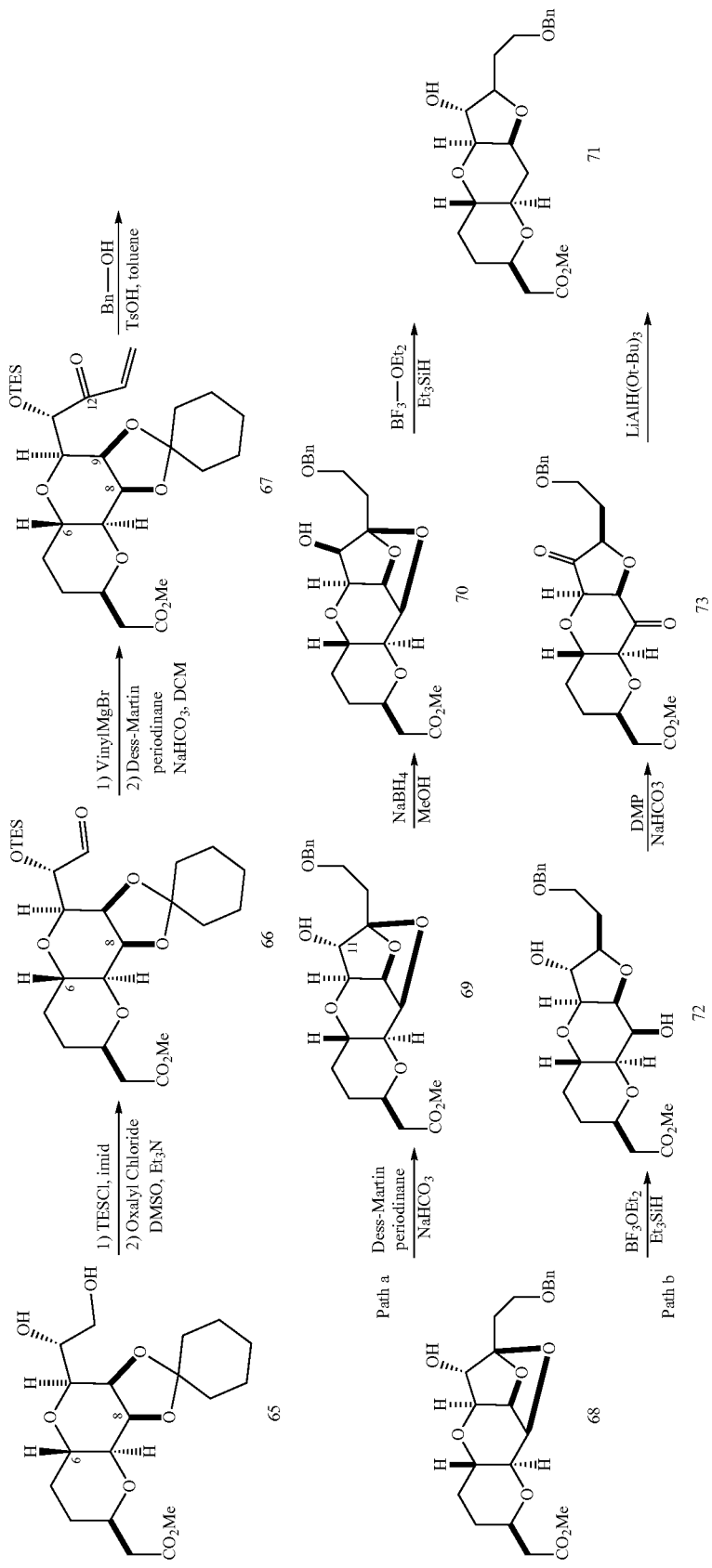

Methyl 2-((3aR,4R,5aS,8R,9aS,9bS)-4-((R)-3,3,8,8-tetraethyl-4,7-dioxa-3,8-disiladecan-5-yl)octahydrospiro[[1,3]dioxolo[4,5-d]pyrano[3,2-b]pyran-2,1'-cyclohexan]-8-yl)acetate

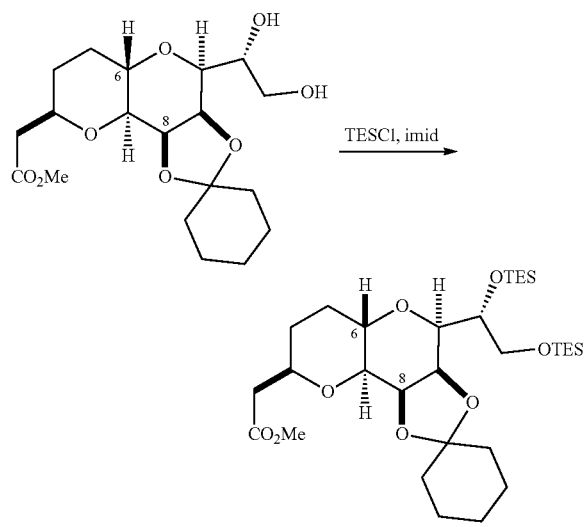

To a solution of methyl 2-((3aR,4S,5aS,8R,9aS,9bS)-4-((R)-1,2-dihydroxyethyl)octahydrospiro[[1,3]dioxolo[4,5-d]pyrano[3,2-b]pyran-2,1'-cyclohexan]-8-yl)acetate (1.1 g, 2.847 mmol) in dichloromethane (11.0 mL) at 0° C. were added imidazole (0.775 g, 11.4 mmol) and chlorotriethylsilane (1.19 ml, 7.12 mmol). The resulting mixture was warmed to ambient temperature and stirred until all starting material was consumed. Upon completion, the reaction was quenched with a sat. aq. NH$_4$Cl solution (10 mL). The resulting mixture was extracted with MTBE (20 mL). The organic layer was washed with 30% (w/v) aqueous NaCl (5 mL) and dried over MgSO$_4$. Filtration, concentration in vacuo, and purification by silica gel column chromatography using a 0-25% gradient of ethyl acetate in n-heptane as eluent provided 1.64 g of the target product as a colorless oil.

$^1$H NMR (400 MHz, CHLOROFORM-d) δ ppm 0.55-0.68 (m, 12H) 0.95 (t, J=8.01 Hz, 13H) 1.14-1.81 (m, 16H) 2.01-2.10 (m, 1H) 2.41 (dd, J=16.02, 6.25 Hz, 1H) 2.71 (dd, J=16.22, 6.84 Hz, 1H) 3.45 (dd, J=10.16, 2.74 Hz, 1H) 3.62-3.65 (m, 1H) 3.66 (s, 3H) 3.74 (d, J=3.91 Hz, 2H) 3.82 (br s, 3H) 4.39-4.45 (m, 1H) 4.45-4.51 (m, 1H)

Methyl 2-((3aR,4R,5aS,8R,9aS,9bS)-4-((S)-2-oxo-1-((triethylsilyl)oxy)ethyl)octahydrospiro[[1,3]dioxolo[4,5-d]pyrano[3,2-b]pyran-2,1'-cyclohexan]-8-yl)acetate

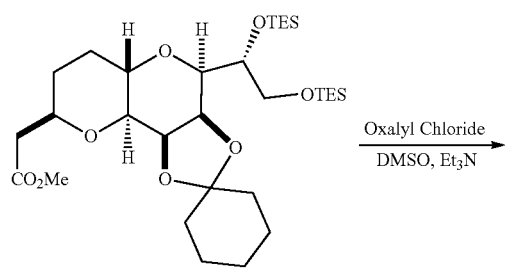

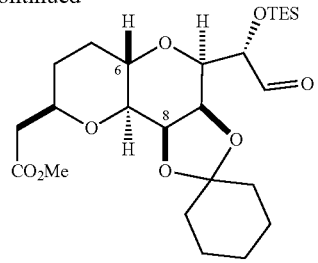

A solution of oxalic chloride (2.67 mL, 5.33 mmol, 2.0 M in dichloromethane) was added dropwise into a solution of DMSO (0.76 mL, 10.7 mmol) in dichloromethane (4.1 mL) at −70° C. After 15 min, methyl 2-((3aR,4R,5aS,8R,9aS,9bS)-4-((R)-3,3,8,8-tetraethyl-4,7-dioxa-3,8-disiladecan-5-yl)octahydrospiro[[1,3]dioxolo[4,5-d]pyrano[3,2-b]pyran-2,1'-cyclohexan]-8-yl)acetate (0.82 g, 1.33 mmol) in dichloromethane (4.1 mL) was added. The reaction solution was stirred for 20 min at −70° C. and for 20 min at −40° C., cooled to −78° C., and treated with TEA (2.2 mL, 16.0 mmol). The resulting mixture was warmed to ambient temperature, treated with water (16.4 mL), and extracted with MTBE (32.8 mL). The organic layer was washed three times with 30% (w/v) aqueous NaCl (24.6 mL) and twice with water (25 mL) and dried over MgSO$_4$. Filtration and concentration in vacuo provided the target product as an oil (100% theoretical yield assumed), which was used in next step without further purification.

Methyl 2-((3aR,4R,5aS,8R,9aS,9bS)-4-((S)-2-oxo-1-((triethylsilyl)oxy)but-3-en-1-yl)octahydrospiro[[1,3]dioxolo[4,5-d]pyrano[3,2-b]pyran-2,1'-cyclohexan]-8-yl)acetate

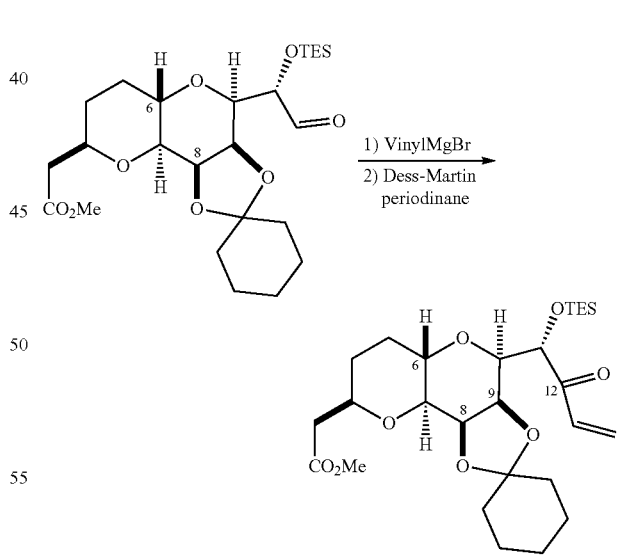

Methyl 2-((3aR,4R,5aS,8R,9aS,9bS)-4-((S)-2-oxo-1-((triethylsilyl)oxy)ethyl)octahydrospiro[[1,3]dioxolo[4,5-d]pyrano[3,2-b]pyran-2,1'-cyclohexan]-8-yl)acetate (0.666 g, 1.33 mmol) was dissolved in THF (13 mL), and the resulting solution was cooled to −25° C. and treated with vinyl magnesium bromide (1.0 M in THF, 1.6 mL, 1.6 mmol). If needed, additional vinyl Grignard reagent was added until all the starting material was consumed. Upon completion, the reaction was quenched with a sat. aq. NH4Cl solution (15 mL) and water (5 mL). The resulting mixture was extracted twice with MTBE (20 mL each). The combined organic layers were washed with 30% (w/v) aqueous NaCl (10 mL) and dried over MgSO4. Filtration and concentration in vacuo provided methyl 2-((3aR,4R,5aS,8R,9aS,9bS)-4-((1R)-2-hydroxy-1-((triethylsilyl)oxy)but-3-en-1-yl)octahydrospiro[[1,3]dioxolo[4,5-d]pyrano[3,2-b]pyran-2,1'-cyclohexan]-8-yl)acetate (100% theoretical yield assumed), which was used in next step without further purification.

The crude product was dissolved in dichloromethane (14 mL). To the solution were added Dess-Martin periodinane (1.01 g, 2.38 mmol) and sodium bicarbonate (0.556 g, 6.62 mmol). The resulting mixture was stirred at ambient temperature until all the starting material was consumed. Upon completion, MTBE (20 mL), a sat. aq. Na2S2O3 solution (20 ml), and water (10 mL) were added, and the resulting mixture was stirred for 1 h. The layers were separated, and the aqueous layer was extracted with MTBE (20 mL). The combined organic layers were washed with a sat. aq. NaHCO3 solution (10 mL) and 30% (w/v) aqueous NaCl (10 mL), and dried over MgSO4. Filtration, concentration in vacuo, and purification by silica gel column chromatography using a 20-66% gradient of ethyl acetate in n-heptane as eluent provided 369 mg of the target product as a colorless oil.

$^1$H NMR (400 MHz, CHLOROFORM-d) δ ppm 0.58-0.66 (m, 6H) 0.90-0.97 (m, 9H) 1.11-1.87 (m, 13H) 2.08-2.14 (m, 1H) 2.41 (dd, J=16.02, 6.25 Hz, 1H) 2.70 (dd, J=16.22, 6.84 Hz, 1H) 3.46 (dd, J=10.16, 3.13 Hz, 1H) 3.66 (s, 3H) 3.77-3.89 (m, 3H) 4.32 (d, J=8.21 Hz, 1H) 4.41-4.51 (m, 2H) 5.67 (dd, J=10.55, 1.56 Hz, 1H) 6.32 (dd, J=17.59, 1.95 Hz, 1H) 6.81 (dd, J=17.59, 10.55 Hz, 1H)

Methyl 2-((2R,3S,3aS,4aS,7R,8aS,9S,9aR)-2-(2-(benzyloxy)ethyl)-3-hydroxydecahydro-2,9-epoxyfuro[3,2-b]pyrano[2,3-e]pyran-7-yl)acetate

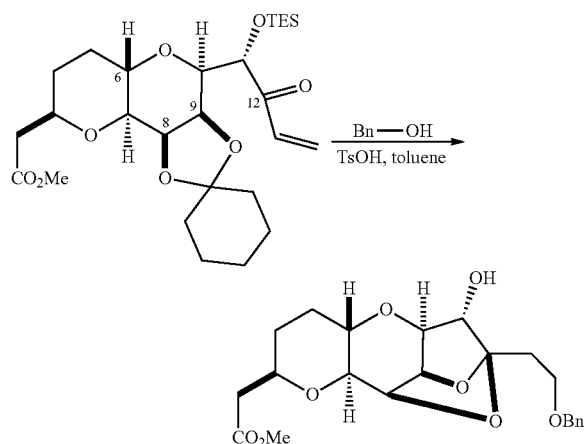

To a solution of methyl 2-((3aR,4R,5aS,8R,9aS,9bS)-4-((S)-2-oxo-1-((triethylsilyl)oxy)but-3-en-1-yl)octahydrospiro[[1,3]dioxolo[4,5-d]pyrano[3,2-b]pyran-2,1'-cyclohexan]-8-yl)acetate (0.123 g, 0.234 mmol) in toluene (6 mL) were added benzyl alcohol (0.3 mL, 2.89 mmol) and p-toluenesulfonic acid monohydrate (8.92 mg, 0.047 mmol). The reaction mixture was heated between 70-80° C. for 5 h, cooled to ambient temperature, and diluted with MTBE (20 mL). The resulting mixture was washed with a sat. aq. NaHCO3 solution (5 mL), 30% (w/v) aqueous NaCl (5 mL) and water (5 mL), and dried over MgSO4. Filtration, concentration in vacuo, and purification by silica gel column chromatography using a 40-80% gradient of ethyl acetate in n-heptane as eluent provided 40 mg of the target product as a white solid.

$^1$H NMR (400 MHz, CHLOROFORM-d) δ ppm 1.42-1.62 (m, 2H) 1.78-1.90 (m, 1H) 2.05-2.11 (m, 1H) 2.15 (ddd, J=15.05, 5.28, 1.95 Hz, 1H) 2.33-2.48 (m, 2H) 2.68 (dd, J=16.02, 7.03 Hz, 1H) 3.08 (d, J=9.38 Hz, 1H) 3.50 (td, J=9.97, 4.30 Hz, 1H) 3.61-3.71 (m, 1H) 3.67 (s, 3H) 3.77-3.82 (m, 1H) 3.83-3.90 (m, 1H) 4.02-4.06 (m, 1H) 4.13-4.19 (m, 2H) 4.45-4.51 (m, 1H) 4.51-4.61 (m, 2H) 7.27-7.43 (m, 5H).

Methyl 2-((2S,3aR,4aS,7R,8aS,9S,9aS)-2-(2-(benzyloxy)ethyl)-3-oxodecahydro-2,9-epoxyfuro[3,2-b]pyrano[2,3-e]pyran-7-yl)acetate

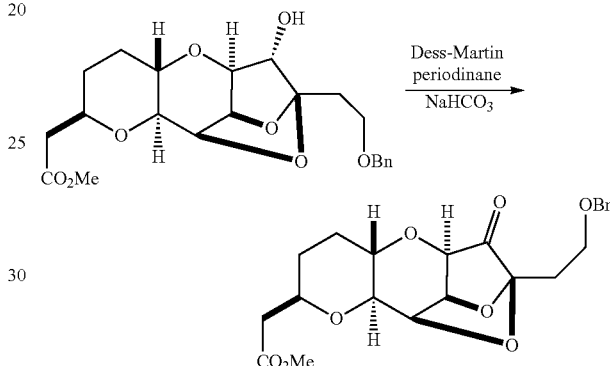

To a solution of methyl 2-((2R,3S,3aS,4aS,7R,8aS,9S,9aR)-2-(2-(benzyloxy)ethyl)-3-hydroxydecahydro-2,9-epoxyfuro[3,2-b]pyrano[2,3-e]pyran-7-yl)acetate (13 mg, 0.031 mmol) in dichloromethane (1 mL) at ambient temperature were added Dess-Martin periodinane (26.2 mg, 0.062 mmol) and sodium bicarbonate (12.99 mg, 0.155 mmol). After being stirred for 1 h, the reaction mixture was diluted with MTBE (5 mL), and treated with sat. aq. Na2S2O3 (3 mL) and water (1 mL). After 30 min stirring, the organic layer was separated, washed with 30% (w/v) aqueous NaCl, and dried over MgSO4. Filtration and concentration in vacuo provided 11 mg of the target product.

$^1$H NMR (400 MHz, CHLOROFORM-d) δ ppm 1.38-1.56 (m, 2H) 1.79-1.88 (m, 1H) 2.10-2.19 (m, 1H) 2.32-2.37 (m, 2H) 2.41 (dd, J=16.02, 5.47 Hz, 1H) 2.65 (dd, J=16.02, 7.43 Hz, 1H) 3.21 (s, 1H) 3.23 (dd, J=9.77, 1.17 Hz, 1H) 3.31-3.40 (m, 1H) 3.67 (s, 3H) 3.66-3.72 (m, 1H) 3.82-3.92 (m, 1H) 4.26 (d, J=5.86 Hz, 1H) 4.34 (br s, 1H) 4.50 (s, 2H) 4.79 (dd, J=5.67, 2.93 Hz, 1H) 7.26-7.41 (m, 5H)

methyl 2-((2R,3R,3aS,4aS,7R,8aS,9S,9aR)-2-(2-(benzyloxy)ethyl)-3-hydroxydecahydro-2,9-epoxyfuro[3,2-b]pyrano[2,3-e]pyran-7-yl)acetate

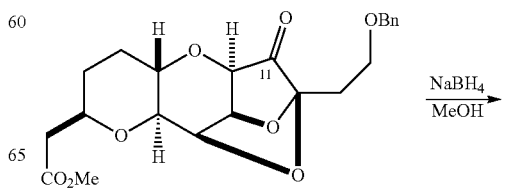

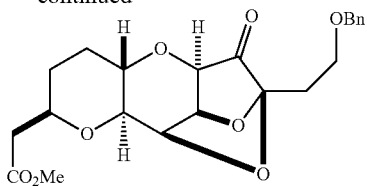

To a solution of methyl 2-((2S,3aR,4aS,7R,8aS,9S,9aS)-2-(2-(benzyloxy)ethyl)-3-oxodecahydro-2,9-epoxyfuro[3,2-b]pyrano[2,3-e]pyran-7-yl)acetate (11 mg, 0.026 mmol) in methanol (1 mL) at 0° C. was added sodium borohydride (2.98 mg, 0.079 mmol). After 15 min, the reaction was quenched with a sat. aq. NH$_4$Cl solution (2 mL) and water (1 mL). The resulting mixture was extracted three times with EtOAc (5 mL each). The combined organic layers were washed with brine (2 mL) and dried over MgSO$_4$. Filtration, concentration in vacuo, and purification by silica gel column chromatography using a 50-80% gradient of ethyl acetate in n-heptane as eluent provided 8.0 mg of the target product as a colorless oil.

$^1$H NMR (400 MHz, CHLOROFORM-d) δ ppm 1.38-1.58 (m, 2H) 1.79-1.86 (m, 1H) 2.12-2.25 (m, 3H) 2.43 (dd, J=16.02, 5.47 Hz, 1H) 2.69 (dd, J=16.02, 7.03 Hz, 1H) 3.13 (dd, J=9.77, 1.17 Hz, 1H) 3.59-3.64 (m, 1H) 3.67 (s, 3H) 3.75-3.80 (m, 1H) 3.83-3.93 (m, 3H) 4.23 (dd, J=8.99, 5.47 Hz, 1H) 4.28-4.30 (m, 1H) 4.36 (td, J=10.36, 4.30 Hz, 1H) 4.50-4.61 (m, 3H) 7.26-7.37 (m, 5H)

Methyl 2-((2R,3S,3aS,4aS,7R,8aR,9S,9aS)-2-(2-(benzyloxy)ethyl)-3,9-dihydroxydecahydrofuro[3,2-b]pyrano[2,3-e]pyran-7-yl)acetate

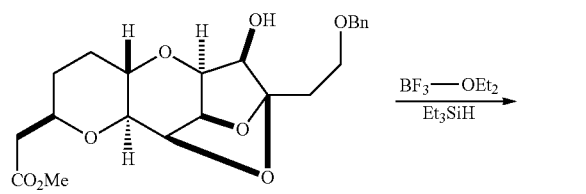

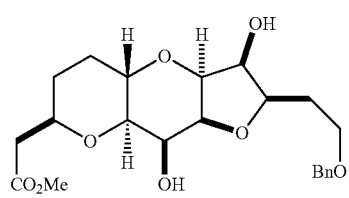

To a solution of methyl 2-((2R,3R,3aS,4aS,7R,8aS,9S,9aR)-2-(2-(benzyloxy)ethyl)-3-hydroxydecahydro-2,9-epoxyfuro[3,2-b]pyrano[2,3-e]pyran-7-yl)acetate (8 mg, 0.019 mmol) in dichloromethane (1 mL) was added triethylsilane (0.1 mL, 0.626 mmol). The resulting solution was cooled to 0° C. and treated with BF$_3$.OEt$_2$ (0.012 mL, 0.095 mmol). The reaction mixture was brought to ambient temperature and stirred until all the starting material was consumed. Upon completion, the reaction was quenched with sat. aq. NaHCO$_3$ (1 mL) and 30% (w/v) aqueous NaCl (1 mL). The resulting mixture was extracted twice with EtOAc (5 mL). The combined organic layers were washed with 30% (w/v) aqueous NaCl (3 mL) and dried over MgSO$_4$. Filtration, concentration in vacuo, and purification by silica gel column chromatography using a 50-100% gradient of ethyl acetate in n-heptane followed by a 0-20% gradient of methanol in ethyl acetate as eluent provided 3.0 mg of the target product.

$^1$H NMR (400 MHz, CHLOROFORM-d) δ ppm 1.37-1.49 (m, 2H) 1.76-1.83 (m, 1H) 1.92-2.10 (m, 2H) 2.12-2.22 (m, 1H) 2.43 (dd, J=15.63, 5.47 Hz, 1H) 2.63 (dd, J=16.02, 7.43 Hz, 1H) 3.05 (dd, J=9.77, 1.95 Hz, 1H) 3.43-3.51 (m, 1H) 3.52-3.65 (m, 2H) 3.66-3.68 (m, 3H) 3.83-3.93 (m, 1H) 3.94-4.07 (m, 3H) 4.09-4.20 (m, 2H) 4.37-4.43 (m, 2H) 4.49-4.52 (m, 2H) 7.27-7.38 (m, 5H)

Methyl 2-((2R,3R,3aS,4aS,7R,8aR,9S,9aS)-2-(2-(benzyloxy)ethyl)-3,9-dihydroxydecahydrofuro[3,2-b]pyrano[2,3-e]pyran-7-yl)acetate

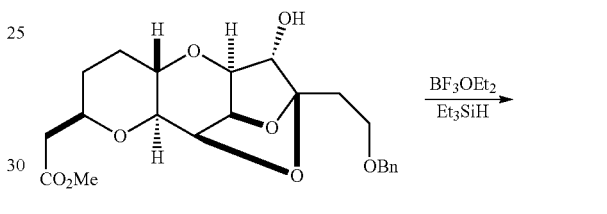

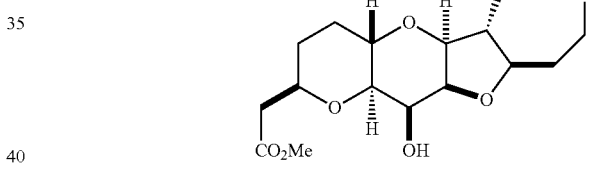

To a solution of methyl 2-((2R,3S,3aS,4aS,7R,8aS,9S,9aR)-2-(2-(benzyloxy)ethyl)-3-hydroxydecahydro-2,9-epoxyfuro[3,2-b]pyrano[2,3-e]pyran-7-yl)acetate (13 mg, 0.031 mmol) in dichloromethane (1 mL) was added triethylsilane (0.1 mL, 0.626 mmol). The resulting solution was cooled to 0° C. and treated with BF$_3$.OEt$_2$ (0.020 mL, 0.155 mmol). The reaction mixture was brought to ambient temperature and stirred until all the starting material was consumed. Upon completion, the reaction was quenched with sat. aq. NaHCO$_3$ (1 mL) and 30% (w/v) aqueous NaCl (1 mL). The resulting mixture was extracted twice with EtOAc (5 mL). The combined organic layers were washed with 30% (w/v) aqueous NaCl (3 mL) and dried over MgSO$_4$. Filtration, concentration in vacuo, and purification by silica gel column chromatography using a 60-100% gradient of ethyl acetate in n-heptane as eluent provided 8.0 mg of the target product.

$^1$H NMR (400 MHz, CHLOROFORM-d) δ ppm 1.37-1.55 (m, 2H) 1.71-1.80 (m, 1H) 1.94-2.02 (m, 1H) 2.04-2.18 (m, 2H) 2.43 (dd, J=15.83, 5.67 Hz, 1H) 2.63 (dd, J=15.83, 7.23 Hz, 1H) 3.08 (dd, J=9.38, 2.34 Hz, 1H) 3.67 (s, 5H) 3.72-3.81 (m, 2H) 3.82-3.91 (m, 1H) 4.02-4.06 (m, 1H) 4.06-4.12 (m, 1H) 4.27 (dd, J=9.38, 7.43 Hz, 1H) 4.34 (dd, J=9.38, 8.21 Hz, 1H) 4.51-4.55 (m, 2H) 7.26-7.38 (m, 5H)

163

Methyl 2-((2R,3aR,4aS,7R,8aS,9aR)-2-(2-(benzyloxy)ethyl)-3,9-dioxodecahydrofuro[3,2-b]pyrano[2,3-e]pyran-7-yl)acetate

164

Methyl 2-((2R,3S,3aS,4aS,7R,8aR,9S,9aS)-2-(2-(benzyloxy)ethyl)-3,9-dihydroxydecahydrofuro[3,2-b]pyrano[2,3-e]pyran-7-yl)acetate

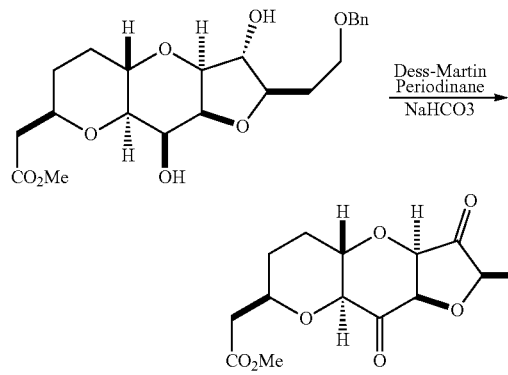

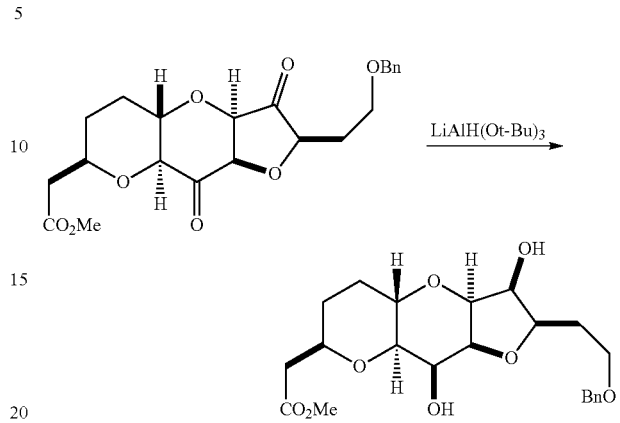

To a solution of methyl 2-((2R,3R,3aS,4aS,7R,8aR,9S,9aS)-2-(2-(benzyloxy)ethyl)-3,9-dihydroxydecahydrofuro[3,2-b]pyrano[2,3-e]pyran-7-yl)acetate (4 mg, 9.468 μmol) in dichloromethane (1 mL) at ambient temperature were added Dess-Martin periodinane (12 mg, 0.028 mmol) and sodium bicarbonate (4 mg, 0.047 mmol). After being stirred for 2 h, the reaction mixture was diluted with MTBE (5 mL), and treated with sat. aq. Na$_2$S$_2$O$_3$ (3 mL) and water (1 mL). After 30 min stirring, the organic layer was separated, washed with 30% (w/v) aqueous NaCl, and dried over MgSO$_4$. Filtration and concentration in vacuo provided 4.0 mg of the target product.

$^1$H NMR (400 MHz, CHLOROFORM-d) δ ppm 1.05-1.18 (m, 1H) 1.64-1.72 (m, 1H) 1.72-1.81 (m, 1H) 1.81-1.89 (m, 1H) 1.90-2.01 (m, 1H) 2.18-2.27 (m, 1H) 2.35-2.44 (m, 1H) 2.70 (dd, J=16.02, 6.64 Hz, 1H) 3.34 (td, J=10.26, 4.89 Hz, 1H) 3.67 (s, 3H) 3.70-3.77 (m, 2H) 3.79-3.86 (m, 1H) 3.89 (d, J=10.16 Hz, 1H) 4.40-4.46 (m, 1H) 4.48 (s, 1H) 4.85 (d, J=10.55 Hz, 1H) 5.07 (dd, J=10.75, 1.37 Hz, 1H) 7.27-7.37 (m, 5H)

To a solution of methyl 2-((2R,3aR,4aS,7R,8aS,9aR)-2-(2-(benzyloxy)ethyl)-3,9-dioxodecahydrofuro[3,2-b]pyrano[2,3-e]pyran-7-yl)acetate (4 mg, 9.464 μmol) in THF (1 mL) at 0° C. was added 1.0 M lithium tri-tert-butoxyaluminum hydride (0.047 mL, 0.047 mmol). The reaction mixture was stirred at ambient temperature until all the starting material was consumed. Upon completion, the reaction mixture was treated with a sat. aq. Rochelle salt solution (3 mL) and extracted with EtOAc (5 mL) twice. The combined organic layers were washed with 30% (w/v) aqueous NaCl (2 mL) and dried over MgSO$_4$. Filtration, concentration in vacuo, and purification by silica gel column chromatography using a 50-100% gradient of ethyl acetate in n-heptane followed by a 0-20% gradient of methanol in ethyl acetate as eluent provided 3.1 mg of the target product.

Example 8—Preparation of Compound (ID)

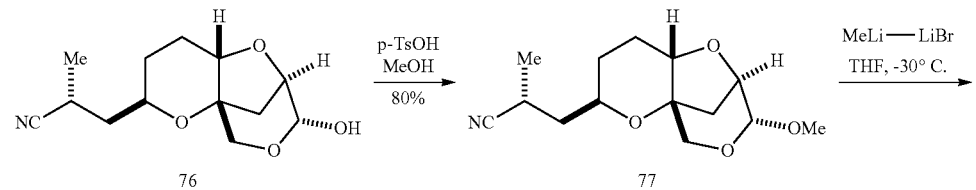

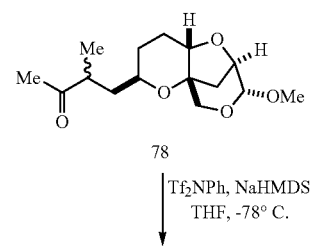

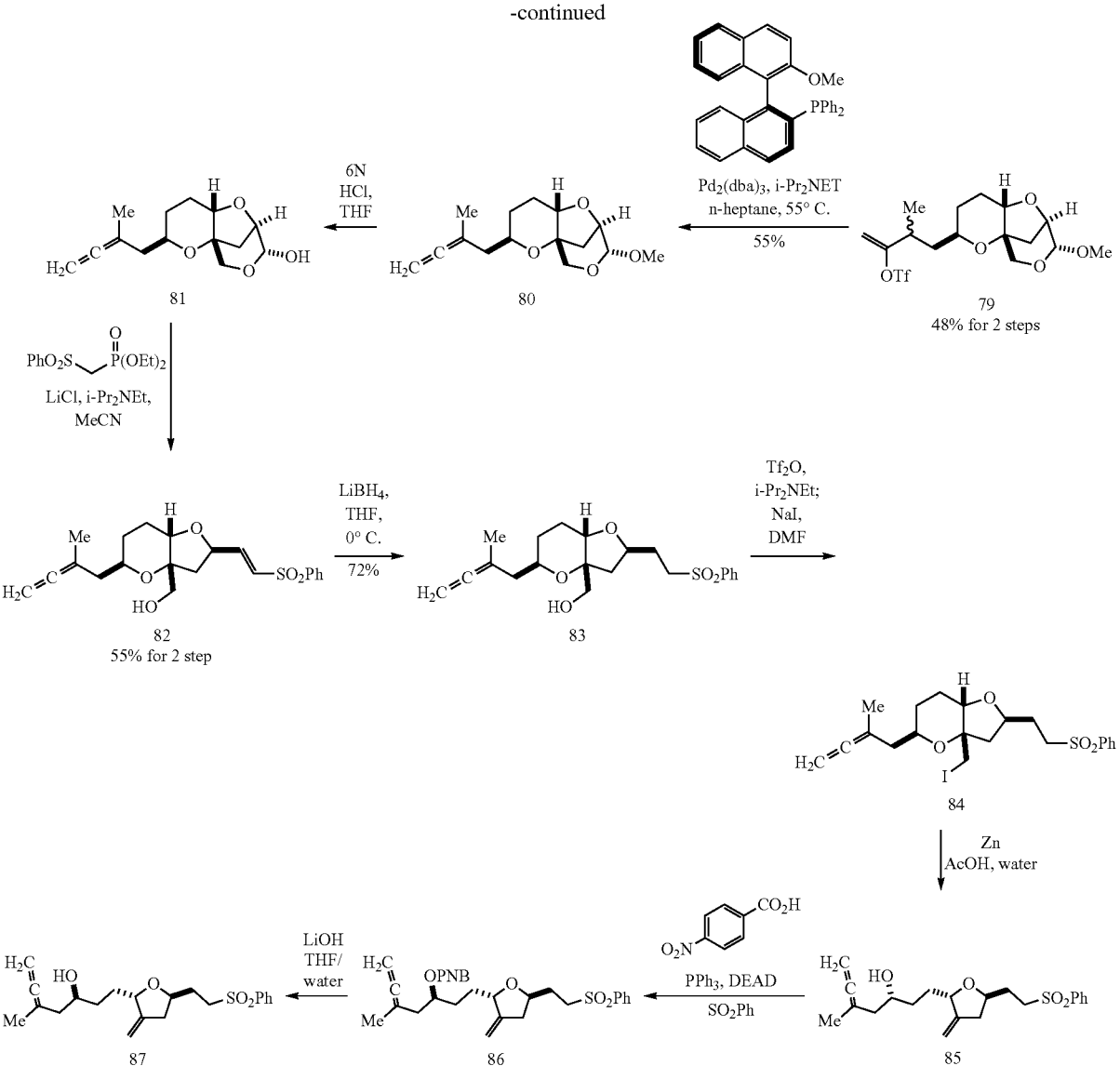

(R)-3-((2R,3R,5aR,7R,9aS)-3-methoxyhexahydro-5H-2,5a-methanopyrano[3,2-e][1,4]dioxepin-7-yl)-2-methylpropanenitrile

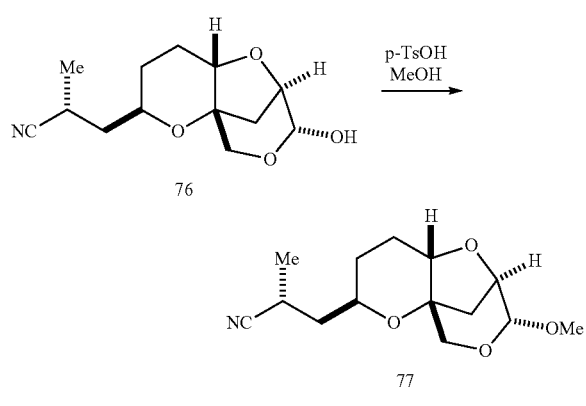

A solution of (R)-3-((2R,3R,5aR,7R,9aS)-3-hydroxyhexahydro-2H-2,5a-methanopyrano[3,2-e][1,4]dioxepin-7-yl)-2-methylpropanenitrile (20 g, 79 mmol) in methanol (200 mL) was treated with p-TsOH (0.751 g, 3.95 mmol) and stirred at 40° C. for 22 h. The mixture was concentrated in vacuo, evaporated again with methanol (100 mL), and azeotroped with toluene (100 mL). The residue was treated with sat. aq. NaHCO$_3$ (100 mL) and extracted twice with MTBE (160 mL). The organic layers were combined, dried over MgSO$_4$, and concentrated in vacuo. The residue was dissolved in MTBE (30 mL) with heating to make a clear solution and treated with n-heptane (60 mL). The resulting suspension was stirred at 65° C. (bath) for 30 min and slowly cooled to room temperature over 1 d. The precipitate was filtered, washed with MTBE/n-heptane=1/5, and dried under a stream of N$_2$ to give the title compound (16.94 g, 80%). $^1$H NMR (400 MHz, CHLOROFORM-d) δ 1.15-1.28 (m, 1H), 1.30 (d, 3H), 1.45-1.59 (m, 3H), 1.61-1.72 (m, 1H), 1.92 (d, 1H), 2.12-2.21 (m, 1H), 2.41-2.49 (m, 1H), 2.82-2.92 (m, 1H), 3.35-3.39 (m, 1H), 3.38 (s, 3H), 3.72-3.80 (m, 3H), 4.12 (dd, 1H), 4.42 (dd, 1H).

4-((2R,3R,5aR,7R,9aS)-3-methoxyhexahydro-5H-2,5a-methanopyrano[3,2-e][1,4]dioxepin-7-yl)-3-methylbutan-2-one

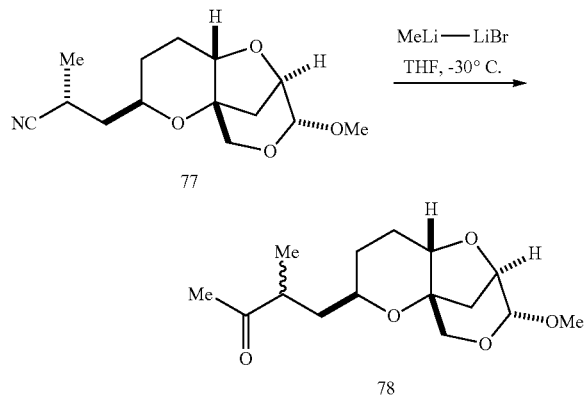

A solution of (R)-3-((2R,3R,5aR,7R,9aS)-3-methoxyhexahydro-2H-2,5a-methanopyrano[3,2-e][1,4]dioxepin-7-yl)-2-methylpropanenitrile (7.0 g, 26 mmol) in THF (105 mL) was cooled to −35° C. and treated with 1.5 M methyllithium as lithium bromide complex in diethyl ether (21.0 mL, 31.4 mmol), while maintaining the internal temperature below −30° C. The mixture was stirred at −30° C. for 2 h. The reaction was quenched with sat. aq. NH₄Cl (70 mL) and warmed to room temperature over 10 min with stirring. The mixture was extracted twice with MTBE (56 mL). The organic layers were combined, dried over MgSO₄, and concentrated in vacuo to give the title compound as a mixture of two isomers (3.43 g 105%).

4-((2R,3R,5aR,7R,9aS)-3-methoxyhexahydro-5H-2,5a-methanopyrano[3,2-e][1,4]dioxepin-7-yl)-3-methylbut-1-en-2-yl trifluoromethanesulfonate

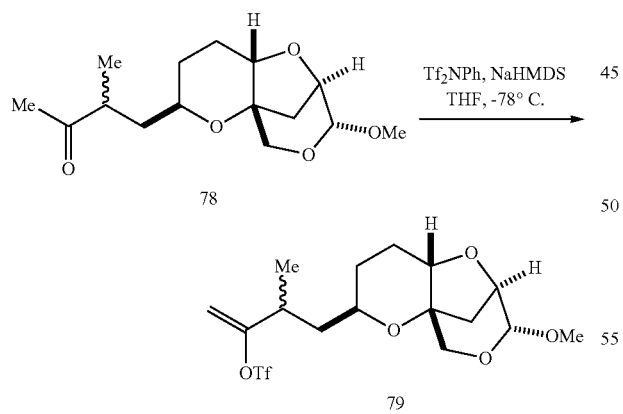

A solution of 4-((2R,3R,5aR,7R,9aS)-3-methoxyhexahydro-2H-2,5a-methanopyrano[3,2-e][1,4]dioxepin-7-yl)-3-methylbutan-2-one (0.13 g, 0.46 mmol) in THF (3.3 mL) was cooled to −78° C. and treated with 1 M NaHMDS in THF (0.50 mL, 0.50 mmol) over 10 min maintaining the internal temperature below −65° C. The mixture was stirred at −78° C. for 30 min. A solution of 1,1,1-trifluoro-N-phenyl-N-(trifluoromethyl)sulfonyl methanesulfonamide (0.245 g, 0.686 mmol) in THF (1.0 mL) was added, and stirring was continued at −78° C. for 1 h. Additional 1 M NaHMDS in THF (0.091 mL, 0.091 mmol) was added, and stirring was continued at −78° C. for another 1 h. The reaction was quenched with sat. aq. NH₄Cl (1.3 mL) and extracted twice with n-heptane (0.9 mL). The organic layers were combined, washed with brine, concentrated in vacuo, and purified by silica gel column chromatography (ethyl acetate in n-heptane=10% to 30%) to give the title compound as a mixture of two isomers (130 mg 68%).

(2R,3R,5aR,7R,9aS)-3-methoxy-7-(2-methylbuta-2,3-dien-1-yl)hexahydro-5H-2,5a-methanopyrano[3,2-e][1,4]dioxepine

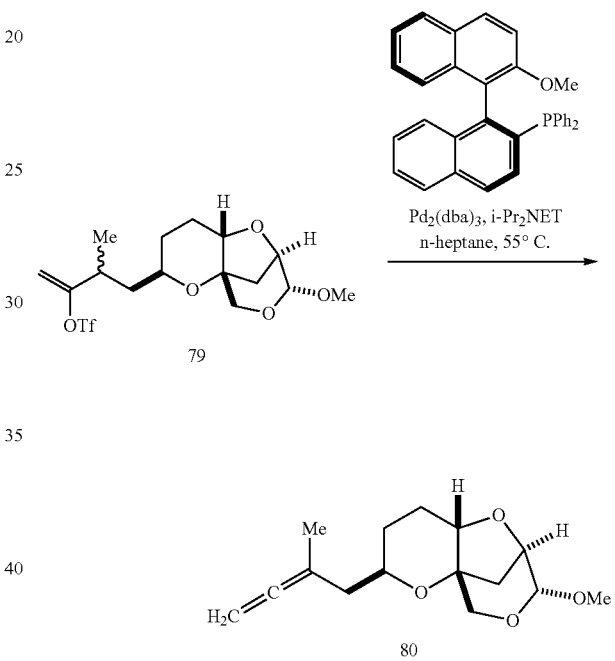

A 100 mL flask was charged with Pd₂(dba)₃ (0.088 g, 0.096 mmol), (S)-(−)-(diphenylphosphino)-2′-methoxy-1,1′-binaphthyl (0.180 g, 0.384 mmol), and n-heptane (32 mL) and heated to 55° C. for 5 min. The mixture was treated with a mixture of 4-((2R,3R,5aR,7R,9aS)-3-methoxyhexahydro-2H-2,5a-methanopyrano[3,2-e][1,4]dioxepin-7-yl)-3-methylbut-1-en-2-yl trifluoromethanesulfonate (2.0 g, 4.8 mmol) and N,N-diisopropylethylamine (1.7 mL, 9.6 mmol) in n-heptane (15 mL). The mixture was stirred at 55° C. for 24 h. After cooling to room temperature, the mixture was filtered through a celite pad and rinsed with n-heptane. The filtrate was concentrated in vacuo and purified by silica gel column chromatography (ethyl acetate in n-heptane=10% to 40%) to give the title compound (700 mg, 55%). ¹H NMR (400 MHz, CHLOROFORM-d) δ 1.12-1.35 (m, 2H), 1.40-1.53 (m, 1H), 1.61-1.66 (m, 1H), 1.68 (t, J=3.13 Hz, 3H), 1.88 (d, J=10.55 Hz, 1H), 1.95-2.05 (m, 1H), 2.06-2.21 (m, 2H), 2.36-2.52 (m, 1H), 3.39 (s, 2H), 3.37-3.42 (dd, J=9.77, 2.74 Hz, 1H), 3.63-3.72 (m, 1H), 3.75 (d, J=9.77 Hz, 1H), 3.79 (dd, J=10.55, 6.64 Hz, 1H), 4.11 (dd, J=6.25, 2.74 Hz, 1H), 4.43 (d, J=2.74 Hz, 1H), 4.53-4.65 (m, 2H).

(2R,3R,5aR,7R,9aS)-7-(2-methylbuta-2,3-dien-1-yl)hexahydro-5H-2,5a-methanopyrano[3,2-e][1,4]dioxepin-3-ol

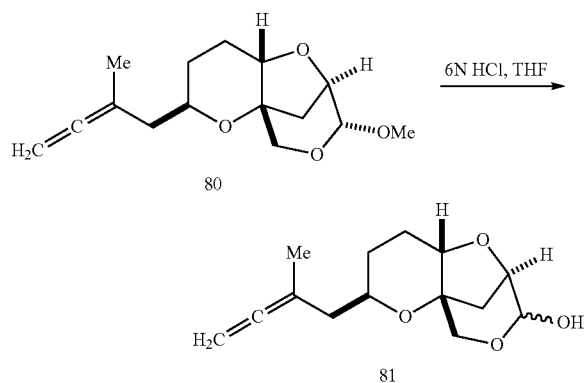

(2R,3R,5aR,7R,9aS)-3-methoxy-7-(2-methylbuta-2,3-dien-1-yl)hexahydro-2H-2,5a-methanopyrano[3,2-e][1,4]dioxepine (0.60 g, 2.25 mmol) was dissolved in THF (9 mL) and treated with 6 N HCl (9.0 mL, 54 mmol). The mixture was stirred at room temperature for 14 h. The mixture was extracted twice with ethyl acetate (9 mL). The organic layers were combined, washed with sat. aq. NaHCO$_3$ (9 mL), dried over MgSO$_4$, and concentrated in vacuo to give the title compound as a mixture of two anomeric isomers (630 mg, 110%).

((2R,3aR,5R,7aS)-5-(2-methylbuta-2,3-dien-1-yl)-2-((E)-2-(phenylsulfonyl)vinyl)hexahydro-3aH-furo[3,2-b]pyran-3a-yl)methanol

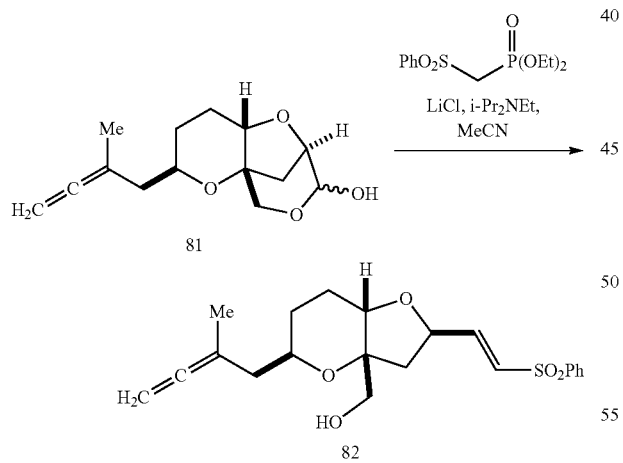

A mixture of (2R,3R,5aR,7R,9aS)-7-(2-methylbuta-2,3-dien-1-yl)hexahydro-2H-2,5a-methanopyrano[3,2-e][1,4]dioxepin-3-ol (0.68 g, 2.7 mmol), diethyl ((phenylsulfonyl)methyl)phosphonate (0.87 g, 3.0 mmol), and lithium chloride (0.17 g, 4.0 mmol) in acetonitrile (13.6 mL) was cooled to 0° C. and treated with N,N-diisopropylethylamine (0.75 mL, 4.3 mmol). The mixture was stirred at 0° C. for 1 h and at room temperature for 4 h. Additional phosphonate (157 mg), lithium chloride (34 mg), and N,N-diisopropylethylamine (0.14 mL) were added, and stirring was continued at room temperature for another 15 h. The reaction mixture was poured into water (6.8 mL) and extracted twice with MTBE (10 mL). The organic layers were combined, dried over MgSO$_4$, concentrated in vacuo, and purified by silica gel column chromatography (ethyl acetate in n-heptane=10% to 50%) to give the title compound (548 mg, 55% for 2 steps). $^1$H NMR (400 MHz, CHLOROFORM-d) δ 1.19-1.34 (m, 1H), 1.60-1.80 (m, 3H), 1.69 (t, J=3.13 Hz, 3H), 1.81-1.95 (m, 1H), 2.00-2.09 (m, 1H), 2.09-2.21 (m, 1H), 2.44-2.60 (m, 1H), 3.40 (s, 2H), 3.68-3.84 (m, 1H), 3.88-4.01 (m, 1H), 4.54-4.67 (m, 2H), 4.76-4.91 (m, 1H), 6.56 (dd, J=14.85, 1.95 Hz, 1H), 6.93 (dd, J=14.85, 3.52 Hz, 1H), 7.46-7.57 (m, 2H), 7.57-7.67 (m, 1H), 7.81-7.92 (m, 2H).

((2R,3aR,5R,7aS)-5-(2-methylbuta-2,3-dien-1-yl)-2-(2-(phenylsulfonyl)ethyl)hexahydro-3aH-furo[3,2-b]pyran-3a-yl)methanol

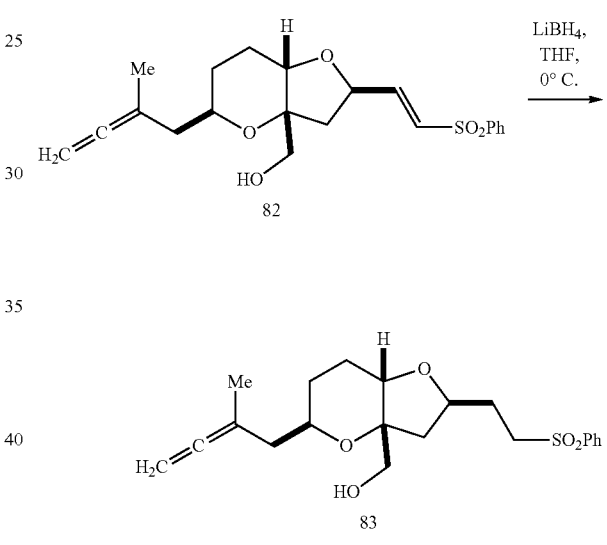

A solution of ((2R,3aR,5R,7aS)-5-(2-methylbuta-2,3-dien-1-yl)-2-((E)-2-(phenylsulfonyl)vinyl)hexahydro-2H-furo[3,2-b]pyran-3a-yl)methanol (0.51 g, 1.3 mmol) in THF (10 mL) was cooled to 0° C. and treated with 2 M LiBH$_4$ in THF (0.98 mL, 2.0 mmol). The mixture was stirred at 0° C. for 4 h. The reaction was quenched with 20% (w/v) citric acid in water (8.16 mL) and extracted twice with MTBE (10 mL). The organic layers were combined, washed with sat. aq. NaHCO$_3$ (5 mL) and then with brine (5 mL), and concentrated in vacuo. The residue was purified by silica gel column chromatography (ethyl acetate in n-heptane=10% to 60%) to give the title compound (370 mg, 72%). $^1$H NMR (400 MHz, CHLOROFORM-d) δ 1.13-1.26 (m, 1H), 1.40 (dd, J=13.87, 6.06 Hz, 1H), 1.53-1.63 (m, 1H), 1.65 (t, J=3.13 Hz, 3H), 1.67-1.72 (m, 1H), 1.74-1.85 (m, 2H), 1.86-1.97 (m, 1H), 1.97-2.05 (m, 1H), 2.05-2.14 (m, 1H), 2.28 (dd, J=14.07, 8.60 Hz, 1H), 3.07 (ddd, J=14.07, 10.94, 5.08 Hz, 1H), 3.24 (ddd, J=14.07, 10.94, 5.08 Hz, 1H), 3.41 (s, 2H), 3.62-3.72 (m, 1H), 3.77 (dd, J=8.60, 5.86 Hz, 1H), 4.12-4.22 (m, 1H), 4.51-4.61 (m, 2H), 7.49-7.58 (m, 2H), 7.59-7.67 (m, 1H), 7.83-7.93 (m, 2H).

171

(2R,3aS,5R,7aS)-3a-(iodomethyl)-5-(2-methylbuta-2,3-dien-1-yl)-2-(2-(phenylsulfonyl)ethyl)hexahydro-2H-furo[3,2-b]pyran

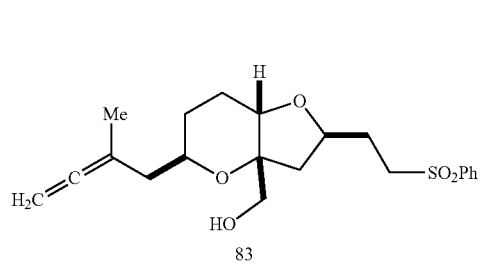

A solution of ((2R,3aR,5R,7aS)-5-(2-methylbuta-2,3-dien-1-yl)-2-(2-(phenylsulfonyl)ethyl)hexahydro-2H-furo[3,2-b]pyran-3a-yl)methanol (0.37 g, 0.94 mmol) in CH$_2$Cl$_2$ (3 mL) was cooled to −5° C. and treated with 2,6-lutidine (0.33 mL, 2.8 mmol) and 1M Tf$_2$O in CH$_2$Cl$_2$ (1.4 mL, 1.4 mmol). After stirring at −5° C. for 1.5 h, the mixture was diluted with DMF (2.78 mL) and treated with sodium iodide (0.42 g, 2.8 mmol). The mixture was stirred at room temperature for 20 h. The mixture was diluted with MTBE (19 mL) and sequentially washed with water (5.6 mL), 1 N HCl (5.6 mL), sat. aq. NaHCO$_3$ (3.7 mL), and 20% (w/v) Na$_2$S$_2$O$_3$ in water (3.7 mL). After concentration, the residue was purified by silica gel column chromatography (ethyl acetate in n-heptane=10% to 40%) to give the title compound (140 mg, 30%). $^1$H NMR (400 MHz, CHLOROFORM-d) δ 1.13-1.32 (m, 1H), 1.54-1.82 (m, 3H), 1.68 (t, J=3.13 Hz, 3H), 1.72-1.82 (m, 1H), 1.82-1.99 (m, 2H), 2.00-2.09 (m, 1H), 2.11-2.23 (m, 1H), 2.43 (dd, J=14.07, 8.21 Hz, 1H), 3.07 (ddd, J=13.97, 10.84, 5.28 Hz, 1H), 3.20-3.30 (m, 1H), 3.27 (d, J=10.16 Hz, 1H), 3.35 (d, J=10.94 Hz, 1H), 3.60-3.70 (m, 1H), 3.77 (dd, J=7.82, 5.47 Hz, 1H), 4.11-4.24 (m, 1H), 4.52-4.60 (m, 2H), 7.51-7.59 (m, 2H), 7.60-7.70 (m, 1H), 7.84-7.96 (m, 2H).

172

(R)-5-methyl-1-((2S,5R)-3-methylene-5-(2-(phenylsulfonyl)ethyl)tetrahydrofuran-2-yl)hepta-5,6-dien-3-ol

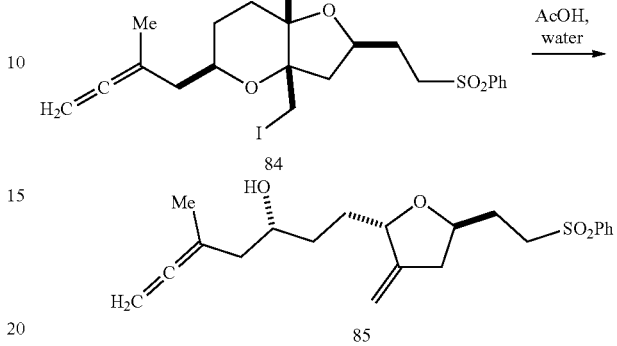

A suspension of zinc dust (0.128 g, 1.95 mmol) in water (0.9 mL) was cooled to 0° C. and treated with acetic acid (0.019 mL, 0.33 mmol). After stirring for 10 min, the mixture was treated with a solution of (2R,3aS,5R,7aS)-3a-(iodomethyl)-5-(2-methylbuta-2,3-dien-1-yl)-2-(2-(phenylsulfonyl)ethyl)hexahydro-2H-furo[3,2-b]pyran (0.14 g, 0.28 mmol) in THF (1.4 mL). After stirring at 0° C. for 1 h, the reaction was quenched with 20% (w/v) citric acid in water (0.84 mL) and stirred at 0° C. for 10 min. The mixture was filtered through a celite pad to remove insoluble zinc and rinsed with MTBE (14 mL). The organic layers were separated, and washed with sat. NaHCO$_3$ (1.4 mL) and brine (1.4 mL). After concentration, the residue was purified by silica gel column chromatography (ethyl acetate in n-heptane=10% to 50%) to give the title compound (76 mg, 72%). $^1$H NMR (400 MHz, CHLOROFORM-d) δ 1.43-1.65 (m, 3H), 1.69 (t, J=3.12 Hz, 3H), 1.70-1.80 (m, 1H), 1.83-1.96 (m, 2H), 1.98-2.12 (m, 2H), 2.19-2.30 (m, 2H), 2.62-2.76 (m, 1H), 3.05-3.19 (m, 1H), 3.21-3.34 (m, 1H), 3.74 (br s, 1H), 4.06 (dt, J=12.88, 6.44 Hz, 1H), 4.28 (br s, 1H), 4.58-4.70 (m, 2H), 4.85 (q, J=2.34 Hz, 1H), 4.98 (q, J=2.34 Hz, 1H), 7.50-7.60 (m, 2H), 7.61-7.69 (m, 1H), 7.87-7.94 (m, 2H).

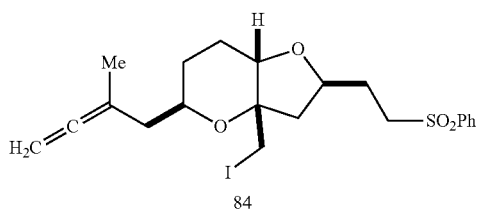

OTHER EMBODIMENTS

Various modifications and variations of the described compositions and methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:
1. A method of preparing a compound of formula (IB), the method comprising reacting a compound of formula (IA) with $R_{12}OH$ and a Lewis acid,
wherein $R_{12}$ is optionally substituted acyl;
wherein the compound of formula (IA) is:

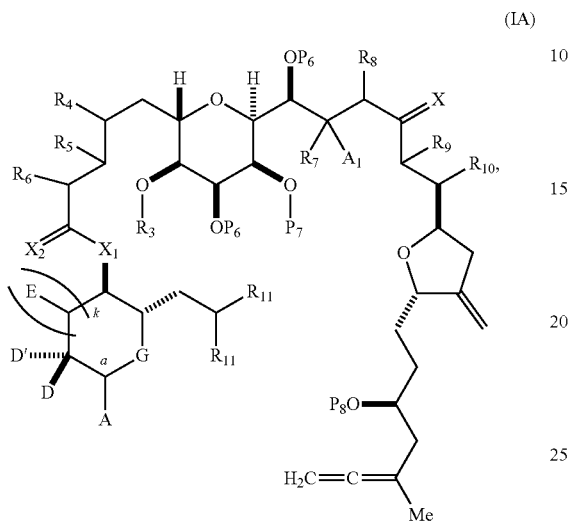

(IA)

or a salt or a tautomer thereof,
wherein
each of D and D' is independently H, optionally substituted alkyl, or $OP_1$, provided that only one of D and D' is $OP_1$, wherein $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

(1)

wherein
L is —(CH(OP$_2$))—, —(C(OH)(OP$_2$))—, or —C(O)—;
$R_1$ is H, or $R_1$ and $P_1$ combine to form a bond;
(i) $R_2$ is H, wherein $P_2$ is absent, H, optionally substituted alkyl, or a hydroxyl protecting group;
(ii) $R_2$ is —(CH$_2$)$_n$NP$_3$P$_4$, wherein $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;
(iii) $R_2$ is —(CH$_2$)$_n$OP$_5$, wherein $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or
(iv) $R_2$ and $P_2$ combine to form an optionally substituted ethylene or a structure selected from the group consisting of:

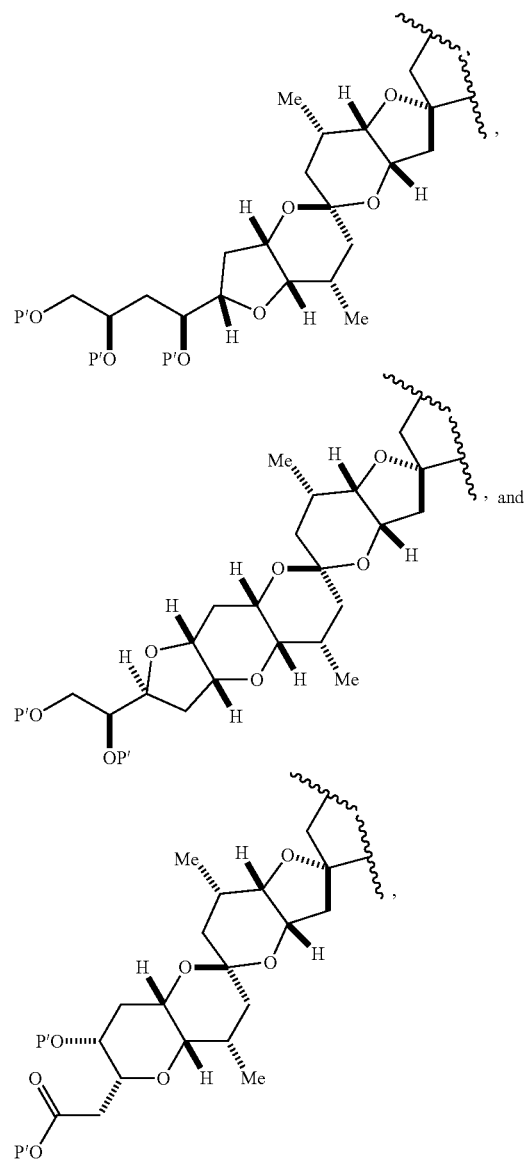

, and wherein each P' is independently H or a hydroxyl protecting group;
E is H, optionally substituted alkyl, or optionally substituted alkoxy;
G is O, S, CH$_2$, or NR$_N$, wherein R$_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, wherein each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$X_1$ is —CH(Y)—, —CH$_2$—, or —O—;
$X_2$ is =O or $X_2$, together with the carbon atom to which it is attached, is —(C(R$_X$)$_2$)—; wherein each R$_X$ is independently H, —OR$_{X1}$, or SR$_{X1}$, provided that at least one $R_X$, when present, is $-OR_{X1}$ or $-SR_{X1}$; wherein each $R_{X1}$ is independently optionally substituted alkyl, or both $R_{X1}$ combine to form optionally substituted alkylene, provided that, when $X_1$ is $-O-$, $X_2$ is $=O$;

Y is $SO_2R_C$ or $COOR_C$, where, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;

$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;

$A_1$ and $R_7$ combine to form oxo, $P_7$ is H or a hydroxyl protecting group, and $R_8$ is H;

or $A_1$ is H or OP''', and:

(a) $P_7$ is H or a hydroxyl protecting group, and $R_7$ and $R_8$, together with the atoms to which each is attached, combine to form a double bond;

or (b) $P_7$ and $R_7$ combine to form a bond, and $R_8$ is H or OP''';

(i) each $P_6$ is independently H or a hydroxyl protecting group, or both $P_6$, together with the atoms to which each is attached, combine to form a ketal or acetal; X is $=O$ or X combines with the carbon atom, to which it is attached, to form $-(CH(OP_9))-$, wherein $P_9$ is H or a hydroxyl protecting group; and each $R_{11}$ is $-OP_{10}$, or both $R_{11}$ combine to form oxo, wherein $P_{10}$ is alkyl or a hydroxyl protecting group;

(ii) both $P_6$ and X, together with the atoms to which each is attached, combine to form ketal, $P_7$ and $R_7$ combine to form a bond, and $R_6$ is H or OP'''; and each $R_{11}$ is $-OP_{10}$, or both $R_{11}$ combine to form oxo, wherein $P_{10}$ is alkyl or a hydroxyl protecting group; or (iii) both $P_6$ and both $R_{11}$, together with the atoms to which they are attached, combine to form acetal; and X is $=O$ or X combines with the carbon atom, to which it is attached, to form $-(CH(OP_9))-$, wherein $P_9$ is H or a hydroxyl protecting group;

$R_9$ is H, OP''', or Y, and $R_{10}$ is H; or $R_9$ and $R_{10}$, together with the atoms to which each is attached, combine to form a double bond;

each P''', when present, is independently H or a hydroxyl protecting group; and $P_8$ is H or silyl; and wherein the compound of formula (IB) is:

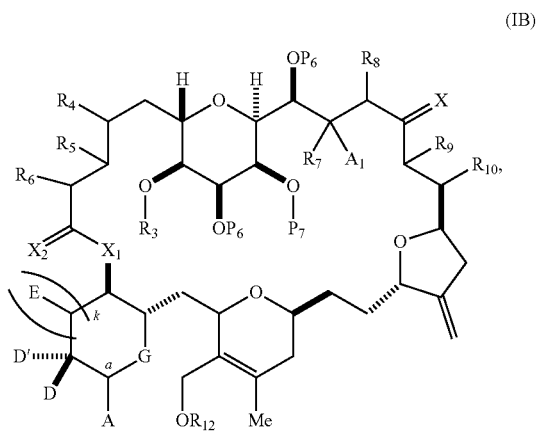

(IB)

or a salt or a tautomer thereof.

2. The method of claim 1, wherein the Lewis acid is an oxophilic Lewis acid.

3. The method of claim 2, wherein the oxophilic Lewis acid is boron trifluoride or a solvate thereof.

4. A method of preparing

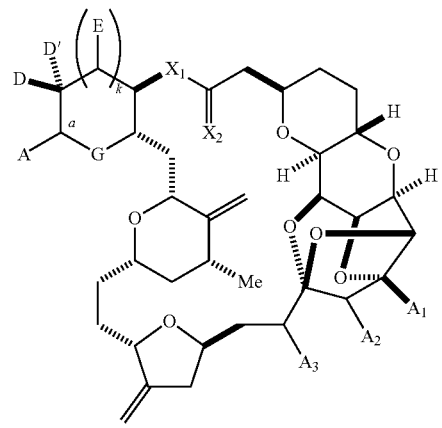

a halichondrin macrolide or an analog thereof, or a salt thereof, wherein each of D and D' is independently H, optionally substituted alkyl, or $OP_1$, provided that only one of D and D' is $OP_1$, wherein $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

(1)

wherein

L is —(CH(OP$_2$))—, —(C(OH)(OP$_2$))—, or —C(O)—;

R$_1$ is H, or R$_1$ and P$_1$ combine to form a bond;

(i) R$_2$ is H, wherein P$_2$ is absent, H, optionally substituted alkyl, or a hydroxyl protecting group;

(ii) R$_2$ is —(CH$_2$)$_n$NP$_3$P$_4$, wherein P$_3$ is H or an N-protecting group, and (a) P$_2$ is absent, H, optionally substituted alkyl, or a hydroxyl protecting group, and P$_4$ is an N-protecting group, or (b) P$_2$ and P$_4$ combine to form an alkylidene, or (c) each of P$_2$ and P$_4$ is H;

(iii) R$_2$ is —(CH$_2$)$_n$OP$_5$, wherein P$_2$ is absent, H, optionally substituted alkyl, or a hydroxyl protecting group, and P$_5$ is H, optionally substituted alkyl, or a hydroxyl protecting group; or P$_2$ and P$_5$, together with the atoms to which each is attached, combine to form a ketal, a cyclic carbonate, a dicarbonyl-dioxo, or silylene-dioxo; or (iv) R$_2$ and P$_2$ combine to form an optionally substituted ethylene or a structure selected from the group consisting of:

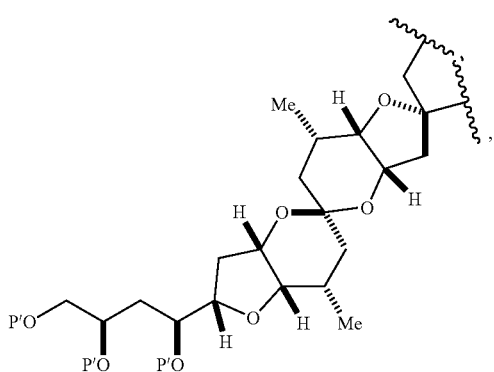

-continued

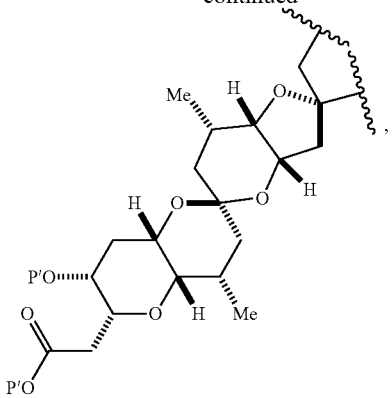

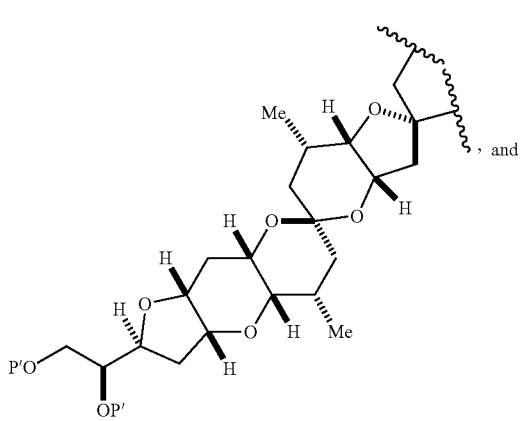, and

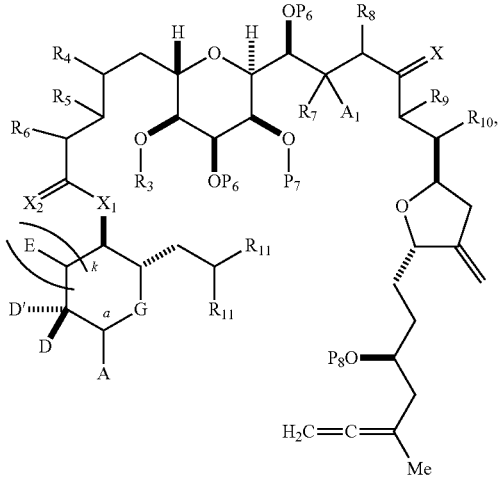

wherein each P' is independently H or a hydroxyl protecting group;

each of A$_1$, A$_2$, and A$_3$ is independently H or OP''', wherein each P''' is independently H or a hydroxyl protecting group;

E is H, optionally substituted alkyl, or optionally substituted alkoxy;

G is O, S, CH$_2$, or NR$_N$, wherein R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, wherein each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1; and

X$_1$ is —CH$_2$— or —O—, and X$_2$ is =O;

the method comprising:

(A) producing a compound of formula (IB) from a compound of formula (IA) and R$_{12}$OH, wherein R$_{12}$ is optionally substituted acyl, and the compound of formula (IA) is of the following structure:

(IA)

or a salt or a tautomer thereof, wherein each of D and D' is independently H, optionally substituted alkyl, or $OP_1$, provided that only one of D and D' is $OP_1$, wherein $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

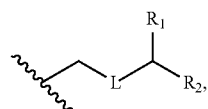
(1)

wherein

L is —(CH($OP_2$))—, —(C(OH)($OP_2$))—, or —C(O)—;

$R_1$ is H, or $R_1$ and $P_1$ combine to form a bond;

(i) $R_2$ is H, wherein $P_2$ is absent, H, optionally substituted alkyl, or a hydroxyl protecting group;

(ii) $R_2$ is —$(CH_2)_n NP_3 P_4$, wherein $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;

(iii) $R_2$ is —$(CH_2)_n OP_5$, wherein $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_2$ and $P_2$ combine to form an optionally substituted ethylene or a structure selected from the group consisting of:

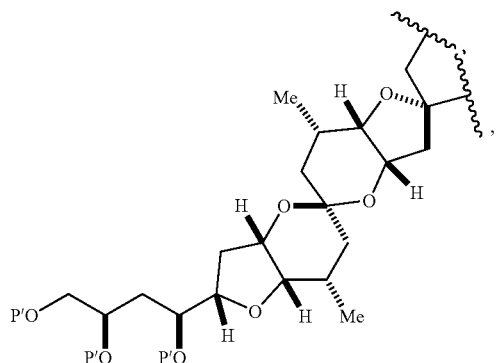

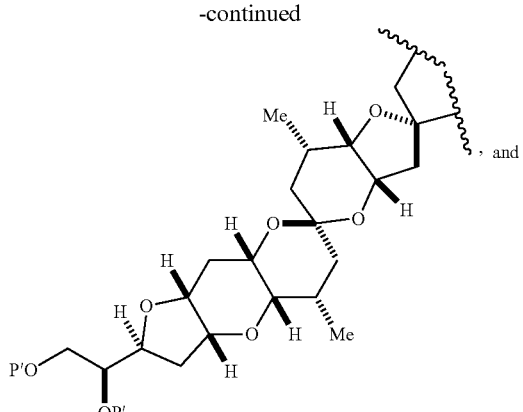

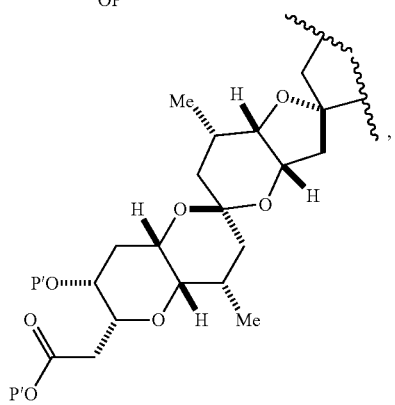

wherein each P' is independently H or a hydroxyl protecting group;

E is H, optionally substituted alkyl, or optionally substituted alkoxy;

G is O, S, $CH_2$, or $NR_N$, wherein $R_N$ is H, an N-protecting group, or optionally substituted alkyl;

each $Q_1$ is independently $OR_A$, $SR_A$, $SO_2R_A$, $OSO_2R_A$, $NR_B R_A$, $NR_B(CO)R_A$, $NR_B(CO)(CO)R_A$, $NR_B(CO)NR_B R_A$, $NR_B(CO)OR_A$, $(CO)OR_A$, $O(CO)R_A$, $(CO)NR_B R_A$, or $O(CO)NR_B R_A$, wherein each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

$X_1$ is —CH(Y)—, —$CH_2$—, or —O—, and $X_2$ is =O or $X_2$, together with the carbon atom to which it is attached, is —$(C(R_X)_2)$—; wherein each $R_X$ is independently H, —$OR_{X1}$, or —$SR_{X1}$, provided that at least one $R_X$, when present, is —$OR_{X1}$ or —$SR_{X1}$; wherein each $R_{X1}$ is independently optionally substituted alkyl, or both $R_{X1}$ combine to form optionally substituted alkylene, provided that, when $X_1$ is —O—, $X_2$ is =O; and wherein Y is $SO_2R_C$ or $COOR_C$, where, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;

$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;

A₁ and R₇ combine to form oxo, P₇ is H or a hydroxyl protecting group, and R₈ is H;
or
A₁ is H or OP''', and:
(i) P₇ is H or a hydroxyl protecting group, and R₇ and R₈, together with the atoms to which each is attached, combine to form a double bond;
or
(ii) P₇ and R₇ combine to form a bond, and R₈ is H or OP''';
(i) each P₆ is independently H or a hydroxyl protecting group, or both P₆, together with the atoms to which each is attached, combine to form a ketal or acetal; X is =O or X combines with the carbon atom, to which it is attached, to form —(CH(OP₉))—, wherein P₉ is H or a hydroxyl protecting group; and each R₁₁ is —OP₁₀, or both R₁₁ combine to form oxo, wherein P₁₀ is alkyl or a hydroxyl protecting group;
(ii) both P₆ and X, together with the atoms to which each is attached, combine to form ketal, P₇ and R₇ combine to form a bond, and R₈ is H or OP'''; and each R₁₁ is —OP₁₀, or both R₁₁ combine to form oxo, wherein P₁₀ is alkyl or a hydroxyl protecting group; or
(iii) both P₆ and both R₁₁, together with the atoms to which they are attached, combine to form acetal; and X is =O or X combines with the carbon atom, to which it is attached, to form —(CH(OP₉))—, wherein P₉ is H or a hydroxyl protecting group;
R₉ is H, OP''', SO₂R_C, or COOR_C, and R₁₀ is H; or R₉ and R₁₀, together with the atoms to which each is attached, combine to form a double bond;
each P''', when present, is independently H or a hydroxyl protecting group; and
P₈ is H or silyl;
and
the compound of formula (IB) is of the following structure:

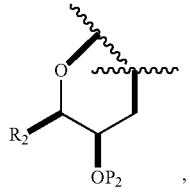

(IB)

or a salt or a tautomer thereof;
wherein
R₁₂ is optionally substituted acyl;
(B) producing the halichondrin macrolide or the analog thereof from compound (IB).

5. The method of claim 4, wherein the producing the compound of formula (IB) comprises reacting the compound of formula (IA) with R₁₂OH and a Lewis acid.

6. The method of claim 5, wherein the Lewis acid is an oxophilic Lewis acid.

7. The method of claim 4, wherein the producing the halichondrin macrolide or the analog thereof comprises reacting the compound of formula (IB) with an allylic reducing agent.

8. The method of claim 1, wherein R₃ and R₅ combine to form a bond, and each of R₄ and R₆ is H; or
wherein R₅ and R₆, together with the atom to which each is attached, combine to form a double bond, R₄ is H, and R₃ is a hydroxyl protecting group;
wherein P₆ is a hydroxyl protecting group, and X is =O or X combines with the carbon atom, to which it is attached, to form —(CH(OP₉))—;
wherein R₇ and P₇ combine to form a bond, and R₈ is H; or
wherein P₇ is a hydroxyl protecting group, and R₇ and R₈, together with the atoms to which each is attached, combine to form a double bond;
wherein R₉ is H or SO₂R_C, and R₁₀ is H;
wherein P₈ is silyl;
wherein each R₁₁ is —OP₁₀, wherein P₁₀ is alkyl;
wherein G is O;
wherein D is H;
wherein D' is OP₁, wherein P₁ is alkyl;
wherein the stereogenic center designated by a is (R), and A is of the following structure:

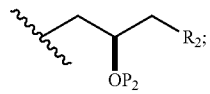

wherein k is 0 and X₁ is —CH₂—; wherein R₂ is —(CH₂)ₙNP₃P₄ or —(CH₂)ₙOP₅, or
wherein n is 0.

9. The method of claim 1, wherein A and D combine to form the following structure:

wherein, the bond to oxygen atom originates at the carbon atom, to which D is attached in formula (IA), and
wherein R₂ is —(CH₂)ₙNP₃P₄ or —(CH₂)ₙOP₅, wherein n is 2.

10. The method of claim 9, wherein k is 1, and E is optionally substituted alkyl or wherein X₁ is —O—.

11. A compound of formula (IA) or (IB):

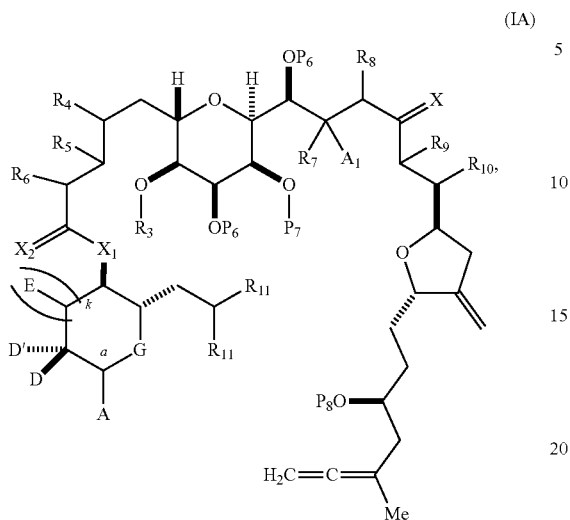
(IA)

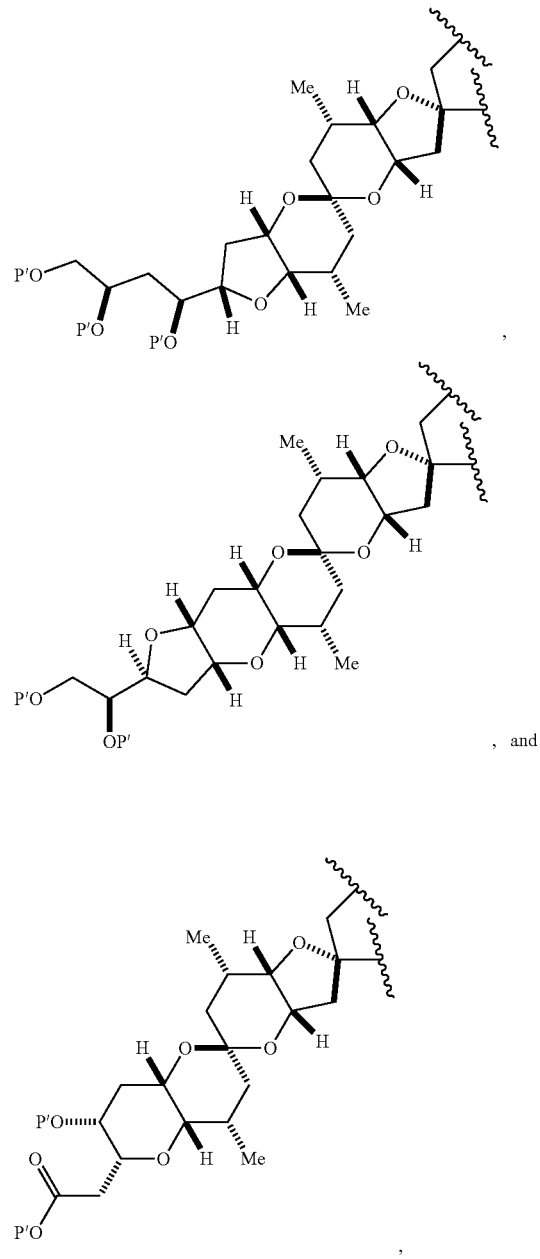

or a salt or a tautomer thereof, wherein each of D and D' is independently H, optionally substituted alkyl, or $OP_1$, provided that only one of D and D' is $OP_1$, wherein $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

(1)

wherein

L is —(CH($OP_2$))—, —(C(OH)($OP_2$))—, or —C(O)—;

$R_1$ is H, or $R_1$ and $P_1$ combine to form a bond;

(i) $R_2$ is H, wherein $P_2$ is absent, H, optionally substituted alkyl, or a hydroxyl protecting group;

(ii) $R_2$ is —$(CH_2)_n NP_3 P_4$, wherein $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;

(iii) $R_2$ is —$(CH_2)_n OP_5$, wherein $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_2$ and $P_2$ combine to form an optionally substituted ethylene or a structure selected from the group consisting of:

wherein each P' is independently H or a hydroxyl protecting group;

E is H, optionally substituted alkyl, or optionally substituted alkoxy;

G is O, S, $CH_2$, or $NR_N$, wherein $R_N$ is H, an N-protecting group, or optionally substituted alkyl;

each $Q_1$ is independently $OR_A$, $SR_A$, $SO_2R_A$, $OSO_2R_A$, $NR_B R_A$, $NR_B(CO)R_A$, $NR_B(CO)(CO)R_A$, $NR_B(CO)NR_B R_A$, $NR_B(CO)OR_A$, $(CO)OR_A$, $O(CO)R_A$, $(CO)NR_B R_A$, or $O(CO)NR_B R_A$, wherein each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

$X_1$ is —CH(Y)—, —CH$_2$—, or —O—;

$X_2$ is =O or $X_2$, together with the carbon atom to which it is attached, is —C($R_X$)$_2$—; wherein each $R_X$ is independently H, —OR$_{X1}$, or —SR$_{X1}$, provided that at least one $R_X$, when present, is —OR$_{X1}$ or —SR$_{X1}$; wherein each $R_{X1}$ is independently optionally substituted alkyl, or both $R_{X1}$ combine to form optionally substituted alkylene, provided that, when $X_1$ is —O—, $X_2$ is =O;

Y is SO$_2$R$_C$ or COOR$_C$, where, when Y is SO$_2$R$_C$, R$_C$ is optionally substituted aryl or optionally substituted non-enolizable alkyl, and when Y is COOR$_C$, R$_C$ is optionally substituted alkyl, optionally substituted aryl, or optionally substituted arylalkyl;

$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;

$A_1$ and $R_7$ combine to form oxo, $P_7$ is H or a hydroxyl protecting group, and $R_8$ is H;

or $A_1$ is H or OP'", and:

(i) $P_7$ is H or a hydroxyl protecting group, and $R_7$ and $R_8$, together with the atoms to which each is attached, combine to form a double bond;

or (ii) $P_7$ and $R_7$ combine to form a bond, and $R_8$ is H or OP'";

(i) each $P_6$ is independently H or a hydroxyl protecting group, or both $P_6$, together with the atoms to which each is attached, combine to form a ketal or acetal; X is =O or X combines with the carbon atom, to which it is attached, to form —(CH(OP$_9$))—, wherein $P_9$ is H or a hydroxyl protecting group; and each $R_{11}$ is —OP$_{10}$, or both $R_{11}$ combine to form oxo, wherein $P_{10}$ is alkyl or a hydroxyl protecting group;

(ii) both $P_6$ and X, together with the atoms to which each is attached, combine to form ketal, $P_7$ and $R_7$ combine to form a bond, and $R_8$ is H or OP'"; and each $R_{11}$ is —OP$_{10}$, or both $R_{11}$ combine to form oxo, wherein $P_{10}$ is alkyl or a hydroxyl protecting group; or (iii) both $P_6$ and both $R_{11}$, together with the atoms to which they are attached, combine to form acetal; and X is =O or X combines with the carbon atom, to which it is attached, to form —(CH(OP$_9$))—, wherein $P_9$ is H or a hydroxyl protecting group;

$R_9$ is H, OP'", or Y, and $R_{10}$ is H; or $R_9$ and $R_{10}$, together with the atoms to which each is attached, combine to form a double bond;

each P'", when present, is independently H or a hydroxyl protecting group; and $P_8$ is H or silyl;

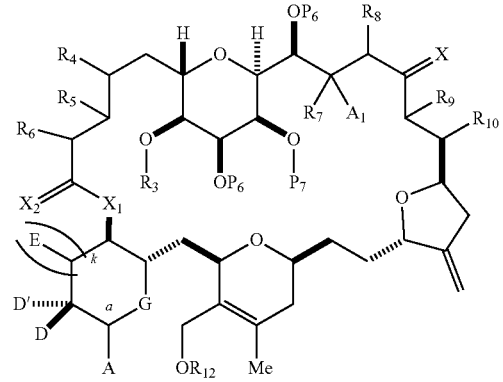

(IB)

or a salt or a tautomer thereof, wherein each of D and D' is independently H, optionally substituted alkyl, or OP$_1$, provided that only one of D and D' is OP$_1$, wherein $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

(1)

wherein

L is —(CH(OP$_2$))—, —(C(OH)(OP$_2$))—, or —C(O)—;

$R_1$ is H, or $R_1$ and $P_1$ combine to form a bond;

(i) $R_2$ is H, wherein $P_2$ is absent, H, optionally substituted alkyl, or a hydroxyl protecting group;

(ii) $R_2$ is —(CH$_2$)$_n$NP$_3$P$_4$, wherein $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;

(iii) $R_2$ is —(CH$_2$)$_n$OP$_5$, wherein $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_2$ and $P_2$ combine to form an optionally substituted ethylene or a structure selected from the group consisting of:

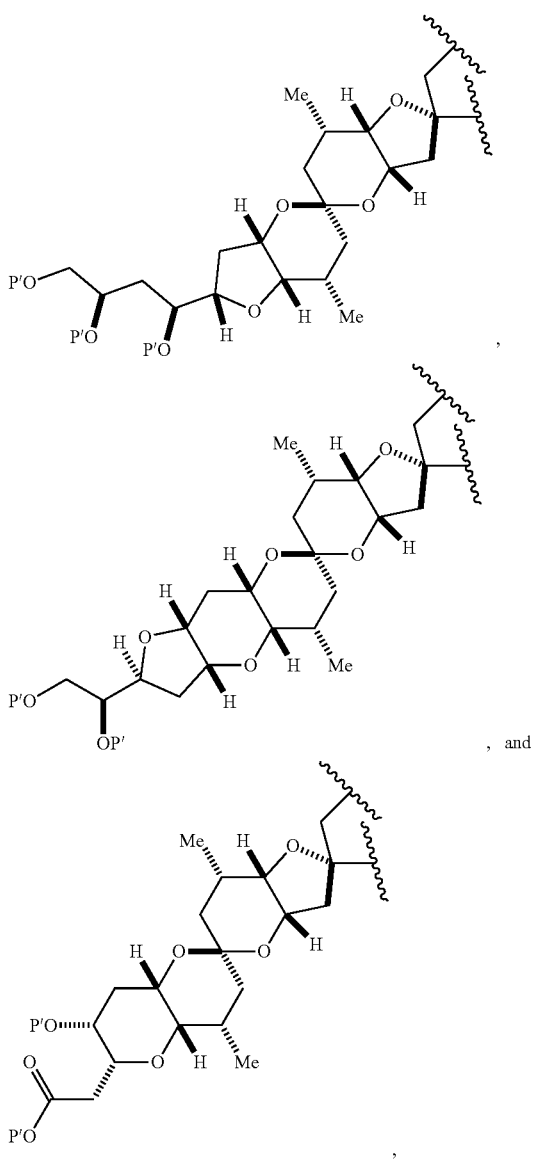
, wherein each P' is independently H or a hydroxyl protecting group;
  E is H, optionally substituted alkyl, or optionally substituted alkoxy;
  G is O, S, CH$_2$, or NR$_N$, wherein R$_N$ is H, an N-protecting group, or optionally substituted alkyl;
  each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, wherein each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
  n, when present, is 0, 1, or 2;
  k is 0 or 1;
  X$_1$ is —CH(Y)—, —CH$_2$—, or —O—;
  X$_2$ is =O or X$_2$, together with the carbon atom to which it is attached, is —(C(R$_X$)$_2$)—; wherein each R$_X$ is independently H, —OR$_{X1}$, or —SR$_{X1}$, provided that at least one R$_X$, when present, is —OR$_{X1}$ or —SR$_{X1}$; wherein each R$_{X1}$ is independently optionally substituted alkyl, or both R$_{X1}$ combine to form optionally substituted alkylene, provided that, when X$_1$ is —O—, X$_2$ is =O;
  Y is SO$_2$R$_C$ or COOR$_C$, where, when Y is SO$_2$R$_C$, R$_C$ is optionally substituted aryl or optionally substituted non-enolizable alkyl, and when Y is COOR$_C$, R$_C$ is optionally substituted alkyl, optionally substituted aryl, or optionally substituted arylalkyl;
  R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;
  A$_1$ and R$_7$ combine to form oxo, P$_7$ is H or a hydroxyl protecting group, and R$_8$ is H;
  or
  A$_1$ is H or OP''', and:
    (a) P$_7$ is H or a hydroxyl protecting group, and R$_7$ and R$_8$, together with the atoms to which each is attached, combine to form a double bond;
    or
    (b) P$_7$ and R$_7$ combine to form a bond, and R$_8$ is H or OP''';
  (i) each P$_6$ is independently H or a hydroxyl protecting group, or both P$_6$, together with the atoms to which each is attached, combine to form a ketal or acetal; X is =O or X combines with the carbon atom, to which it is attached, to form —(CH(OP$_9$))—, wherein P$_9$ is H or a hydroxyl protecting group; or
  (ii) both P$_6$ and X, together with the atoms to which each is attached, combine to form ketal, P$_7$ and R$_7$ combine to form a bond, and R$_8$ is H or OP''';
  R$_9$ is H, OP''', or Y, and R$_{10}$ is H; or R$_9$ and R$_{10}$, together with the atoms to which each is attached, combine to form a double bond;
  each P''', when present, is independently H or a hydroxyl protecting group; and
  R$_{12}$ is optionally substituted acyl.

12. The compound of claim 11, wherein P$_8$ is silyl; wherein each R$_{11}$ is —OP$_{10}$, wherein P$_{10}$ is alkyl; wherein R$_9$ is H or SO$_2$R$_C$, and R$_{10}$ is H; wherein P$_6$ is a hydroxyl protecting group, and X is =O or X combines with the carbon atom, to which it is attached, to form —(CH(OP$_9$))—; wherein A$_1$ is H; wherein the stereogenic center designated by a is (R), and A is of the following structure:

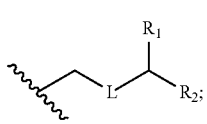
  (1)

wherein k is 0 and X$_1$ is —CH$_2$—;
  wherein R$_2$ is —(CH$_2$)$_n$NP$_3$P$_4$ or —(CH$_2$)$_n$OP$_5$, wherein n is 0;
  wherein R$_5$ and R$_6$, together with the atom to which each is attached, combine to form a double bond, R$_4$ is H, and R$_3$ is a hydroxyl protecting group;
  wherein R$_7$ and P$_7$ combine to form a bond, and R$_8$ is H; or wherein P₇ is a hydroxyl protecting group, and R₇ and R₈, together with the atoms to which each is attached, combine to form a double bond.

13. A compound of formula (IC), (IE), (IJ), or (IN):

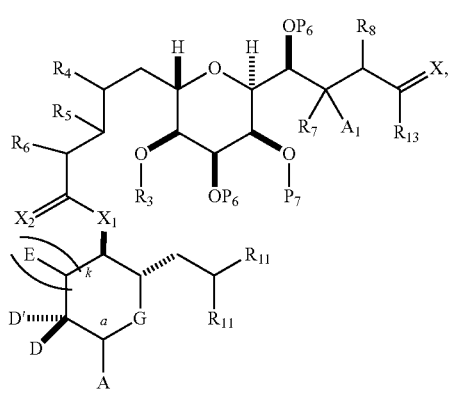

(IC)

or a salt or tautomer thereof, wherein each of D and D' is independently H, optionally substituted alkyl, or OP₁, provided that only one of D and D' is OP₁, wherein P₁ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, and $Q_1$, the group of formula (1) having the structure:

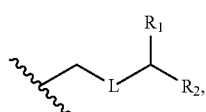

(1)

wherein

L is —(CH(OP₂))— or —C(O)—;

R₁ is H, or R₁ and P₁ combine to form a bond;

(i) R₂ is H, wherein P₂ is absent, H, optionally substituted alkyl, or a hydroxyl protecting group;

(ii) R₂ is —(CH₂)ₙNP₃P₄, wherein P₃ is an N-protecting group, and (a) P₂ is absent, H, optionally substituted alkyl, or a hydroxyl protecting group, and P₄ is an N-protecting group, or (b) P₂ and P₄ combine to form an alkylidene;

(iii) R₂ is —(CH₂)ₙOP₅, wherein P₂ is absent, H, optionally substituted alkyl, or a hydroxyl protecting group, and P₅ is optionally substituted alkyl or a hydroxyl protecting group; or P₂ and P₅, together with the atoms to which each is attached, combine to form a ketal, a cyclic carbonate, a dicarbonyl-dioxo, or silylene-dioxo; or (iv) R₂ and P₂ combine to form an optionally substituted ethylene or a structure selected from the group consisting of:

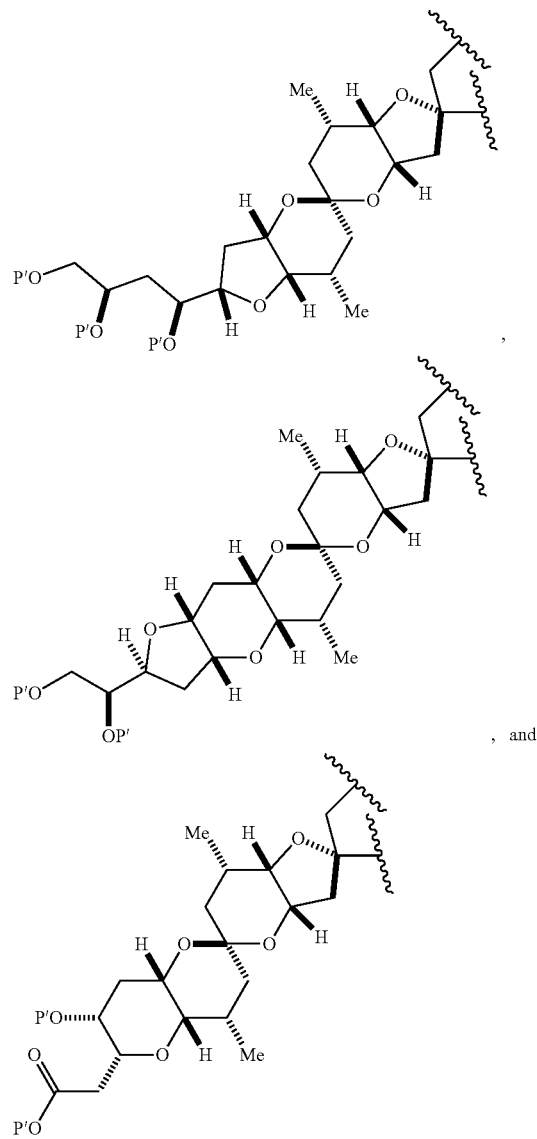

, and wherein each P' is independently a hydroxyl protecting group;

E is H, optionally substituted alkyl, or optionally substituted alkoxy;

G is O, S, CH₂, or NR_N, wherein R_N is H, an N-protecting group, or optionally substituted alkyl;

each $Q_1$ is independently OR_A, SR_A, SO₂R_A, OSO₂R_A, NR_BR_A, NR_B(CO)R_A, NR_B(CO)(CO)R_A, NR_B(CO)NR_BR_A, NR_B(CO)OR_A, (CO)OR_A, O(CO)R_A, (CO)NR_BR_A, or O(CO)NR_BR_A, wherein each of R_A and R_B is independently alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

X₁ is —CH(Y)— or —CH₂—;

X₂ is =O or X₂, together with the carbon atom to which it is attached, is —(C(R_X)₂)—; wherein each R_X is independently H, —OR_{X1}, or —SR_{X1}, provided that at least one $R_X$, when present, is $-OR_{X1}$ or $-SR_{X1}$; wherein each $R_{X1}$ is independently optionally substituted alkyl, or both $R_{X1}$ combine to form optionally substituted alkylene;

Y is $SO_2R_C$ or $COOR_C$, wherein, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;

$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;
  (i) each $P_6$ is independently a hydroxyl protecting group, or both $P_6$, together with the atoms to which each is attached, combine to form a ketal or acetal; each is independently $-OP_{10}$, or
    both combine to form oxo, wherein $P_{10}$ is alkyl or a hydroxyl protecting group;
  or
  (ii) both $P_6$ and both together with the atoms to which they are attached, combine to form an acetal;

$R_{13}$ is H or $-CH_2P(O)(OR_E)_2$, wherein each $R_E$, when present, is independently optionally substituted alkyl, optionally substituted aryl, or optionally substituted arylalkyl;

X is $=O$ or X combines with the carbon atom, to which it is attached, to form $-(CH(OP_9))-$, wherein $P_9$ is H or a hydroxyl protecting group;

$A_1$ and $R_7$ combine to form oxo, $P_7$ is H or a hydroxyl protecting group, and $R_8$ is H;
or
$A_1$ is H or OP''', and:
  (i) $P_7$ is H or a hydroxyl protecting group, and $R_7$ and $R_8$, together with the atoms to which each is attached, combine to form a double bond;
  or
  (ii) $P_7$ and $R_7$ combine to form a bond, and $R_8$ is H or OP''';
and
each P''', when present, is independently H or a hydroxyl protecting group;

(IE)

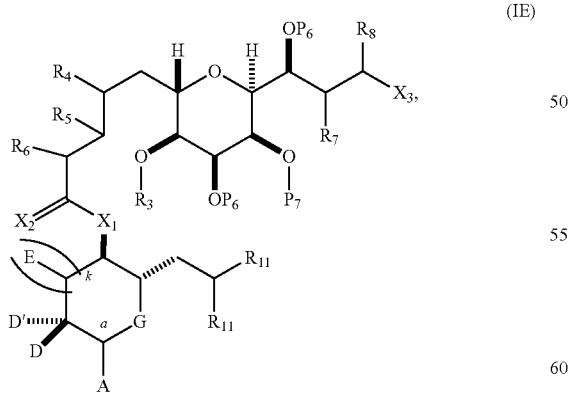

or a salt or tautomer thereof,
wherein
each of D and D' is independently H, optionally substituted alkyl, or $OP_1$, provided that only one of D and D' is $OP_1$, wherein $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, and $Q_1$, the group of formula (1) having the structure:

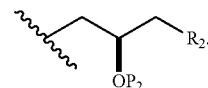

wherein

L is $-(CH(OP_2))-$ or $-C(O)-$;

$R_1$ is H, or $R_1$ and $P_1$ combine to form a bond;
  (i) $R_2$ is H, wherein $P_2$ is absent, H, optionally substituted alkyl, or a hydroxyl protecting group;
  (ii) $R_2$ is $-(CH_2)_nNP_3P_4$, wherein $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;
  (iii) $R_2$ is $-(CH_2)_nOP_5$, wherein $P_2$ is absent, H, optionally substituted alkyl, or a hydroxyl protecting group, and $P_5$ is optionally substituted alkyl or a hydroxyl protecting group; or $P_2$ and $P_5$, together with the atoms to which each is attached, combine to form a ketal, a cyclic carbonate, a dicarbonyl-dioxo, or silylene-dioxo; or
  (iv) $R_2$ and $P_2$ combine to form an optionally substituted ethylene or a structure selected from the group consisting of:

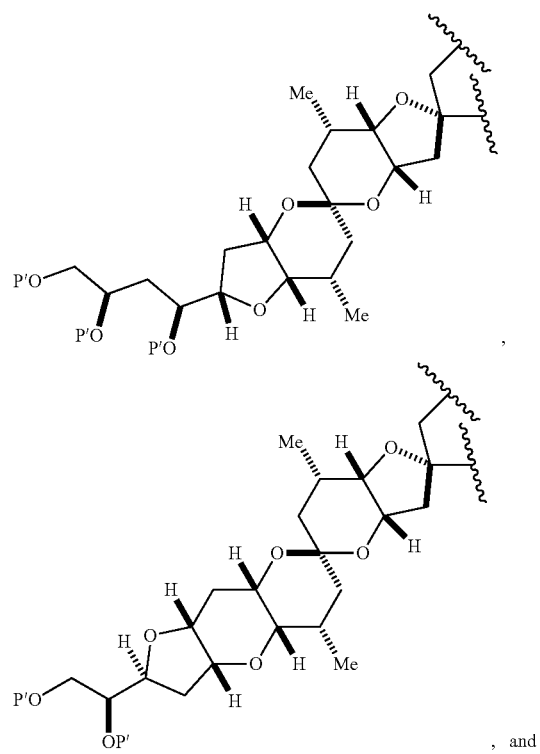

, and

-continued

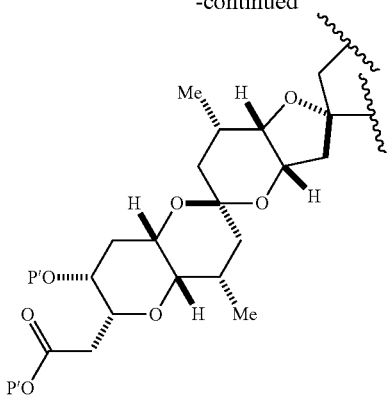

wherein each P' is independently a hydroxyl protecting group;
E is H, optionally substituted alkyl, or optionally substituted alkoxy;
G is O, S, $CH_2$, or $NR_N$, wherein $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, wherein each of $R_A$ and $R_B$ is independently alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$X_1$ is —CH(Y)— or —$CH_2$—,
$X_2$ is =O or $X_2$, together with the carbon atom to which it is attached, is —$(C(R_X)_2)$—; wherein each $R_X$ is independently H, —$OR_{X1}$, or —$SR_{X1}$, provided that at least one $R_X$, when present, is —$OR_{X1}$ or —$SR_{X1}$; wherein each $R_{X1}$ is independently optionally substituted alkyl, or both $R_{X1}$ combine to form optionally substituted alkylene;
Y is $SO_2R_C$ or $COOR_C$, wherein, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;
$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;
$R_7$ and $P_7$ combine to form a bond, and $R_8$ is H; or $P_7$ is a hydroxyl protecting group, and $R_7$ and $R_8$, together with the atoms to which each is attached, combine to form a double bond;
(i) each $P_6$ is independently a hydroxyl protecting group, or both $P_6$, together with the atoms to which each is attached, combine to form a ketal or acetal; each is independently —$OP_{10}$, or
both $R_{11}$ combine to form oxo, wherein $P_{10}$ is alkyl or a hydroxyl protecting group;
or
(ii) both $P_5$ and both $R_{11}$ together with the atoms to which they are attached, combine to form an acetal;

$X_3$ is —$CH_2OP_A$, —CH=$CH_2$, or —$CH(OP_A)CH_2OP_A$, wherein each $R_E$ is optionally substituted alkyl, optionally substituted aryl, or optionally substituted arylalkyl, and wherein each $P_A$ is independently H or a hydroxyl protecting group, or both $P_A$ combine to form a cyclic protected diol;

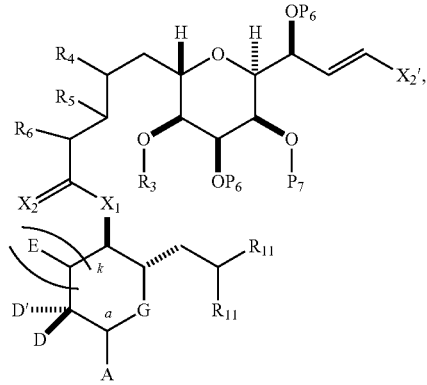

(IJ)

where
each of D and D' is independently H, optionally substituted alkyl, or $OP_1$, provided that only one of D and D' is $OP_1$, wherein $P_1$ is H, alkyl, or a hydroxyl protecting group; and A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, and $Q_1$, the group of formula (1) having the structure:

(1)

where
L is —(CH($OP_2$))— or —C(O)—;
$R_1$ is H, or $R_1$ and $P_1$ combine to form a bond;
(i) $R_2$ is H, wherein $P_2$ is absent, H, optionally substituted alkyl, or a hydroxyl protecting group;
(ii) $R_2$ is —$(CH_2)_nNP_3P_4$, wherein $P_3$ is an N-protecting group, and (a) $P_2$ is absent, H, optionally substituted alkyl, or a hydroxyl protecting group, and $P_4$ is an N-protecting group, or (b) $P_2$ and $P_4$ combine to form an alkylidene;
(iii) $R_2$ is —$(CH_2)_nOP_5$, wherein $P_2$ is absent, H, optionally substituted alkyl, or a hydroxyl protecting group, and $P_5$ is optionally substituted alkyl or a hydroxyl protecting group; or $P_2$ and $P_5$, together with the atoms to which each is attached, combine to form a ketal, a cyclic carbonate, a dicarbonyl-dioxo, or silylene-dioxo; or
(iv) $R_2$ and $P_2$ combine to form an optionally substituted ethylene or a structure selected from the group consisting of:

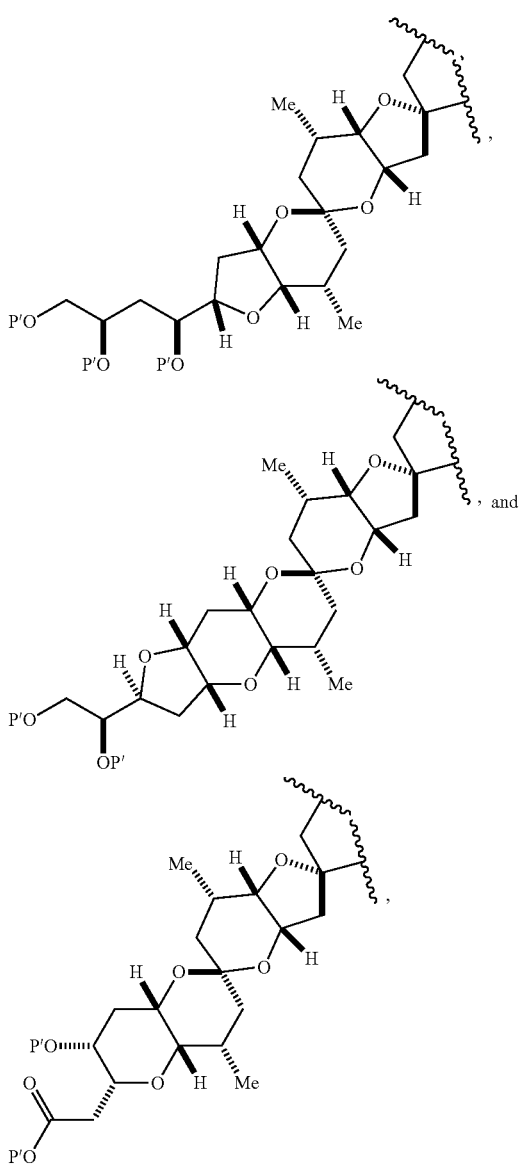

wherein each P' is independently a hydroxyl protecting group;
  E is H, optionally substituted alkyl, or optionally substituted alkoxy;
  G is O, S, $CH_2$, or $NR_N$, wherein $R_N$ is H, an N-protecting group, or optionally substituted alkyl;
  each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, wherein each of $R_A$ and $R_B$ is independently alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
  n, when present, is 0, 1, or 2;
  k is 0 or 1;
  $X_1$ is —CH(Y)—, —$CH_2$—, or —O—;
  $X_2$ is =O or $X_2$, together with the carbon atom to which it is attached, is —$(C(R_X)_2)$—; wherein each $R_X$ is independently H, —$OR_{X1}$, or —$SR_{X1}$, provided that at least one $R_X$, when present, is —$OR_{X1}$ or —$SR_{X1}$; wherein each $R_{X1}$ is independently optionally substituted alkyl, or both $R_{X1}$ combine to form optionally substituted alkylene, provided that, when $X_1$ is —O—, $X_2$ is =O;
  Y is $SO_2R_C$ or $COOR_C$, where, when Y is $SO_2R_C$, $R_C$ is optionally substituted aryl or optionally substituted non-enolizable alkyl, and when Y is $COOR_C$, $R_C$ is optionally substituted alkyl, optionally substituted aryl, or optionally substituted arylalkyl;
  $R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;
    (i) each $P_6$ is independently a hydroxyl protecting group, or both $P_6$, together with the atoms to which each is attached, combine to form a ketal or acetal; each $R_{11}$ is independently —$OP_{10}$, or both $R_{11}$ combine to form oxo, wherein $P_{10}$ is alkyl or a hydroxyl protecting group;
    or
    (ii) both $P_6$ and both $R_{11}$, together with the atoms to which they are attached, combine to form an acetal;
  each $P_7$ is independently a hydroxyl protecting group; and
  $X_2'$ is a halogen or pseudohalogen; or (IN)

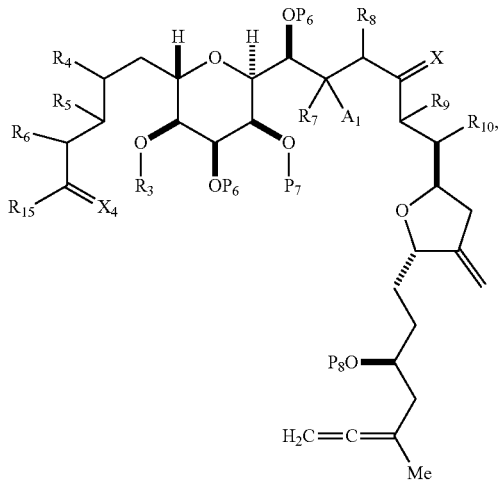

or a salt or tautomer thereof,
wherein
  $R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H;
  $A_1$ and $R_7$ combine to form oxo, $P_7$ is H or a hydroxyl protecting group, and $R_8$ is H;
  or
  $A_1$ is H or OP″, and:
    (i) $P_7$ is H or a hydroxyl protecting group, and $R_7$ and $R_8$, together with the atoms to which each is attached, combine to form a double bond;
    or
    (ii) $P_7$ and $R_7$ combine to form a bond, and $R_8$ is H or OP″;

each P'', when present, is independently H or a hydroxyl protecting group;

each $P_6$ is independently H or a hydroxyl protecting group, or both $P_6$, together with the atoms to which each is attached, combine to form a ketal or acetal, and X is =O or X combines with the carbon atom, to which it is attached, to form —(CH(OP$_9$))—, wherein $P_9$ is H or a hydroxyl protecting group; or both $P_6$ and X, together with the atoms to which each is attached, combine to form ketal; where, when both $P_6$ and X, together with the atoms to which each is attached, combine to form ketal, $P_7$ and $R_7$ combine to form a bond, and $R_8$ is H or OP'';

$R_9$ is H, SO$_2$R$_C$, or COOR$_C$, and $R_{10}$ is H, where, when $R_9$ is SO$_2$R$_C$, $R_C$ is optionally substituted aryl or optionally substituted non-enolizable alkyl, and when $R_9$ is COOR$_C$, $R_C$ is optionally substituted alkyl, optionally substituted aryl, or optionally substituted arylalkyl; or $R_9$ and $R_{10}$, together with the atoms to which each is attached, combine to form a double bond;

$R_{15}$ is H or —OP$_1$, wherein $P_{11}$ is H, a hydroxyl protecting group, or optionally substituted alkyl;

$X_4$ is =O or, together with the carbon atom to which it is attached, is —CH$_2$—, provided that when $R_{15}$ is H, $X_4$ is =O; and $P_8$ is H or silyl.

14. The compound of claim 13, wherein $A_1$ is H; wherein, in compound (IE), each $P_A$ is H, or both $P_A$ combine to form a cyclic protected diol; or wherein each $R_{11}$ is —OP$_{10}$, wherein $P_{10}$ is alkyl.

15. The compound of claim 11, wherein A and D combine to form the following structure:

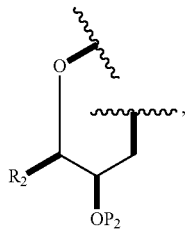

wherein, the bond to oxygen atom originates at the carbon atom, to which D is attached in formula (IA), and wherein $R_2$ is —(CH$_2$)$_n$NP$_3$P$_4$ or —(CH$_2$)$_n$OP$_5$, wherein n is 2.

16. The compound of claim 15, wherein k is 1, and E is optionally substituted alkyl or wherein $X_1$ is —O—.

17. The compound of claim 13, wherein, in compound (IN): $R_9$ is H or SO$_2$R$_C$, and $R_{10}$ is H; $P_8$ is silyl;

$P_6$ is a hydroxyl protecting group, and X is =O or X combines with the carbon atom, to which it is attached, to form —(CH(OP$_9$))—; or $R_3$ and $R_5$ combine to form a bond, and each of $R_4$ and $R_6$ is H.

18. A compound of formula (ID), (IDa), (IDb), (IDc), or (IDd):

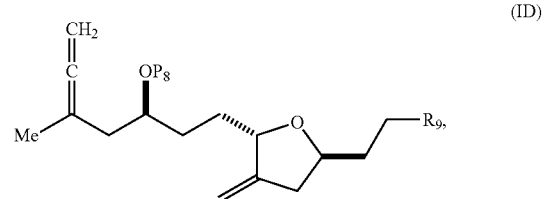

(ID)

wherein
$P_8$ is H or a hydroxyl protecting group; and
$R_9$ is SO$_2$R$_C$ or COOR$_C$, when $R_9$ is SO$_2$R$_C$, $R_C$ is optionally substituted aryl or optionally substituted non-enolizable alkyl, and when $R_9$ is COOR$_C$, $R_C$ is optionally substituted alkyl, optionally substituted aryl, or optionally substituted arylalkyl;

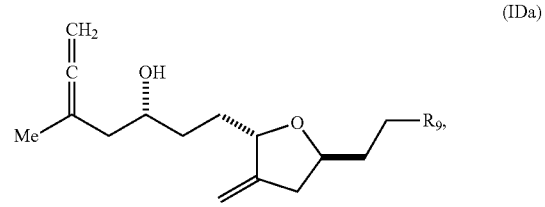

(IDa)

wherein
$R_9$ is SO$_2$R$_C$ or COOR$_C$, when $R_9$ is SO$_2$R$_C$, $R_C$ is optionally substituted aryl or optionally substituted non-enolizable alkyl, and when $R_9$ is COOR$_C$, $R_C$ is optionally substituted alkyl, optionally substituted aryl, or optionally substituted arylalkyl;

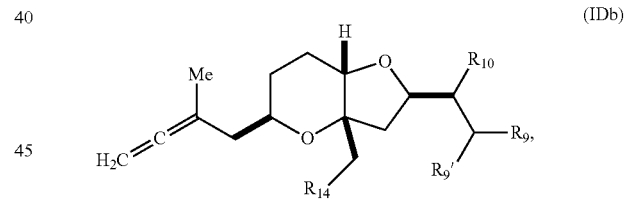

(IDb)

wherein
$R_9'$ and $R_{10}$ are both H, or $R_9'$ and $R_{10}$ combine to form a double bond; $R_{14}$ is hydroxyl, a halogen, or a pseudo-halogen; and
$R_9$ is SO$_2$R$_C$ or COOR$_C$, when $R_9$ is SO$_2$R$_C$, $R_C$ is optionally substituted aryl or optionally substituted non-enolizable alkyl, and when $R_9$ is COOR$_C$, $R_C$ is optionally substituted alkyl, optionally substituted aryl, or optionally substituted arylalkyl;

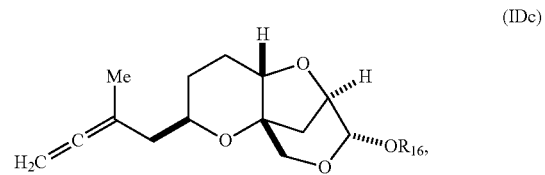

(IDc)

wherein
R$_{16}$ is H, a hydroxyl protecting group, or an optionally substituted alkyl;

(IDd)

wherein
X$_6$ is —C(R$_{17}$)=CH$_2$ or —C(O)-Me, wherein R$_{17}$ is a pseudohalogen or halogen; and
R$_{16}$ is H, a hydroxyl protecting group, or an optionally substituted alkyl.

19. The compound of claim 18, wherein in compound (ID), (IDa), or (IDb), R$_9$ is SO$_2$R$_C$.

20. A compound of formula (IF), (IH), (IHa), or (IHb):

(IF)

wherein
X$_3$ is —CHO, —CH$_2$OP$_A$, —CH=CH$_2$, or —CH(OP$_A$)CH$_2$OP$_A$, wherein each P$_A$ is independently H or a hydroxyl protecting group, or both P$_A$ combine to form a cyclic protected diol;
R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;
R$_7$ and P$_7$ combine to form a bond, and R$_8$ is H; or P$_7$ is a hydroxyl protecting group, and R$_7$ and R$_8$, together with the atoms to which each is attached, combine to form a double bond; and
each P$_6$ is independently a hydroxyl protecting group, or both P$_6$, together with the atoms to which each is attached, combine to form a ketal or acetal;

(IH)

or a salt thereof,
where
X$_3$ is —CHO, —CH$_2$OP$_A$, —CH=CH$_2$, or —CH(OP$_A$)CH$_2$OP$_A$;

X$_4$ is =O or X$_4$, together with the carbon atom to which it is attached, combine to form —CH$_2$—;
R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;
R$_7$ and P$_7$ combine to form a bond, and R$_8$ is H; or P$_7$ is a hydroxyl protecting group, and R$_7$ and R$_8$, together with the atoms to which each is attached, combine to form a double bond;
each P$_6$ is independently a hydroxyl protecting group, or both P$_6$, together with the atoms to which each is attached, combine to form a ketal or acetal;
each P$_A$ is independently H or a hydroxyl protecting group, or both P$_A$ combine to form a cyclic protected diol; and
P$_B$ is H, a hydroxyl protecting group, or optionally substituted alkyl;

(IHa)

wherein
a identifies the carbon-oxygen bond as | or ⋮,
X$_3$ is —CHO, —CH$_2$OP$_A$, —CH=CH$_2$, or —CH(OP$_A$)CH$_2$OP$_A$;
X$_5$ is —CH=CH$_2$ or —CH(R$_4$)—CH(R$_5$)—CH(R$_6$)—C(X$_4$)OP$_B$;
X$_4$ is =O or X$_4$, together with the carbon atom to which it is attached, combine to form —CH$_2$—;
R$_3$ and R$_5$ combine to form a bond, and each of R$_4$ and R$_6$ is H; or R$_3$ is H or a hydroxyl protecting group, R$_5$ and one of R$_4$ and R$_6$, together with the atoms to which each is attached, combine to form a double bond, and the remaining R$_4$ or R$_6$ is H;
P$_6$ is a hydroxyl protecting group;
each P$_A$ is independently H or a hydroxyl protecting group, or both P$_A$ combine to form a cyclic protected diol; and
P$_B$ is H, a hydroxyl protecting group, or optionally substituted alkyl; and
R$_8$ is H; or (IHb)

wherein
X$_5$ is —CH=CH$_2$ or —CH(R$_4$)—CH(R$_5$)—CH(R$_6$)—C(X$_4$)OP$_B$;

$X_4$ is =O or $X_4$, together with the carbon atom to which it is attached, combine to form —$CH_2$—;

$P_B$ is H, a hydroxyl protecting group, or optionally substituted alkyl;

$R_3$ and $R_5$ combine to form a bond, and each of $R_4$ and $R_6$ is H; or $R_3$ is H or a hydroxyl protecting group, $R_5$ and one of $R_4$ and $R_6$, together with the atoms to which each is attached, combine to form a double bond, and the remaining $R_4$ or $R_6$ is H; and each of $P_6$ and $P_7$ is independently a hydroxyl protecting group, or one $P_6$ and $P_7$, together with the atoms to which each is attached, combine to form a ketal, and the remaining $P_6$ is a hydroxyl protecting group; or both $P_6$, together with the atoms to which each is attached, combine to form a ketal, and $P_7$ is a hydroxyl protecting group.

21. A compound selected from the group consisting of:

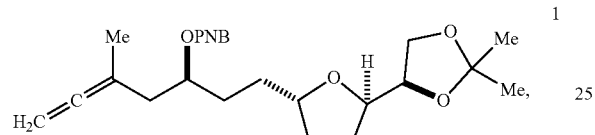

1

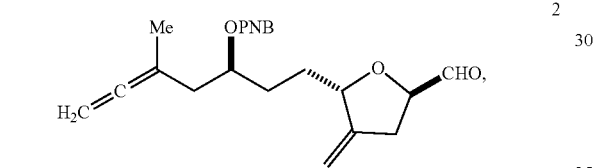

2

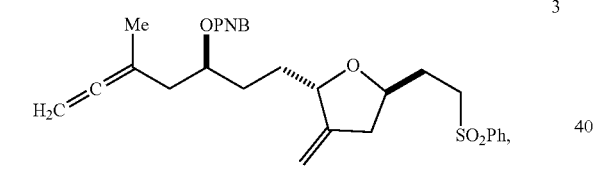

3

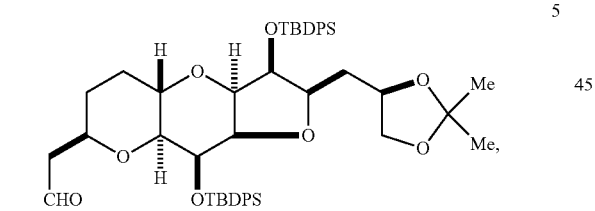

5

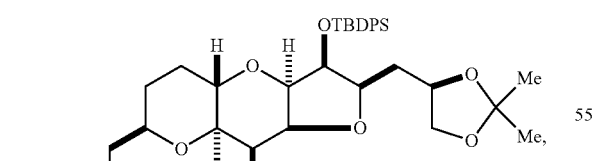

7

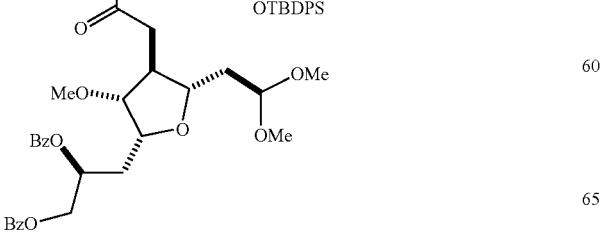

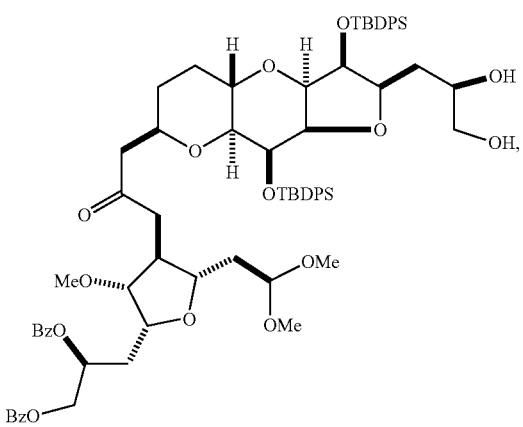

7a

8

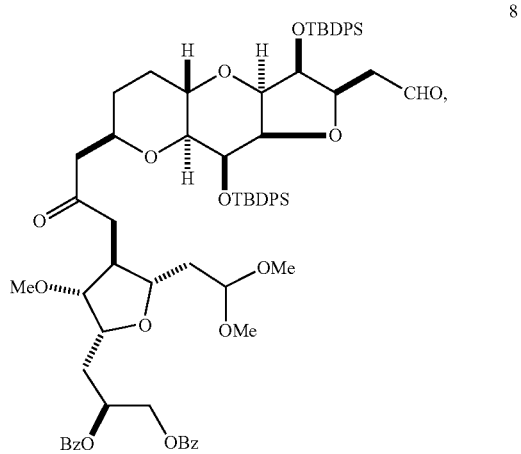

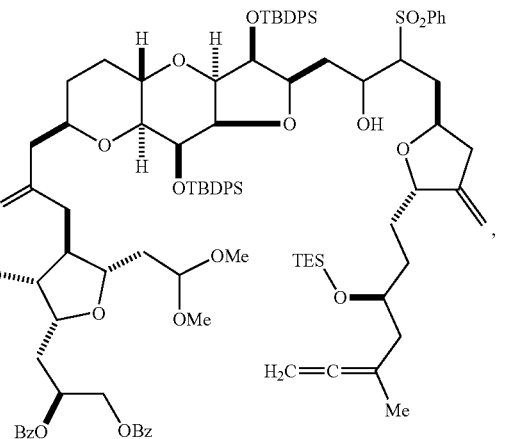

9

203
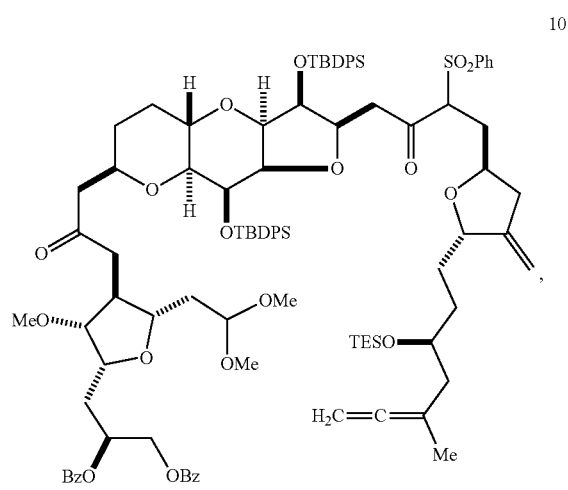
10
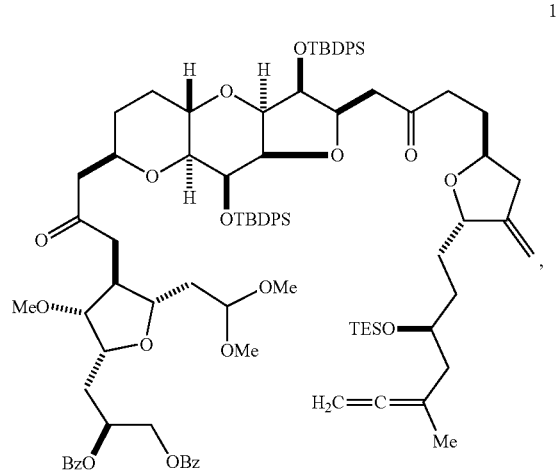
11
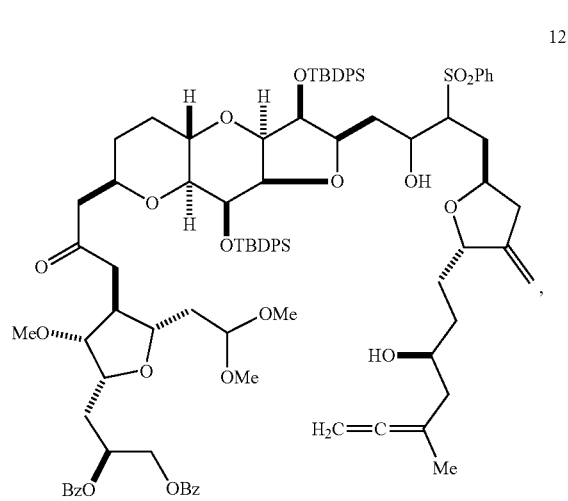
12
204
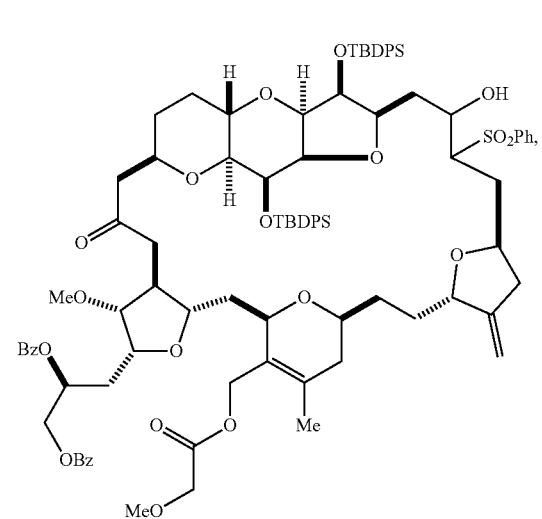
13
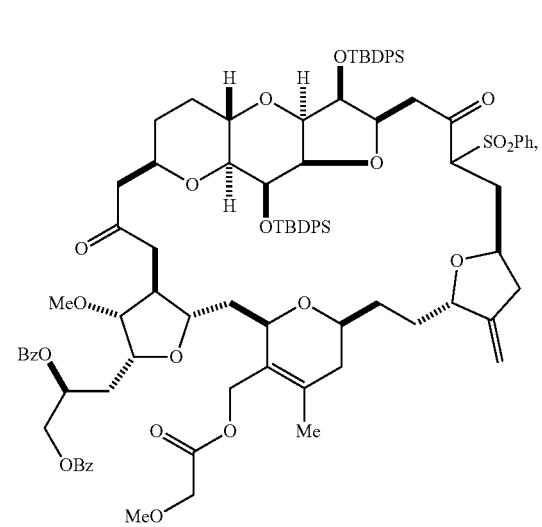
14
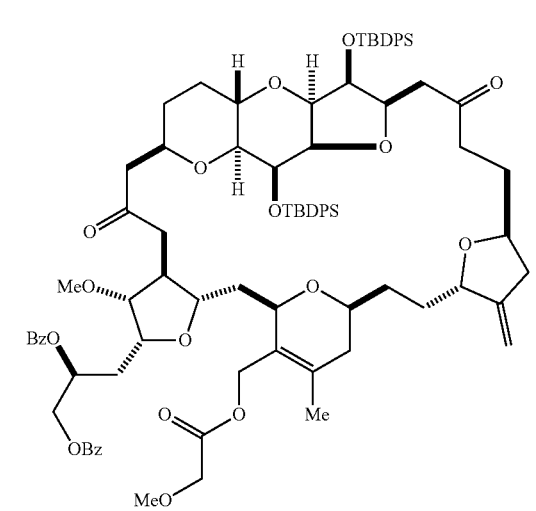
15

205
-continued
16
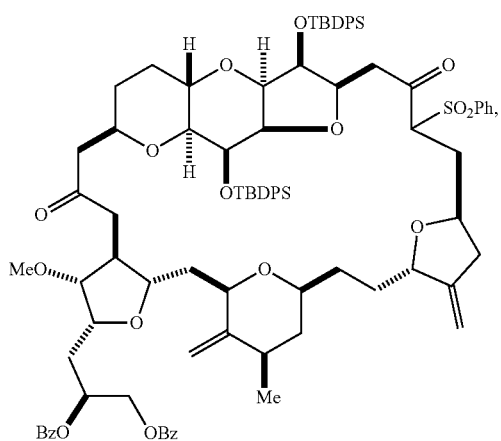
17
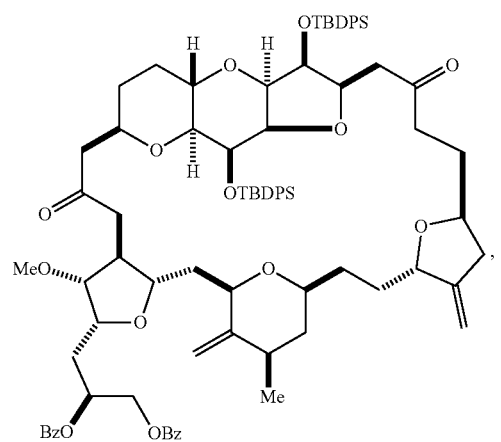
18
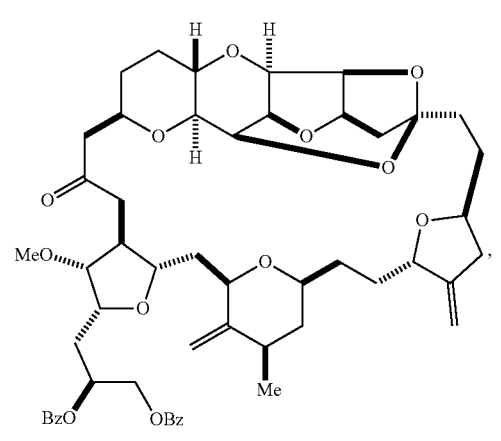
206
-continued
21
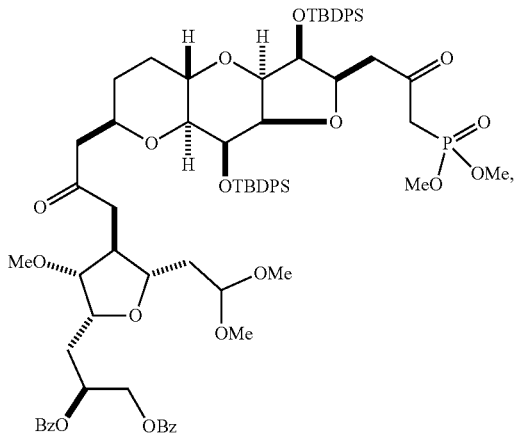
23
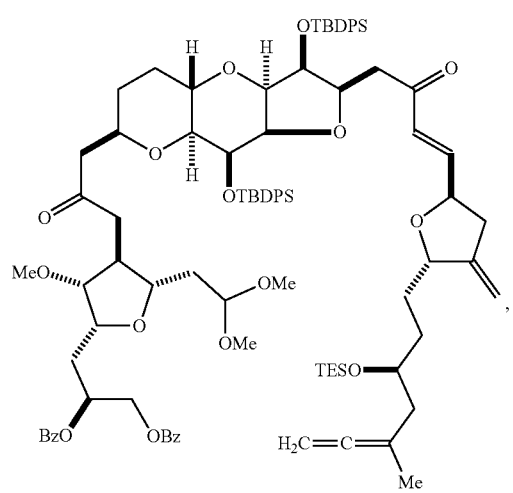
24
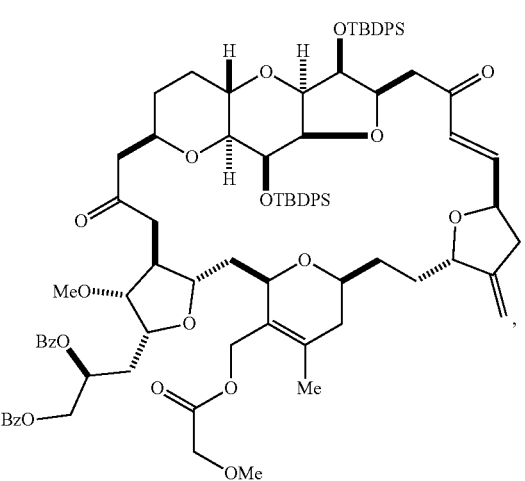

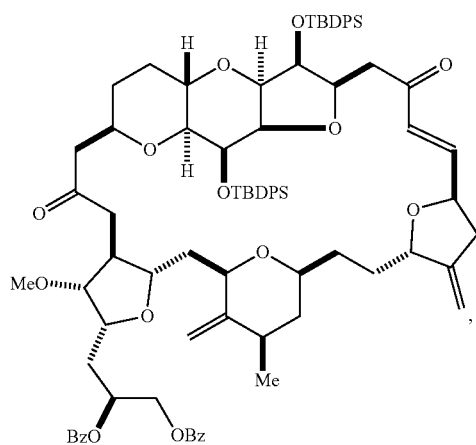
25
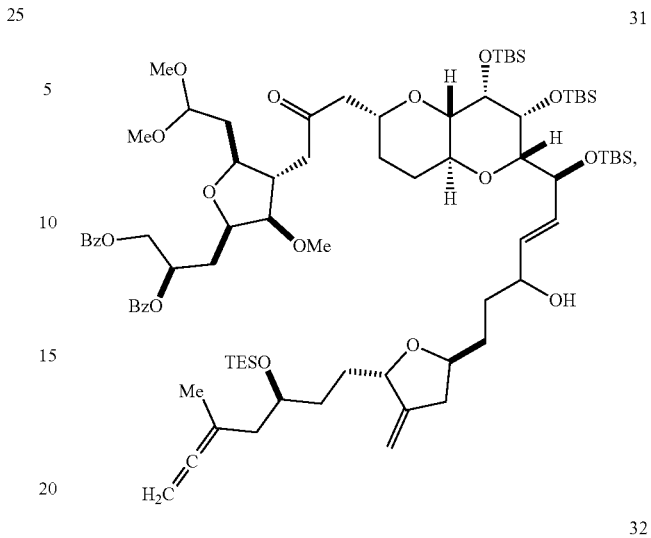
31
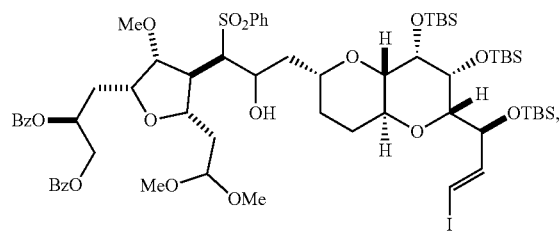
27
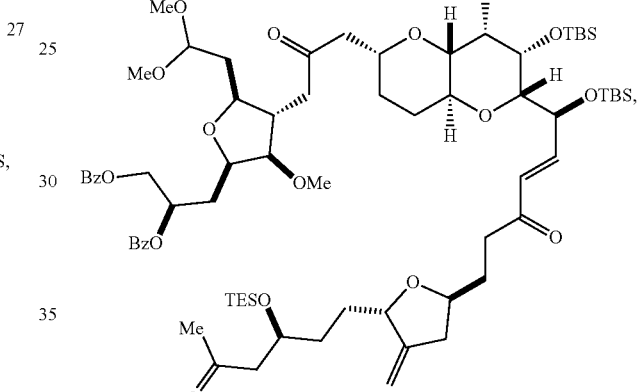
32
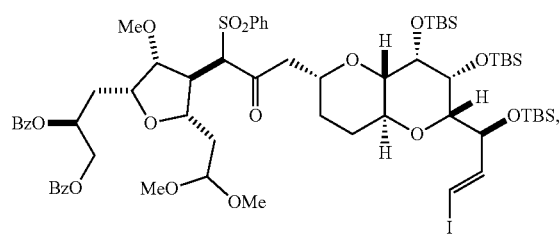
28
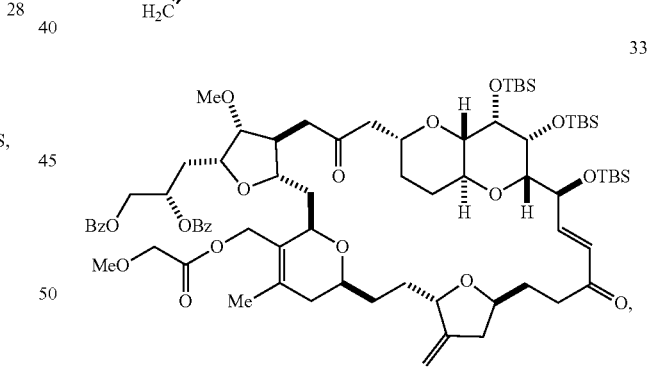
33
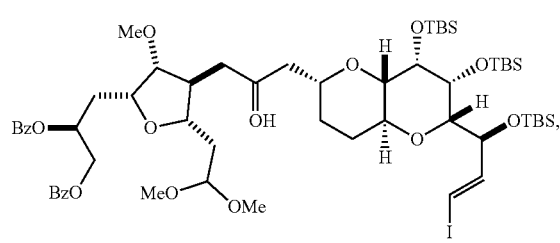
29
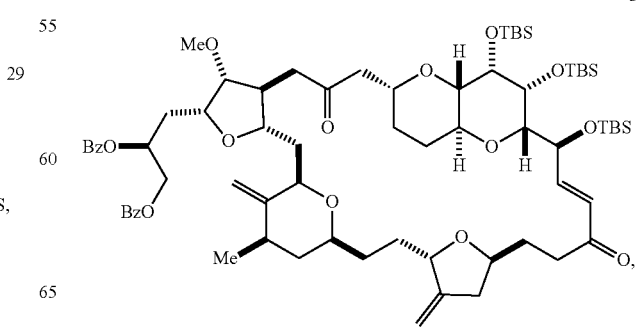
34

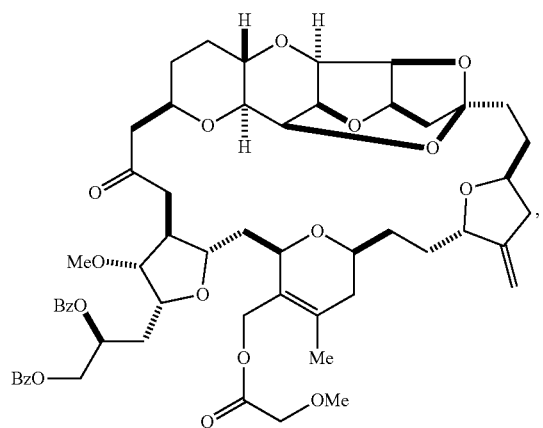
35
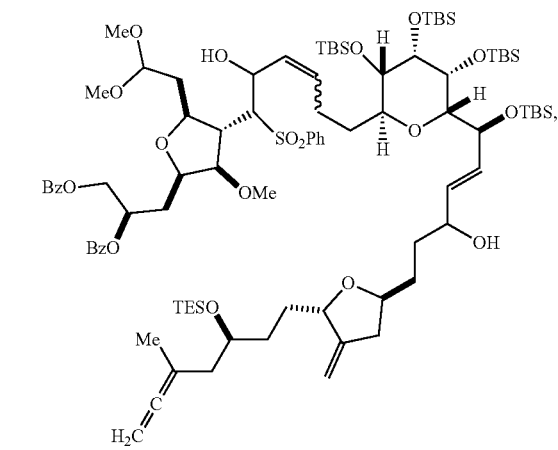
38
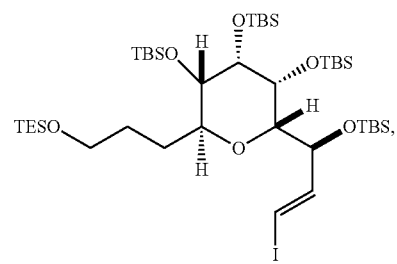
36
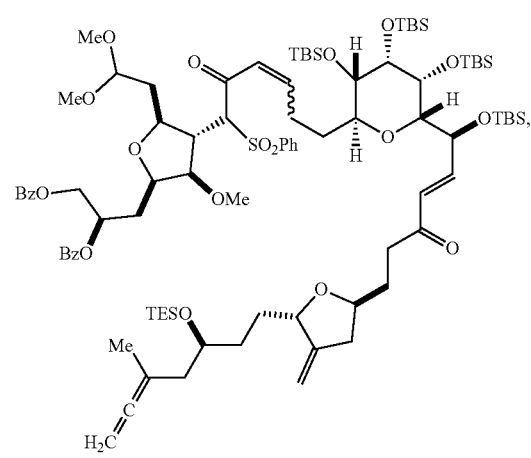
39
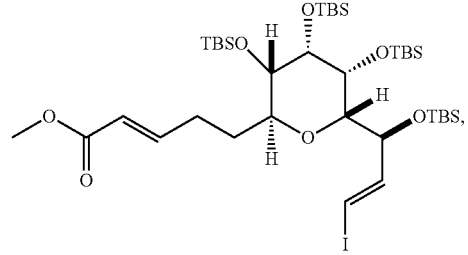
36b
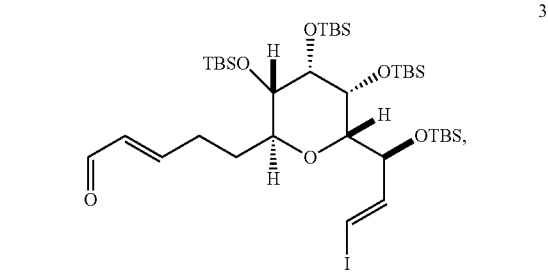
36c
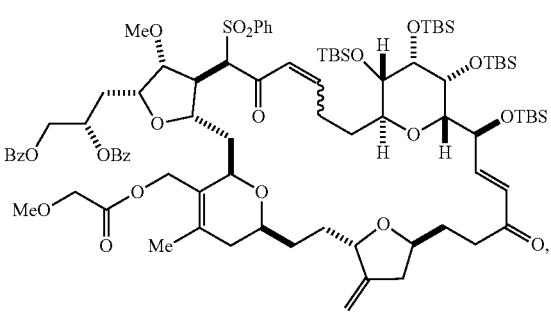
40
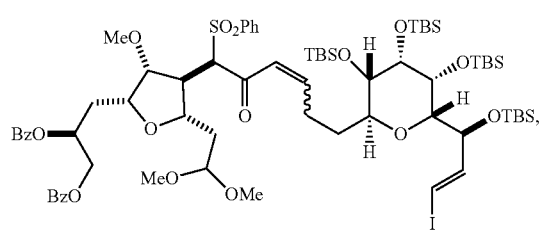
37
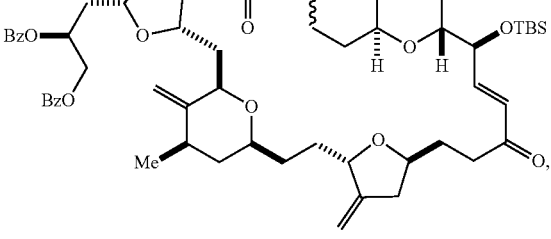
41

43
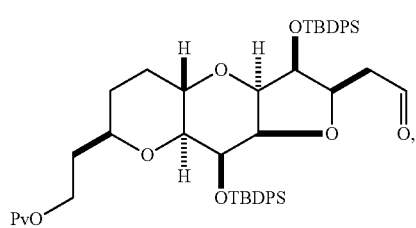
44
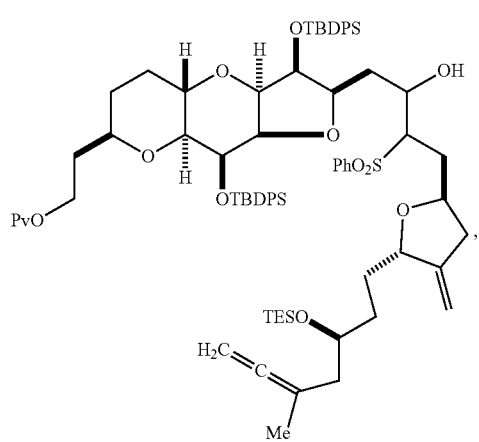
44a
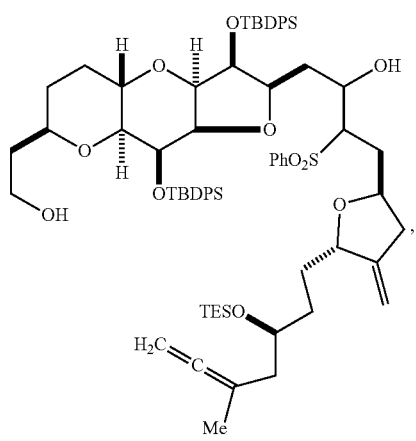
45
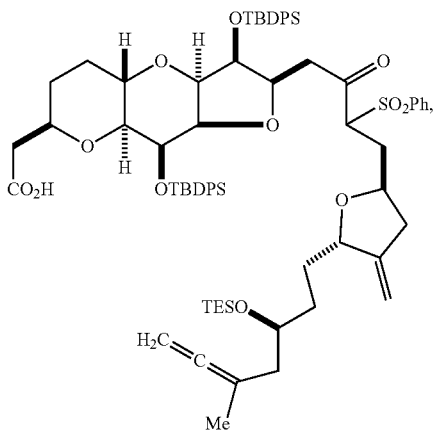
47
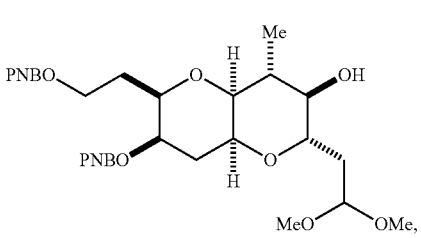
47a
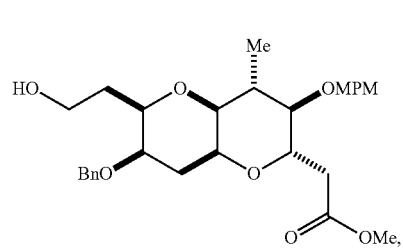
47b
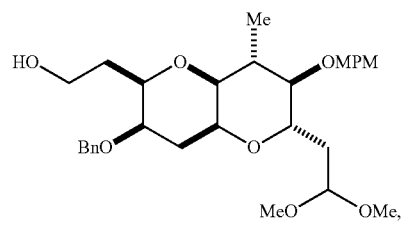
47c
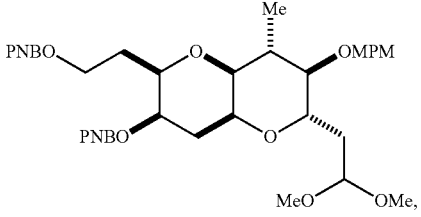
48
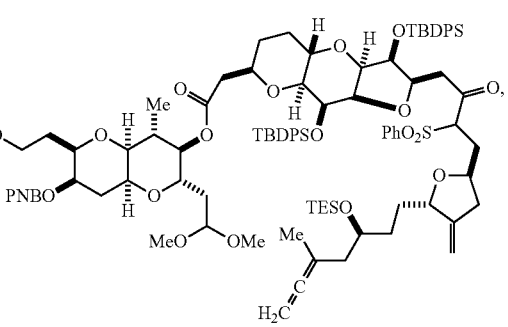

49
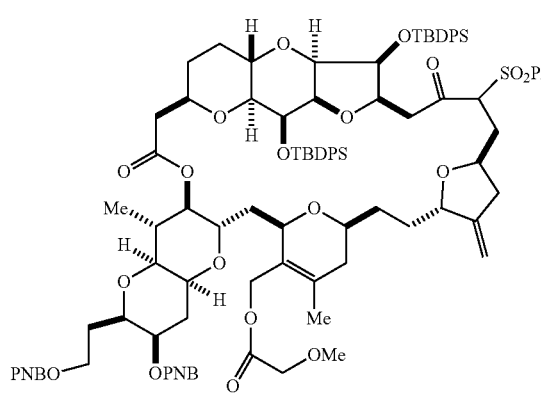
50
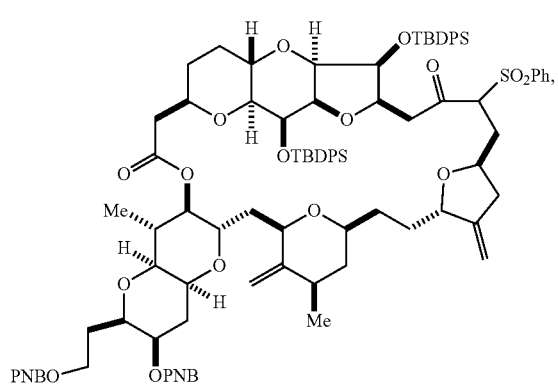
50a
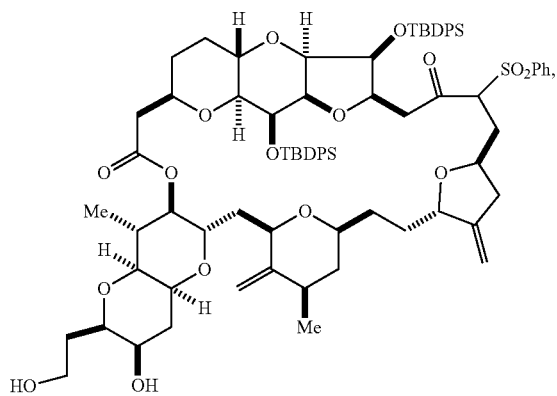
51
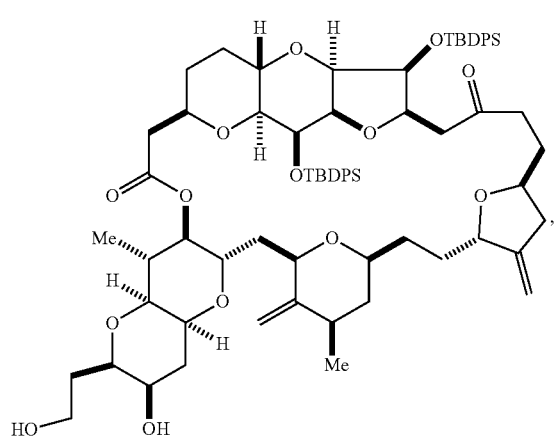
53
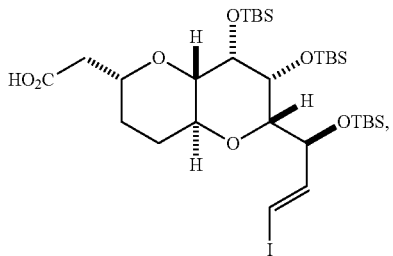
54
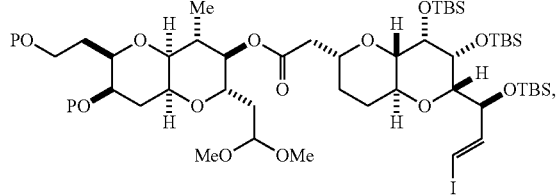
55
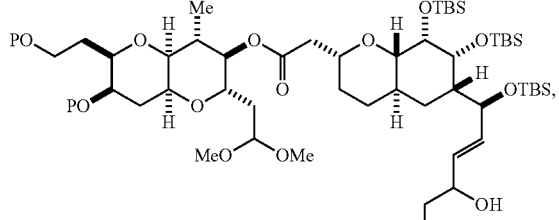
56
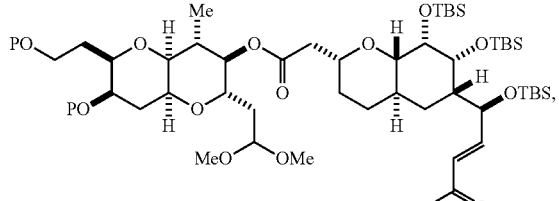
57
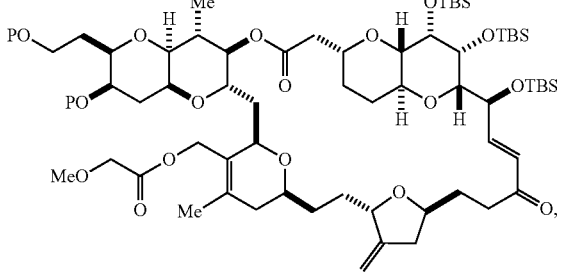

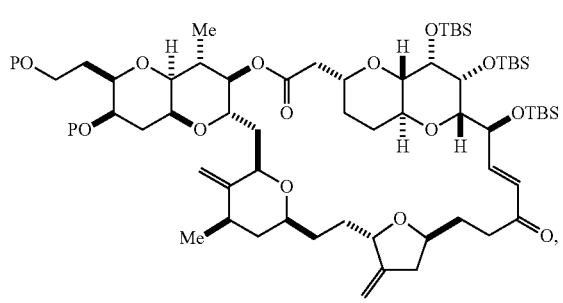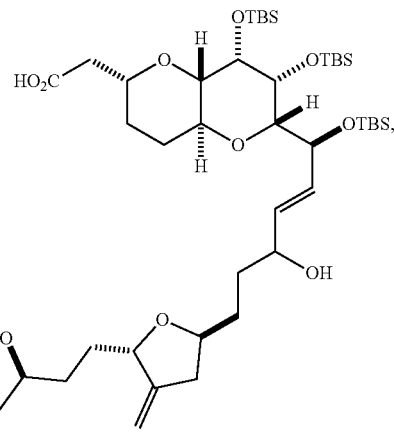

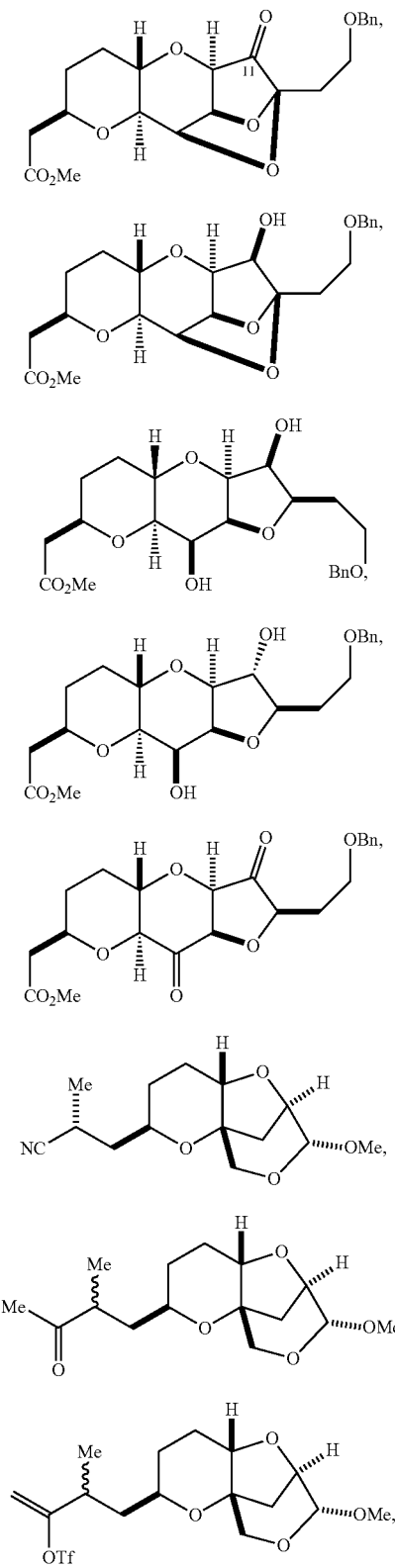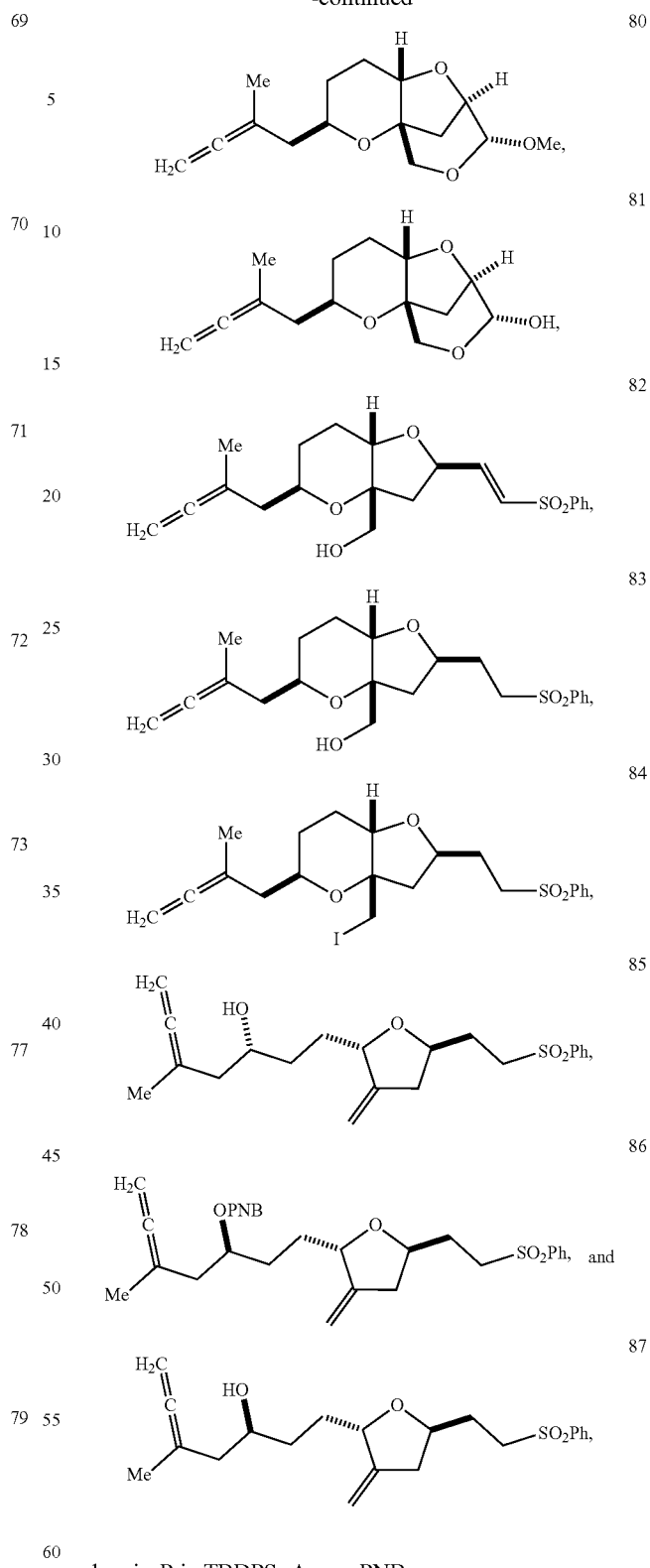
wherein P is TBDPS, Ac, or PNB.
* * * * *

UNITED STATES PATENT AND TRADEMARK OFFICE
CERTIFICATE OF CORRECTION

PATENT NO.         : 11,136,335 B2
APPLICATION NO.    : 16/313196
DATED              : October 5, 2021
INVENTOR(S)        : Charles E. Chase et al.

Page 1 of 11

It is certified that error appears in the above-identified patent and that said Letters Patent is hereby corrected as shown below:

In the Specification

Column 2, Lines 5-24, replace " 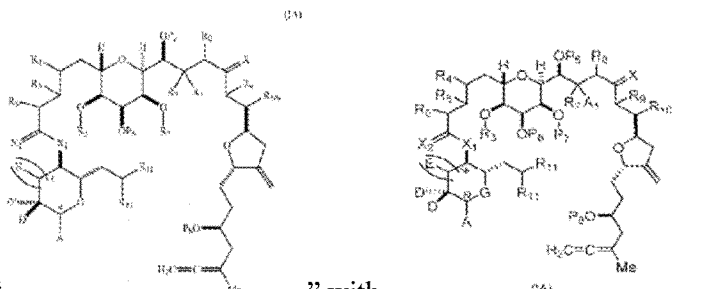 " with -- --

Column 5, Lines 1-18, replace " 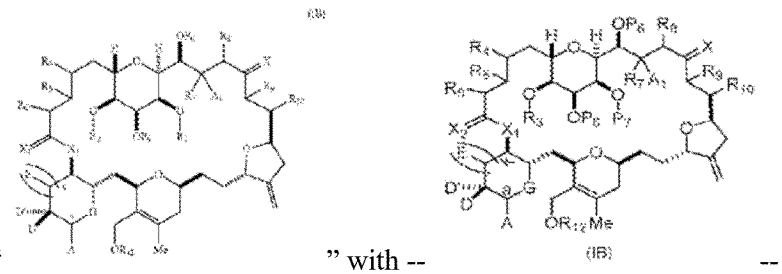 " with -- --

Column 6, Lines 52-65, replace " 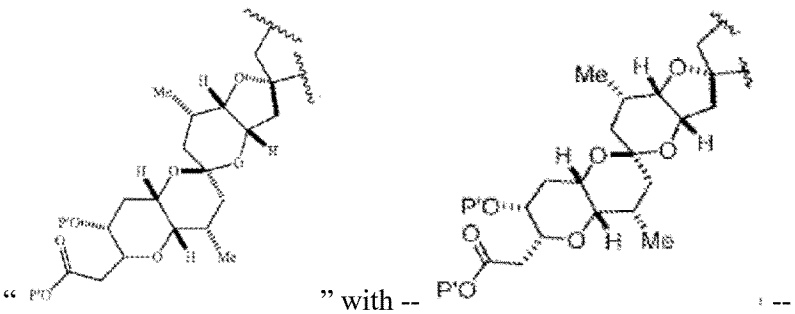 " with -- --

Signed and Sealed this
Thirtieth Day of July, 2024

Katherine Kelly Vidal
*Director of the United States Patent and Trademark Office*

Column 7, Lines 35-55, replace " 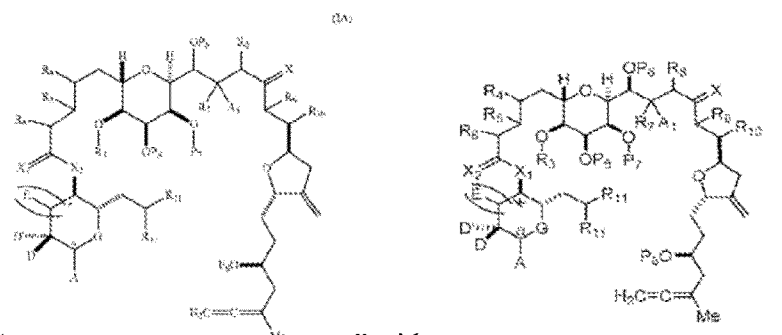 " with -- --
Column 9, Lines 1-15, replace " 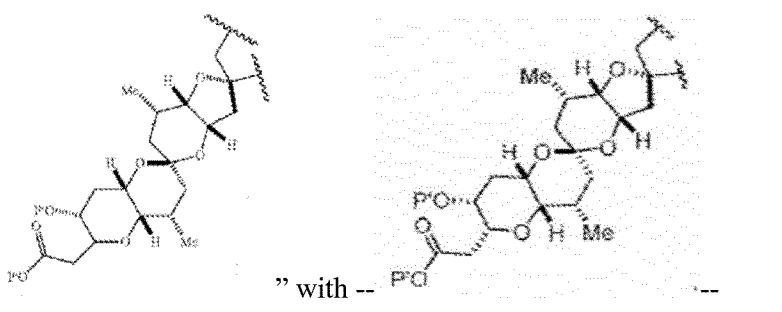 " with -- --
Column 10, Lines 26-43, replace " 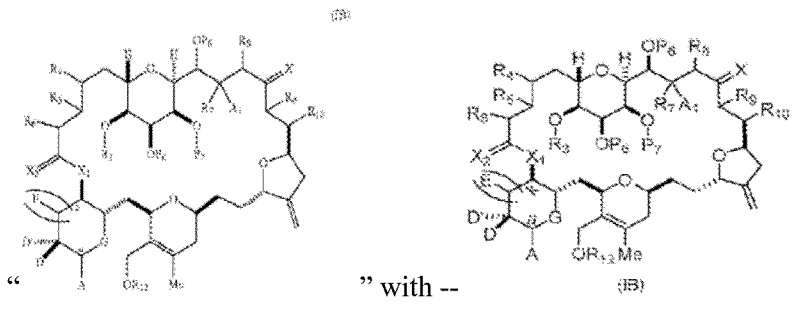 " with -- --
Column 12, Lines 25-47, replace " 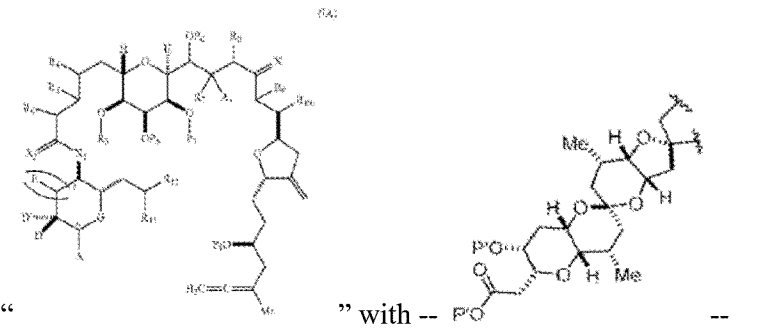 " with -- --

CERTIFICATE OF CORRECTION (continued)
U.S. Pat. No. 11,136,335 B2

Column 13, Lines 50-65 " 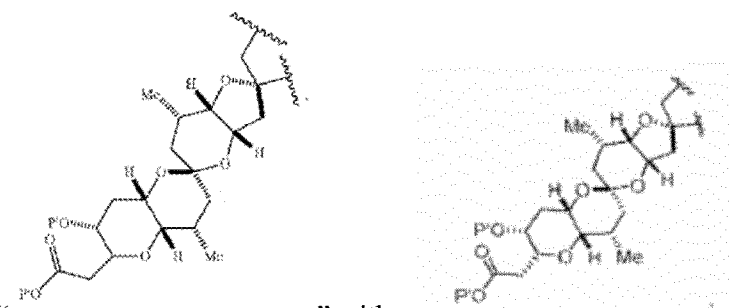 " with -- --

Column 14, Line 53, replace "or both R combine" with --or both $R_{11}$ combine--
　　　　Line 58, replace "or both $R_1$ combine" with --or both $R_{11}$ combine--

Column 16, Lines 33-45, replace " 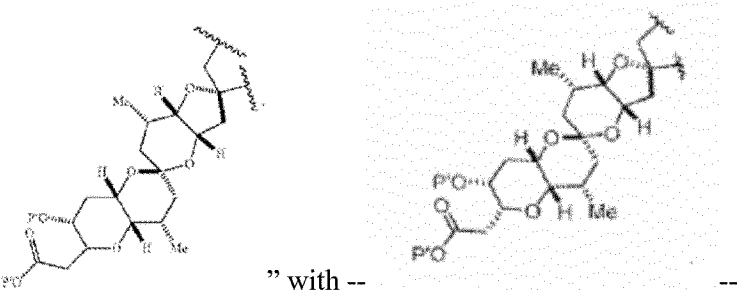 " with -- --

Column 27, Lines 1-14, replace " 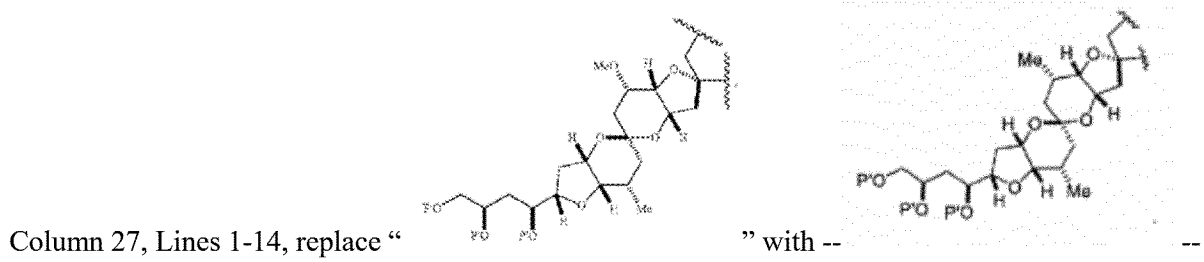 " with -- --

Lines 15-29, replace " 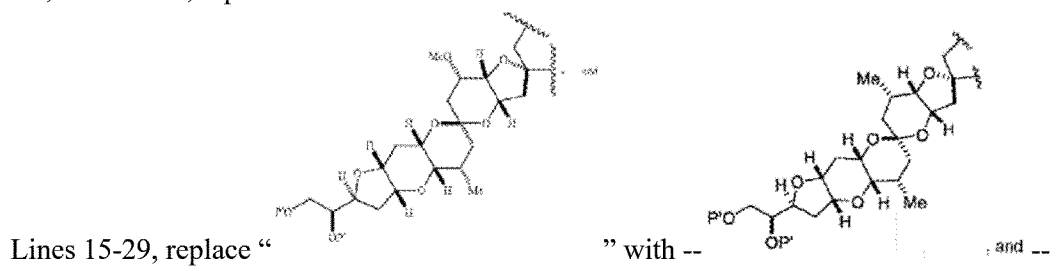 " with -- , and --

Lines 30-44, replace " 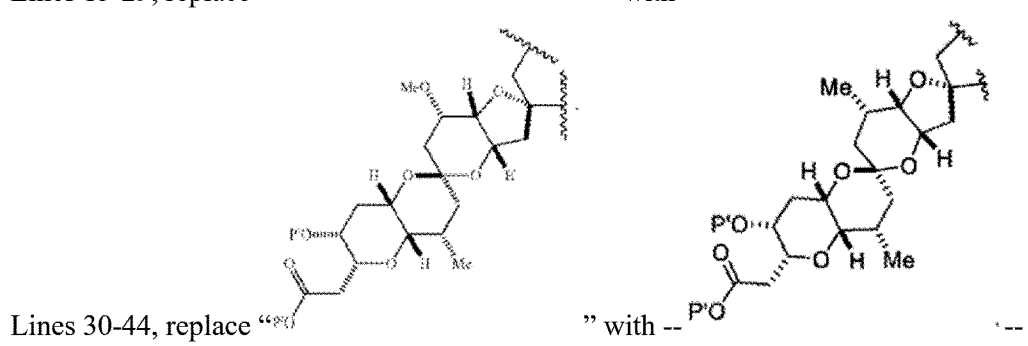 " with -- --

CERTIFICATE OF CORRECTION (continued)
U.S. Pat. No. 11,136,335 B2

Column 31, Line 5, replace "$^{13}O$" with --$^{13}C$--

Column 37, Lines 37-38, replace "13-(trimethylsilyl)" with --β(trimethylsilyl)--

Column 42, Lines 1-14, replace " " with -- 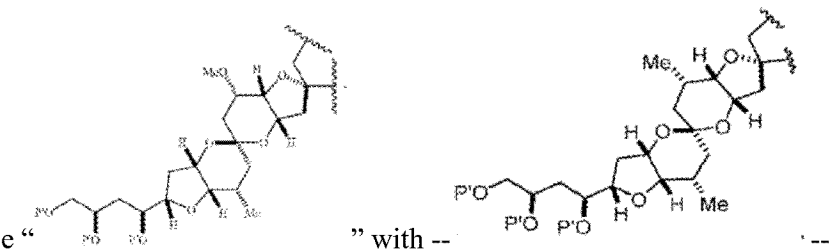 --

Lines 15-29, replace " " with -- 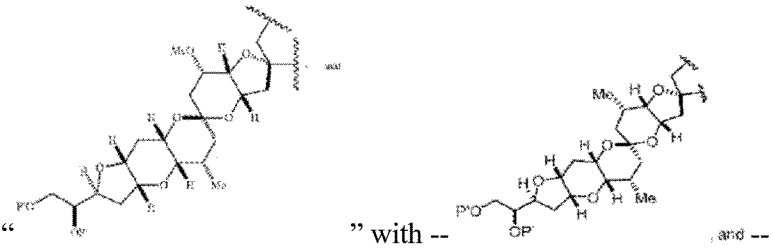, and --

Lines 30-43, replace " " with -- 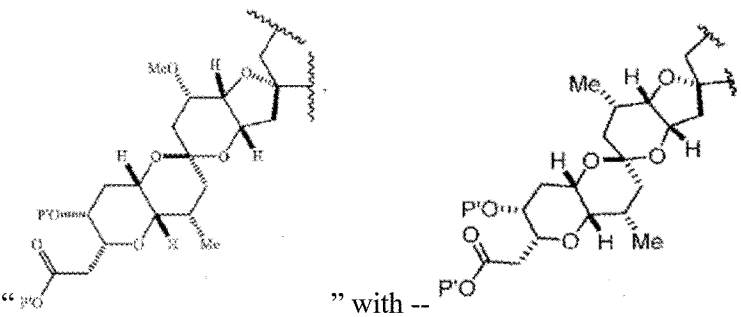 --

Column 44, Lines 1-15, replace " " with -- 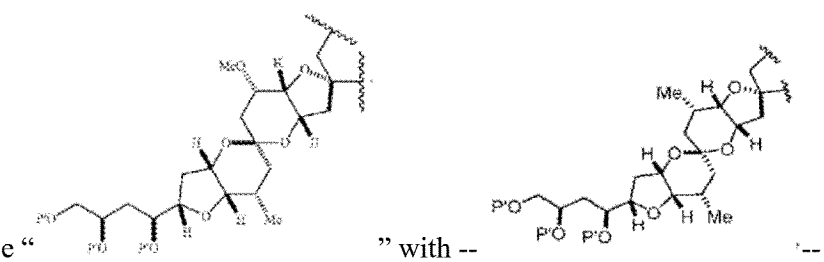 --

Lines 16-34, replace " " with -- 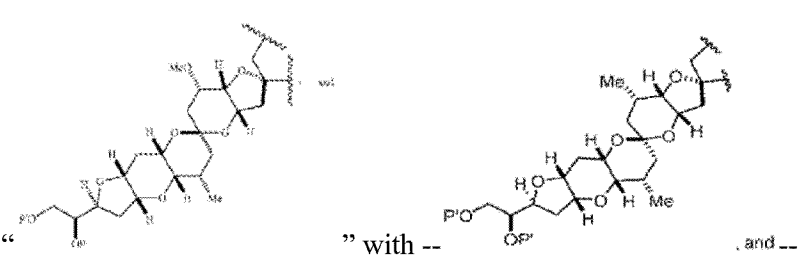, and --

Lines 35-50, replace " 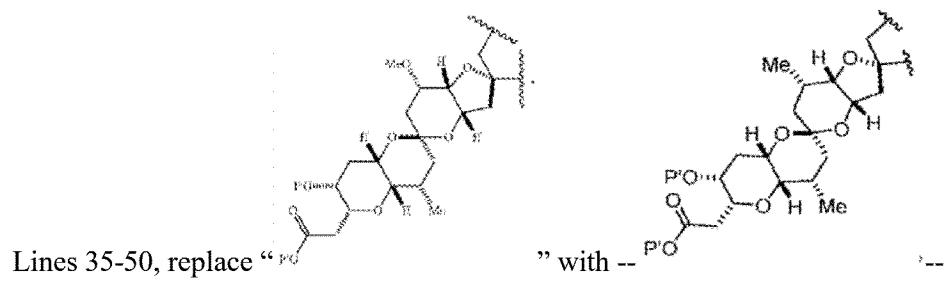 " with -- --
Column 49, Lines 50-65, replace " 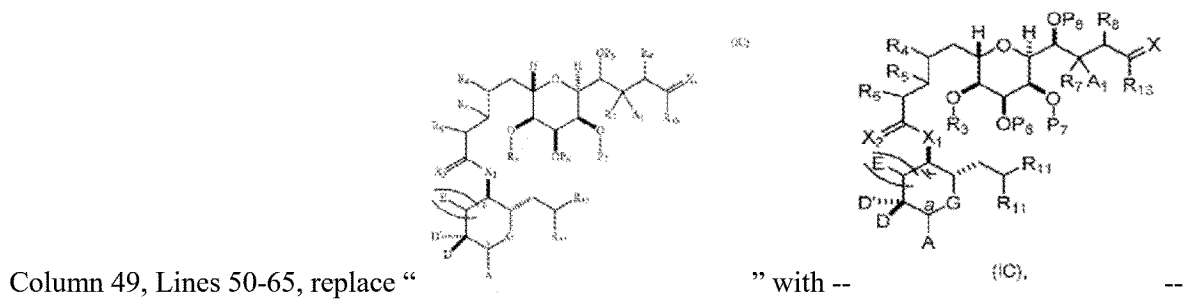 " with -- --
Column 51, Lines 17-30, replace " 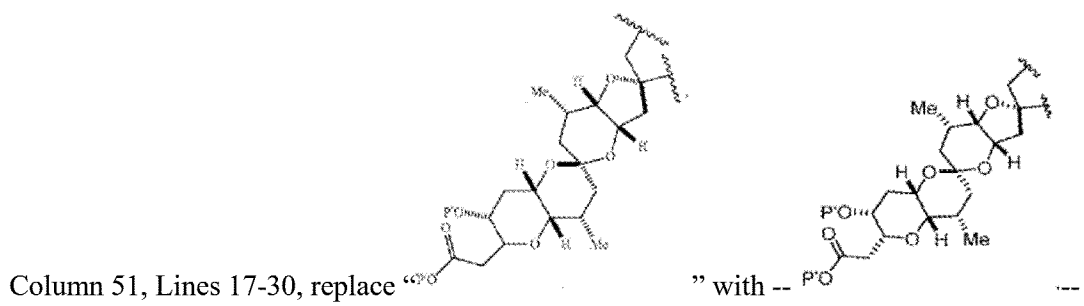 " with -- --
Column 53, Lines 50-65, replace " 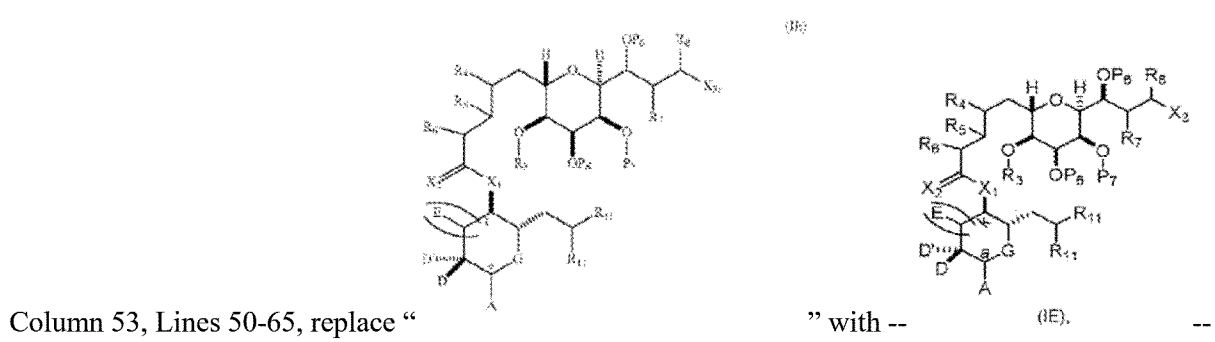 " with -- --
Column 55, Lines 5-15, replace " 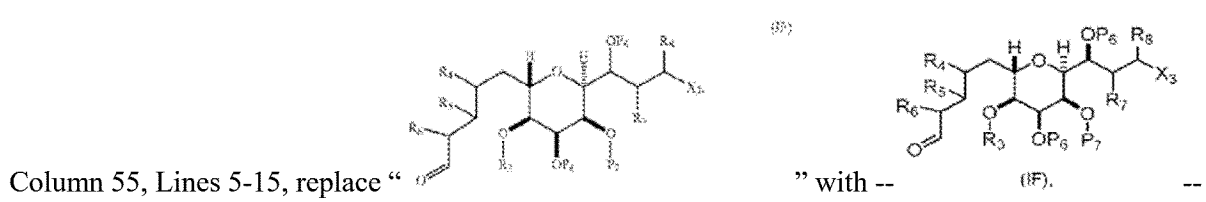 " with -- --

Column 56, Lines 5-15, replace " " with --  --
Column 57, Line 44, replace "$R^D$" with --$R_D$--
Column 62, Line 27, replace "both $P_6$ and $R_{11}$ both together" with --both $P_6$ and both $R_{11}$, together--
Column 63, Line 65, replace "—$OP_1$" with -- —$OP_{11}$--
Column 66, Line 61, replace "in which A," with --in which $A_1$--
Column 75, Compounds 10-12, replace " " with 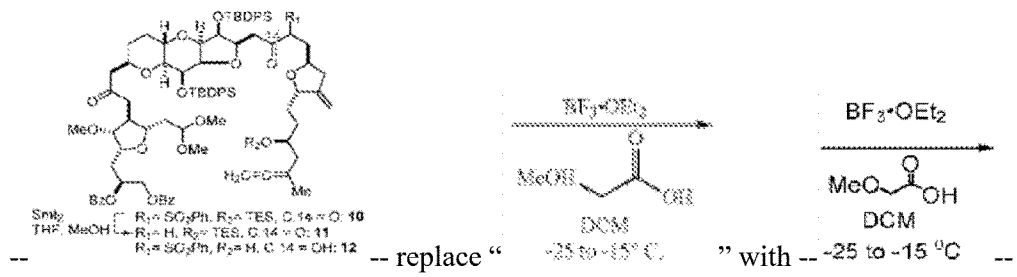 -- replace " 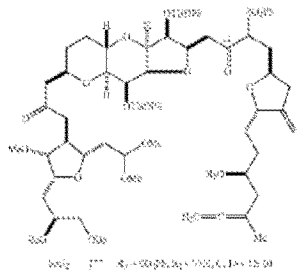 " with --$-25$ to $-15\ ^0C$ --
Column 92, Lines 10-25, replace " " with -- 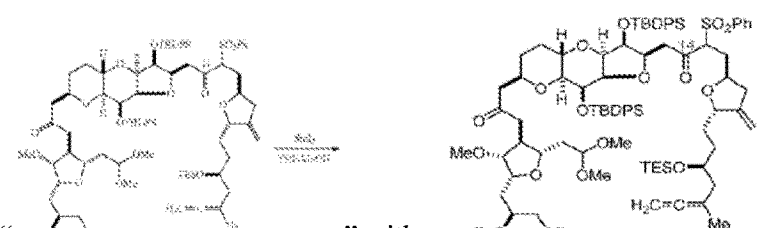 --
Lines 26-42, replace " " with -- 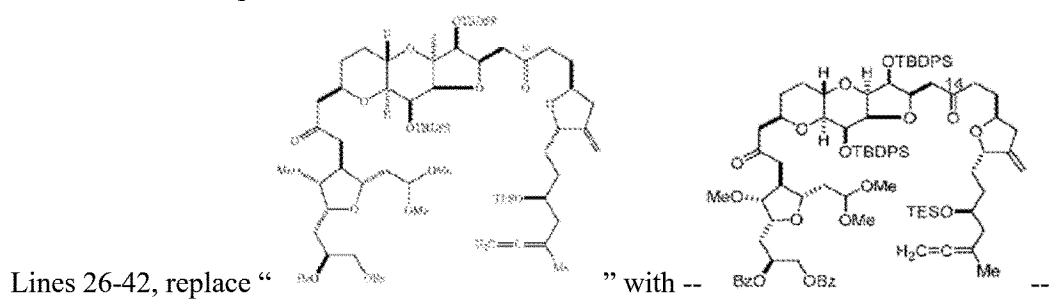 --

Column 123, Compound 40, replace " 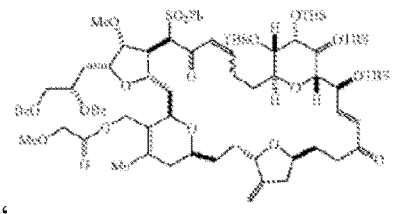 " with
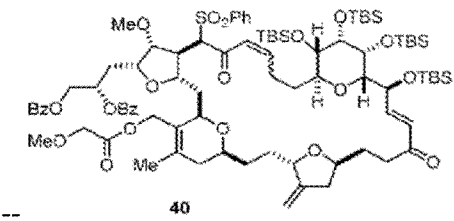
--
Compound 35, replace " 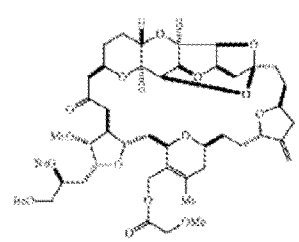 " with -- 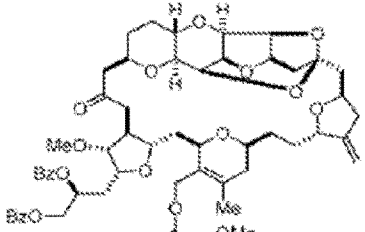 --
Column 124, Compound 18, replace " 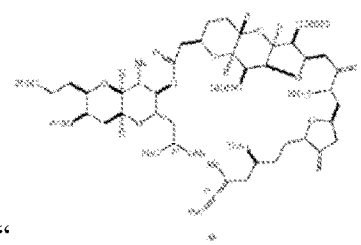 " with -- 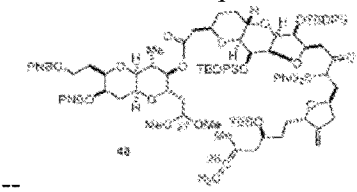 --
Column 127, Compound 48, replace " " with
-- --

CERTIFICATE OF CORRECTION (continued)
U.S. Pat. No. 11,136,335 B2

Column 128, Compound 47, replace " 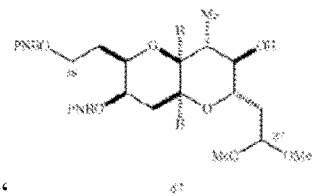 " with -- 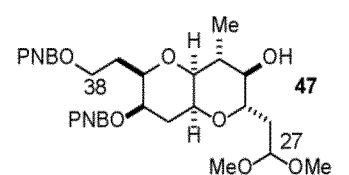 --

Columns 145-146, Compound 53, replace " 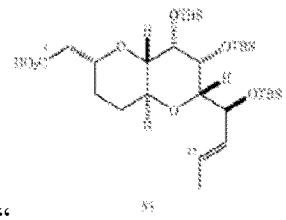 " with -- 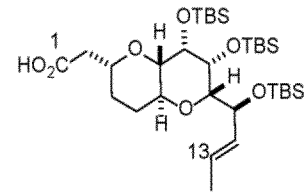 --

Compound 54, replace " 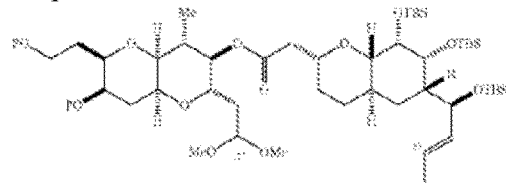 " with

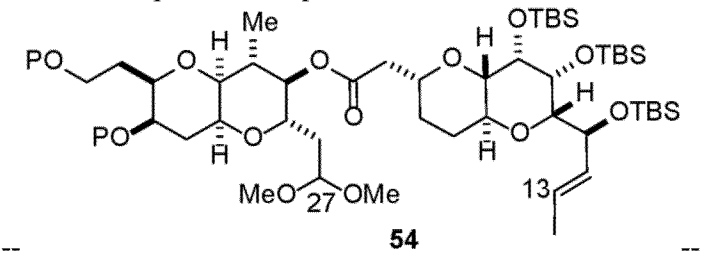

--

Column 147, Compound 57, replace " 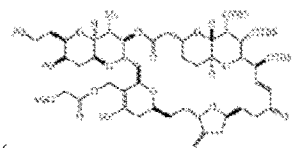 " with

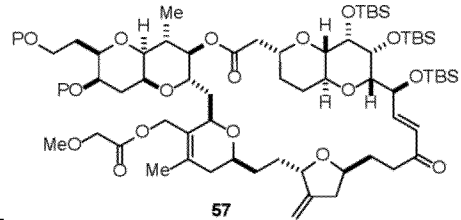

--

Column 149, Compound 60, replace " 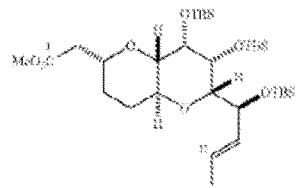 " with -- 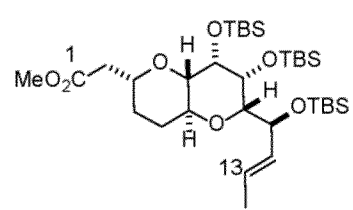 --

Column 151, Compound 63, replace " " with -- 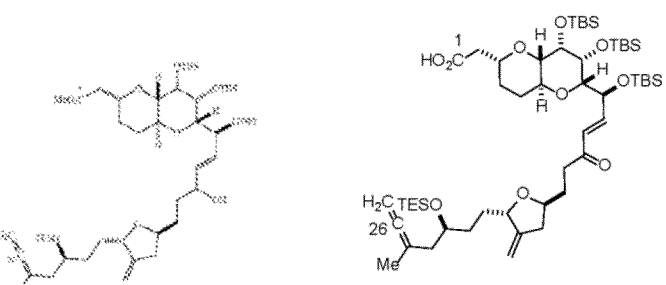 --
Columns 153-154, Compound 57, replace " " with 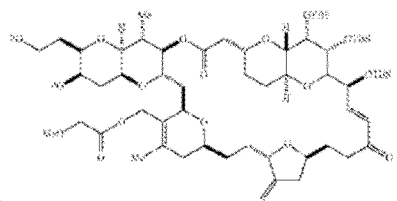
-- 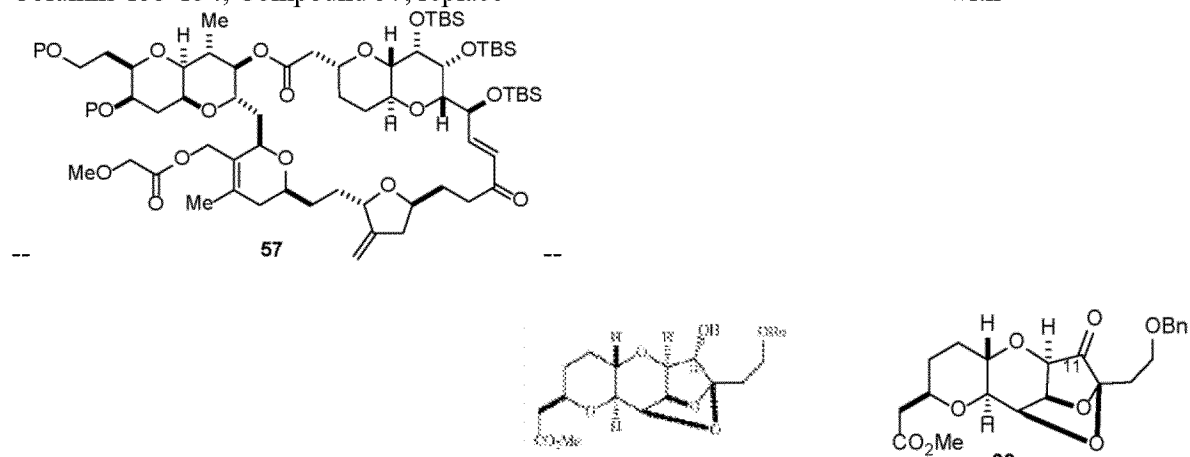 --
Columns 155-156, Compound 69, replace " " with -- 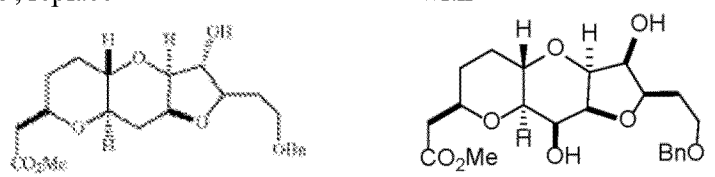 --
Compound 71, replace " " with -- 71 --
Column 161, Lines 1-9, replace " " with -- 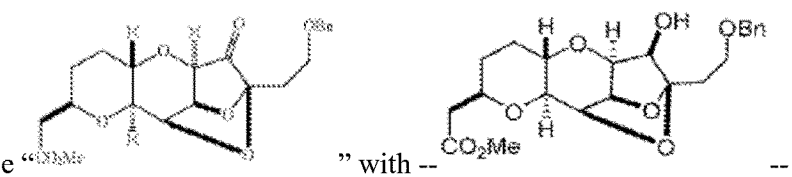 --

Column 166, Compounds 86 and 85, replace

" 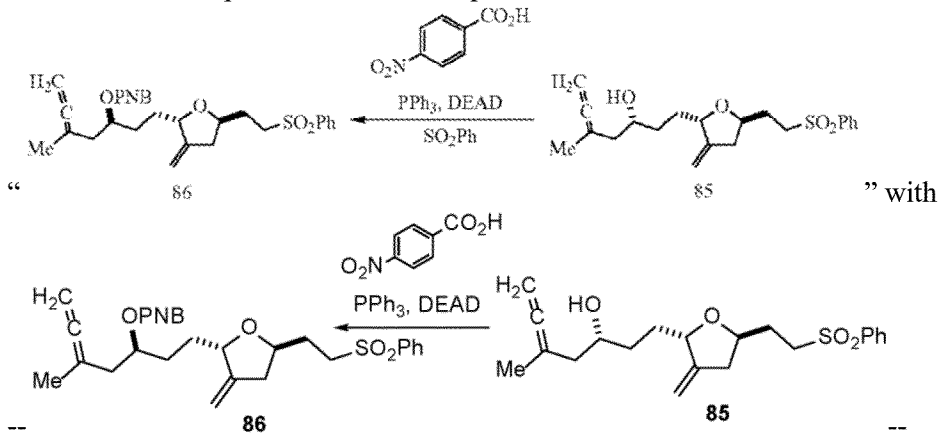 " with

-- 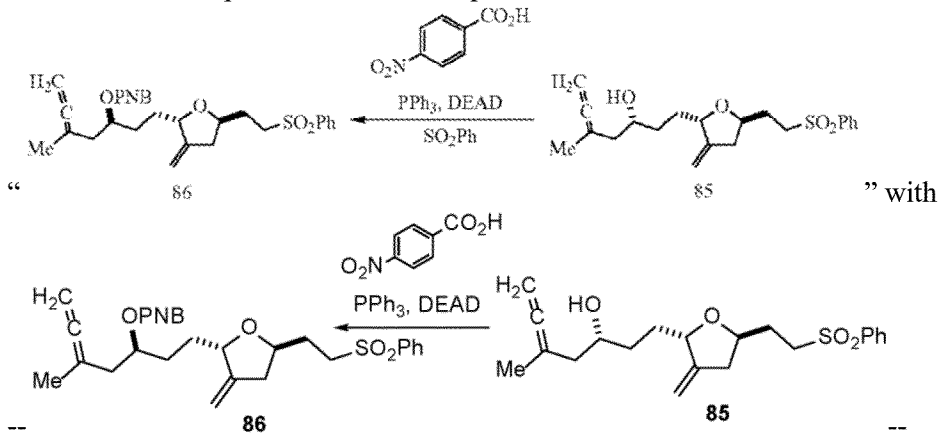 --

Column 174, Line 67, replace "SR$_{x1}$" with -- — SR$_{x1}$--

Column 175, Line 48, replace "R$_6$ is H or OP";" with --R$_8$ is H or OP";--

Column 176, Lines 2-20, replace " 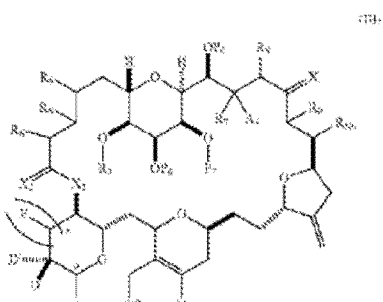 " with

-- 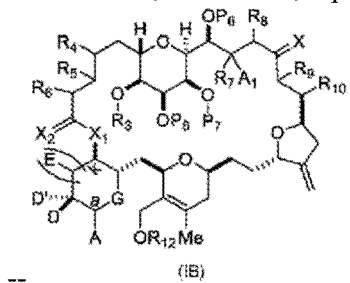 --

Column 188, Lines 52-59, replace " 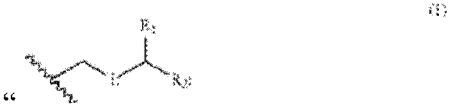 " with

-- 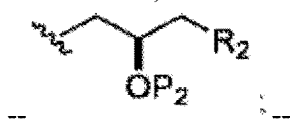 --

Column 191, Line 19, replace "each is independently" with --each R$_{11}$ is independently--
    Line 20, replace "both combine to form" with --both R$_{11}$ combine to form--
    Line 23, replace "and both together" with --and both R$_{11}$ together--

Column 192, Lines 7-14, replace " 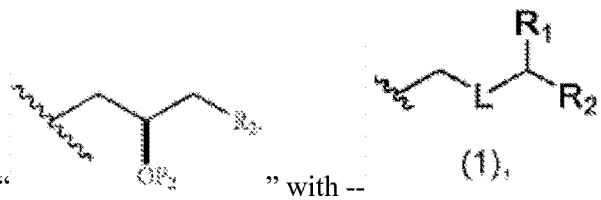 " with -- --
Column 193, Line 62, replace "each is independently" with --each $R_{11}$ is independently--
Line 66, replace "both $P_5$ and" with --both $P_6$ and--
Column 197, Line 21, replace "—$OP_1$" with -- —$OP_{11}$--
Column 199, Lines 55-63, replace "  " with -- --
Column 207, Lines 55-67, replace " 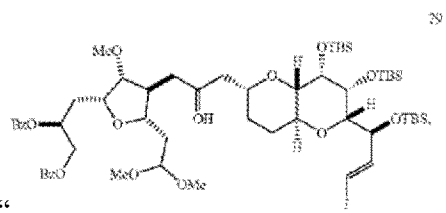 " with
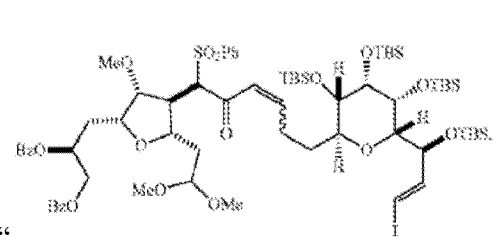
--  29  --
Column 209, Lines 57-67, replace " " with
37
--